(12) United States Patent
Dicks et al.

(10) Patent No.: US 9,714,435 B2
(45) Date of Patent: Jul. 25, 2017

US009714435B2

(54) SIMIAN ADENOVIRUS AND HYBRID ADENOVIRAL VECTORS

(75) Inventors: Matthew Douglas James Dicks, Oxford (GB); Matthew Guy Cottingham, Oxford (GB); Adrian Vivian Sinton Hill, Oxford (GB); Sarah Gilbert, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 0 days.

(21) Appl. No.: 14/119,413

(22) PCT Filed: May 25, 2012

(86) PCT No.: PCT/GB2012/000467
§ 371 (c)(1),
(2), (4) Date: Mar. 19, 2014

(87) PCT Pub. No.: WO2012/172277
PCT Pub. Date: Dec. 20, 2012

(65) Prior Publication Data
US 2015/0044766 A1    Feb. 12, 2015

(30) Foreign Application Priority Data
May 25, 2011 (GB) .................................. 1108879.6

(51) Int. Cl.
| C12N 15/861 | (2006.01) |
| C12N 15/11  | (2006.01) |
| A61K 39/235 | (2006.01) |
| C12N 15/86  | (2006.01) |
| C12N 7/00   | (2006.01) |

(52) U.S. Cl.
CPC ............... *C12N 15/86* (2013.01); *C12N 7/00* (2013.01); *C12N 2710/10021* (2013.01); *C12N 2710/10042* (2013.01); *C12N 2710/10044* (2013.01); *C12N 2800/204* (2013.01)

(58) Field of Classification Search
None
See application file for complete search history.

(56) References Cited

U.S. PATENT DOCUMENTS

| 2004/0136963 | A1  | 7/2004  | Wilson et al. |
| 2008/0090281 | A1* | 4/2008  | Wilson et al. ............ 435/235.1 |
| 2009/0110695 | A1* | 4/2009  | Havenga et al. .......... 424/199.1 |
| 2010/0303859 | A1* | 12/2010 | Williams ................... 424/215.1 |
| 2011/0217332 | A1* | 9/2011  | Colloca et al. ............ 424/233.1 |

OTHER PUBLICATIONS

Dicks et al, , 2) 90% identical to nucleotides 18302-21130 of SEQ ID No. 1, 3) 90% identical to nucleotides 13891-15486 of SEQ ID No. 1, 4) is 90% identical to nucleotides 32290-33621 of SEQ ID No. 1 or 5) a nucleic acid that hybridizes to any of these sequences, PLOS one, 2012, vol. 7(7), pp. 1-12.*
Yan et al, Developing Novel Oncolytic Adenoviruses through Bioselection, Journal of Virology, Feb. 2003, p. 2640-2650.*
Guo et al, Protein tolerance to random amino acid change, PNAS, 2004, vol. 101 (25), pp. 9205-9210.*
Lesk et al, Prediction of Protein Function from Protein Sequence and Structure, p. 27 and 28, downloaded Sep. 16, 2007.*
Farina, Steven F., Gao, Guang-Ping, Xian, Z.Q., Rux, John J., Burnett, Roger M., Alvira, Mauricio R., Marsh, Jonathan, Ertl, Hildegund C.J., and Wilson, James M. "Replication-Defective Vector Based on a Chimpanzee Adenovirus", Journal of Virology, Dec. 201, pp. 11603-11613; Copyright ©2001, American Society of Microbiology, All Rights Reserved.; vol. 75, No. 23.; Received Jun. 21, 2001/Accepted Aug. 30, 2001.
Hillis, William D. and Goodman, Rosanne "Serologic Classification of Chimpanzee Adenoviruses By Hemagglutination And Hemagglutination Inhibition"; The Journal of Immunology, Copyright ©1969 by The Williams & Wilkins Co.; vol. 103, No. 5, Nov. 1, 1969, 103(5) pp. 1089-1095; Printed in U.S.A., Received Apr. 21, 1969.

* cited by examiner

*Primary Examiner* — Maria Marvich
(74) *Attorney, Agent, or Firm* — Avery N. Goldstein; Blue Filament Law PLLC

(57) ABSTRACT

The present invention provides recombinant adenoviral vectors, immunogenic compositions thereof and their use in medicine, and methods for generating recombinant adenoviral vectors. In particular, the present invention provides an adenovirus vector comprising a capsid derived from chimpanzee adenovirus AdY25, wherein said capsid encapsidates a nucleic acid molecule comprising an exogeneous nucleotide sequence of interest.

13 Claims, 9 Drawing Sheets

SEQUENCE LISTING

<160> NUMBER OF SEQ ID NOS: 49

<210> SEQ ID NO 1
<211> LENGTH: 36711
<212> TYPE: DNA
<213> ORGANISM: Chimpanzee adenovirus AdY25
<220> FEATURE:
<221> NAME/KEY: source
<222> LOCATION: 1..36711
<223> OTHER INFORMATION: /mol_type="DNA"
    /organism="Chimpanzee adenovirus AdY25"

<400> SEQUENCE: 1

```
ccatcatcaa taatatacct caaacttttt gtgcgcgtta atatgcaaat gaggcgtttg      60
aatttgggaa gggaggaagg tgattggccg agagaagggc gaccgttagg ggcggggcga     120
gtgacgtttt tgatgacgtga ccgcgaggag gagccagttt gcaagttctc gtgggaaaag    180
tgacgtcaaa cgaggtgtgg tttgaacacg gaaatactca attttcccgc gctctctgac     240
aggaaatgag gtgtttctag gcggatgcaa gtgaaaacgg gccattttcg cgcgaaaact     300
gaatgaggaa gtgaaaatct gagtaatttc gcgtttatga cagggaggag tatttgccga     360
gggccgagta gactttgacc gattacgtgg gggtttcgat taccgtgttt ttcacctaaa     420
tttccgcgta cggtgtcaaa gtccggtgtt tttacgtagg tgtcagctga tcgccagggt     480
atttaaacct gcgctctcca gtcaagaggc cactcttgag tgccagcgag aagagttttc     540
tcctccgcgc cgcgagtcag atctacactt tgaaagatga ggcacctgag agacctgccc     600
gatgagaaaa tcatcatcgc ttccgggaac gagattctgg aactggtggt aaatgccatg     660
atgggcgacg accctccgga gcccccacc ccatttgagg caccttcgct acacgatttg     720
tatgatctgg aggtggatgt gcccgaggac gaccccaacg aggaggcggt aaatgattta     780
tttagcgatg ccgcgctgct agctgccgag gaggcttcga gccctagctc agacagcgac     840
tcttcactgc ataccctag accccggcaga ggtgagaaaa agatccccga gcttaaaggg     900
gaagagatgg acttgcgctg ctatgaggaa tgcttgcccc cgagcgatga tgaggacgag     960
caggcgatcc agaacgcagc gagccaggga atgcaagccg ccagcgagag ttttgcgctg    1020
gactgcccgc ctctgcccgg acacggctgt aagtcttgtg aatttcatcg cttgaatact    1080
ggagataaag ctgtgttatg tgcactttgc tatatgagag cttacaacca ttgtgtttac    1140
agtaagtgtg attaagttga actttagagg gaggcagaga gcagggtgac tgggcgatga    1200
ctggtttatt tatgtatata tgttcttat ataggtcccg tctctgacgc agatgatgag    1260 accccccacta cagagtccac ttcgtcaccc ccagaaattg gcacatctcc acctgagaat    1320
attgttagac cagttcctgt tagagccact gggaggagag cagctgtgga atgtttggat    1380
gacttgctac aggctgggga tgaacctttg gacttgtgta cccggaaacg ccccaggcac    1440
```

```
taagtgccac acatgtgtgt ttacttgagg tgatgtcagt atttataggg tgtggagtgc    1500
aataaaaaat gtgttgactt taagtgcgtg gtttatgact caggggtggg gactgtgggt    1560
atataagcag gtgcagacct gtgtggttag ctcagagcgg catggagatt tggacgatct    1620
tggaagatct tcacaagact agacagctgc tagagaacgc ctcgaacgga gtctctcacc    1680
tgtggagatt ctgcttcggt ggcgacctag ctaagctagt ctatagggcc aaacaggatt    1740
atagcgaaca atttgaggtt attttgagag agtgtccggg tcttttttgac gctcttaatt    1800 tgggtcatca gactcacttt aaccagagga ttgtaagagc ccttgatttt actactcccg    1860
gcagatccac tgcggcagta gcctttttttg cttttcttct tgacaaatgg agtcaagaaa    1920
cccatttcag cagggattac cagctggatt tcttagcagt agctttgtgg agaacatgga    1980
aatcccagcg cctgaatgca atctcaggct acttgccggt acagccacta gacactctga    2040
agatcctgaa tctccaggag agtcccaggg cacgccaacg tcgccggcag cagcagcggc    2100
agcaggagga ggatcaagaa gagaacccga gagccggcct ggaccctccg gcggaggagg    2160
agtagctgac ctgtttcctg aactgcgccg ggtgctgact aggtcttcga gtggtcggga    2220
gagggggatt aagcgggaga ggcatgatga gactaatcac agaactgaac tgactgtggg    2280
tctgatgagc cgcaagcgtc cagaaacagt gtggtggcat gaggtgcagt cgactggcac    2340
agatgaggtg tcagtgatgc atgagaggtt ttccctagaa caagtcaaga cttgttggtt    2400
agagcctgag gatgattggg aggtagccat caggaattat gccaagctgg ctctgaggcc    2460
agacaagaag tacaagatta ctaagctgat aaatatcaga aatgcctgct acatctcagg    2520
gaatggggct gaagtggaga tctgtcttca ggaaagggtg gctttcagat gctgcatgat    2580
gaatatgtac ccgggagtgg tgggcatgga tggggtcacc tttatgaaca tgaggttcag    2640
gggagatggg tataatggca cggtctttat ggccaatacc aagctgacag ttcatggctg    2700
ctccttcttt gggtttaata cacctgcat tgaggcctgg ggtcaggttg gtgtgagggg    2760
ctgtagtttt tcagccaact ggatgggggt cgtgggcagg accaagagta tgctgtccgt    2820
gaagaaatgc ttgttcgaga ggtgccacct gggggtgatg agcgagggcg aagccagaat    2880
ccgccactgc gcctctaccg agacgggctg ttttgtgctg tgcaagggca atgctaagat    2940
caagcataat atgatctgtg gagcctcgga cgagcgcggc taccagatgc tgacctgcgc    3000
cggtgggaac agccatatgc tggccaccgt gcatgtggcc tcccatgccc gcaagccctg    3060
gcccgagttc gagcacaatg tcatgaccag gtgcaatatg catctggggt cccgccgagg    3120
catgttcatg ccctatcagt gcaacctgaa ttatgtgaag gtgctgctgg agcccgatgc    3180
catgtccaga gtgagcctga cggggtgtt tgacatgaat gtggaggtgt ggaagattct    3240
gagatatgat gaatccaaga ccaggtgccg agcctgcgag tgcggaggga agcatgccag    3300
gttccagccc gtgtgtgtgg aggtgacgga ggacctgcga cccgatcatt tggtgttgtc    3360
ctgcaccggg acggagttcg gttccagcgg ggaagaatct gactagagtg agtagtgttc    3420
tggggcgggg gaggacctgc atgagggcca gaatgactga aatctgtgct tttctgtgtg    3480
ttgcagcatc atgagcggaa gcggctcctt tgagggaggg gtattcagcc cttatctgac    3540
ggggcgtctc ccctcctggg cgggagtgcg tcagaatgtg atgggatcca cggtggacgg    3600
ccggcccgtg cagcccgcga actcttcaac cctgacctat gcaaccctga gctcttcgtc    3660
ggtggacgca gctgccgccc cagctgctgc atccgccgcc agcgccgtgc gcggaatggc    3720
catgggcgcc ggctactacg gcactctggt ggccaactcg agttccacca ataatcccgc    3780
cagcctgaac gaggagaagc tgctgctgct gatggcccag cttgaggcct tgacccagcg    3840
```

-continued

```
cctgggcgag ctgacccagc aggtggctca gctgcaggag cagacgcggg ccgcggttgc    3900
cacggtgaaa tccaaataaa aaatgaatca ataaataaac ggagacggtt gttgatttta    3960
acacagagtc tgaatcttta tttgattttt cgcgcgcggt aggccctgga ccaccggtct    4020
cgatcattga gcacccggtg gatcttttcc aggacccggt agaggtgggc ttggatgttg    4080
aggtacatgg gcatgagccc gtcccggggg tggaggtagc tccattgcag ggcctcgtgc    4140
tcggggggtgg tgttgtaaat cacccagtca tagcaggggc gcaggggcgtg gtgttgcaca    4200
atatctttga ggaggagact gatggccacg gcagcccctt tggtgtaggt gtttacaaat    4260
ctgttgagct gggagggatg catgcggggg gagatgaggt gcatcttggc ctggatcttg    4320
agattggcga tgttaccgcc cagatcccgc ctggggttca tgttgtgcag gaccaccagc    4380
acggtgtatc cggtgcactt ggggaattta tcatgcaact tggaagggaa ggcgtgaaag    4440
aatttggcga cgcccttgtg tccgcccagg ttttccatgc actcatccat gatgatggca    4500
atgggcccgt gggcggcggc ctgggcaaag acgtttcggg ggtcggacac atcatagttg    4560
tggtcctggg tgaggtcatc ataggccatt ttaatgaatt tggggcggag ggtgccggac    4620
tgggggacaa aggtaccctc gatcccgggg gcgtagttcc cctcacagat ctgcatctcc    4680
caggctttga gctcagaggg ggggatcatg tccacctgcg gggcgataaa gaacacggtt    4740
tccggggcgg gggagatgag ctgggccgaa agcaagttcc ggagcagctg ggacttgccg    4800
cagccggtgg ggccgtaaat gaccccgatg accggctgca ggtggtagtt gagggagaga    4860
cagctgccgt cctcccggag gaggggggcc acctcgttca tcatctcgcg cacgtgcatg    4920
ttctcgcgca ccagttccgc caggaggcgc tctcccccca gagataggag ctcctggagc    4980
gaggcgaagt ttttcagcgg cttgagtccg tcggccatgg gcattttgga gagggtctgt    5040
tgcaagagtt ccaagcggtc ccagagctcg gtgatgtgct ctacggcatc tcgatccagc    5100
agacctcctc gtttcgcggg ttgggacgac tgcgggagta gggcaccaga cgatgggcgt    5160
ccagcgcagc cagggtccgg tccttccagg gccgcagcgt ccgcgtcagg gtggtctccg    5220
tcacggtgaa ggggtgcgcg ccgggctggg cgcttgcgag ggtgcgcttc aggctcatcc    5280
ggctggtcga aaaccgctcc cgatcggcgc cctgcgcgtc ggccaggtag caattgacca    5340
tgagttcgta gttgagcgcc tcggccgcgt ggcctttggc gcggagctta cctttggaag    5400
tctgcccgca ggcgggacag aggagggact tgagggcgta gagcttgggg gcgaggaaga    5460
cggaatcggg ggcgtaggcg tccgcgccgc agtgggcgca gacggtctcg cactccacga    5520
gccaggtgag gtcgggctgg tcggggtcaa aaaccagttt cccgccgttc tttttgatgc    5580
gtttcttacc tttggtctcc atgagctcgt gtcccgctg ggtgacaaag aggctgtccg    5640
tgtccccgta gaccgacttt atgggccggt cctcgagcgg tgtgccgcgg tcctcctcgt    5700
agaggaaccc cgcccactcc gagacgaaag cccgggtcca ggccagcacg aaggaggcca    5760
cgtgggacgg gtagcggtcg ttgtccacca gcgggtccac ttttccagg gtatgcaaac    5820
acatgtcccc ctcgtccaca tccaggaagg tgattggctt gtaagtgtag gccacgtgac    5880
cggggtccc ggccgggggg gtataaaagg gggcgggccc ctgctcgtcc tcactgtctt    5940
ccggatcgct gtccaggagc gccagctgtt ggggtaggta ttccctctcg aaggcgggca    6000
tgacctcggc actcaggttg tcagtttcta gaaacgagga ggatttgata ttgacggtgc    6060
cagcggagat gcctttcaag agcccctcgt ccatctggtc agaaaagacg atttttttgt    6120
tgtcgagctt ggtggcgaag gagccgtaga gggcgttgga aaggagcttg gcgatggagc    6180
```

```
gcatggtctg gttttttttcc ttgtcggcgc gctccttggc cgcgatgttg agctgcacgt   6240
actcgcgcgc cacgcacttc cattcgggga agacggtggt catctcgtcg ggcacgattc   6300
tgacctgcca acctcgatta tgcagggtga tgaggtccac actggtggcc acctcgccgc   6360
gcaggggctc gttggtccag cagaggcggc cgcccttgcg cgagcagaag gggggcagag   6420
ggtccagcat gacctcgtcg gggggtcgg catcgatggt gaagatgccg gcaggagat    6480 cggggtcgaa gtagctgatg gaagtggcca gatcgtccag ggaagcttgc cattcgcgca   6540
cggccagcgc gcgctcgtag ggactgaggg gcgtgcccca gggcatgggg tgggtgagcg   6600
cggaggcgta catgccgcag atgtcgtaga cgtagagggg ctcctcgagg atgccgatgt   6660
aggtggggta gcagcgcccc ccgcggatgc tggcgcgcac gtagtcatac agctcgtgcg   6720
agggcgcgag gagccccggg cccaggttgg tgcgactggg cttttcggcg cggtagacga   6780
tctggcgaaa gatggcatgc gagttggagg agatggtggg cctttggaag atgttgaagt   6840
gggcgtgggg gaggccgacc gagtcgcgga tgaagtgggc gtaggagtct tgcagtttgg   6900
cgacgagctc ggcggtgacg aggacgtcca gagcgcagta gtcgagggtc tcctggatga   6960
tgtcatactt gagctggccc ttttgttttcc acagctcgcg gttgagaagg aactcttcgc   7020
ggtccttcca gtactcttcg aggggaaacc cgtcctgatc tgcacggtaa gagcctagca   7080
tgtagaactg gttgacggcc ttgtaggcgc agcagcccctt ctccacgggg agggcgtagg   7140
cctgggcggc cttgcgcagg gaggtgtgcg tgagggcgaa ggtgtccctg accatgacct   7200
tgaggaactg gtgcttgaaa tcgatatcgt cgcagccccc ctgctcccag agctggaagt   7260
ccgtgcgctt cttgtaggcg gggttgggca aagcgaaagt aacatcgttg aaaaggatct   7320
tgcccgcgcg gggcataaag ttgcgagtga tgcggaaagg ctgggcacc tcggcccggt   7380 tgttgatgac ctgggcggcg agcacgatct cgtcgaaacc gttgatgttg tggcccacga   7440
tgtagagttc cacgaatcgc gggcggccct tgacgtgggg cagcttcttg agctcctcgt   7500
aggtgagctc gtcggggtcg ctgagaccgt gctgctcgag cgcccagtcg gcgagatggg   7560
ggttggcgcg gaggaaggaa gtccagagat ccacggccag ggcggtttgc agacggtccc   7620
ggtactgacg gaactgctgc ccgacggcca ttttttcggg ggtgacgcag tagaaggtgc   7680
gggggtcccc gtgccagcgg tcccatttga gctggagggc gagatcgagg gcgagctcga   7740
cgaggcggtc gtccctgag agtttcatga ccagcatgaa gggacgagc tgcttgccga    7800 aggaccccat ccaggtgtag gtttccacat cgtaggtgag gaagagcctt tcggtgcgag   7860
gatgcgagcc gatggggaag aactggatct cctgccacca attggaggaa tggctgttga   7920
tgtgatggaa gtagaaatgc cgacggcgcg ccgaacactc gtgcttgtgt ttatacaagc   7980
ggccacagtg ctcgcaacgc tgcacgggat gcacgtgctg cacgagctgt acctgagttc   8040
ctttgacgag gaatttcagt gggaagtgga gtcgtggcgc ctgcatctcg tgctgtacta   8100
cgtcgtggtg gtcggcctgg ccctcttctg cctcgatggt ggtcatgctg acgagcccgc   8160
gcgggaggca ggtccagacc tcggcgcgag cgggtcggaa agcgaggacg agggcgcgca   8220
ggccggagct gtccagggtc ctgagacgct gcggagtcag gtcagtgggc agcggcggcg   8280
cgcggttgac ttgcaggagt ttttccaggg gcgcgggag gtcagatgg tacttgatct    8340 ccaccgcgcc gttggtggcg acgtcgatgg cttgcagggt cccgtgcccc tggggtgtga   8400
ccaccgtccc ccgtttcttc ttgggcggct ggggcgacgg gggcggtgcc tcttccatgg   8460
ttagaagcgg cggcgaggac gcgcgccggg cggcagaggc ggctcggggc ccggaggcag   8520
gggcggcagg ggcacgtcgg cgccgcgcgc gggtaggttc tggtactgcg cccggagaag   8580
```

```
actggcgtga gcgacgacgc gacggttgac gtcctggatc tgacgcctct gggtgaaggc   8640
cacgggaccc gtgagtttga acctgaaaga gagttcgaca gaatcaatct cggtatcgtt   8700
gacggcggcc tgccgcagga tctcttgcac gtcgcccgag ttgtcctggt aggcgatctc   8760
ggtcatgaac tgctcgatct cctcctcctg aaggtctccg cgaccggcgc gctccacggt   8820
ggccgcgagg tcgttggaga tgcggcccat gagctgcgag aaggcgttca tgcccgcctc   8880
gttccagacg cggctgtaga ccacgacgcc ctcgggatcg cgggcgcgca tgaccacctg   8940
ggcgaggttg agctccacgt ggcgcgtgaa gaccgcgtag ttgcagaggc gctggtagag   9000
gtagttgagc gtggtggcga tgtgctcggt gacgaagaaa tacatgatcc agcggcggag   9060
cggcatctcg ctgacgtcgc ccagcgcctc aagcgttcc atggcctcgt aaaagtccac    9120
ggcgaagttg aaaaactggg agttgcgcgc cgagacggtc aactcctcct ccagaagacg   9180
gatgagctcg gcgatggtgg cgcgcacctc gcgctcgaag gccccggga gttcctccac    9240
ttcctcctct tcttcctcct ccactaacat ctcttctact tcctcctcag gcggtggtgg   9300
tggcggggga gggggcctgc gtcgccggcg gcgcacgggc agacggtcga tgaagcgctc   9360
gatggtctcg ccgcgccggc gtcgcatggt ctcggtgacg gcgcgcccgt cctcgcgggg   9420
ccgcagcgtg aagacgccgc cgcgcatctc caggtggccg gggggtccc cgttgggcag    9480
ggagagggcg ctgacgatgc atcttatcaa ttgccccgta gggactccgc gcaaggacct   9540
gagcgtctcg agatccacgg gatctgaaaa ccgttgaacg aaggcttcga gccagtcgca   9600
gtcgcaaggt aggctgagca cggtttcttc tgccgggtca tgttggggag cggggcgggc   9660
gatgctgctg gtgatgaagt tgaaataggc ggttctgaga cggcggatgg tggcgaggag   9720
caccaggtct ttgggcccgg cttgctggat gcgcagacgg tcggccatgc ccaggcgtg    9780
gtcctgacac ctggccaggt ccttgtagta gtcctgcatg agccgctcca cgggcacctc   9840
ctcctcgccc gcgcggccgt gcatgcgcgt gagcccgaag ccgcgctggg gctggacgag   9900
cgccaggtcg gcgacgacgc gctcggcgag gatggcctgc tggatctggg tgagggtggt   9960
ctggaagtcg tcaaagtcga cgaagcggtg gtaggctccg gtgttgatgg tgtaggagca  10020
gttggccatg acgaccagt tgacggtctg gtggcccgga cgcacgagct cgtggtactt   10080
gaggcgcgag taggcgcgcg tgtcgaagat gtagtcgttg caggtgcgca ccaggtactg  10140
gtagccgatg aggaagtgcg gcggcggctg gcggtagagc ggccatcgct cggtggcggg  10200
ggcgccgggc gcgaggtcct cgagcatggt gcggtggtag ccgtagatgt acctggacat  10260
ccaggtgatg ccggcggcgg tggtggaggc gcgcgggaac tcgcggacgc ggttccagat  10320
gttgcgcagc ggcaggaagt agttcatggt gggcacggtc tggcccgtga ggcgcgcgca  10380
gtcgtggatg ctctatacgg gcaaaaacga aagcggtcag cggctcgact ccgtggcctg  10440
gaggctaagc gaacgggttg ggctgcgcgt gtaccccggt tcgaatctcg aatcaggctg  10500
gagccgcagc taacgtggta ctggcactcc cgtctcgacc caagcctgca ccaaccctcc  10560
aggatacgga ggcgggtcgt tttgcaactt tttttggagg ccggaaatga aactagtaag  10620
cgcgaaaagc ggccgaccgc gatggctcgc tgccgtagtc tggagaagaa tcgccagggt  10680
tgcgttgcgg tgtgccccgg ttcgaggccg gccggattcc gcggctaacg agggcgtggc  10740
tgccccgtcg tttccaagac cccatagcca gccgacttct ccagttacgg agcgagcccc  10800
tcttttgttt tgtttgtttt tgccagatgc atcccgtact gcggcagatg cgccccacc   10860
accctccacc gcaacaacag cccctcctc cacagccggc gcttctgccc ccgcccagc    10920
```

```
agcagcagca acttccagcc acgaccgccg cggccgccgt gagcgggcgct ggacagactt   10980
ctcagtatga tcacctggcc ttggaagagg gcgaggggct ggcgcgcctg ggggcgtcgt   11040
cgccggagcg gcacccgcgc gtgcagatga aaagggacgc tcgcgaggcc tacgtgccca   11100
agcagaacct gttcagagac aggagcgcg aggagcccga ggagatgcgc gcggcccggt    11160
tccacgcggg gcgggagctg cggcgcggcc tggaccgaaa gagggtgctg agggacgagg   11220
atttcgaggc ggacgagctg acggggatca gccccgcgcg cgcgcacgtg gccgcggcca   11280
acctggtcac ggcgtacgag cagaccgtga aggaggagag caacttccaa aaatccttca   11340
acaaccacgt gcgcaccctg atcgcgcgcg aggaggtgac cctgggcctg atgcacctgt   11400
gggacctgct ggaggccatc gtgcagaacc ccaccagcaa gccgctgacg gcgcagctgt   11460
tcctggtggt gcagcatagt cgggacaacg aggcgttcag ggaggcgctg ctgaatatca   11520
ccgagcccga gggccgctgg ctcctggacc tggtgaacat tctgcagagc atcgtggtgc   11580
aggagcgcgg ggctgccgctg tccgagaagc tggcggccat caacttctcg gtgctgagtc   11640
tgggcaagta ctacgctagg aagatctaca agacccccgta cgtgcccata gacaaggagg   11700
tgaagatcga cgggttttac atgcgcatga ccctgaaagt gctgaccctg agcgacgatc   11760
tggggggtgta ccgcaacgac aggatgcacc gcgcggtgag cgccagcagg cggcgcgagc   11820
tgagcgacca ggagctgatg cacagcctgc agcgggccct gaccggggcc gggaccgagg   11880
gggagagcta ctttgacatg ggcgcggacc tgcactggca gcccagccgc cgggccttgg   11940
aggcggcagg cggtcccccc tacatagaag aggtggacga tgaggtggac gaggagggcg   12000
agtacctgga agactgatgg cgcgaccgta ttttgctag atgcaacaac agccacctcc     12060
tgatcccgcg atgcgggcgg cgctgcagag ccagccgtcc ggcattaact cctcggacga   12120
ttggaccccag gccatgcaac gcatcatggc gctgacgacc cgcaacccccg aagcctttag   12180
acagcagccc caggccaacc ggctctcggc catcctggag gccgtggtgc cctcgcgctc    12240
caaccccacg cacgagaagg tcctggccat cgtgaacgcg ctggtggaga acaaggccat    12300
ccgcggcgac gaggccggcc tggtgtacaa cgcgctgctg gagcgcgtgg cccgctacaa    12360
cagcaccaac gtgcagacca acctggaccg catggtgacc gacgtgcgcg aggccgtggc    12420
ccagcgcgag cggttccacc gcgagtccaa cctgggatcc atggtggcgc tgaacgcctt    12480
cctcagcacc cagcccgcca acgtgccccg gggccaggag gactacacca acttcatcag    12540
cgccctgcgc ctgatggtga ccgaggtgcc ccagagcgag gtgtaccagt ccgggccgga    12600
ctacttcttc cagaccagtc gccagggctt gcagaccgtg aacctgagcc aggcgttcaa    12660
gaacttgcag ggcctgtggg gcgtgcaggc cccggtcggg gaccgcgcga cggtgtcgag    12720
cctgctgacg ccgaactcgc gcctgctgct gctgctggtg gccccccttca cggacagcgg    12780
cagcatcaac cgcaactcgt acctgggcta cctgattaac ctgtaccgcg aggccatcgg   12840
ccaggcgcac gtgacagagc agacctacca ggagatcacc cacgtgagcc gcgccctggg   12900
ccaggacgac ccgggcaatc tggaagccac cctgaacttt tgctgaccca accggtcgca   12960
gaagatcccg ccccagtaca cgctcagcgc cgaggaggag cgcatcctgc gatacgtgca   13020
gcagagcgtg ggcctgttcc tgatgcagga ggggccacc cccagcgccg cgctcgacat   13080
gaccgcgcgc aacatggagc ccagcatgta cgccagcaac cgcccgttca tcaataaact   13140
gatggactac ttgcatcggg cggccgccat gaactctgac tatttcacca acgccatcct   13200
gaatccccac tggctcccgc cgccgggggtt ctacacgggc gagtacgaca tgcccgaccc   13260
caatgacggg ttcctgtggg acgatgtgga cagcagcgtg ttctccccccc gaccgggtgc   13320
```

```
taacgagcgc cccttgtgga agaaggaagg cagcgaccga cgcccgtcct cggcgctgtc   13380
cggccgcgag ggtgctgccg cggcggtgcc cgaggccgcc agtcctttcc cgagcttgcc   13440
cttctcgctg aacagtattc gcagcagcga gctgggcagg atcacgcgcc cgcgcttgct   13500
gggcgaggag gagtacttga atgactcgct gttgagaccc gagcgggaga agaacttccc   13560
caataacggg atagagagcc tggtggacaa gatgagccgc tggaagacgt atgcgcagga   13620
gcacagggac gatccgtcgc aggggccac gagccgggc agcgccgccc gtaaacgccg   13680
gtggcacgac aggcagcggg gactgatgtg ggacgatgag gattccgccg acgacagcag   13740
cgtgttggac ttgggtggga gtggtaaccc gttcgctcac ctgcgccccc gcatcgggcg   13800
catgatgtaa gagaaaccga aaataaatga tactcaccaa ggccatggcg accagcgtgc   13860
gttcgtttct tctctgttgt tgtatctagt atgatgaggc gtgcgtaccc ggagggtcct   13920
cctccctcgt acgagagcgt gatgcagcag gcgatggcgg cggcggcggc gatgcagccc   13980
ccgctggagg ctccttacgt gccccgcgcg tacctggcgc ctacggaggg gcggaacagc   14040
attcgttact cggagctggc acccttgtac gataccaccc ggttgtacct ggtggacaac   14100
aagtcggcgg acatcgcctc gctgaactac cagaacgacc acagcaactt cctgaccacc   14160
gtggtgcaga acaatgactt caccccacg gaggccagca cccagaccat caactttgac   14220
gagcgctcgc ggtggggcgg tcagctgaaa accatcatgc acaccaacat gcccaacgtg   14280
aacgagttca tgtacagcaa caagttcaag gcgcgggtga tggtctcccg caagaccccc   14340
aacggggtga cagtgacaga tggtagtcag gatatcttgg agtatgaatg ggtggagttt   14400
gagctgcccg aaggcaactt ctcggtgacc atgaccatcg acctgatgaa caacgccatc   14460
atcgacaatt acttggcggt ggggcggcag aacggggtcc tggagagcga tatcggcgtg   14520
aagttcgaca ctaggaactt caggctgggc tgggaccccg tgaccgagct ggtcatgccc   14580
ggggtgtaca ccaacgaggc cttccacccc gatattgtct tgctgccggg ctgcggggtg   14640
gacttcaccg agagccgcct cagcaacctg ctgggcattc gcaagaggca gcccttccag   14700
gagggcttcc agatcatgta cgaggatctg gaggggggca acatccccgc gctcctggat   14760
gtcgacgcct atgagaaaag caaggaggag agcgccgccg cggcgactgc agctgtagcc   14820
accgcctcta ccgaggtcag gggcgataat tttgccagcc ctgcagcagt ggcagcggcc   14880
gaggcggctg aaaccgaaag taagatagtc attcagccgg tggagaagga tagcaaggac   14940
aggagctaca acgtgctgcc ggacaagata aacaccgcct accgcagctg gtacctggcc   15000
tacaactatg gcgaccccga gaagggcgtg cgctcctgga cgctgctcac cacctcggac   15060
gtcacctgcg gcgtggagca agtctactgg tcgctgcccg acatgatgca agacccggtc   15120
accttccgct ccacgcgtca agttagcaac taccgtggg tgggcgccga gctcctgccc   15180
gtctactcca agagcttctt caacgagcag gccgtctact cgcagcagct gcgcgccttc   15240
acctcgctca cgcacgtctt caaccgcttc cccgagaacc agatcctcgt ccgcccgccc   15300
gcgcccacca ttaccaccgt cagtgaaaac gttcctgctc tcacagatca cgggaccctg   15360
ccgctgcgca gcagtatccg gggagtccag cgcgtgaccg ttactgacgc cagacgccgc   15420
acctgcccct acgtctacaa ggccctgggc atagtcgcgc cgcgcgtcct ctcgagccgc   15480
accttctaaa aaatgtccat tctcatctcg cccagtaata acaccggttg gggcctgcgc   15540
gcgcccagca gatgtacgg aggcgctcgc caacgctcca cgcaacaccc cgtgcgcgtg   15600
cgcgggcact tccgcgctcc ctggggcgcc ctcaagggcc gcgtgcggtc gcgcaccacc   15660
```

```
gtcgacgacg tgatcgacca ggtggtggcc gacgcgcgca actacacccc cgccgccgcg    15720
cccgtctcca ccgtggacgc cgtcatcgac agcgtggtgg ccgacgcgcg ccggtacgcc    15780
cgcgccaaga gccggcggcg gcgcatcgcc cggcggcacc ggagcacccc cgccatgcgc    15840
gcggcgcgag ccttgctgcg cagggccagg cgcacgggac gcagggccat gctcagggcg    15900
gccagacgcg cggcttcagg cgccagcgcc ggcaggaccc ggagacgcgc ggccacggcg    15960
gcggcagcgg ccatcgccag catgtcccgc ccgcggcgag ggaacgtgta ctgggtgcgc    16020
gacgccgcca ccggtgtgcg cgtgcccgtg cgcacccgcc ccctcgcac ttgaagatgt    16080 tcacttcgcg atgttgatgt gtcccagcgg cgaggaggat gtccaagcgc aaattcaagg    16140
aagagatgct ccaggtcatc gcgcctgaga tctacggccc cgcggtggtg aaggaggaaa    16200
gaaagcccCg caaaatcaag cgggtcaaaa aggacaaaaa ggaagaagat gacgatctgg    16260
tggagtttgt gcgcgagttc gccccccggc ggcgcgtgca gtggcgcggg cggaaagtgc    16320
acccggtgct gagacccggc accaccgtgg tcttcacgcc cggcgagcgc tccggcagcg    16380
cttccaagcg ctcctacgac gaggtgtacg gggacgagga catcctcgag caggcggccg    16440
agcgcctggg cgagtttgct tacggcaagc gcagccgccc cgccctgaag gaagaggcgg    16500
tgtccatccc gctggaccac ggcaaccCca cgccgagcct caagcccgtg accctgcagc    16560
aggtgctgcc gagcgcagcg ccgcgccggg ggttcaagcg cgagggcgag gatctgtacc    16620
ccaccatgca gctgatggtg cccaagcgcc agaagctgga agacgtgctg gagaccatga    16680
aggtggaccc ggacgtgcag cccgaggtca aggtgcggcc catcaagcag gtggccccgg    16740
gcctgggcgt gcagaccgtg gacatcaaga tccccacgga gcccatggaa acgcagaccg    16800
agcccatgat caagcccagc accagcacca tggaggtgca gacggatccc tggatgccat    16860
cggctcctag ccgaagaccc cggcgcaagt acggcgcggc cagcctgctg atgcccaact    16920
acgcgctgca tccttccatc atccccacgc cgggctaccg cggcacgcgc ttctaccgcg    16980
gtcatacaac cagccgccgc cgcaagacca ccacccgccg ccgccgtcgc cgcacagccg    17040
ctgcatctac ccctgccgcc ctggtgcgga gagtgtaccg ccgcggccgc gcgcctctga    17100
ccctaccgcg cgcgcgctac cacccgagca tcgccattta aactttcgcc tgctttgcag    17160
atggccctca catgccgcct ccgcgttccc attacgggct accgaggaag aaaaccgcgc    17220
cgtagaaggc tggcggggaa cgggatgcgt cgccaccacc atcggcggcg gcgcgccatc    17280
agcaagcggt tgggggagg cttcctgccc gcgctgatcc ccatcatcgc cgcggcgatc    17340
ggggcgatcc ccggcattgc ttccgtggcg gtgcaggcct ctcagcgcca ctgagacact    17400
tggaaaacat cttgtaataa accaatggac tctgacgctc ctggtcctgt gatgtgtttt    17460
cgtagacaga tggaagacat caattttcg tccctggctc cgcgacacgg cacgcggccg    17520
ttcatgggca cctggagcga catcggcacc agccaactga acggggcgc cttcaattgg    17580 agcagtctct ggagcgggct taagaatttc gggtccacgc ttaaaaccta tggcagcaag    17640
gcgtggaaca gcaccacagg gcaggcgctg agggataagc tgaaagagca gaacttccag    17700
cagaaggtgg tcgatgggct cgcctcgggc atcaacgggg tggtggacct ggccaaccag    17760
gccgtgcagc ggcagatcaa cagccgcctg gaccgggtgc cgcccgccgg ctccgtggag    17820
atgccgcagg tggaggagga gctgcctccc ctggacaagc ggggcgagaa gcgacccgc    17880 ccgacgcgg aggagacgct gctgacgcac acgacgagc cgccccgta cgaggaggcg    17940 gtgaaactgg gtctgccac cacgcggccc atcgcgcccc tggccaccgg ggtgctgaaa    18000
cccgaaagta ataagcccgc gaccctggac ttgcctcctc ccgcttcccg cccctctaca    18060
```

```
gtggctaagc ccctgccgcc ggtggccgtg gcccgcgcgc gacccggggg ctccgcccgc   18120
cctcatgcga actggcagag cactctgaac agcatcgtgg gtctgggagt gcagagtgtg   18180
aagcgccgcc gctgctatta aacctaccgt agcgcttaac ttgcttgtct gtgtgtgtat   18240
gtattatgtc gccgctgtcc gccagaagga ggagtgaaga ggcgcgtcgc cgagttgcaa   18300
gatggccacc ccatcgatgc tgccccagtg ggcgtacatg cacatcgccg gacaggacgc   18360
ttcggagtac ctgagtccgg gtctggtgca gttcgcccgc gccacagaca cctacttcag   18420
tctggggaac aagtttagga accccacggt ggcgcccacg cacgatgtga ccaccgaccg   18480
cagccagcgg ctgacgctgc gcttcgtgcc cgtggaccgc gaggacaaca cctactcgta   18540
caaagtgcgc tacacgctgg ccgtgggcga caaccgcgtg ctggacatgg ccagcaccta   18600
ctttgacatc cgcggcgtgc tggatcgggg ccctagcttc aaaccctact ccggcaccgc   18660
ctacaacagc ctggctccca agggagcgcc caattccagc cagtgggagc aaaaaaaggc   18720
aggcaatggt gacactatgg aaacacacac atttggtgtg gccccaatgg gcggtgagaa   18780
tattacaatc gacggattac aaattggaac tgacgctaca gctgatcagg ataaaccaat   18840
ttatgctgac aaaacattcc agcctgaacc tcaagtagga gaagaaaatt ggcaagaaac   18900
tgaaagcttt tatggcggta gggctcttaa aaaagacaca agcatgaaac cttgctatgg   18960
ctcctatgct agacccacca atgtaaaggg aggtcaagct aaacttaaag ttggagctga   19020
tggagttcct accaaagaat ttgacataga cctggctttc tttgatactc ccggtggcac   19080
agtgaatgga caagatgagt ataaagcaga cattgtcatg tataccgaaa acacgtatct   19140
ggaaactcca gacacgcatg tggtatacaa accaggcaag gatgatgcaa gttctgaaat   19200
taacctggtt cagcagtcca tgcccaatag acccaactat attgggttca gagacaactt   19260
tattgggctc atgtattaca acagtactgg caatatgggg gtgctggctg tcaggcctc   19320 acagctgaat gctgtggtcg acttgcaaga cagaaacacc gagctgtcat accagctctt   19380
gcttgactct ttgggtgaca gaacccggta tttcagtatg tggaatcagg cggtggacag   19440
ttatgatcct gatgtgcgca ttattgaaaa ccatggtgtg gaagacgaac ttcccaacta   19500
ttgcttcccc ctggatgggt ctggcactaa tgccgcttac caaggtgtga agtaaaaaaa   19560
tggtaacgat ggtgatgttg agagcgaatg ggaaaatgat gatactgtcg cagctcgaaa   19620
tcaattatgc aagggcaaca tttttgccat ggaaattaac ctccaagcca acctgtggag   19680
aagtttcctc tactcgaacg tggccctgta cctgcccgac tcttacaagt cacgccagc   19740 caacatcacc ctgcccacca acaccaacac ttatgattac atgaacggga gagtggtgcc   19800
tccctcgctg gtggacgcct acatcaacat cggggcgcgc tggtcgctgg accccatgga   19860
caacgtcaat cccttcaacc accaccgcaa cgcgggcctg cgctaccgct ccatgctcct   19920
gggcaacggg cgctacgtgc ccttccacat ccaggtgccc cagaaatttt cgccatcaa    19980 gagcctcctg ctcctgcccg gtcctacac ctacagtgg aacttccgca aggacgtcaa    20040
catgatcctg cagagctccc tcggcaacga cctgcgcacg gacggggcct ccatctcctt   20100
caccagcatc aacctctacg ccaccttctt ccccatggcg cacaacacgg cctccacgct   20160
cgaggccatg ctgcgcaacg acaccaacga ccagtccttc aacgactacc tctcggcggc   20220
caacatgctc taccccatcc cggccaacgc caccaacgtg cccatctcca tccctcgcg    20280 caactgggcc gccttccgcg gctggtcctt cacgcgcctc aagaccaagg agacgccctc   20340
gctgggctcc gggttcgacc cctacttcgt ctactcgggc tccatcccct acctcgacgg   20400
```

```
caccttctac ctcaaccaca ccttcaagaa ggtctccatc accttcgact cctccgtcag   20460
ctggcccggc aacgaccggc tcctgacgcc aacgagttc  gaaatcaagc gcaccgtcga   20520
cggcgaggga tacaacgtgg cccagtgcaa catgaccaag gactggttcc tggtccagat   20580
gctggcccac tacaacatcg gctaccaggg cttctacgtg cccgagggct acaaggaccg   20640
catgtactcc ttcttccgca acttccagcc catgagccgc caggtggtgg acgaggtcaa   20700
ctacaaggac taccaggccg tcaccctggc ctaccagcac aacaactcgg gcttcgtcgg   20760
ctacctcgcg cccaccatgc gccagggcca gccctacccc gccaactacc cgtacccgct   20820
catcggcaag agcgccgtca ccagcgtcac ccagaaaaag ttcctctgcg acagggtcat   20880
gtggcgcatc cccttctcca gcaacttcat gtccatgggc gcgctcaccg acctcggcca   20940
gaacatgctc tatgccaact ccgcccacgc gctagacatg aatttcgaag tcgaccccat   21000
ggatgagtcc acccttctct atgttgtctt cgaagtcttc gacgtcgtcc gagtgcacca   21060
gccccaccgc ggcgtcatcg aggccgtcta cctgcgcacc cccttctcgg ccggtaacgc   21120
caccacctaa attgctactt gcatgatggc tgagcccaca ggctccggcg agcaggagct   21180
cagggccatc atccgcgacc tgggctgcgg gccctacttc ctgggcacct tcgataagcg   21240
cttcccggga ttcatggccc cgcacaagct ggcctgcgcc atcgtcaaca cggccggccg   21300
cgagaccggg ggcgagcact ggctggcctt cgcctggaac ccgcgctcga cacctgcta   21360 cctcttcgac cccttcgggt tctcggacga gcgcctcaag cagatctacc agttcgagta   21420
cgagggcctg ctgcgccgta gcgccctggc caccgaggac cgctgcgtca ccctggaaaa   21480
gtccacccag accgtgcagg gtccgcgctc ggccgcctgc gggctcttct gctgcatgtt   21540
cctgcacgcc ttcgtgcact ggcccgaccg ccccatggac aagaaccccca ccatgaactt   21600 gctgacgggg gtgcccaacg gcatgctcca gtcgccccag gtggaaccca ccctgcgccg   21660
caaccaggag gcgctctacc gcttcctcaa ctcccactcc gcctactttc gctcccaccg   21720
cgcgcgcatc gagaaggcca ccgccttcga ccgcatgaac aatcaagaca tgtaaaccgt   21780
gtgtgtatgt ttaaaatatc ttttaataaa cagcacttta atgttacaca tgcatctgag   21840 atgatttat  tttagaaatc gaaagggttc tgccgggtct cggcatggcc cgcgggcagg   21900
gacacgttgc ggaactggta cttggccagc cacttgaact cggggatcag cagtttgggc   21960
agcggggtgt cggggaagga gtcggtccac agcttccgcg tcagctgcag ggcgcccagc   22020
aggtcgggcg cggagatctt gaaatcgcag ttgggacccg cgttctgcgc gcgagagttg   22080
cggtacacgg ggttgcagca ctggaacacc atcagggccg ggtgcttcac gctcgccagc   22140
accgccgcgt cggtgatgct ctccacgtcg aggtcctcgg cgttggccat cccgaagggg   22200
gtcatcttgc aggtctgcct tcccatggtg ggcacgcacc cgggcttgtg gttgcaatcg   22260
cagtgcaggg ggatcagcat catctgggcc tggtcggcgt tcatccccgg gtacatggcc   22320
ttcatgaaag cctccaattg cctgaacgcc tgctgggcct tggctccctc ggtgaagaag   22380
accccgcagg acttgctaga gaactggttg gtggcacagc cggcatcgtg cacgcagcag   22440
cgcgcgtcgt tgttggccag ctgcaccacg ctgcgccccc agcggttctg ggtgatcttg   22500
gcccggtcgg ggttctcctt cagcgcgcgc tgcccgttct cgctcgccac atccatctcg   22560
atcatgtgct ccttctggat catggtggtc ccgtgcaggc accgcagttt gccctcggcc   22620
tcggtgcacc cgtgcagcca cagcgcgcac ccggtgcact cccagttctt gtgggcgatc   22680
tgggaatgcg cgtgcacgaa cccttgcagg aagcggccca tcatggtcgt cagggtcttg   22740
ttgctagtga aggtcaacgg gatgccgcgg tgctcctcgt tgatgtacag gtggcagatg   22800
```

```
cggcggtaca cctcgccctg ctcgggcatc agttggaagt tggctttcag gtcggtctcc   22860
acgcggtagc ggtccatcag catagtcatg atttccatgc ccttctccca ggccgagacg   22920
atgggcaggc tcatagggtt cttcaccatc atcttagcac tagcagccgc ggccaggggg   22980
tcgctctcat ccagggtctc aaagctccgc ttgccgtcct tctcggtgat ccgcaccggg   23040
gggtagctga agcccacggc cgccagctcc tcctcggcct gtctttcgtc ctcgctgtcc   23100
tggctgacgt cctgcatgac cacatgcttg gtcttgcggg gtttcttctt gggcggcagt   23160
ggcggcggag atgcttgtgg cgaggggag cgcgagttct cgctcaccac tactatctct   23220
tcctcttctt ggtccgaggc cacgcggcgg taggtatgtc tcttcggggg cagaggcgga   23280
ggcgacgggc tctcgccgcc gcgacttggc ggatggctgg cagagcccct tccgcgttcg   23340
ggggtgcgct cccggcggcg ctctgactga cttcctccgc ggccggccat tgtgttctcc   23400
tagggaggaa caacaagcat ggagactcag ccatcgccaa cctcgccatc tgccccacc   23460 gccgcgacg agaagcagca gcagcagaat gaaagcttaa ccgccccgcc gcccagcccc   23520
gcctccgacg cagccgcggt cccagacatg caagagatgg aggaatccat cgagattgac   23580
ctgggctatg tgacgcccgc ggagcatgag gaggagctgg cagtgcgctt tcaatcgtca   23640
agccaggaag ataaagaaca gccagagcag gaagcagaga cgagcagag tcaggctggg   23700 ctcgagcatg gcgactacct ccacctgagc ggggaggagg acgcgctcat caagcatctg   23760
gcccggcagg ccaccatcgt caaggacgcg ctgctcgacc gcaccgaggt gcccctcagc   23820
gtggaggagc tcagccgcgc ctacgagctc aacctcttct cgccgcgcgt gccccccaag   23880
cgccagccca acggcacctg cgagcccaac ccccgcctca acttctaccc ggtcttcgcg   23940
gtgcccgagg ccctgccac ctaccacatc tttttcaaga accaaaagat ccccgtctcc   24000
tgccgcgcca accgcacccg cgccgacgcc ctcttcaacc tgggtcccgg cgcccgccta   24060
cctgatatcg cctccttgga agaggttccc aagatcttcg agggtctggg cagcgacgag   24120
actcgggccg cgaacgctct gcaaggagaa ggaggaggag agcatgagca ccacagcgcc   24180
ctggtcgagt tggaaggcga caacgcgcgg ctggcggtgc tcaaacgcac ggtcgagctg   24240
acccatttcg cctaccggc tctgaacctg cccccgaaag tcatgagcgc ggtcatggac   24300
caggtgctca tcaagcgcgc gtcgcccatc tccgaggacg agggcatgca agactccgag   24360
gagggcaagc ccgtggtcag cgacgagcag ctggcccggt ggctgggtcc taatgctacc   24420
cctcaaagtt tggaagagcg gcgcaagctc atgatggccg tggtcctggt gaccgtggag   24480
ctggagtgcc tgcgccgctt cttcgccgac gcggagaccc tgcgcaaggt cgaggagaac   24540
ctgcactacc tcttcaggca cgggttcgtg cgccaggcct gcaagatctc caacgtggag   24600
ctgaccaacc tggtctccta catgggcatc ttgcacgaga accgcctggg gcagaacgtg   24660
ctgcacacca ccctgcgcgg ggaggcccgc cgcgactaca tccgcgactg cgtctacctc   24720
tacctctgcc acacctggca gacgggcatg ggcgtgtggc agcagtgtct ggaggagcag   24780
aacctgaaag agctctgcaa gctcctgcaa aagaacctca agggtctgtg gaccgggttc   24840
gacgagcgga ccaccgcctc ggacctggcc gacctcatct tccccgagcg cctcaggctg   24900
acgctgcgca acggcctgcc cgactttatg agccaaagca tgttgcaaaa ctttcgctct   24960
ttcatcctcg aacgctccgg aatcctgccc gccacctgct ccgcgctgcc ctcggacttc   25020
gtgccgctga ccttccgcga gtgccccccg ccgctgtgga gccactgcta cctgctgcgc   25080
ctggccaact acctggccta ccactcggac gtgatcgagg acgtcagcgg cgagggcctg   25140
```

```
ctcgagtgcc actgccgctg caacctctgc acgccgcacc gctccctggc ctgcaacccc    25200
cagctgctga gcgagaccca gatcatcggc accttcgagt tgcaagggcc cagcgagggc    25260
gagggagcca agggggtct gaaactcacc ccggggctgt ggacctcggc ctacttgcgc     25320
aagttcgtgc ccgaggatta ccatcccttc gagatcaggt tctacgagga ccaatcccag    25380
ccgcccaagg ccgagctgtc ggcctgcgtc atcacccagg gggcgatcct ggcccaattg    25440
caagccatcc agaaatcccg ccaagaattc ttgctgaaaa agggccgcgg ggtctacctc    25500
gaccccagaa ccggtgagga gctcaacccc ggcttccccc aggatgcccc gaggaaacaa    25560
gaagctgaaa gtggagctgc cgcccgtgga ggatttggag gaagactggg agaacagcag    25620
tcaggcagag gagatggagg aagactggga cagcactcag gcagaggagg acagcctgca    25680
agacagtctg gaggaagacg aggaggaggc agaggaggag gtggaagaag cagccgccgc    25740
cagaccgtcg tcctcggcgg gggagaaagc aagcagcacg gataccatct ccgctccggg    25800
tcggggtccc gctcggcccc acagtagatg ggacgagacc gggcgattcc cgaacccac     25860 cacccagacc ggtaagaagg agcggcaggg atacaagtcc tggcggggg caaaaaacgc     25920 catcgtctcc tgcttgcagg cctgcggggg caacatctcc ttcacccggc gctacctgct    25980
cttccaccgc ggggtgaact tccccccgcaa catcttgcat tactaccgtc acctccacag    26040
cccctactac ttccaagaag aggcagcagc agcagaaaaa gaccagaaaa ccagctagaa     26100
aatccacagc ggcggcagcg gcaggtggac tgaggatcgc ggcgaacgag ccggcgcaga    26160
cccgggagct gaggaaccgg atctttccca ccctctatgc catcttccag cagagtcggg    26220
ggcaggagca ggaactgaaa gtcaagaacc gttctctgcg ctcgctcacc cgcagttgtc    26280
tgtatcacaa gagcgaagac caacttcagc gcactctcga ggacgccgag gctctcttca    26340
acaagtactg cgccgctcact cttaaagagt agcccgcgcc cgcccagtcg cagaaaaagg    26400
cgggaattac gtcacctgtg cccttcgccc tagccgcctc cacccagcac cgccatgagc    26460
aaagagattc ccacgcctta catgtggagc taccagcccc agatgggcct ggccgccggc    26520
gccgcccagg actactccac ccgcatgaat tggctcagcg ccgggcccgc gatgatctca    26580
cgggtgaatg acatccgcgc ccaccgaaac cagatactcc tagaacagtc agcgctcacc    26640
gccacgcccc gcaatcacct caatccgcgt aattggcccg ccgccctggt gtaccaggaa    26700
attccccagc ccacgaccgt actacttccg cgagacgccc aggccgaagt ccagctgact    26760
aactcaggtg tccagctggc gggcggcgcc accctgtgtc gtcaccgccc cgctcagggt    26820
ataaagcggc tggtgatccg gggcagaggc acacagctca cgacgaggt ggtgagctct     26880 tcgctgggtc tgcgacctga cggagtcttc caactcgccg gatcggggag atcttccttc    26940
acgcctcgtc aggcggtcct gactttggag agttcgtcct cgcagccccg ctcgggcggc    27000
atcggcactc tccagttcgt ggaggagttc actccctcgg tctacttcaa ccccttctcc    27060 ggctccccg gccactaccc ggacgagttc atcccgaact ttgacgccat cagcgagtcg    27120
gtggacggct acgattgaat gtcccatggt ggcgcggctg acctagctcg gcttcgacac    27180
ctggaccact gccgccgctt tcgctgcttc gctcgggacc tcgccgagtt cacctacttt    27240
gagctgcccg aggagcatcc tcagggcccg gcccacggga tgcggatcgt cgtcgaaggg    27300
ggcctagact cccacctgct tcggatcttc agccagcgcc cgatcctggt cgagcgccaa    27360
cagggcaaca ccctcctgac cctctactgc atctgcgacc accccggcct gcatgaaagt    27420
ctttgttgtc tgctgtgtac tgagtataat aaaagctgag atcagcgact actccggact    27480
caactgtggt gtttctgcat ccatcaatcg gtctctgacc ttcaccggga acgagaccga    27540
```

```
gctccaggtc cagtgtaagc cccacaagaa gtacctcacc tggctgtacc agggctcccc    27600
gatcgccgtt gttaaccact gcgacgacga cggagtcctg ctgaacggcc ccgccaacct    27660 tacttttcc acccgcagaa gcaagctact gctcttccga cccttcctcc ccggcaccta    27720
tcagtgcatc tcgggaccct gccatcacac cttccacctg atcccgaata ccacctcttc    27780
cccagcaccg ctccccacta acaaccaaac taaccaccac caacgctacc gacgcgacct    27840
cgtttctgaa tctaatacca cccacaccgg aggtgagctc cgaggtcgca aaccctctgg    27900
gatttattac ggcccctggg aggtggtggg gttaatagct ttaggcttag tggcgggtgg    27960
gcttttggct ctctgctacc tatacctccc ttgcttttcc tacttagtgg tgctttgttg    28020
ctggtttaag aaatggggaa gatcaccta gtgtgcggtg tgctggtgac ggtggtgctt    28080
tcgattctgg gaggggaag cgcggctgta gtgacggaga agaaggccga tccctgcttg    28140
actttcaacc ccgataaatg ccggctgagt tttcagcccg atggcaatcg gtgcgcggtg    28200
ttgatcaagt gcggatggga atgcgagagc gtgttggtcc agtataaaa caagacctgg    28260 aacaatactc tcgcgtccac atggcagccc ggggaccccg agtggtacac cgtctctgtc    28320
cctggtgctg acggctccct ccgcacggtg aacaacactt tcattttga gcacatgtgc    28380 gagaccgcca tgttcatgag caagcagtac ggtatgtggc ccccacgtaa agagaatatc    28440
gtggtcttct ccatcgctta cagcgcgtgc acggtgctaa tcaccgcgat cgtgtgcctg    28500
agcattcaca tgctcatcgc tattcgcccc agaaataatg ccgagaaaga gaaacagcca    28560
taacacactt tcacatacc tttttcgac catggcctct gttacaatcc ttattattt    28620 tttgggactt gtgggcacta gcagcacttt tcagcatata aacaaactg tttatgctgg    28680 ttcaaattct gtgttagctg gacatcagtc ataccagaaa gtttcatggt actggtatga    28740 taaaatcaa acaccgtta cactctgcaa gggtccacaa cagccgctaa accgtagtgg    28800
gatttttttt agctgtaatc ataataatat cacactactt tcaattacaa agcactatgc    28860 tggaactttac tatggaacca atttcaatat caaacatgac acttactata gtgtcagagt    28920
attggatcca actacccta gaacaactac aaagcccacc acaactaaga agcccactac    28980
acctaagaag cctaccacgc ccaaaaccac taagacaact actaagacca ctaccacaga    29040
gccaaccaca accagcaccc cacttgcta taactacaca cacacacaca cactgagctg    29100
acctcacagg caactactga aatggttttt gccctgttac aaaagggga aacagtagc    29160 agcagtcctc tgcctaccac ccccagtgag gaaataccta aatccatggt tggcattatc    29220
gctgctgtag tggtgtgtat gctgattatc atcttgtgca tgatgtacta tgcctgctac    29280
tacagaaaac acaggctgaa caacaagctg accccctac tgaatgttga ttttaattt    29340 tttagaacca tgaagatcct aagccttttt tgttttcta taattattac ctctgctatt    29400
tgtaactcag tggataagga cgttactgtc accactggct ctaattatac actgaaagga    29460
cctccctcag gtatgctttc gtggtattgc tattttggaa ctgatgtttc acaaactgaa    29520
ttgtgtaatt ttcaaaaagg caaaacccaa aatcctaaaa ttcataacta tcaatgcaat    29580
ggtactgatt tagtactgtt caatatcacg aaaacatatg ctggaagtta ttactgcccg    29640
ggagataatg ttgacaatat gatttttac gaattacaag tagttgatcc cactactcca    29700
gcaccaccca ccacaactac caaggcacat agcacagaca cacaggaaac cactccagag    29760
gcagaagtag cagagttagc aaagcagatt catgaagatt cctttgttgc caatacccc    29820 acacaccccg gaccgcaatg tccagggcca ttagtcagcg gcattgtcgg tgtgctttgc    29880
```

```
gggttagcag ttataatcat ctgcatgttc attttttgctt gctgctacag aaggcttcac   29940
cgacaaaaat cagacccact gctgaacctc tatgtttaat ttttgatttt ccagagccat   30000
gaaggcactt agcactttag ttttttttgac cttgattggc attgttttta atagtaaaat   30060
taccagggtt agctttctca aacatgttaa tgttactgaa ggaaataata tcacactagt   30120
aggtgtagaa ggtgctcaaa acaccacctg gacaaaatac catctcgggt ggaaagatat   30180
ttgcacctgg aatgtcactt atttttgcat aggagttaat cttaccattg ttaatgctaa   30240
tcaatctcag aatggattaa ttaaagggca gagcgtgagt gttaccagtg atgggtacta   30300
tacccagcat aatttcaact acaacattac tgttatacca ctgccaacac ctagcccacc   30360
tagcactact cagaccacac aaacaactca cactacacag agctccacaa ctaccatgca   30420
gaccactcag acaaccacat acactacttc ccctcagccc accaccacta cagcagaggc   30480
gagtagctca cccaccatca aagtggcatt tttaatgctg gccccatcta gcagtccac   30540
tgctagtacc aatgagcaga ctactgaatt tttgtccact attcagagca gcaccacagc   30600
tacctcgagt gccttctcta gcaccgccaa tctcacctcg ctttcctcta tgccaatcag   30660
taatgctact acctcccccg ctcctcttcc cactcctctg aagcaatccg agtccagcac   30720
gcagctgcag atcaccctgc tcattgtgat cggggtggtc atcctggcag tgctgctcta   30780
ctttatcttc tgccgtcgca tccccaacgc aaagccggcc tacaagccca ttgttatcgg   30840
gacgccgag ccgcttcagg tggagggagg tctaaggaat cttctcttct cttttacagt   30900
atggtgattt gaactatgat tcctagacat ttcattatca cttctctaat ctgtgtgctc   30960
caagtctgtg ccaccctcgc tctcgtggct aacgcgagtc cagactgcat ggagcgttc   31020
gcctcctacg tgctctttgc cttcatcacc tgcatctgct gctgtagcat agtctgcctg   31080
cttatcacct tcttccagtt cgttgactgg gtctttgtgc gcatcgccta cctgcgccac   31140
cacccccagt accgcgacca gagagtggcg caactgttga gactcatctg atgataagca   31200
tgcgggctct gctactactt ctcgcgcttc tgctagctcc cctcgccgcc ccctatccc   31260
tcaaatcccc cacccagtcc cctgaagagg ttcgaaaatg taaattccaa gaaccctgga   31320
aattcctttc atgctacaaa ctcaaatcag aaatgcaccc cagctggatc atgatcgttg   31380
gaatcgtgaa catccttgcc tgtaccctct tctcctttgt gatttacccc cgctttgact   31440
ttgggtggaa cgcacccgag gcgctctggc tcccgcctga tcccgacaca ccaccacagc   31500
agcagcagca aaatcaggca caggcacacg caccaccaca gcctaggcca caatacatgc   31560
ccatcttaaa ctatgaggcc gaggcacagc gagccatgct tcctgctatt agttacttca   31620
atctaaccgg cggagatgac tgaccccatg gccaacaaca ccgtcaacga cctcctggac   31680
atggacggcc gcgcctcgga gcagcgactc gcccaactcc gcatccgcca gcagcaggag   31740
agagccgtca aggagctgca ggatgcggtg gccatccacc agtgcaagag aggcatcttc   31800
tgcctggtga agcaggccaa gatctccttc gaggtcacgt ccaccgacca tcgcctctcc   31860
tacgagctcc tgcagcagcg ccagaagttc acctgcctgg tcggagtcaa ccccatcgtc   31920
atcacccagc agtctggcga taccaagggt tgcatccact gctcctgcga ctcccccgag   31980
tgcgttcaca ccctgatcaa gaccctctgc ggcctccgcg acctcctccc catgaactaa   32040
tcaactaacc ccctacccct ttaccctcca gtaaaaataa agattaaaaa tgattgaatt   32100
gatcaataaa gaatcactta cttgaaatct gaaaccaggt ctctgtccat gttttctgtc   32160
agcagcactt cactcccctc ttcccaactc tggtactgca ggccccggcg ggctgcaaac   32220
ttcctccaca ctctgaaggg gatgtcaaat tcctcctgtc cctcaatctt cattttttatc   32280
```

| | |
|---|---|
| ttctatcaga tgtccaaaaa gcgcgcgcgg gtggatgatg gcttcgaccc cgtgtacccc | 32340 |
| tacgatgcag acaacgcacc gactgtgccc ttcatcaacc ctcccttcgt ctcttcagat | 32400 |
| ggattccaag aaaagcccct gggggtgttg tccctgcgac tggccgaccc cgtcaccacc | 32460 |
| aagaatgggg ctgtcaccct caagctgggg gaggggtgg acctcgacga ctcgggaaaa | 32520 |
| ctcatctcca aaaatgccac caaggccact gcccctctca gtatttccaa cggcaccatt | 32580 |
| tcccttaaca tggctgcccc ttttacaac aacaatggaa cgttaagtct caatgtttct | 32640 |
| acaccattag cagtatttcc cactttaac actttaggta tcagtcttgg aaacggtctt | 32700 |
| caaacttcta ataagttgct gactgtacag ttaactcatc ctcttacatt cagctcaaat | 32760 |
| agcatcacag taaaaacaga caaaggactc tatattaatt ctagtggaaa cagagggctt | 32820 |
| gaggctaaca taagcctaaa aagaggactg attttttgatg gtaatgctat tgcaacatac | 32880 |
| cttggaagtg gtttagacta tggatcctat gatagcgatg ggaaaacaag acccatcatc | 32940 |
| accaaaattg gagcaggttt gaattttgat gctaataatg ccatggctgt gaagctaggc | 33000 |
| acaggtttaa gttttgactc tgccggtgcc ttaacagctg gaaacaaaga ggatgacaag | 33060 |
| ctaacacttt ggactacacc tgacccaagc cctaattgtc aattactttc agacagagat | 33120 |
| gccaaattta ccctatgtct tacaaaatgc ggtagtcaaa tactaggcac tgttgcagta | 33180 |
| gctgctgtta ctgtaggttc agcactaaat ccaattaatg acacagtaaa aagcgccata | 33240 |
| gtattcctta gatttgactc tgacggtgtg ctcatgtcaa actcatcaat ggtaggtgat | 33300 |
| tactggaact ttagggaagg acagaccacc caaagtgtgg cctatacaaa tgctgtggga | 33360 |
| ttcatgccca atctaggtgc atatcctaaa acccaaagca aaacaccaaa aaatagtata | 33420 |
| gtaagtcagg tatatttaaa tggagaaact actatgccaa tgacactgac aataactttc | 33480 |
| aatggcactg atgaaaaaga cacaacacct gtgagcactt actccatgac ttttacatgg | 33540 |
| cagtggactg gagactataa ggacaagaat attaccttttg ctaccaactc ctttactttc | 33600 |
| tcctacatgg cccaagaata aaccctgcat gccaaccccca ttgttcccac cactatggaa | 33660 |
| aactctgaag cagaaaaaaa taaagttcaa gtgtttttatt gattcaacag ttttcacaga | 33720 |
| attcgagtag ttatttttccc tcctccctcc caactcatgg aatacaccac cctctcccca | 33780 |
| cgcacagcct taaacatctg aatgccattg gtaatggaca tggttttggt ctccacattc | 33840 |
| cacacagttt cagagcgagc cagtctcggg tcggtcaggg agatgaaacc ctcgggcac | 33900 |
| tcctgcatct gcacctcaaa gttcagtagc tgagggctgt cctcggtggt cgggatcaca | 33960 |
| gttatctgga agaagagcgg tgagagtcat aatccgcgaa cgggatcggg cggttgtggc | 34020 |
| gcatcaggcc ccgcagcagt cgctgtctgc gccgctccgt caagctgctg ctcaaggggt | 34080 |
| ctgggtccag ggactccctg cgcatgatgc cgatggccct gagcatcagt cgcctggtgc | 34140 |
| ggcgggcgca gcagcggatg cggatctcac tcaggtcgga gcagtacgtg cagcacagca | 34200 |
| ctaccaagtt gttcaacagt ccatagttca acgtgctcca gccaaaactc atctgtggaa | 34260 |
| ctatgctgcc cacatgtcca tcgtaccaga tcctgatgta aatcaggtgg cgccccctcc | 34320 |
| agaacacact gccatgtac atgatctcct tgggcatgtg caggttcacc acctcccggt | 34380 |
| accacatcac ccgctggttg aacatgcagc cctggataat cctgcggaac cagatggcca | 34440 |
| gcaccgcccc gcccgccatg cagcgcaggg accccgggtc ctggcaatgg cagtggagca | 34500 |
| cccaccgctc acgccgtgg attaactggg agctgaacaa gtctatgttg gcacagcaca | 34560 |
| ggcacacgct catgcatgtc ttcagcactc tcagttcctc gggggtcagg accatgtccc | 34620 |

```
agggcacggg gaactcttgc aggacagtga acccggcaga acagggcagc cctcgcacac    34680
aacttacatt gtgcatggac agggtatcgc aatcaggcag caccggatga tcctccacca    34740
gagaagcgcg ggtctcggtc tcctcacagc gaggtaaggg ggccggcggt tggtacggat    34800 gatgcggga tgacgctaat cgtgttctgg atcgtgtcat gatggagctg tttcctgaca     34860
ttttcgtact tcacgaagca gaacctggta cgggcactgc acaccgctcg ccggcgacgg    34920
tctcggcgct tcgagcgctc ggtgttgaag ttatagaaca gccactccct cagagcgtgc    34980
agtatctcct gagcctcttg ggtgatgaaa atcccatccg ctctgatggc tctgatcaca    35040
tcggccacgg tggaatgggc cagacccagc cagatgatgc aattttgttg ggtttcggtg    35100
acggagggag agggaagaac aggaagaacc atgattaact ttattccaaa cggtctcgga    35160
gcacttcaaa atgcaggtcc cggaggtggc acctctcgcc cccactgtgt tggtggaaaa    35220
taacagccag gtcaaaggtg acacggttct cgagatgttc cacggtggct tccagcaaag    35280
cctccacgcg cacatccaga aacaagagga cagcgaaagc gggagcgttt tctaattcct    35340
caatcatcat attacactcc tgcaccatcc ccagataatt ttcattttc cagccttgaa     35400 tgattcgtat tagttcctga ggtaaatcca agccagccat gataaaagc tcgcgcagag     35460 cgccctccac cggcattctt aagcacaccc tcataattcc aagagattct gctcctggtt    35520
cacctgcagc agattaacaa tgggaatatc aaaatctctg ccgcgatccc taagctcctc    35580
cctcaacaat aactgtatgt aatctttcat atcatctccg aaattttag ccataggcc      35640 gccaggaata gagcagggc aagccacatt acagataaag cgaagtcctc cccagtgagc     35700
attgccaaat gtaagattga aataagcatg ctggctagac cctgtgatat cttccagata    35760
actggacaga aaatcaggca agcaattttt aagaaaatca acaaaagaaa agtcgtccag    35820
gtgcaggttt agagcctcag gaacaacgat ggaataagtg caaggagtgc gttccagcat    35880
ggttagtgtt tttttggtga tctgtagaac aaaaaataaa catgcaatat taaaccatgc    35940
tagcctggcg aacaggtggg taaatcactc tttccagcac caggcaggct acggggtctc    36000
cggcgcgacc ctcgtagaag ctgtcgccat gattgaaaag catcaccgag agaccttccc    36060
ggtggccggc atggatgatt cgagaagaag catacactcc gggaacattg gcatccgtga    36120
gtgaaaaaaa gcgacctata aagcctcggg gcactacaat gctcaatctc aattccagca    36180
aagccacccc atgcggatgg agcacaaaat tggcaggtgc gtaaaaaatg taattactcc    36240
cctcctgcac aggcagcaaa gccccgctc cctccagaaa cacatacaaa gcctcagcgt     36300
ccatagctta ccgagcacgg caggcgcaag agtcagagaa aaggctgagc tctaacctga    36360
ctgcccgctc ctgtgctcaa tatatagccc taacctacac tgacgtaaag gccaaagtct    36420 aaaaatacc gccaaaatga cacacacgcc cagcacacgc ccagaaaccg gtgacacact     36480
caaaaaaata cgtgcgcttc ctcaaacgcc caaaccggcg tcatttccgg gttcccacgc    36540
tacgtcaccg ctcagcgact ttcaaattcc gtcgaccgtt aaaaacgtca ctcgccccgc    36600
ccctaacggt cgcccttctc tcggccaatc accttcctcc cttcccaaat tcaaacgcct    36660
catttgcata ttaacgcgca caaaaagttt gaggtatata tttgaatgat g             36711
```

<210> SEQ ID NO 2
<211> LENGTH: 942
<212> TYPE: PRT
<213> ORGANISM: Chimpanzee adenovirus AdY25
<220> FEATURE:
<221> NAME/KEY: SOURCE
<222> LOCATION: 1..942
<223> OTHER INFORMATION: /mol_type="protein"

/organism="Chimpanzee adenovirus AdY25"

<400> SEQUENCE: 2

```
Met Ala Thr Pro Ser Met Leu Pro Gln Trp Ala Tyr Met His Ile Ala
1               5                   10                  15

Gly Gln Asp Ala Ser Glu Tyr Leu Ser Pro Gly Leu Val Gln Phe Ala
            20                  25                  30

Arg Ala Thr Asp Thr Tyr Phe Ser Leu Gly Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Val Pro Val Asp Arg Glu Asp Asn Thr Tyr Ser Tyr
65                  70                  75                  80

Lys Val Arg Tyr Thr Leu Ala Val Gly Asp Asn Arg Val Leu Asp Met
                85                  90                  95

Ala Ser Thr Tyr Phe Asp Ile Arg Gly Val Leu Asp Arg Gly Pro Ser
            100                 105                 110

Phe Lys Pro Tyr Ser Gly Thr Ala Tyr Asn Ser Leu Ala Pro Lys Gly
        115                 120                 125

Ala Pro Asn Ser Ser Gln Trp Glu Gln Lys Ala Gly Asn Gly Asp
    130                 135                 140

Thr Met Glu Thr His Thr Phe Gly Val Ala Pro Met Gly Gly Glu Asn
145                 150                 155                 160

Ile Thr Ile Asp Gly Leu Gln Ile Gly Thr Asp Ala Thr Ala Asp Gln
                165                 170                 175

Asp Lys Pro Ile Tyr Ala Asp Lys Thr Phe Gln Pro Glu Pro Gln Val
            180                 185                 190

Gly Glu Glu Asn Trp Gln Glu Thr Glu Ser Phe Tyr Gly Gly Arg Ala
        195                 200                 205

Leu Lys Lys Asp Thr Ser Met Lys Pro Cys Tyr Gly Ser Tyr Ala Arg
    210                 215                 220

Pro Thr Asn Val Lys Gly Gly Gln Ala Lys Leu Lys Val Gly Ala Asp
225                 230                 235                 240

Gly Val Pro Thr Lys Glu Phe Asp Ile Asp Leu Ala Phe Phe Asp Thr
                245                 250                 255

Pro Gly Gly Thr Val Asn Gly Asp Glu Tyr Lys Ala Asp Ile Val
            260                 265                 270

Met Tyr Thr Glu Asn Thr Tyr Leu Glu Thr Pro Asp Thr His Val Val
        275                 280                 285

Tyr Lys Pro Gly Lys Asp Asp Ala Ser Ser Glu Ile Asn Leu Val Gln
    290                 295                 300

Gln Ser Met Pro Asn Arg Pro Asn Tyr Ile Gly Phe Arg Asp Asn Phe
305                 310                 315                 320

Ile Gly Leu Met Tyr Tyr Asn Ser Thr Gly Asn Met Gly Val Leu Ala
                325                 330                 335

Gly Gln Ala Ser Gln Leu Asn Ala Val Val Asp Leu Gln Asp Arg Asn
            340                 345                 350

Thr Glu Leu Ser Tyr Gln Leu Leu Leu Asp Ser Leu Gly Asp Arg Thr
        355                 360                 365

Arg Tyr Phe Ser Met Trp Asn Gln Ala Val Asp Ser Tyr Asp Pro Asp
    370                 375                 380

Val Arg Ile Ile Glu Asn His Gly Val Glu Asp Glu Leu Pro Asn Tyr
385                 390                 395                 400
```

-continued

```
Cys Phe Pro Leu Asp Gly Ser Gly Thr Asn Ala Ala Tyr Gln Gly Val
                405                 410                 415

Lys Val Lys Asn Gly Asn Asp Gly Asp Val Glu Ser Glu Trp Glu Asn
            420                 425                 430

Asp Asp Thr Val Ala Ala Arg Asn Gln Leu Cys Lys Gly Asn Ile Phe
        435                 440                 445

Ala Met Glu Ile Asn Leu Gln Ala Asn Leu Trp Arg Ser Phe Leu Tyr
    450                 455                 460

Ser Asn Val Ala Leu Tyr Leu Pro Asp Ser Tyr Lys Tyr Thr Pro Ala
465                 470                 475                 480

Asn Ile Thr Leu Pro Thr Asn Thr Asn Thr Tyr Asp Tyr Met Asn Gly
                485                 490                 495

Arg Val Val Pro Pro Ser Leu Val Asp Ala Tyr Ile Asn Ile Gly Ala
            500                 505                 510

Arg Trp Ser Leu Asp Pro Met Asp Asn Val Asn Pro Phe Asn His His
        515                 520                 525

Arg Asn Ala Gly Leu Arg Tyr Arg Ser Met Leu Leu Gly Asn Gly Arg
    530                 535                 540

Tyr Val Pro Phe His Ile Gln Val Pro Gln Lys Phe Phe Ala Ile Lys
545                 550                 555                 560

Ser Leu Leu Leu Pro Gly Ser Tyr Thr Tyr Glu Trp Asn Phe Arg
                565                 570                 575

Lys Asp Val Asn Met Ile Leu Gln Ser Ser Leu Gly Asn Asp Leu Arg
            580                 585                 590

Thr Asp Gly Ala Ser Ile Ser Phe Thr Ser Ile Asn Leu Tyr Ala Thr
        595                 600                 605

Phe Phe Pro Met Ala His Asn Thr Ala Ser Thr Leu Glu Ala Met Leu
    610                 615                 620

Arg Asn Asp Thr Asn Asp Gln Ser Phe Asn Asp Tyr Leu Ser Ala Ala
625                 630                 635                 640

Asn Met Leu Tyr Pro Ile Pro Ala Asn Ala Thr Asn Val Pro Ile Ser
                645                 650                 655

Ile Pro Ser Arg Asn Trp Ala Ala Phe Arg Gly Trp Ser Phe Thr Arg
            660                 665                 670

Leu Lys Thr Lys Glu Thr Pro Ser Leu Gly Ser Gly Phe Asp Pro Tyr
        675                 680                 685

Phe Val Tyr Ser Gly Ser Ile Pro Tyr Leu Asp Gly Thr Phe Tyr Leu
    690                 695                 700

Asn His Thr Phe Lys Lys Val Ser Ile Thr Phe Asp Ser Ser Val Ser
705                 710                 715                 720

Trp Pro Gly Asn Asp Arg Leu Leu Thr Pro Asn Glu Phe Glu Ile Lys
                725                 730                 735

Arg Thr Val Asp Gly Glu Gly Tyr Asn Val Ala Gln Cys Asn Met Thr
            740                 745                 750

Lys Asp Trp Phe Leu Val Gln Met Leu Ala His Tyr Asn Ile Gly Tyr
        755                 760                 765

Gln Gly Phe Tyr Val Pro Glu Gly Tyr Lys Asp Arg Met Tyr Ser Phe
    770                 775                 780

Phe Arg Asn Phe Gln Pro Met Ser Arg Gln Val Asp Glu Val Asn
785                 790                 795                 800

Tyr Lys Asp Tyr Gln Ala Val Thr Leu Ala Tyr Gln His Asn Asn Ser
                805                 810                 815

Gly Phe Val Gly Tyr Leu Ala Pro Thr Met Arg Gln Gly Gln Pro Tyr
```

```
                820                 825                 830
Pro Ala Asn Tyr Pro Tyr Pro Leu Ile Gly Lys Ser Ala Val Thr Ser
            835                 840                 845

Val Thr Gln Lys Lys Phe Leu Cys Asp Arg Val Met Trp Arg Ile Pro
850                 855                 860

Phe Ser Ser Asn Phe Met Ser Met Gly Ala Leu Thr Asp Leu Gly Gln
865                 870                 875                 880

Asn Met Leu Tyr Ala Asn Ser Ala His Ala Leu Asp Met Asn Phe Glu
            885                 890                 895

Val Asp Pro Met Asp Glu Ser Thr Leu Leu Tyr Val Val Phe Glu Val
                900                 905                 910

Phe Asp Val Val Arg Val His Gln Pro His Arg Gly Val Ile Glu Ala
            915                 920                 925

Val Tyr Leu Arg Thr Pro Phe Ser Ala Gly Asn Ala Thr Thr
        930                 935                 940

<210> SEQ ID NO 3
<211> LENGTH: 532
<212> TYPE: PRT
<213> ORGANISM: Chimpanzee adenovirus AdY25
<220> FEATURE:
<221> NAME/KEY: SOURCE
<222> LOCATION: 1..532
<223> OTHER INFORMATION: /mol_type="protein"
      /organism="Chimpanzee adenovirus AdY25"

<400> SEQUENCE: 3

Met Met Arg Arg Ala Tyr Pro Glu Gly Pro Pro Ser Tyr Glu Ser
1               5                   10                  15

Val Met Gln Gln Ala Met Ala Ala Ala Ala Met Gln Pro Pro Leu
            20                  25                  30

Glu Ala Pro Tyr Val Pro Pro Arg Tyr Leu Ala Pro Thr Glu Gly Arg
            35                  40                  45

Asn Ser Ile Arg Tyr Ser Glu Leu Ala Pro Leu Tyr Asp Thr Thr Arg
    50                  55                  60

Leu Tyr Leu Val Asp Asn Lys Ser Ala Asp Ile Ala Ser Leu Asn Tyr
65                  70                  75                  80

Gln Asn Asp His Ser Asn Phe Leu Thr Thr Val Val Gln Asn Asn Asp
                85                  90                  95

Phe Thr Pro Thr Glu Ala Ser Thr Gln Thr Ile Asn Phe Asp Glu Arg
            100                 105                 110

Ser Arg Trp Gly Gly Gln Leu Lys Thr Ile Met His Thr Asn Met Pro
        115                 120                 125

Asn Val Asn Glu Phe Met Tyr Ser Asn Lys Phe Lys Ala Arg Val Met
130                 135                 140

Val Ser Arg Lys Thr Pro Asn Gly Val Thr Val Thr Asp Gly Ser Gln
145                 150                 155                 160

Asp Ile Leu Glu Tyr Glu Trp Val Glu Phe Glu Leu Pro Glu Gly Asn
                165                 170                 175

Phe Ser Val Thr Met Thr Ile Asp Leu Met Asn Asn Ala Ile Ile Asp
            180                 185                 190

Asn Tyr Leu Ala Val Gly Arg Gln Asn Gly Val Leu Glu Ser Asp Ile
        195                 200                 205

Gly Val Lys Phe Asp Thr Arg Asn Phe Arg Leu Gly Trp Asp Pro Val
    210                 215                 220

Thr Glu Leu Val Met Pro Gly Val Tyr Thr Asn Glu Ala Phe His Pro
```

```
                225                 230                 235                 240

Asp Ile Val Leu Leu Pro Gly Cys Gly Val Asp Phe Thr Glu Ser Arg
                    245                 250                 255

Leu Ser Asn Leu Leu Gly Ile Arg Lys Arg Gln Pro Phe Gln Glu Gly
            260                 265                 270

Phe Gln Ile Met Tyr Glu Asp Leu Glu Gly Gly Asn Ile Pro Ala Leu
        275                 280                 285

Leu Asp Val Asp Ala Tyr Glu Lys Ser Lys Glu Ser Ala Ala Ala
    290                 295                 300

Ala Thr Ala Ala Val Ala Thr Ala Ser Thr Glu Val Arg Gly Asp Asn
305                 310                 315                 320

Phe Ala Ser Pro Ala Ala Val Ala Ala Ala Glu Ala Ala Glu Thr Glu
                    325                 330                 335

Ser Lys Ile Val Ile Gln Pro Val Glu Lys Asp Ser Lys Asp Arg Ser
                340                 345                 350

Tyr Asn Val Leu Pro Asp Lys Ile Asn Thr Ala Tyr Arg Ser Trp Tyr
            355                 360                 365

Leu Ala Tyr Asn Tyr Gly Asp Pro Glu Lys Gly Val Arg Ser Trp Thr
        370                 375                 380

Leu Leu Thr Thr Ser Asp Val Thr Cys Gly Val Glu Gln Val Tyr Trp
385                 390                 395                 400

Ser Leu Pro Asp Met Met Gln Asp Pro Val Thr Phe Arg Ser Thr Arg
                    405                 410                 415

Gln Val Ser Asn Tyr Pro Val Val Gly Ala Glu Leu Leu Pro Val Tyr
                420                 425                 430

Ser Lys Ser Phe Phe Asn Glu Gln Ala Val Tyr Ser Gln Gln Leu Arg
            435                 440                 445

Ala Phe Thr Ser Leu Thr His Val Phe Asn Arg Phe Pro Glu Asn Gln
        450                 455                 460

Ile Leu Val Arg Pro Pro Ala Pro Thr Ile Thr Thr Val Ser Glu Asn
465                 470                 475                 480

Val Pro Ala Leu Thr Asp His Gly Thr Leu Pro Leu Arg Ser Ser Ile
                    485                 490                 495

Arg Gly Val Gln Arg Val Thr Val Thr Asp Ala Arg Arg Arg Thr Cys
                500                 505                 510

Pro Tyr Val Tyr Lys Ala Leu Gly Ile Val Ala Pro Arg Val Leu Ser
            515                 520                 525

Ser Arg Thr Phe
        530

<210> SEQ ID NO 4
<211> LENGTH: 443
<212> TYPE: PRT
<213> ORGANISM: Chimpanzee adenovirus AdY25
<220> FEATURE:
<221> NAME/KEY: SOURCE
<222> LOCATION: 1..443
<223> OTHER INFORMATION: /mol_type="protein"
      /organism="Chimpanzee adenovirus AdY25"

<400> SEQUENCE: 4

Met Ser Lys Lys Arg Ala Arg Val Asp Asp Gly Phe Asp Pro Val Tyr
1               5                   10                  15

Pro Tyr Asp Ala Asp Asn Ala Pro Thr Val Pro Phe Ile Asn Pro Pro
            20                  25                  30

Phe Val Ser Ser Asp Gly Phe Gln Glu Lys Pro Leu Gly Val Leu Ser
```

```
             35                  40                  45
Leu Arg Leu Ala Asp Pro Val Thr Thr Lys Asn Gly Ala Val Thr Leu
 50                  55                  60
Lys Leu Gly Glu Gly Val Asp Leu Asp Asp Ser Gly Lys Leu Ile Ser
 65                  70                  75                  80
Lys Asn Ala Thr Lys Ala Thr Ala Pro Leu Ser Ile Ser Asn Gly Thr
                 85                  90                  95
Ile Ser Leu Asn Met Ala Ala Pro Phe Tyr Asn Asn Asn Gly Thr Leu
                100                 105                 110
Ser Leu Asn Val Ser Thr Pro Leu Ala Val Phe Pro Thr Phe Asn Thr
                115                 120                 125
Leu Gly Ile Ser Leu Gly Asn Gly Leu Gln Thr Ser Asn Lys Leu Leu
                130                 135                 140
Thr Val Gln Leu Thr His Pro Leu Thr Phe Ser Ser Asn Ser Ile Thr
145                 150                 155                 160
Val Lys Thr Asp Lys Gly Leu Tyr Ile Asn Ser Ser Gly Asn Arg Gly
                165                 170                 175
Leu Glu Ala Asn Ile Ser Leu Lys Arg Gly Leu Ile Phe Asp Gly Asn
                180                 185                 190
Ala Ile Ala Thr Tyr Leu Gly Ser Gly Leu Asp Tyr Gly Ser Tyr Asp
                195                 200                 205
Ser Asp Gly Lys Thr Arg Pro Ile Ile Thr Lys Ile Gly Ala Gly Leu
                210                 215                 220
Asn Phe Asp Ala Asn Asn Ala Met Ala Val Lys Leu Gly Thr Gly Leu
225                 230                 235                 240
Ser Phe Asp Ser Ala Gly Ala Leu Thr Ala Gly Asn Lys Glu Asp Asp
                245                 250                 255
Lys Leu Thr Leu Trp Thr Thr Pro Asp Pro Ser Pro Asn Cys Gln Leu
                260                 265                 270
Leu Ser Asp Arg Asp Ala Lys Phe Thr Leu Cys Leu Thr Lys Cys Gly
                275                 280                 285
Ser Gln Ile Leu Gly Thr Val Ala Val Ala Ala Val Thr Val Gly Ser
                290                 295                 300
Ala Leu Asn Pro Ile Asn Asp Thr Val Lys Ser Ala Ile Val Phe Leu
305                 310                 315                 320
Arg Phe Asp Ser Asp Gly Val Leu Met Ser Asn Ser Ser Met Val Gly
                325                 330                 335
Asp Tyr Trp Asn Phe Arg Glu Gly Gln Thr Thr Gln Ser Val Ala Tyr
                340                 345                 350
Thr Asn Ala Val Gly Phe Met Pro Asn Leu Gly Ala Tyr Pro Lys Thr
                355                 360                 365
Gln Ser Lys Thr Pro Lys Asn Ser Ile Val Ser Gln Val Tyr Leu Asn
                370                 375                 380
Gly Glu Thr Thr Met Pro Met Thr Leu Thr Ile Thr Phe Asn Gly Thr
385                 390                 395                 400
Asp Glu Lys Asp Thr Thr Pro Val Ser Thr Tyr Ser Met Thr Phe Thr
                405                 410                 415
Trp Gln Trp Thr Gly Asp Tyr Lys Asp Lys Asn Ile Thr Phe Ala Thr
                420                 425                 430
Asn Ser Phe Thr Phe Ser Tyr Met Ala Gln Glu
                435                 440

<210> SEQ ID NO 5
```

```
<211> LENGTH: 257
<212> TYPE: PRT
<213> ORGANISM: Chimpanzee adenovirus AdY25
<220> FEATURE:
<221> NAME/KEY: SOURCE
<222> LOCATION: 1..257
<223> OTHER INFORMATION: /mol_type="protein"
      /organism="Chimpanzee adenovirus AdY25"

<400> SEQUENCE: 5
```

Met Arg His Leu Arg Asp Leu Pro Asp Glu Lys Ile Ile Ile Ala Ser
1               5                   10                  15

Gly Asn Glu Ile Leu Glu Leu Val Val Asn Ala Met Met Gly Asp Asp
            20                  25                  30

Pro Pro Glu Pro Pro Thr Pro Phe Glu Ala Pro Ser Leu His Asp Leu
        35                  40                  45

Tyr Asp Leu Glu Val Asp Val Pro Glu Asp Pro Asn Glu Glu Ala
    50                  55                  60

Val Asn Asp Leu Phe Ser Asp Ala Ala Leu Leu Ala Ala Glu Ala
65                  70                  75                  80

Ser Ser Pro Ser Ser Asp Ser Ser Leu His Thr Pro Arg Pro
                85                  90                  95

Gly Arg Gly Glu Lys Lys Ile Pro Glu Leu Lys Gly Glu Met Asp
            100                 105                 110

Leu Arg Cys Tyr Glu Glu Cys Leu Pro Pro Ser Asp Glu Asp Glu
        115                 120                 125

Gln Ala Ile Gln Asn Ala Ala Ser Gln Gly Met Gln Ala Ala Ser Glu
130                 135                 140

Ser Phe Ala Leu Asp Cys Pro Pro Leu Pro Gly His Gly Cys Lys Ser
145                 150                 155                 160

Cys Glu Phe His Arg Leu Asn Thr Gly Asp Lys Ala Val Leu Cys Ala
                165                 170                 175

Leu Cys Tyr Met Arg Ala Tyr Asn His Cys Val Tyr Ser Pro Val Ser
            180                 185                 190

Asp Ala Asp Asp Glu Thr Pro Thr Thr Glu Ser Thr Ser Ser Pro Pro
        195                 200                 205

Glu Ile Gly Thr Ser Pro Pro Glu Asn Ile Val Arg Pro Val Pro Val
    210                 215                 220

Arg Ala Thr Gly Arg Arg Ala Ala Val Glu Cys Leu Asp Asp Leu Leu
225                 230                 235                 240

Gln Ala Gly Asp Glu Pro Leu Asp Leu Cys Thr Arg Lys Arg Pro Arg
                245                 250                 255

His

```
<210> SEQ ID NO 6
<211> LENGTH: 187
<212> TYPE: PRT
<213> ORGANISM: Chimpanzee adenovirus AdY25
<220> FEATURE:
<221> NAME/KEY: SOURCE
<222> LOCATION: 1..187
<223> OTHER INFORMATION: /mol_type="protein"
      /organism="Chimpanzee adenovirus AdY25"

<400> SEQUENCE: 6
```

Met Glu Ile Trp Thr Ile Leu Glu Asp Leu His Lys Thr Arg Gln Leu
1               5                   10                  15

Leu Glu Asn Ala Ser Asn Gly Val Ser His Leu Trp Arg Phe Cys Phe
            20                  25                  30

-continued

```
Gly Gly Asp Leu Ala Lys Leu Val Tyr Arg Ala Lys Gln Asp Tyr Ser
         35                  40                  45

Glu Gln Phe Glu Val Ile Leu Arg Glu Cys Pro Gly Leu Phe Asp Ala
 50                  55                  60

Leu Asn Leu Gly His Gln Thr His Phe Asn Gln Arg Ile Val Arg Ala
 65                  70                  75                  80

Leu Asp Phe Thr Thr Pro Gly Arg Ser Thr Ala Ala Val Ala Phe Phe
                 85                  90                  95

Ala Phe Leu Leu Asp Lys Trp Ser Gln Glu Thr His Phe Ser Arg Asp
                100                 105                 110

Tyr Gln Leu Asp Phe Leu Ala Val Ala Leu Trp Arg Thr Trp Lys Ser
            115                 120                 125

Gln Arg Leu Asn Ala Ile Ser Gly Tyr Leu Pro Val Gln Pro Leu Asp
        130                 135                 140

Thr Leu Lys Ile Leu Asn Leu Gln Glu Ser Pro Arg Ala Arg Gln Arg
145                 150                 155                 160

Arg Arg Gln Gln Gln Arg Gln Gln Glu Glu Asp Gln Glu Glu Asn Pro
                165                 170                 175

Arg Ala Gly Leu Asp Pro Pro Ala Glu Glu Glu
            180                 185
```

<210> SEQ ID NO 7
<211> LENGTH: 499
<212> TYPE: PRT
<213> ORGANISM: Chimpanzee adenovirus AdY25
<220> FEATURE:
<221> NAME/KEY: SOURCE
<222> LOCATION: 1..499
<223> OTHER INFORMATION: /mol_type="protein"
      /organism="Chimpanzee adenovirus AdY25"

<400> SEQUENCE: 7

```
Met Glu Ser Arg Asn Pro Phe Gln Gln Gly Leu Pro Ala Gly Phe Leu
 1               5                  10                  15

Ser Ser Ser Phe Val Glu Asn Met Glu Ile Pro Ala Pro Glu Cys Asn
             20                  25                  30

Leu Arg Leu Leu Ala Gly Thr Ala Thr Arg His Ser Glu Asp Pro Glu
         35                  40                  45

Ser Pro Gly Glu Ser Gln Gly Thr Pro Thr Ser Pro Ala Ala Ala Ala
     50                  55                  60

Ala Ala Gly Gly Gly Ser Arg Arg Glu Pro Glu Ser Arg Pro Gly Pro
 65                  70                  75                  80

Ser Gly Gly Gly Val Ala Asp Leu Phe Pro Glu Leu Arg Arg Val
                 85                  90                  95

Leu Thr Arg Ser Ser Gly Arg Glu Arg Gly Ile Lys Arg Glu Arg
             100                 105                 110

His Asp Glu Thr Asn His Arg Thr Glu Leu Thr Val Gly Leu Met Ser
         115                 120                 125

Arg Lys Arg Pro Glu Thr Val Trp Trp His Glu Val Gln Ser Thr Gly
        130                 135                 140

Thr Asp Glu Val Ser Val Met His Glu Arg Phe Ser Leu Glu Gln Val
145                 150                 155                 160

Lys Thr Cys Trp Leu Glu Pro Glu Asp Asp Trp Glu Val Ala Ile Arg
                165                 170                 175

Asn Tyr Ala Lys Leu Ala Leu Arg Pro Asp Lys Lys Tyr Lys Ile Thr
            180                 185                 190
```

```
Lys Leu Ile Asn Ile Arg Asn Ala Cys Tyr Ile Ser Gly Asn Gly Ala
        195                 200                 205
Glu Val Glu Ile Cys Leu Gln Glu Arg Val Ala Phe Arg Cys Cys Met
    210                 215                 220
Met Asn Met Tyr Pro Gly Val Gly Met Asp Gly Val Thr Phe Met
225                 230                 235                 240
Asn Met Arg Phe Arg Gly Asp Gly Tyr Asn Gly Thr Val Phe Met Ala
                245                 250                 255
Asn Thr Lys Leu Thr Val His Gly Cys Ser Phe Phe Gly Phe Asn Asn
                260                 265                 270
Thr Cys Ile Glu Ala Trp Gly Gln Val Gly Val Arg Gly Cys Ser Phe
                275                 280                 285
Ser Ala Asn Trp Met Gly Val Val Gly Arg Thr Lys Ser Met Leu Ser
                290                 295                 300
Val Lys Lys Cys Leu Phe Glu Arg Cys His Leu Gly Val Met Ser Glu
305                 310                 315                 320
Gly Glu Ala Arg Ile Arg His Cys Ala Ser Thr Glu Thr Gly Cys Phe
                325                 330                 335
Val Leu Cys Lys Gly Asn Ala Lys Ile Lys His Asn Met Ile Cys Gly
                340                 345                 350
Ala Ser Asp Glu Arg Gly Tyr Gln Met Leu Thr Cys Ala Gly Gly Asn
                355                 360                 365
Ser His Met Leu Ala Thr Val His Val Ala Ser His Ala Arg Lys Pro
        370                 375                 380
Trp Pro Glu Phe Glu His Asn Val Met Thr Arg Cys Asn Met His Leu
385                 390                 395                 400
Gly Ser Arg Arg Gly Met Phe Met Pro Tyr Gln Cys Asn Leu Asn Tyr
                405                 410                 415
Val Lys Val Leu Leu Glu Pro Asp Ala Met Ser Arg Val Ser Leu Thr
                420                 425                 430
Gly Val Phe Asp Met Asn Val Glu Val Trp Lys Ile Leu Arg Tyr Asp
        435                 440                 445
Glu Ser Lys Thr Arg Cys Arg Ala Cys Glu Cys Gly Gly Lys His Ala
    450                 455                 460
Arg Phe Gln Pro Val Cys Val Glu Val Thr Glu Asp Leu Arg Pro Asp
465                 470                 475                 480
His Leu Val Leu Ser Cys Thr Gly Thr Glu Phe Gly Ser Ser Gly Glu
                485                 490                 495
Glu Ser Asp

<210> SEQ ID NO 8
<211> LENGTH: 142
<212> TYPE: PRT
<213> ORGANISM: Chimpanzee adenovirus AdY25
<220> FEATURE:
<221> NAME/KEY: SOURCE
<222> LOCATION: 1..142
<223> OTHER INFORMATION: /mol_type="protein"
      /organism="Chimpanzee adenovirus AdY25"

<400> SEQUENCE: 8

Met Ser Gly Ser Gly Ser Phe Glu Gly Gly Val Phe Ser Pro Tyr Leu
1               5                   10                  15
Thr Gly Arg Leu Pro Ser Trp Ala Gly Val Arg Gln Asn Val Met Gly
            20                  25                  30
```

```
Ser Thr Val Asp Gly Arg Pro Val Gln Pro Ala Asn Ser Ser Thr Leu
         35                  40                  45

Thr Tyr Ala Thr Leu Ser Ser Ser Val Asp Ala Ala Ala Ala
 50                  55                  60

Ala Ala Ala Ser Ala Ala Ser Ala Val Arg Gly Met Ala Met Gly Ala
 65                  70                  75                  80

Gly Tyr Tyr Gly Thr Leu Val Ala Asn Ser Ser Ser Thr Asn Asn Pro
                 85                  90                  95

Ala Ser Leu Asn Glu Glu Lys Leu Leu Leu Met Ala Gln Leu Glu
             100                 105                 110

Ala Leu Thr Gln Arg Leu Gly Glu Leu Thr Gln Gln Val Ala Gln Leu
         115                 120                 125

Gln Glu Gln Thr Arg Ala Ala Val Ala Thr Val Lys Ser Lys
     130                 135                 140
```

<210> SEQ ID NO 9
<211> LENGTH: 449
<212> TYPE: PRT
<213> ORGANISM: Chimpanzee adenovirus AdY25
<220> FEATURE:
<221> NAME/KEY: SOURCE
<222> LOCATION: 1..449
<223> OTHER INFORMATION: /mol_type="protein"
      /organism="Chimpanzee adenovirus AdY25"

<400> SEQUENCE: 9

```
Met Glu Thr Lys Gly Arg Arg Ser Gly Ala Val Phe Asp Gln Pro
 1               5                  10                  15

Asp Glu Pro Glu Ala His Pro Arg Lys Arg Pro Ala Arg Ala Pro
                 20                  25                  30

Leu His Arg Asp Gly Asp His Pro Asp Ala Asp Ala Ala Ala Leu Glu
                 35                  40                  45

Gly Pro Asp Pro Gly Cys Ala Gly Arg Pro Ser Ser Gly Ala Leu Leu
 50                  55                  60

Pro Gln Ser Ser Gln Pro Ala Lys Arg Gly Gly Leu Leu Asp Arg Asp
 65                  70                  75                  80

Ala Val Glu His Ile Thr Glu Leu Trp Asp Arg Leu Glu Leu Leu Gln
                 85                  90                  95

Gln Thr Leu Ser Lys Met Pro Met Ala Asp Gly Leu Lys Pro Leu Lys
             100                 105                 110

Asn Phe Ala Ser Leu Gln Glu Leu Leu Ser Leu Gly Gly Glu Arg Leu
         115                 120                 125

Leu Ala Glu Leu Val Arg Glu Asn Met His Val Arg Glu Met Met Asn
 130                 135                 140

Glu Val Ala Pro Leu Leu Arg Glu Asp Gly Ser Cys Leu Ser Leu Asn
145                 150                 155                 160

Tyr His Leu Gln Pro Val Ile Gly Val Ile Tyr Gly Pro Thr Gly Cys
                 165                 170                 175

Gly Lys Ser Gln Leu Leu Arg Asn Leu Leu Ser Ala Gln Leu Ile Ser
             180                 185                 190

Pro Ala Pro Glu Thr Val Phe Phe Ile Ala Pro Gln Val Asp Met Ile
         195                 200                 205

Pro Pro Ser Glu Leu Lys Ala Trp Glu Met Gln Ile Cys Glu Gly Asn
 210                 215                 220

Tyr Ala Pro Gly Ile Glu Gly Thr Phe Val Pro Gln Ser Gly Thr Leu
225                 230                 235                 240
```

```
Arg Pro Lys Phe Ile Lys Met Ala Tyr Asp Asp Leu Thr Gln Asp His
            245                 250                 255

Asn Tyr Asp Val Ser Asp Pro Arg Asn Val Phe Ala Gln Ala Ala Ala
        260                 265                 270

His Gly Pro Ile Ala Ile Ile Met Asp Glu Cys Met Glu Asn Leu Gly
        275                 280                 285

Gly His Lys Gly Val Ala Lys Phe Phe His Ala Phe Pro Ser Lys Leu
        290                 295                 300

His Asp Lys Phe Pro Lys Cys Thr Gly Tyr Thr Val Leu Val Val Leu
305                 310                 315                 320

His Asn Met Asn Pro Arg Arg Asp Leu Gly Gly Asn Ile Ala Asn Leu
                325                 330                 335

Lys Ile Gln Ala Lys Met His Leu Ile Ser Pro Arg Met His Pro Ser
            340                 345                 350

Gln Leu Asn Arg Phe Val Asn Thr Tyr Thr Lys Gly Leu Pro Val Ala
        355                 360                 365

Ile Ser Leu Leu Leu Lys Asp Ile Val Gln His Ala Leu Arg Pro
370                 375                 380

Cys Tyr Asp Trp Val Ile Tyr Asn Thr Thr Pro Glu His Glu Ala Leu
385                 390                 395                 400

Gln Trp Ser Tyr Leu His Pro Arg Asp Gly Leu Met Pro Met Tyr Leu
                405                 410                 415

Asn Ile Gln Ala His Leu Tyr Arg Val Leu Glu Lys Ile His Arg Val
            420                 425                 430

Leu Asn Asp Arg Asp Arg Trp Ser Arg Ala Tyr Arg Ala Arg Lys Ile
        435                 440                 445

Lys

<210> SEQ ID NO 10
<211> LENGTH: 1196
<212> TYPE: PRT
<213> ORGANISM: Chimpanzee adenovirus AdY25
<220> FEATURE:
<221> NAME/KEY: SOURCE
<222> LOCATION: 1..1196
<223> OTHER INFORMATION: /mol_type="protein"
      /organism="Chimpanzee adenovirus AdY25"

<400> SEQUENCE: 10

Met Ala Leu Val Gln Thr His Gly Ser Arg Gly Leu His Pro Glu Ala
1               5                   10                  15

Ser Asp Pro Gly Arg Gln Pro Ser Arg Arg Ser Arg Gln Ser Ser
            20                  25                  30

Pro Gly Ala Val Pro Glu Pro Thr Arg Ala Arg Arg Arg Ala Pro
            35                  40                  45

Ala Ala Pro Ala Ser Gly Pro Arg Ala Ala Ser Ala Ala Arg Arg Ala
    50                  55                  60

Ser Ser Pro Pro Leu Leu Thr Met Glu Glu Ala Pro Pro Ser Pro
65                  70                  75                  80

Gln Pro Pro Lys Lys Lys Arg Gly Thr Val Val Thr Pro Gln Gly His
                85                  90                  95

Gly Thr Leu Gln Ala Ile Asp Val Ala Thr Asn Gly Ala Val Glu Ile
            100                 105                 110

Lys Tyr His Leu Asp Leu Pro Arg Ala Leu Glu Lys Leu Leu Gln Val
        115                 120                 125

Asn Arg Ala Pro Pro Leu Pro Thr Asp Leu Thr Pro Gln Arg Leu Arg
```

```
                130                 135                 140
Thr Leu Asp Ser Ser Gly Leu Arg Ala Leu Val Leu Ala Leu Arg Pro
145                 150                 155                 160

Ala Arg Ala Glu Val Trp Thr Cys Leu Pro Arg Gly Leu Val Ser Met
                165                 170                 175

Thr Thr Ile Glu Ala Glu Gly Gln Ala Asp His His Asp Val Val
                180                 185                 190

Gln His Glu Met Gln Ala Pro Arg Leu His Phe Pro Leu Lys Phe Leu
                195                 200                 205

Val Lys Gly Thr Gln Val Gln Leu Val Gln His Val His Pro Val Gln
                210                 215                 220

Arg Cys Glu His Cys Gly Arg Leu Tyr Lys His Lys His Glu Cys Ser
225                 230                 235                 240

Ala Arg Arg Arg His Phe Tyr Phe His His Ile Asn Ser His Ser Ser
                245                 250                 255

Asn Trp Trp Gln Glu Ile Gln Phe Phe Pro Ile Gly Ser His Pro Arg
                260                 265                 270

Thr Glu Arg Leu Phe Leu Thr Tyr Asp Val Glu Thr Tyr Thr Trp Met
                275                 280                 285

Gly Ser Phe Gly Lys Gln Leu Val Pro Phe Met Leu Val Met Lys Leu
                290                 295                 300

Ser Gly Asp Asp Arg Leu Val Glu Leu Ala Leu Asp Leu Ala Leu Gln
305                 310                 315                 320

Leu Lys Trp Asp Arg Trp His Gly Asp Pro Arg Thr Phe Tyr Cys Val
                325                 330                 335

Thr Pro Glu Lys Met Ala Val Gly Gln Gln Phe Arg Gln Tyr Arg Asp
                340                 345                 350

Arg Leu Gln Thr Ala Leu Ala Val Asp Leu Trp Thr Ser Phe Leu Arg
                355                 360                 365

Ala Asn Pro His Leu Ala Asp Trp Ala Leu Glu Gln His Gly Leu Ser
                370                 375                 380

Asp Pro Asp Glu Leu Thr Tyr Glu Glu Leu Lys Lys Leu Pro His Val
385                 390                 395                 400

Lys Gly Arg Pro Arg Phe Val Glu Leu Tyr Ile Val Gly His Asn Ile
                405                 410                 415

Asn Gly Phe Asp Glu Ile Val Leu Ala Ala Gln Val Ile Asn Asn Arg
                420                 425                 430

Ala Glu Val Pro Gln Pro Phe Arg Ile Thr Arg Asn Phe Met Pro Arg
                435                 440                 445

Ala Gly Lys Ile Leu Phe Asn Asp Val Thr Phe Ala Leu Pro Asn Pro
450                 455                 460

Ala Tyr Lys Lys Arg Thr Asp Phe Gln Leu Trp Glu Gln Gly Gly Cys
465                 470                 475                 480

Asp Asp Ile Asp Phe Lys His Gln Phe Leu Lys Val Met Val Arg Asp
                485                 490                 495

Thr Phe Ala Leu Thr His Thr Ser Leu Arg Lys Ala Ala Gln Ala Tyr
                500                 505                 510

Ala Leu Pro Val Glu Lys Gly Cys Cys Ala Tyr Lys Ala Val Asn Gln
                515                 520                 525

Phe Tyr Met Leu Gly Ser Tyr Arg Ala Asp Gln Asp Gly Phe Pro Leu
                530                 535                 540

Glu Glu Tyr Trp Lys Asp Arg Glu Glu Phe Leu Leu Asn Arg Glu Leu
545                 550                 555                 560
```

-continued

```
Trp Lys Gln Lys Gly Gln Leu Lys Tyr Asp Ile Ile Gln Glu Thr Leu
                565                 570                 575

Asp Tyr Cys Ala Leu Asp Val Leu Val Thr Ala Glu Leu Val Ala Lys
            580                 585                 590

Leu Gln Asp Ser Tyr Ala His Phe Ile Arg Asp Ser Val Gly Leu Pro
        595                 600                 605

His Ala His Phe Asn Ile Phe Gln Arg Pro Thr Ile Ser Ser Asn Ser
    610                 615                 620

His Ala Ile Phe Arg Gln Ile Val Tyr Arg Ala Glu Lys Pro Ser Arg
625                 630                 635                 640

Thr Asn Leu Gly Pro Gly Leu Leu Ala Pro Ser His Glu Leu Tyr Asp
                645                 650                 655

Tyr Val Arg Ala Ser Ile Arg Gly Gly Arg Cys Tyr Pro Thr Tyr Ile
            660                 665                 670

Gly Ile Leu Glu Glu Pro Leu Tyr Val Tyr Asp Ile Cys Gly Met Tyr
        675                 680                 685

Ala Ser Ala Leu Thr His Pro Met Pro Trp Gly Thr Pro Leu Ser Pro
    690                 695                 700

Tyr Glu Arg Ala Leu Ala Val Arg Glu Trp Gln Ala Ser Leu Asp Asp
705                 710                 715                 720

Leu Ala Thr Ser Ile Ser Tyr Phe Asp Pro Asp Leu Leu Pro Gly Ile
                725                 730                 735

Phe Thr Ile Asp Ala Asp Pro Pro Asp Glu Val Met Leu Asp Pro Leu
            740                 745                 750

Pro Pro Phe Cys Ser Arg Lys Gly Gly Arg Leu Cys Trp Thr Asn Glu
        755                 760                 765

Pro Leu Arg Gly Glu Val Ala Thr Ser Val Asp Leu Ile Thr Leu His
    770                 775                 780

Asn Arg Gly Trp Gln Val Arg Ile Val Pro Asp Glu Met Thr Val
785                 790                 795                 800

Phe Pro Glu Trp Lys Cys Val Ala Arg Glu Tyr Val Gln Leu Asn Ile
                805                 810                 815

Ala Ala Lys Glu Arg Ala Asp Lys Glu Lys Asn Gln Thr Met Arg Ser
            820                 825                 830

Ile Ala Lys Leu Leu Ser Asn Ala Leu Tyr Gly Ser Phe Ala Thr Lys
        835                 840                 845

Leu Asp Asn Lys Lys Ile Val Phe Ser Asp Gln Met Asp Glu Gly Leu
    850                 855                 860

Leu Lys Gly Ile Ser Ala Gly Thr Val Asn Ile Lys Ser Ser Ser Phe
865                 870                 875                 880

Leu Glu Thr Asp Asn Leu Ser Ala Glu Val Met Pro Ala Phe Glu Arg
                885                 890                 895

Glu Tyr Leu Pro Gln Gln Leu Ala Leu Leu Asp Ser Asp Pro Glu Asp
            900                 905                 910

Ser Glu Asp Glu Gln Gly Pro Ala Pro Phe Tyr Thr Pro Pro Ala Gly
        915                 920                 925

Thr Pro Gly His Val Ala Tyr Thr Tyr Lys Pro Ile Thr Phe Leu Asp
    930                 935                 940

Val Asp Glu Gly Asp Met Cys Leu His Thr Leu Glu Lys Val Asp Pro
945                 950                 955                 960

Leu Val Asp Asn Asp Arg Tyr Pro Ser His Val Ala Ser Phe Val Leu
                965                 970                 975
```

```
Ala Trp Thr Arg Ala Phe Val Ser Glu Trp Ala Gly Phe Leu Tyr Glu
            980                 985                 990

Glu Asp Arg Gly Thr Pro Leu Glu Asp Arg Pro Ile Lys Ser Val Tyr
        995                1000                1005

Gly Asp Thr Asp Ser Leu Phe Val Thr Gln Arg Gly His Glu Leu Met
    1010                1015                1020

Glu Thr Lys Gly Lys Lys Arg Ile Lys Lys Asn Gly Gly Lys Leu Val
1025                1030                1035                1040

Phe Asp Pro Asp Gln Pro Asp Leu Thr Trp Leu Val Glu Cys Glu Thr
                1045                1050                1055

Val Cys Ala His Cys Gly Ala Asp Ala Tyr Ala Pro Asp Ser Val Phe
            1060                1065                1070

Leu Ala Pro Lys Leu Tyr Ala Leu Lys Ser Leu Leu Cys Pro Ala Cys
        1075                1080                1085

Gly Gln Thr Ser Lys Gly Lys Leu Arg Ala Lys Gly His Ala Ala Glu
    1090                1095                1100

Ala Leu Asn Tyr Glu Leu Met Val Asn Cys Tyr Leu Ala Asp Ala Gln
1105                1110                1115                1120

Gly Ala Asp Arg Glu Arg Phe Ser Thr Ser Arg Met Ser Leu Lys Arg
                1125                1130                1135

Thr Leu Ala Ser Ala Gln Pro Gly Ala His Pro Phe Thr Val Thr Glu
            1140                1145                1150

Thr Thr Leu Thr Arg Thr Leu Arg Pro Trp Lys Asp Arg Thr Leu Ala
        1155                1160                1165

Ala Leu Asp Ala His Arg Leu Val Pro Tyr Ser Arg Ser Arg Pro Asn
    1170                1175                1180

Pro Arg Asn Glu Glu Val Cys Trp Ile Glu Met Pro
1185                1190                1195

<210> SEQ ID NO 11
<211> LENGTH: 646
<212> TYPE: PRT
<213> ORGANISM: Chimpanzee adenovirus AdY25
<220> FEATURE:
<221> NAME/KEY: SOURCE
<222> LOCATION: 1..646
<223> OTHER INFORMATION: /mol_type="protein"
      /organism="Chimpanzee adenovirus AdY25"

<400> SEQUENCE: 11

Met Ala Leu Ser Ile His Asp Cys Ala Arg Leu Thr Gly Gln Thr Val
1               5                   10                  15

Pro Thr Met Asn Tyr Phe Leu Pro Leu Arg Asn Ile Trp Asn Arg Val
            20                  25                  30

Arg Glu Phe Pro Arg Ala Ser Thr Thr Ala Ala Gly Ile Thr Trp Met
        35                  40                  45

Ser Arg Tyr Ile Tyr Gly Tyr His Arg Thr Met Leu Glu Asp Leu Ala
    50                  55                  60

Pro Gly Ala Pro Ala Thr Glu Arg Trp Pro Leu Tyr Arg Gln Pro Pro
65                  70                  75                  80

Pro His Phe Leu Ile Gly Tyr Gln Tyr Leu Val Arg Thr Cys Asn Asp
                85                  90                  95

Tyr Ile Phe Asp Thr Arg Ala Tyr Ser Arg Leu Lys Tyr His Glu Leu
            100                 105                 110

Val Arg Pro Gly His Gln Thr Val Asn Trp Ser Val Met Ala Asn Cys
        115                 120                 125
```

```
Ser Tyr Thr Ile Asn Thr Gly Ala Tyr His Arg Phe Val Asp Phe Asp
    130                 135                 140

Asp Phe Gln Thr Thr Leu Thr Gln Ile Gln Gln Ala Ile Leu Ala Glu
145                 150                 155                 160

Arg Val Val Ala Asp Leu Ala Leu Val Gln Pro Gln Arg Gly Phe Gly
                165                 170                 175

Leu Thr Arg Met His Gly Arg Ala Gly Glu Glu Val Pro Val Glu
            180                 185                 190

Arg Leu Met Gln Asp Tyr Tyr Lys Asp Leu Ala Arg Cys Gln Asp His
            195                 200                 205

Ala Trp Gly Met Ala Asp Arg Leu Arg Ile Gln Gln Ala Gly Pro Lys
210                 215                 220

Asp Leu Val Leu Leu Ala Thr Ile Arg Arg Leu Arg Thr Ala Tyr Phe
225                 230                 235                 240

Asn Phe Ile Thr Ser Ile Ala Arg Pro Ala Pro Gln His Asp Pro
                245                 250                 255

Ala Glu Glu Thr Val Leu Ser Leu Pro Cys Asp Cys Asp Trp Leu Glu
            260                 265                 270

Ala Phe Val Gln Arg Phe Ser Asp Pro Val Asp Leu Glu Thr Leu Arg
            275                 280                 285

Ser Leu Arg Gly Val Pro Thr Gly Gln Leu Ile Arg Cys Ile Val Ser
    290                 295                 300

Ala Leu Ser Leu Pro Asn Gly Asp Pro Pro Gly His Leu Glu Met Arg
305                 310                 315                 320

Gly Gly Val Phe Thr Leu Arg Pro Arg Glu Asp Gly Arg Ala Val Thr
                325                 330                 335

Glu Thr Met Arg Arg Arg Arg Gly Glu Thr Ile Glu Arg Phe Ile Asp
            340                 345                 350

Arg Leu Pro Val Arg Arg Arg Arg Pro Pro Pro Pro Pro
            355                 360                 365

Pro Pro Pro Glu Glu Val Glu Glu Met Leu Val Glu Glu Glu
    370                 375                 380

Glu Glu Glu Val Glu Glu Leu Pro Gly Ala Phe Glu Arg Glu Val Arg
385                 390                 395                 400

Ala Thr Ile Ala Glu Leu Ile Arg Leu Leu Glu Glu Glu Leu Thr Val
                405                 410                 415

Ser Ala Arg Asn Ser Gln Phe Phe Asn Phe Ala Val Asp Phe Tyr Glu
            420                 425                 430

Ala Met Glu Arg Leu Glu Ala Leu Gly Asp Val Ser Glu Met Pro Leu
            435                 440                 445

Arg Arg Trp Ile Met Tyr Phe Phe Val Thr Glu His Ile Ala Thr Thr
    450                 455                 460

Leu Asn Tyr Leu Tyr Gln Arg Leu Cys Asn Tyr Ala Val Phe Thr Arg
465                 470                 475                 480

His Val Glu Leu Asn Leu Ala Gln Val Val Met Arg Ala Arg Asp Pro
                485                 490                 495

Glu Gly Val Val Val Tyr Ser Arg Val Trp Asn Glu Ala Gly Met Asn
            500                 505                 510

Ala Phe Ser Gln Leu Met Gly Arg Ile Ser Asn Asp Leu Ala Ala Thr
            515                 520                 525

Val Glu Arg Ala Gly Arg Gly Asp Leu Gln Glu Glu Ile Glu Gln
    530                 535                 540

Phe Met Thr Glu Ile Ala Tyr Gln Asp Asn Ser Gly Asp Val Gln Glu
```

```
                    545                 550                 555                 560
Ile Leu Arg Gln Ala Ala Val Asn Asp Thr Glu Ile Asp Ser Val Glu
                565                 570                 575

Leu Ser Phe Arg Phe Lys Leu Thr Gly Pro Val Ala Phe Thr Gln Arg
                580                 585                 590

Arg Gln Ile Gln Asp Val Asn Arg Val Val Ala His Ala Ser Leu
                595                 600                 605

Leu Arg Ala Gln Tyr Gln Asn Leu Pro Ala Arg Gly Ala Asp Val Pro
610                 615                 620

Leu Pro Pro Leu Pro Pro Gly Pro Glu Pro Pro Leu Pro Pro Gly Ala
625                 630                 635                 640

Arg Pro Arg Arg Arg Phe
                645

<210> SEQ ID NO 12
<211> LENGTH: 396
<212> TYPE: PRT
<213> ORGANISM: Chimpanzee adenovirus AdY25
<220> FEATURE:
<221> NAME/KEY: SOURCE
<222> LOCATION: 1..396
<223> OTHER INFORMATION: /mol_type="protein"
      /organism="Chimpanzee adenovirus AdY25"

<400> SEQUENCE: 12

Met His Pro Val Leu Arg Gln Met Arg Pro His Pro Pro Gln
1               5                   10                  15

Gln Gln Pro Pro Pro Gln Pro Ala Leu Leu Pro Pro Gln Gln
                20                  25                  30

Gln Gln Gln Leu Pro Ala Thr Thr Ala Ala Ala Val Ser Gly Ala
            35                  40                  45

Gly Gln Thr Ser Gln Tyr Asp His Leu Ala Leu Glu Glu Gly Glu Gly
        50                  55                  60

Leu Ala Arg Leu Gly Ala Ser Ser Pro Glu Arg His Pro Arg Val Gln
65                  70                  75                  80

Met Lys Arg Asp Ala Arg Glu Ala Tyr Val Pro Lys Gln Asn Leu Phe
                85                  90                  95

Arg Asp Arg Ser Gly Glu Glu Pro Glu Glu Met Arg Ala Ala Arg Phe
                100                 105                 110

His Ala Gly Arg Glu Leu Arg Arg Gly Leu Asp Arg Lys Arg Val Leu
            115                 120                 125

Arg Asp Glu Asp Phe Glu Ala Asp Glu Leu Thr Gly Ile Ser Pro Ala
130                 135                 140

Arg Ala His Val Ala Ala Ala Asn Leu Val Thr Ala Tyr Glu Gln Thr
145                 150                 155                 160

Val Lys Glu Glu Ser Asn Phe Gln Lys Ser Phe Asn Asn His Val Arg
                165                 170                 175

Thr Leu Ile Ala Arg Glu Glu Val Thr Leu Gly Leu Met His Leu Trp
                180                 185                 190

Asp Leu Leu Glu Ala Ile Val Gln Asn Pro Thr Ser Lys Pro Leu Thr
            195                 200                 205

Ala Gln Leu Phe Leu Val Val Gln His Ser Arg Asp Asn Glu Ala Phe
        210                 215                 220

Arg Glu Ala Leu Leu Asn Ile Thr Glu Pro Glu Gly Arg Trp Leu Leu
225                 230                 235                 240

Asp Leu Val Asn Ile Leu Gln Ser Ile Val Val Gln Glu Arg Gly Leu
```

```
                    245                 250                 255
Pro Leu Ser Glu Lys Leu Ala Ala Ile Asn Phe Ser Val Leu Ser Leu
            260                 265                 270
Gly Lys Tyr Tyr Ala Arg Lys Ile Tyr Lys Thr Pro Tyr Val Pro Ile
            275                 280                 285
Asp Lys Glu Val Lys Ile Asp Gly Phe Tyr Met Arg Met Thr Leu Lys
            290                 295                 300
Val Leu Thr Leu Ser Asp Asp Leu Gly Val Tyr Arg Asn Asp Arg Met
305                 310                 315                 320
His Arg Ala Val Ser Ala Ser Arg Arg Glu Leu Ser Asp Gln Glu
                325                 330                 335
Leu Met His Ser Leu Gln Arg Ala Leu Thr Gly Ala Gly Thr Glu Gly
            340                 345                 350
Glu Ser Tyr Phe Asp Met Gly Ala Asp Leu His Trp Gln Pro Ser Arg
            355                 360                 365
Arg Ala Leu Glu Ala Ala Gly Gly Pro Pro Tyr Ile Glu Glu Val Asp
            370                 375                 380
Asp Glu Val Asp Glu Glu Gly Glu Tyr Leu Glu Asp
385                 390                 395
```

<210> SEQ ID NO 13
<211> LENGTH: 589
<212> TYPE: PRT
<213> ORGANISM: Chimpanzee adenovirus AdY25
<220> FEATURE:
<221> NAME/KEY: SOURCE
<222> LOCATION: 1..589
<223> OTHER INFORMATION: /mol_type="protein"
      /organism="Chimpanzee adenovirus AdY25"

<400> SEQUENCE: 13

```
Met Gln Gln Gln Pro Pro Asp Pro Ala Met Arg Ala Ala Leu Gln
1               5                   10                  15
Ser Gln Pro Ser Gly Ile Asn Ser Ser Asp Asp Trp Thr Gln Ala Met
            20                  25                  30
Gln Arg Ile Met Ala Leu Thr Thr Arg Asn Pro Glu Ala Phe Arg Gln
        35                  40                  45
Gln Pro Gln Ala Asn Arg Leu Ser Ala Ile Leu Glu Ala Val Val Pro
    50                  55                  60
Ser Arg Ser Asn Pro Thr His Glu Lys Val Leu Ala Ile Val Asn Ala
65                  70                  75                  80
Leu Val Glu Asn Lys Ala Ile Arg Gly Asp Glu Ala Gly Leu Val Tyr
                85                  90                  95
Asn Ala Leu Leu Glu Arg Val Ala Arg Tyr Asn Ser Thr Asn Val Gln
            100                 105                 110
Thr Asn Leu Asp Arg Met Val Thr Asp Val Arg Glu Ala Val Ala Gln
        115                 120                 125
Arg Glu Arg Phe His Arg Glu Ser Asn Leu Gly Ser Met Val Ala Leu
    130                 135                 140
Asn Ala Phe Leu Ser Thr Gln Pro Ala Asn Val Pro Arg Gly Gln Glu
145                 150                 155                 160
Asp Tyr Thr Asn Phe Ile Ser Ala Leu Arg Leu Met Val Thr Glu Val
                165                 170                 175
Pro Gln Ser Glu Val Tyr Gln Ser Gly Pro Asp Tyr Phe Phe Gln Thr
            180                 185                 190
Ser Arg Gln Gly Leu Gln Thr Val Asn Leu Ser Gln Ala Phe Lys Asn
```

```
                195                 200                 205
Leu Gln Gly Leu Trp Gly Val Gln Ala Pro Val Gly Asp Arg Ala Thr
210                 215                 220
Val Ser Ser Leu Leu Thr Pro Asn Ser Arg Leu Leu Leu Leu Leu Val
225                 230                 235                 240
Ala Pro Phe Thr Asp Ser Gly Ser Ile Asn Arg Asn Ser Tyr Leu Gly
                245                 250                 255
Tyr Leu Ile Asn Leu Tyr Arg Glu Ala Ile Gly Gln Ala His Val Asp
                260                 265                 270
Glu Gln Thr Tyr Gln Glu Ile Thr His Val Ser Arg Ala Leu Gly Gln
                275                 280                 285
Asp Asp Pro Gly Asn Leu Glu Ala Thr Leu Asn Phe Leu Leu Thr Asn
290                 295                 300
Arg Ser Gln Lys Ile Pro Pro Gln Tyr Thr Leu Ser Ala Glu Glu Glu
305                 310                 315                 320
Arg Ile Leu Arg Tyr Val Gln Gln Ser Val Gly Leu Phe Leu Met Gln
                325                 330                 335
Glu Gly Ala Thr Pro Ser Ala Ala Leu Asp Met Thr Ala Arg Asn Met
                340                 345                 350
Glu Pro Ser Met Tyr Ala Ser Asn Arg Pro Phe Ile Asn Lys Leu Met
                355                 360                 365
Asp Tyr Leu His Arg Ala Ala Met Asn Ser Asp Tyr Phe Thr Asn
370                 375                 380
Ala Ile Leu Asn Pro His Trp Leu Pro Pro Gly Phe Tyr Thr Gly
385                 390                 395                 400
Glu Tyr Asp Met Pro Asp Pro Asn Asp Gly Phe Leu Trp Asp Asp Val
                405                 410                 415
Asp Ser Ser Val Phe Ser Pro Arg Pro Gly Ala Asn Glu Arg Pro Leu
                420                 425                 430
Trp Lys Lys Glu Gly Ser Asp Arg Arg Pro Ser Ser Ala Leu Ser Gly
                435                 440                 445
Arg Glu Gly Ala Ala Ala Val Pro Glu Ala Ala Ser Pro Phe Pro
450                 455                 460
Ser Leu Pro Phe Ser Leu Asn Ser Ile Arg Ser Ser Glu Leu Gly Arg
465                 470                 475                 480
Ile Thr Arg Pro Arg Leu Leu Gly Glu Glu Tyr Leu Asn Asp Ser
                485                 490                 495
Leu Leu Arg Pro Glu Arg Glu Lys Asn Phe Pro Asn Asn Gly Ile Glu
                500                 505                 510
Ser Leu Val Asp Lys Met Ser Arg Trp Lys Thr Tyr Ala Gln Glu His
                515                 520                 525
Arg Asp Asp Pro Ser Gln Gly Ala Thr Ser Arg Gly Ser Ala Ala Arg
                530                 535                 540
Lys Arg Arg Trp His Asp Arg Gln Arg Gly Leu Met Trp Asp Glu
545                 550                 555                 560
Asp Ser Ala Asp Asp Ser Ser Val Leu Asp Leu Gly Gly Ser Gly Asn
                565                 570                 575
Pro Phe Ala His Leu Arg Pro Arg Ile Gly Arg Met Met
                580                 585

<210> SEQ ID NO 14
<211> LENGTH: 193
<212> TYPE: PRT
<213> ORGANISM: Chimpanzee adenovirus AdY25
```

<220> FEATURE:
<221> NAME/KEY: SOURCE
<222> LOCATION: 1..193
<223> OTHER INFORMATION: /mol_type="protein"
      /organism="Chimpanzee adenovirus AdY25"

<400> SEQUENCE: 14

Met Ser Ile Leu Ile Ser Pro Ser Asn Asn Thr Gly Trp Gly Leu Arg
1               5                   10                  15

Ala Pro Ser Lys Met Tyr Gly Gly Ala Arg Gln Arg Ser Thr Gln His
            20                  25                  30

Pro Val Arg Val Arg Gly His Phe Arg Ala Pro Trp Gly Ala Leu Lys
        35                  40                  45

Gly Arg Val Arg Ser Arg Thr Thr Val Asp Asp Val Ile Asp Gln Val
    50                  55                  60

Val Ala Asp Ala Arg Asn Tyr Thr Pro Ala Ala Ala Pro Val Ser Thr
65                  70                  75                  80

Val Asp Ala Val Ile Asp Ser Val Val Ala Asp Ala Arg Arg Tyr Ala
                85                  90                  95

Arg Ala Lys Ser Arg Arg Arg Ile Ala Arg His Arg Ser Thr
            100                 105                 110

Pro Ala Met Arg Ala Ala Arg Ala Leu Leu Arg Arg Ala Arg Arg Thr
            115                 120                 125

Gly Arg Arg Ala Met Leu Arg Ala Ala Arg Ala Ala Ser Gly Ala
    130                 135                 140

Ser Ala Gly Arg Thr Arg Arg Ala Ala Thr Ala Ala Ala Ala
145                 150                 155                 160

Ile Ala Ser Met Ser Arg Pro Arg Arg Gly Asn Val Tyr Trp Val Arg
                165                 170                 175

Asp Ala Ala Thr Gly Val Arg Val Pro Val Arg Thr Arg Pro Pro Arg
            180                 185                 190

Thr

<210> SEQ ID NO 15
<211> LENGTH: 340
<212> TYPE: PRT
<213> ORGANISM: Chimpanzee adenovirus AdY25
<220> FEATURE:
<221> NAME/KEY: SOURCE
<222> LOCATION: 1..340
<223> OTHER INFORMATION: /mol_type="protein"
      /organism="Chimpanzee adenovirus AdY25"

<400> SEQUENCE: 15

Met Ser Lys Arg Lys Phe Lys Glu Glu Met Leu Gln Val Ile Ala Pro
1               5                   10                  15

Glu Ile Tyr Gly Pro Ala Val Val Lys Glu Arg Lys Pro Arg Lys
            20                  25                  30

Ile Lys Arg Val Lys Lys Asp Lys Lys Glu Glu Asp Asp Asp Leu Val
            35                  40                  45

Glu Phe Val Arg Glu Phe Ala Pro Arg Arg Val Gln Trp Arg Gly
    50                  55                  60

Arg Lys Val His Pro Val Leu Arg Pro Gly Thr Thr Val Phe Thr
65                  70                  75                  80

Pro Gly Glu Arg Ser Gly Ser Ala Ser Lys Arg Ser Tyr Asp Glu Val
                85                  90                  95

Tyr Gly Asp Glu Asp Ile Leu Glu Gln Ala Ala Glu Arg Leu Gly Glu
            100                 105                 110

```
Phe Ala Tyr Gly Lys Arg Ser Arg Pro Ala Leu Lys Glu Glu Ala Val
            115                 120                 125

Ser Ile Pro Leu Asp His Gly Asn Pro Thr Pro Ser Leu Lys Pro Val
        130                 135                 140

Thr Leu Gln Gln Val Leu Pro Ser Ala Ala Pro Arg Arg Gly Phe Lys
145                 150                 155                 160

Arg Glu Gly Glu Asp Leu Tyr Pro Thr Met Gln Leu Met Val Pro Lys
                165                 170                 175

Arg Gln Lys Leu Glu Asp Val Leu Glu Thr Met Lys Val Asp Pro Asp
                180                 185                 190

Val Gln Pro Glu Val Lys Val Arg Pro Ile Lys Gln Val Ala Pro Gly
            195                 200                 205

Leu Gly Val Gln Thr Val Asp Ile Lys Ile Pro Thr Glu Pro Met Glu
        210                 215                 220

Thr Gln Thr Glu Pro Met Ile Lys Pro Ser Thr Ser Thr Met Glu Val
225                 230                 235                 240

Gln Thr Asp Pro Trp Met Pro Ser Ala Pro Ser Arg Arg Pro Arg Arg
                245                 250                 255

Lys Tyr Gly Ala Ala Ser Leu Leu Met Pro Asn Tyr Ala Leu His Pro
                260                 265                 270

Ser Ile Ile Pro Thr Pro Gly Tyr Arg Gly Thr Arg Phe Tyr Arg Gly
                275                 280                 285

His Thr Thr Ser Arg Arg Arg Lys Thr Thr Thr Arg Arg Arg Arg Arg
                290                 295                 300

Arg Thr Ala Ala Ala Ser Thr Pro Ala Ala Leu Val Arg Arg Val Tyr
305                 310                 315                 320

Arg Arg Gly Arg Ala Pro Leu Thr Leu Pro Arg Ala Arg Tyr His Pro
                325                 330                 335

Ser Ile Ala Ile
            340

<210> SEQ ID NO 16
<211> LENGTH: 77
<212> TYPE: PRT
<213> ORGANISM: Chimpanzee adenovirus AdY25
<220> FEATURE:
<221> NAME/KEY: SOURCE
<222> LOCATION: 1..77
<223> OTHER INFORMATION: /mol_type="protein"
      /organism="Chimpanzee adenovirus AdY25"

<400> SEQUENCE: 16

Met Ala Leu Thr Cys Arg Leu Arg Val Pro Ile Thr Gly Tyr Arg Gly
1               5                   10                  15

Arg Lys Pro Arg Arg Arg Leu Ala Gly Asn Gly Met Arg Arg His
                20                  25                  30

His His Arg Arg Arg Arg Ala Ile Ser Lys Arg Leu Gly Gly Gly Phe
            35                  40                  45

Leu Pro Ala Leu Ile Pro Ile Ile Ala Ala Ala Ile Gly Ala Ile Pro
    50                  55                  60

Gly Ile Ala Ser Val Ala Val Gln Ala Ser Gln Arg His
65                  70                  75

<210> SEQ ID NO 17
<211> LENGTH: 243
<212> TYPE: PRT
<213> ORGANISM: Chimpanzee adenovirus AdY25
```

```
<220> FEATURE:
<221> NAME/KEY: SOURCE
<222> LOCATION: 1..243
<223> OTHER INFORMATION: /mol_type="protein"
      /organism="Chimpanzee adenovirus AdY25"

<400> SEQUENCE: 17

Met Glu Asp Ile Asn Phe Ser Ser Leu Ala Pro Arg His Gly Thr Arg
1               5                   10                  15

Pro Phe Met Gly Thr Trp Ser Asp Ile Gly Thr Ser Gln Leu Asn Gly
            20                  25                  30

Gly Ala Phe Asn Trp Ser Ser Leu Trp Ser Gly Leu Lys Asn Phe Gly
        35                  40                  45

Ser Thr Leu Lys Thr Tyr Gly Ser Lys Ala Trp Asn Ser Thr Thr Gly
    50                  55                  60

Gln Ala Leu Arg Asp Lys Leu Lys Glu Gln Asn Phe Gln Gln Lys Val
65                  70                  75                  80

Val Asp Gly Leu Ala Ser Gly Ile Asn Gly Val Val Asp Leu Ala Asn
                85                  90                  95

Gln Ala Val Gln Arg Gln Ile Asn Ser Arg Leu Asp Pro Val Pro Pro
            100                 105                 110

Ala Gly Ser Val Glu Met Pro Gln Val Glu Glu Leu Pro Pro Leu
        115                 120                 125

Asp Lys Arg Gly Glu Lys Arg Pro Arg Pro Asp Ala Glu Glu Thr Leu
130                 135                 140

Leu Thr His Thr Asp Glu Pro Pro Pro Tyr Glu Glu Ala Val Lys Leu
145                 150                 155                 160

Gly Leu Pro Thr Thr Arg Pro Ile Ala Pro Leu Ala Thr Gly Val Leu
                165                 170                 175

Lys Pro Glu Ser Asn Lys Pro Ala Thr Leu Asp Leu Pro Pro Pro Ala
            180                 185                 190

Ser Arg Pro Ser Thr Val Ala Lys Pro Leu Pro Pro Val Ala Val Ala
        195                 200                 205

Arg Ala Arg Pro Gly Gly Ser Ala Arg Pro His Ala Asn Trp Gln Ser
    210                 215                 220

Thr Leu Asn Ser Ile Val Gly Leu Gly Val Gln Ser Val Lys Arg Arg
225                 230                 235                 240

Arg Cys Tyr

<210> SEQ ID NO 18
<211> LENGTH: 209
<212> TYPE: PRT
<213> ORGANISM: Chimpanzee adenovirus AdY25
<220> FEATURE:
<221> NAME/KEY: SOURCE
<222> LOCATION: 1..209
<223> OTHER INFORMATION: /mol_type="protein"
      /organism="Chimpanzee adenovirus AdY25"

<400> SEQUENCE: 18

Met Ala Glu Pro Thr Gly Ser Gly Glu Gln Glu Leu Arg Ala Ile Ile
1               5                   10                  15

Arg Asp Leu Gly Cys Gly Pro Tyr Phe Leu Gly Thr Phe Asp Lys Arg
            20                  25                  30

Phe Pro Gly Phe Met Ala Pro His Lys Leu Ala Cys Ala Ile Val Asn
        35                  40                  45

Thr Ala Gly Arg Glu Thr Gly Gly Glu His Trp Leu Ala Phe Ala Trp
    50                  55                  60
```

```
Asn Pro Arg Ser Asn Thr Cys Tyr Leu Phe Asp Pro Phe Gly Phe Ser
 65                  70                  75                  80

Asp Glu Arg Leu Lys Gln Ile Tyr Gln Phe Glu Tyr Glu Gly Leu Leu
                 85                  90                  95

Arg Arg Ser Ala Leu Ala Thr Glu Asp Arg Cys Val Thr Leu Glu Lys
            100                 105                 110

Ser Thr Gln Thr Val Gln Gly Pro Arg Ser Ala Ala Cys Gly Leu Phe
        115                 120                 125

Cys Cys Met Phe Leu His Ala Phe Val His Trp Pro Asp Arg Pro Met
130                 135                 140

Asp Lys Asn Pro Thr Met Asn Leu Leu Thr Gly Val Pro Asn Gly Met
145                 150                 155                 160

Leu Gln Ser Pro Gln Val Glu Pro Thr Leu Arg Arg Asn Gln Glu Ala
                165                 170                 175

Leu Tyr Arg Phe Leu Asn Ser His Ser Ala Tyr Phe Arg Ser His Arg
            180                 185                 190

Ala Arg Ile Glu Lys Ala Thr Ala Phe Asp Arg Met Asn Asn Gln Asp
        195                 200                 205

Met

<210> SEQ ID NO 19
<211> LENGTH: 512
<212> TYPE: PRT
<213> ORGANISM: Chimpanzee adenovirus AdY25
<220> FEATURE:
<221> NAME/KEY: SOURCE
<222> LOCATION: 1..512
<223> OTHER INFORMATION: /mol_type="protein"
      /organism="Chimpanzee adenovirus AdY25"

<400> SEQUENCE: 19

Met Ala Gly Arg Gly Gly Ser Gln Ser Glu Arg Arg Arg Glu Arg Thr
  1               5                  10                  15

Pro Glu Arg Gly Arg Gly Ser Ala Ser His Pro Ser Arg Gly Gly Gly
                 20                  25                  30

Glu Ser Pro Ser Pro Pro Leu Pro Pro Lys Arg His Thr Tyr Arg Arg
             35                  40                  45

Arg Val Ala Ser Asp Gln Glu Glu Glu Ile Val Val Val Ser Glu
         50                  55                  60

Asn Ser Arg Ser Pro Ser Pro Gln Ala Ser Pro Pro Leu Pro Pro
 65                  70                  75                  80

Lys Lys Lys Pro Arg Lys Thr Lys His Val Val Met Gln Asp Val Ser
                 85                  90                  95

Gln Asp Ser Glu Asp Glu Arg Gln Ala Glu Glu Leu Ala Ala Val
            100                 105                 110

Gly Phe Ser Tyr Pro Pro Val Arg Ile Thr Glu Lys Asp Gly Lys Arg
        115                 120                 125

Ser Phe Glu Thr Leu Asp Glu Ser Asp Pro Leu Ala Ala Ala Ala Ser
130                 135                 140

Ala Lys Met Met Val Lys Asn Pro Met Ser Leu Pro Ile Val Ser Ala
145                 150                 155                 160

Trp Glu Lys Gly Met Glu Ile Met Thr Met Leu Met Asp Arg Tyr Arg
                165                 170                 175

Val Glu Thr Asp Leu Lys Ala Asn Phe Gln Leu Met Pro Glu Gln Gly
            180                 185                 190
```

```
Glu Val Tyr Arg Arg Ile Cys His Leu Tyr Ile Asn Glu His Arg
            195                 200                 205
Gly Ile Pro Leu Thr Phe Thr Ser Asn Lys Thr Leu Thr Thr Met Met
210                 215                 220
Gly Arg Phe Leu Gln Gly Phe Val His Ala His Ser Gln Ile Ala His
225                 230                 235                 240
Lys Asn Trp Glu Cys Thr Gly Cys Ala Leu Trp Leu His Gly Cys Thr
            245                 250                 255
Glu Ala Glu Gly Lys Leu Arg Cys Leu His Gly Thr Thr Met Ile Gln
            260                 265                 270
Lys Glu His Met Ile Glu Met Asp Val Ala Ser Glu Asn Gly Gln Arg
            275                 280                 285
Ala Leu Lys Glu Asn Pro Asp Arg Ala Lys Ile Thr Gln Asn Arg Trp
290                 295                 300
Gly Arg Ser Val Val Gln Leu Ala Asn Asn Asp Ala Arg Cys Cys Val
305                 310                 315                 320
His Asp Ala Gly Cys Ala Thr Asn Gln Phe Ser Ser Lys Ser Cys Gly
            325                 330                 335
Val Phe Phe Thr Glu Gly Ala Lys Ala Gln Gln Ala Phe Arg Gln Leu
            340                 345                 350
Glu Ala Phe Met Lys Ala Met Tyr Pro Gly Met Asn Ala Asp Gln Ala
            355                 360                 365
Gln Met Met Leu Ile Pro Leu His Cys Asp Cys Asn His Lys Pro Gly
            370                 375                 380
Cys Val Pro Thr Met Gly Arg Gln Thr Cys Lys Met Thr Pro Phe Gly
385                 390                 395                 400
Met Ala Asn Ala Glu Asp Leu Asp Val Glu Ser Ile Thr Asp Ala Ala
                405                 410                 415
Val Leu Ala Ser Val Lys His Pro Ala Leu Met Val Phe Gln Cys Cys
                420                 425                 430
Asn Pro Val Tyr Arg Asn Ser Arg Ala Gln Asn Ala Gly Pro Asn Cys
            435                 440                 445
Asp Phe Lys Ile Ser Ala Pro Asp Leu Leu Gly Ala Leu Gln Leu Thr
450                 455                 460
Arg Lys Leu Trp Thr Asp Ser Phe Pro Asp Thr Pro Leu Pro Lys Leu
465                 470                 475                 480
Leu Ile Pro Glu Phe Lys Trp Leu Ala Lys Tyr Gln Phe Arg Asn Val
                485                 490                 495
Ser Leu Pro Ala Gly His Ala Glu Thr Arg Gln Asn Pro Phe Asp Phe
            500                 505                 510

<210> SEQ ID NO 20
<211> LENGTH: 802
<212> TYPE: PRT
<213> ORGANISM: Chimpanzee adenovirus AdY25
<220> FEATURE:
<221> NAME/KEY: SOURCE
<222> LOCATION: 1..802
<223> OTHER INFORMATION: /mol_type="protein"
      /organism="Chimpanzee adenovirus AdY25"

<400> SEQUENCE: 20

Met Glu Thr Gln Pro Ser Pro Thr Ser Pro Ala Pro Thr Ala Gly
1               5                   10                  15
Asp Glu Lys Gln Gln Gln Asn Glu Ser Leu Thr Ala Pro Pro
            20                  25                  30
```

-continued

```
Ser Pro Ala Ser Asp Ala Ala Ala Val Pro Asp Met Gln Glu Met Glu
         35                  40                  45

Glu Ser Ile Glu Ile Asp Leu Gly Tyr Val Thr Pro Ala Glu His Glu
 50                  55                  60

Glu Glu Leu Ala Val Arg Phe Gln Ser Ser Gln Glu Asp Lys Glu
 65                  70                  75                  80

Gln Pro Glu Gln Glu Ala Glu Asn Glu Gln Ser Gln Ala Gly Leu Glu
                 85                  90                  95

His Gly Asp Tyr Leu His Leu Ser Gly Glu Asp Ala Leu Ile Lys
             100                 105                 110

His Leu Ala Arg Gln Ala Thr Ile Val Lys Asp Ala Leu Leu Asp Arg
             115                 120                 125

Thr Glu Val Pro Leu Ser Val Glu Glu Leu Ser Arg Ala Tyr Glu Leu
130                 135                 140

Asn Leu Phe Ser Pro Arg Val Pro Pro Lys Arg Gln Pro Asn Gly Thr
145                 150                 155                 160

Cys Glu Pro Asn Pro Arg Leu Asn Phe Tyr Pro Val Phe Ala Val Pro
                165                 170                 175

Glu Ala Leu Ala Thr Tyr His Ile Phe Phe Lys Asn Gln Lys Ile Pro
            180                 185                 190

Val Ser Cys Arg Ala Asn Arg Thr Arg Ala Asp Ala Leu Phe Asn Leu
            195                 200                 205

Gly Pro Gly Ala Arg Leu Pro Asp Ile Ala Ser Leu Glu Glu Val Pro
        210                 215                 220

Lys Ile Phe Glu Gly Leu Gly Ser Asp Glu Thr Arg Ala Ala Asn Ala
225                 230                 235                 240

Leu Gln Gly Glu Gly Gly Glu His Glu His His Ser Ala Leu Val
                245                 250                 255

Glu Leu Glu Gly Asp Asn Ala Arg Leu Ala Val Leu Lys Arg Thr Val
            260                 265                 270

Glu Leu Thr His Phe Ala Tyr Pro Ala Leu Asn Leu Pro Pro Lys Val
            275                 280                 285

Met Ser Ala Val Met Asp Gln Val Leu Ile Lys Arg Ala Ser Pro Ile
290                 295                 300

Ser Glu Asp Glu Gly Met Gln Asp Ser Glu Glu Gly Lys Pro Val Val
305                 310                 315                 320

Ser Asp Glu Gln Leu Ala Arg Trp Leu Gly Pro Asn Ala Thr Pro Gln
                325                 330                 335

Ser Leu Glu Glu Arg Arg Lys Leu Met Met Ala Val Val Leu Val Thr
            340                 345                 350

Val Glu Leu Glu Cys Leu Arg Arg Phe Phe Ala Asp Ala Glu Thr Leu
            355                 360                 365

Arg Lys Val Glu Glu Asn Leu His Tyr Leu Phe Arg His Gly Phe Val
        370                 375                 380

Arg Gln Ala Cys Lys Ile Ser Asn Val Glu Leu Thr Asn Leu Val Ser
385                 390                 395                 400

Tyr Met Gly Ile Leu His Glu Asn Arg Leu Gly Gln Asn Val Leu His
                405                 410                 415

Thr Thr Leu Arg Gly Glu Ala Arg Arg Asp Tyr Ile Arg Asp Cys Val
            420                 425                 430

Tyr Leu Tyr Leu Cys His Thr Trp Gln Thr Gly Met Gly Val Trp Gln
            435                 440                 445

Gln Cys Leu Glu Glu Gln Asn Leu Lys Glu Leu Cys Lys Leu Leu Gln
```

```
            450                 455                 460
Lys Asn Leu Lys Gly Leu Trp Thr Gly Phe Asp Glu Arg Thr Thr Ala
465                 470                 475                 480

Ser Asp Leu Ala Asp Leu Ile Phe Pro Glu Arg Leu Arg Leu Thr Leu
                485                 490                 495

Arg Asn Gly Leu Pro Asp Phe Met Ser Gln Ser Met Leu Gln Asn Phe
            500                 505                 510

Arg Ser Phe Ile Leu Glu Arg Ser Gly Ile Leu Pro Ala Thr Cys Ser
            515                 520                 525

Ala Leu Pro Ser Asp Phe Val Pro Leu Thr Phe Arg Glu Cys Pro Pro
            530                 535                 540

Pro Leu Trp Ser His Cys Tyr Leu Leu Arg Leu Ala Asn Tyr Leu Ala
545                 550                 555                 560

Tyr His Ser Asp Val Ile Glu Asp Val Ser Gly Glu Gly Leu Leu Glu
                565                 570                 575

Cys His Cys Arg Cys Asn Leu Cys Thr Pro His Arg Ser Leu Ala Cys
            580                 585                 590

Asn Pro Gln Leu Leu Ser Glu Thr Gln Ile Ile Gly Thr Phe Glu Leu
            595                 600                 605

Gln Gly Pro Ser Glu Gly Glu Gly Ala Lys Gly Gly Leu Lys Leu Thr
            610                 615                 620

Pro Gly Leu Trp Thr Ser Ala Tyr Leu Arg Lys Phe Val Pro Glu Asp
625                 630                 635                 640

Tyr His Pro Phe Glu Ile Arg Phe Tyr Glu Asp Gln Ser Gln Pro Pro
                645                 650                 655

Lys Ala Glu Leu Ser Ala Cys Val Ile Thr Gln Gly Ala Ile Leu Ala
            660                 665                 670

Gln Leu Gln Ala Ile Gln Lys Ser Arg Gln Glu Phe Leu Leu Lys Lys
            675                 680                 685

Gly Arg Gly Val Tyr Leu Asp Pro Gln Thr Gly Glu Glu Leu Asn Pro
690                 695                 700

Gly Phe Pro Gln Asp Ala Pro Arg Lys Gln Glu Ala Glu Ser Gly Ala
705                 710                 715                 720

Ala Ala Arg Gly Gly Phe Gly Gly Arg Leu Gly Gln Gln Ser Gly
                725                 730                 735

Arg Gly Asp Gly Gly Arg Leu Gly Gln His Ser Gly Arg Gly Gly Gln
            740                 745                 750

Pro Ala Arg Gln Ser Gly Gly Arg Arg Gly Gly Arg Gly Gly Gly
            755                 760                 765

Gly Arg Ser Ser Arg Arg Gln Thr Val Val Leu Gly Gly Gly Glu Ser
770                 775                 780

Lys Gln His Gly Tyr His Leu Arg Ser Gly Ser Gly Ser Arg Ser Ala
785                 790                 795                 800

Pro Gln

<210> SEQ ID NO 21
<211> LENGTH: 184
<212> TYPE: PRT
<213> ORGANISM: Chimpanzee adenovirus AdY25
<220> FEATURE:
<221> NAME/KEY: SOURCE
<222> LOCATION: 1..184
<223> OTHER INFORMATION: /mol_type="protein"
      /organism="Chimpanzee adenovirus AdY25"

<400> SEQUENCE: 21
```

```
Met Pro Arg Gly Asn Lys Lys Leu Lys Val Glu Leu Pro Pro Val Glu
1               5                   10                  15

Asp Leu Glu Glu Asp Trp Glu Asn Ser Ser Gln Ala Glu Glu Met Glu
                20                  25                  30

Glu Asp Trp Asp Ser Thr Gln Ala Glu Glu Asp Ser Leu Gln Asp Ser
            35                  40                  45

Leu Glu Glu Asp Glu Glu Ala Glu Glu Val Glu Glu Ala Ala
    50                  55                  60

Ala Ala Arg Pro Ser Ser Ser Ala Gly Glu Lys Ala Ser Ser Thr Asp
65                  70                  75                  80

Thr Ile Ser Ala Pro Gly Arg Gly Pro Ala Arg Pro His Ser Arg Trp
                85                  90                  95

Asp Glu Thr Gly Arg Phe Pro Asn Pro Thr Thr Gln Thr Gly Lys Lys
                100                 105                 110

Glu Arg Gln Gly Tyr Lys Ser Trp Arg Gly His Lys Asn Ala Ile Val
            115                 120                 125

Ser Cys Leu Gln Ala Cys Gly Gly Asn Ile Ser Phe Thr Arg Arg Tyr
            130                 135                 140

Leu Leu Phe His Arg Gly Val Asn Phe Pro Arg Asn Ile Leu His Tyr
145                 150                 155                 160

Tyr Arg His Leu His Ser Pro Tyr Tyr Phe Gln Glu Ala Ala Ala
                165                 170                 175

Ala Glu Lys Asp Gln Lys Thr Ser
            180
```

<210> SEQ ID NO 22
<211> LENGTH: 219
<212> TYPE: PRT
<213> ORGANISM: Chimpanzee adenovirus AdY25
<220> FEATURE:
<221> NAME/KEY: SOURCE
<222> LOCATION: 1..219
<223> OTHER INFORMATION: /mol_type="protein"
      /organism="Chimpanzee adenovirus AdY25"

<400> SEQUENCE: 22

```
Met Pro Arg Gly Asn Lys Lys Leu Lys Val Glu Leu Pro Pro Val Glu
1               5                   10                  15

Asp Leu Glu Glu Asp Trp Glu Asn Ser Ser Gln Ala Glu Glu Met Glu
                20                  25                  30

Glu Asp Trp Asp Ser Thr Gln Ala Glu Glu Asp Ser Leu Gln Asp Ser
            35                  40                  45

Leu Glu Glu Asp Glu Glu Ala Glu Glu Val Glu Glu Ala Ala
    50                  55                  60

Ala Ala Arg Pro Ser Ser Ser Ala Gly Glu Lys Ala Ser Ser Thr Asp
65                  70                  75                  80

Thr Ile Ser Ala Pro Gly Arg Gly Pro Ala Arg Pro His Ser Arg Trp
                85                  90                  95

Asp Glu Thr Gly Arg Phe Pro Asn Pro Thr Thr Gln Thr Ala Pro Thr
                100                 105                 110

Thr Ser Lys Lys Arg Gln Gln Gln Lys Lys Thr Arg Lys Pro Ala
            115                 120                 125

Arg Lys Ser Thr Ala Ala Ala Ala Gly Gly Leu Arg Ile Ala Ala
            130                 135                 140

Asn Glu Pro Ala Gln Thr Arg Glu Leu Arg Asn Arg Ile Phe Pro Thr
145                 150                 155                 160
```

-continued

Leu Tyr Ala Ile Phe Gln Gln Ser Arg Gly Gln Gln Glu Leu Lys
            165                 170                 175

Val Lys Asn Arg Ser Leu Arg Ser Leu Thr Arg Ser Cys Leu Tyr His
        180                 185                 190

Lys Ser Glu Asp Gln Leu Gln Arg Thr Leu Glu Asp Ala Glu Ala Leu
    195                 200                 205

Phe Asn Lys Tyr Cys Ala Leu Thr Leu Lys Glu
    210                 215

<210> SEQ ID NO 23
<211> LENGTH: 227
<212> TYPE: PRT
<213> ORGANISM: Chimpanzee adenovirus AdY25
<220> FEATURE:
<221> NAME/KEY: SOURCE
<222> LOCATION: 1..227
<223> OTHER INFORMATION: /mol_type="protein"
      /organism="Chimpanzee adenovirus AdY25"

<400> SEQUENCE: 23

Met Ser Lys Glu Ile Pro Thr Pro Tyr Met Trp Ser Tyr Gln Pro Gln
1               5                   10                  15

Met Gly Leu Ala Ala Gly Ala Ala Gln Asp Tyr Ser Thr Arg Met Asn
            20                  25                  30

Trp Leu Ser Ala Gly Pro Ala Met Ile Ser Arg Val Asn Asp Ile Arg
        35                  40                  45

Ala His Arg Asn Gln Ile Leu Leu Glu Gln Ser Ala Leu Thr Ala Thr
    50                  55                  60

Pro Arg Asn His Leu Asn Pro Arg Asn Trp Pro Ala Ala Leu Val Tyr
65                  70                  75                  80

Gln Glu Ile Pro Gln Pro Thr Thr Val Leu Leu Pro Arg Asp Ala Gln
                85                  90                  95

Ala Glu Val Gln Leu Thr Asn Ser Gly Val Gln Leu Ala Gly Gly Ala
            100                 105                 110

Thr Leu Cys Arg His Arg Pro Ala Gln Gly Ile Lys Arg Leu Val Ile
        115                 120                 125

Arg Gly Arg Gly Thr Gln Leu Asn Asp Glu Val Val Ser Ser Ser Leu
    130                 135                 140

Gly Leu Arg Pro Asp Gly Val Phe Gln Leu Ala Gly Ser Gly Arg Ser
145                 150                 155                 160

Ser Phe Thr Pro Arg Gln Ala Val Leu Thr Leu Glu Ser Ser Ser Ser
                165                 170                 175

Gln Pro Arg Ser Gly Gly Ile Gly Thr Leu Gln Phe Val Glu Glu Phe
            180                 185                 190

Thr Pro Ser Val Tyr Phe Asn Pro Phe Ser Gly Ser Pro Gly His Tyr
        195                 200                 205

Pro Asp Glu Phe Ile Pro Asn Phe Asp Ala Ile Ser Glu Ser Val Asp
    210                 215                 220

Gly Tyr Asp
225

<210> SEQ ID NO 24
<211> LENGTH: 106
<212> TYPE: PRT
<213> ORGANISM: Chimpanzee adenovirus AdY25
<220> FEATURE:
<221> NAME/KEY: SOURCE
<222> LOCATION: 1..106

```
<223> OTHER INFORMATION: /mol_type="protein"
      /organism="Chimpanzee adenovirus AdY25"

<400> SEQUENCE: 24

Met Ser His Gly Gly Ala Ala Asp Leu Ala Arg Leu Arg His Leu Asp
1               5                   10                  15

His Cys Arg Arg Phe Arg Cys Phe Ala Arg Asp Leu Ala Glu Phe Thr
            20                  25                  30

Tyr Phe Glu Leu Pro Glu Glu His Pro Gln Gly Pro Ala His Gly Val
        35                  40                  45

Arg Ile Val Val Glu Gly Gly Leu Asp Ser His Leu Leu Arg Ile Phe
    50                  55                  60

Ser Gln Arg Pro Ile Leu Val Glu Arg Gln Gln Gly Asn Thr Leu Leu
65                  70                  75                  80

Thr Leu Tyr Cys Ile Cys Asp His Pro Gly Leu His Glu Ser Leu Cys
                85                  90                  95

Cys Leu Leu Cys Thr Glu Tyr Asn Lys Ser
            100                 105

<210> SEQ ID NO 25
<211> LENGTH: 212
<212> TYPE: PRT
<213> ORGANISM: Chimpanzee adenovirus AdY25
<220> FEATURE:
<221> NAME/KEY: SOURCE
<222> LOCATION: 1..212
<223> OTHER INFORMATION: /mol_type="protein"
      /organism="Chimpanzee adenovirus AdY25"

<400> SEQUENCE: 25

Met Lys Val Phe Val Val Cys Cys Val Leu Ser Ile Ile Lys Ala Glu
1               5                   10                  15

Ile Ser Asp Tyr Ser Gly Leu Asn Cys Gly Val Ser Ala Ser Ile Asn
            20                  25                  30

Arg Ser Leu Thr Phe Thr Gly Asn Glu Thr Glu Leu Gln Val Gln Cys
        35                  40                  45

Lys Pro His Lys Lys Tyr Leu Thr Trp Leu Tyr Gln Gly Ser Pro Ile
    50                  55                  60

Ala Val Val Asn His Cys Asp Asp Gly Val Leu Leu Asn Gly Pro
65                  70                  75                  80

Ala Asn Leu Thr Phe Ser Thr Arg Arg Ser Lys Leu Leu Leu Phe Arg
                85                  90                  95

Pro Phe Leu Pro Gly Thr Tyr Gln Cys Ile Ser Gly Pro Cys His His
            100                 105                 110

Thr Phe His Leu Ile Pro Asn Thr Thr Ser Ser Pro Ala Pro Leu Pro
        115                 120                 125

Thr Asn Asn Gln Thr Asn His His Gln Arg Tyr Arg Arg Asp Leu Val
    130                 135                 140

Ser Glu Ser Asn Thr Thr His Thr Gly Gly Glu Leu Arg Gly Arg Lys
145                 150                 155                 160

Pro Ser Gly Ile Tyr Tyr Gly Pro Trp Glu Val Val Gly Leu Ile Ala
                165                 170                 175

Leu Gly Leu Val Ala Gly Gly Leu Leu Ala Leu Cys Tyr Leu Tyr Leu
            180                 185                 190

Pro Cys Phe Ser Tyr Leu Val Val Leu Cys Cys Trp Phe Lys Lys Trp
        195                 200                 205

Gly Arg Ser Pro
```

<210> SEQ ID NO 26
<211> LENGTH: 176
<212> TYPE: PRT
<213> ORGANISM: Chimpanzee adenovirus AdY25
<220> FEATURE:
<221> NAME/KEY: SOURCE
<222> LOCATION: 1..176
<223> OTHER INFORMATION: /mol_type="protein"
       /organism="Chimpanzee adenovirus AdY25"

<400> SEQUENCE: 26

```
Met Gly Lys Ile Thr Leu Val Cys Gly Val Leu Val Thr Val Leu
1               5                   10                  15

Ser Ile Leu Gly Gly Gly Ser Ala Ala Val Val Thr Glu Lys Lys Ala
                20                  25                  30

Asp Pro Cys Leu Thr Phe Asn Pro Asp Lys Cys Arg Leu Ser Phe Gln
            35                  40                  45

Pro Asp Gly Asn Arg Cys Ala Val Leu Ile Lys Cys Gly Trp Glu Cys
        50                  55                  60

Glu Ser Val Leu Val Gln Tyr Lys Asn Lys Thr Trp Asn Asn Thr Leu
65                  70                  75                  80

Ala Ser Thr Trp Gln Pro Gly Asp Pro Glu Trp Tyr Thr Val Ser Val
                85                  90                  95

Pro Gly Ala Asp Gly Ser Leu Arg Thr Val Asn Asn Thr Phe Ile Phe
            100                 105                 110

Glu His Met Cys Glu Thr Ala Met Phe Met Ser Lys Gln Tyr Gly Met
        115                 120                 125

Trp Pro Pro Arg Lys Glu Asn Ile Val Val Phe Ser Ile Ala Tyr Ser
    130                 135                 140

Ala Cys Thr Val Leu Ile Thr Ala Ile Val Cys Leu Ser Ile His Met
145                 150                 155                 160

Leu Ile Ala Ile Arg Pro Arg Asn Asn Ala Glu Lys Glu Lys Gln Pro
                165                 170                 175
```

<210> SEQ ID NO 27
<211> LENGTH: 209
<212> TYPE: PRT
<213> ORGANISM: Chimpanzee adenovirus AdY25
<220> FEATURE:
<221> NAME/KEY: SOURCE
<222> LOCATION: 1..209
<223> OTHER INFORMATION: /mol_type="protein"
       /organism="Chimpanzee adenovirus AdY25"

<400> SEQUENCE: 27

```
Met Lys Ile Leu Ser Leu Phe Cys Phe Ser Ile Ile Ile Thr Ser Ala
1               5                   10                  15

Ile Cys Asn Ser Val Asp Lys Asp Val Thr Val Thr Thr Gly Ser Asn
                20                  25                  30

Tyr Thr Leu Lys Gly Pro Pro Ser Gly Met Leu Ser Trp Tyr Cys Tyr
            35                  40                  45

Phe Gly Thr Asp Val Ser Gln Thr Glu Leu Cys Asn Phe Gln Lys Gly
        50                  55                  60

Lys Thr Gln Asn Pro Lys Ile His Asn Tyr Gln Cys Asn Gly Thr Asp
65                  70                  75                  80

Leu Val Leu Phe Asn Ile Thr Lys Thr Tyr Ala Gly Ser Tyr Tyr Cys
                85                  90                  95
```

```
Pro Gly Asp Asn Val Asp Asn Met Ile Phe Tyr Glu Leu Gln Val Val
            100                 105                 110

Asp Pro Thr Thr Pro Ala Pro Thr Thr Thr Lys Ala His Ser
        115                 120                 125

Thr Asp Thr Gln Glu Thr Thr Pro Glu Ala Glu Val Ala Glu Leu Ala
        130                 135                 140

Lys Gln Ile His Glu Asp Ser Phe Val Ala Asn Thr Pro Thr His Pro
145                 150                 155                 160

Gly Pro Gln Cys Pro Gly Pro Leu Val Ser Gly Ile Val Gly Val Leu
                165                 170                 175

Cys Gly Leu Ala Val Ile Ile Ile Cys Met Phe Ile Phe Ala Cys Cys
            180                 185                 190

Tyr Arg Arg Leu His Arg Gln Lys Ser Asp Pro Leu Leu Asn Leu Tyr
            195                 200                 205

Val

<210> SEQ ID NO 28
<211> LENGTH: 302
<212> TYPE: PRT
<213> ORGANISM: Chimpanzee adenovirus AdY25
<220> FEATURE:
<221> NAME/KEY: SOURCE
<222> LOCATION: 1..302
<223> OTHER INFORMATION: /mol_type="protein"
      /organism="Chimpanzee adenovirus AdY25"

<400> SEQUENCE: 28

Met Lys Ala Leu Ser Thr Leu Val Phe Leu Thr Leu Ile Gly Ile Val
1               5                   10                  15

Phe Asn Ser Lys Ile Thr Arg Val Ser Phe Leu Lys His Val Asn Val
                20                  25                  30

Thr Glu Gly Asn Asn Ile Thr Leu Val Gly Val Glu Gly Ala Gln Asn
            35                  40                  45

Thr Thr Trp Thr Lys Tyr His Leu Gly Trp Lys Asp Ile Cys Thr Trp
        50                  55                  60

Asn Val Thr Tyr Phe Cys Ile Gly Val Asn Leu Thr Ile Val Asn Ala
65                  70                  75                  80

Asn Gln Ser Gln Asn Gly Leu Ile Lys Gly Gln Ser Val Ser Val Thr
                85                  90                  95

Ser Asp Gly Tyr Tyr Thr Gln His Asn Phe Asn Tyr Asn Ile Thr Val
            100                 105                 110

Ile Pro Leu Pro Thr Pro Ser Pro Pro Ser Thr Thr Gln Thr Thr Gln
        115                 120                 125

Thr Thr His Thr Thr Gln Ser Ser Thr Thr Thr Met Gln Thr Thr Gln
        130                 135                 140

Thr Thr Thr Tyr Thr Thr Ser Pro Gln Pro Thr Thr Thr Thr Ala Glu
145                 150                 155                 160

Ala Ser Ser Ser Pro Thr Ile Lys Val Ala Phe Leu Met Leu Ala Pro
                165                 170                 175

Ser Ser Ser Pro Thr Ala Ser Thr Asn Glu Gln Thr Thr Glu Phe Leu
            180                 185                 190

Ser Thr Ile Gln Ser Ser Thr Thr Ala Thr Ser Ser Ala Phe Ser Ser
            195                 200                 205

Thr Ala Asn Leu Thr Ser Leu Ser Ser Met Pro Ile Ser Asn Ala Thr
        210                 215                 220

Thr Ser Pro Ala Pro Leu Pro Thr Pro Leu Lys Gln Ser Glu Ser Ser
```

```
                225                 230                 235                 240

Thr Gln Leu Gln Ile Thr Leu Leu Ile Val Ile Gly Val Val Ile Leu
            245                 250                 255

Ala Val Leu Leu Tyr Phe Ile Phe Cys Arg Arg Ile Pro Asn Ala Lys
            260                 265                 270

Pro Ala Tyr Lys Pro Ile Val Ile Gly Thr Pro Glu Pro Leu Gln Val
            275                 280                 285

Glu Gly Gly Leu Arg Asn Leu Leu Phe Ser Phe Thr Val Trp
            290                 295                 300

<210> SEQ ID NO 29
<211> LENGTH: 91
<212> TYPE: PRT
<213> ORGANISM: Chimpanzee adenovirus AdY25
<220> FEATURE:
<221> NAME/KEY: SOURCE
<222> LOCATION: 1..91
<223> OTHER INFORMATION: /mol_type="protein"
      /organism="Chimpanzee adenovirus AdY25"

<400> SEQUENCE: 29

Met Ile Pro Arg His Phe Ile Ile Thr Ser Leu Ile Cys Val Leu Gln
1               5                   10                  15

Val Cys Ala Thr Leu Ala Leu Val Ala Asn Ala Ser Pro Asp Cys Ile
            20                  25                  30

Gly Ala Phe Ala Ser Tyr Val Leu Phe Ala Phe Ile Thr Cys Ile Cys
            35                  40                  45

Cys Cys Ser Ile Val Cys Leu Leu Ile Thr Phe Gln Phe Val Asp
        50                  55                  60

Trp Val Phe Val Arg Ile Ala Tyr Leu Arg His His Pro Gln Tyr Arg
65              70                  75                  80

Asp Gln Arg Val Ala Gln Leu Leu Arg Leu Ile
            85                  90

<210> SEQ ID NO 30
<211> LENGTH: 147
<212> TYPE: PRT
<213> ORGANISM: Chimpanzee adenovirus AdY25
<220> FEATURE:
<221> NAME/KEY: SOURCE
<222> LOCATION: 1..147
<223> OTHER INFORMATION: /mol_type="protein"
      /organism="Chimpanzee adenovirus AdY25"

<400> SEQUENCE: 30

Met Arg Ala Leu Leu Leu Leu Ala Leu Leu Ala Pro Leu Ala
1               5                   10                  15

Ala Pro Leu Ser Leu Lys Ser Pro Thr Gln Ser Pro Glu Glu Val Arg
            20                  25                  30

Lys Cys Lys Phe Gln Glu Pro Trp Lys Phe Leu Ser Cys Tyr Lys Leu
            35                  40                  45

Lys Ser Glu Met His Pro Ser Trp Ile Met Ile Val Gly Ile Val Asn
        50                  55                  60

Ile Leu Ala Cys Thr Leu Phe Ser Phe Val Ile Tyr Pro Arg Phe Asp
65              70                  75                  80

Phe Gly Trp Asn Ala Pro Glu Ala Leu Trp Leu Pro Asp Pro Asp
            85                  90                  95

Thr Pro Pro Gln Gln Gln Gln Asn Gln Ala Gln Ala His Ala Pro
            100                 105                 110
```

-continued

```
Pro Gln Pro Arg Pro Gln Tyr Met Pro Ile Leu Asn Tyr Glu Ala Glu
            115                 120                 125

Ala Gln Arg Ala Met Leu Pro Ala Ile Ser Tyr Phe Asn Leu Thr Gly
        130                 135                 140

Gly Asp Asp
145

<210> SEQ ID NO 31
<211> LENGTH: 134
<212> TYPE: PRT
<213> ORGANISM: Chimpanzee adenovirus AdY25
<220> FEATURE:
<221> NAME/KEY: SOURCE
<222> LOCATION: 1..134
<223> OTHER INFORMATION: /mol_type="protein"
      /organism="Chimpanzee adenovirus AdY25"

<400> SEQUENCE: 31

Met Thr Asp Pro Met Ala Asn Asn Thr Val Asn Asp Leu Leu Asp Met
1               5                   10                  15

Asp Gly Arg Ala Ser Glu Gln Arg Leu Ala Gln Leu Arg Ile Arg Gln
            20                  25                  30

Gln Gln Glu Arg Ala Val Lys Glu Leu Gln Asp Ala Val Ala Ile His
        35                  40                  45

Gln Cys Lys Arg Gly Ile Phe Cys Leu Val Lys Gln Ala Lys Ile Ser
    50                  55                  60

Phe Glu Val Thr Ser Thr Asp His Arg Leu Ser Tyr Glu Leu Leu Gln
65                  70                  75                  80

Gln Arg Gln Lys Phe Thr Cys Leu Val Gly Val Asn Pro Ile Val Ile
                85                  90                  95

Thr Gln Gln Ser Gly Asp Thr Lys Gly Cys Ile His Cys Ser Cys Asp
            100                 105                 110

Ser Pro Glu Cys Val His Thr Leu Ile Lys Thr Leu Cys Gly Leu Arg
        115                 120                 125

Asp Leu Leu Pro Met Asn
    130

<210> SEQ ID NO 32
<211> LENGTH: 141
<212> TYPE: PRT
<213> ORGANISM: Chimpanzee adenovirus AdY25
<220> FEATURE:
<221> NAME/KEY: SOURCE
<222> LOCATION: 1..141
<223> OTHER INFORMATION: /mol_type="protein"
      /organism="Chimpanzee adenovirus AdY25"

<400> SEQUENCE: 32

Met Ser Gly Asn Ser Ser Ile Met Thr Arg Ser Arg Thr Arg Leu Ala
1               5                   10                  15

Ser Ser Arg His His Pro Tyr Gln Pro Pro Ala Pro Leu Pro Arg Cys
            20                  25                  30

Glu Glu Thr Glu Thr Arg Ala Ser Leu Val Glu Asp His Pro Val Leu
        35                  40                  45

Pro Asp Cys Asp Thr Leu Ser Met His Asn Ile Thr Val Ile Pro Thr
    50                  55                  60

Thr Glu Asp Ser Pro Gln Leu Leu Asn Phe Glu Val Gln Met Gln Glu
65                  70                  75                  80

Cys Pro Glu Gly Phe Ile Ser Leu Thr Asp Pro Arg Leu Ala Arg Ser
                85                  90                  95
```

```
Glu Thr Val Trp Asn Val Glu Thr Lys Thr Met Ser Ile Thr Asn Gly
            100                 105                 110

Ile Gln Met Phe Lys Ala Val Arg Gly Glu Arg Val Tyr Ser Met
        115                 120                 125

Ser Trp Glu Gly Gly Lys Ile Thr Thr Arg Ile Leu
    130                 135                 140

<210> SEQ ID NO 33
<211> LENGTH: 299
<212> TYPE: PRT
<213> ORGANISM: Chimpanzee adenovirus AdY25
<220> FEATURE:
<221> NAME/KEY: SOURCE
<222> LOCATION: 1..299
<223> OTHER INFORMATION: /mol_type="protein"
      /organism="Chimpanzee adenovirus AdY25"

<400> SEQUENCE: 33

Met Ser Gly Asn Ser Ser Ile Met Thr Arg Ser Arg Thr Arg Leu Ala
1               5                   10                  15

Ser Ser Arg His His Pro Tyr Gln Pro Pro Ala Pro Leu Pro Arg Cys
            20                  25                  30

Glu Glu Thr Glu Thr Arg Ala Ser Leu Val Glu Asp His Pro Val Leu
        35                  40                  45

Pro Asp Cys Asp Thr Leu Ser Met His Asn Val Ser Cys Val Arg Gly
50                  55                  60

Leu Pro Cys Ser Ala Gly Phe Thr Val Leu Gln Glu Phe Pro Val Pro
65                  70                  75                  80

Trp Asp Met Val Leu Thr Pro Glu Glu Leu Arg Val Leu Lys Thr Cys
                85                  90                  95

Met Ser Val Cys Leu Cys Cys Ala Asn Ile Asp Leu Phe Ser Ser Gln
            100                 105                 110

Leu Ile His Gly Arg Glu Arg Trp Val Leu His Cys His Cys Gln Asp
        115                 120                 125

Pro Gly Ser Leu Arg Cys Met Ala Gly Gly Ala Val Leu Ala Ile Trp
    130                 135                 140

Phe Arg Arg Ile Ile Gln Gly Cys Met Phe Asn Gln Arg Val Met Trp
145                 150                 155                 160

Tyr Arg Glu Val Val Asn Leu His Met Pro Lys Glu Ile Met Tyr Met
                165                 170                 175

Gly Ser Val Phe Trp Arg Gly Arg His Leu Ile Tyr Ile Arg Ile Trp
            180                 185                 190

Tyr Asp Gly His Val Gly Ser Ile Val Pro Gln Met Ser Phe Gly Trp
        195                 200                 205

Ser Thr Leu Asn Tyr Gly Leu Leu Asn Asn Leu Val Leu Cys Cys
    210                 215                 220

Thr Tyr Cys Ser Asp Leu Ser Glu Ile Arg Ile Arg Cys Cys Ala Arg
225                 230                 235                 240

Arg Thr Arg Arg Leu Met Leu Arg Ala Ile Gly Ile Met Arg Arg Glu
                245                 250                 255

Ser Leu Asp Pro Asp Pro Leu Ser Ser Leu Thr Glu Arg Arg Arg
            260                 265                 270

Gln Arg Leu Leu Arg Gly Leu Met Arg His Asn Arg Pro Ile Pro Phe
        275                 280                 285

Ala Asp Tyr Asp Ser His Arg Ser Ser Arg
    290                 295
```

```
<210> SEQ ID NO 34
<211> LENGTH: 122
<212> TYPE: PRT
<213> ORGANISM: Chimpanzee adenovirus AdY25
<220> FEATURE:
<221> NAME/KEY: SOURCE
<222> LOCATION: 1..122
<223> OTHER INFORMATION: /mol_type="protein"
      /organism="Chimpanzee adenovirus AdY25"

<400> SEQUENCE: 34

Met Val Leu Pro Val Leu Pro Ser Pro Ser Val Thr Glu Thr Gln Gln
1               5                   10                  15

Asn Cys Ile Ile Trp Leu Gly Leu Ala His Ser Thr Val Ala Asp Val
            20                  25                  30

Ile Arg Ala Ile Arg Ala Asp Gly Ile Phe Ile Thr Gln Glu Ala Gln
        35                  40                  45

Glu Ile Leu His Ala Leu Arg Glu Trp Leu Phe Tyr Asn Phe Asn Thr
    50                  55                  60

Glu Arg Ser Lys Arg Arg Asp Arg Arg Arg Ala Val Cys Ser Ala
65                  70                  75                  80

Arg Thr Arg Phe Cys Phe Val Lys Tyr Glu Asn Val Arg Lys Gln Leu
                85                  90                  95

His His Asp Thr Ile Gln Asn Thr Ile Ser Val Ile Pro Pro Ser Ser
            100                 105                 110

Val Pro Thr Ala Gly Pro Leu Thr Ser Leu
        115                 120

<210> SEQ ID NO 35
<211> LENGTH: 117
<212> TYPE: PRT
<213> ORGANISM: Chimpanzee adenovirus AdY25
<220> FEATURE:
<221> NAME/KEY: SOURCE
<222> LOCATION: 1..117
<223> OTHER INFORMATION: /mol_type="protein"
      /organism="Chimpanzee adenovirus AdY25"

<400> SEQUENCE: 35

Met Arg Val Cys Leu Arg Met Pro Val Glu Gly Ala Leu Arg Glu Leu
1               5                   10                  15

Phe Ile Met Ala Gly Leu Asp Leu Pro Gln Glu Leu Ile Arg Ile Ile
            20                  25                  30

Gln Gly Trp Lys Asn Glu Asn Tyr Leu Gly Met Val Gln Glu Cys Asn
        35                  40                  45

Met Met Ile Glu Glu Leu Glu Asn Ala Pro Ala Phe Ala Val Leu Leu
    50                  55                  60

Phe Leu Asp Val Arg Val Glu Ala Leu Leu Glu Ala Thr Val Glu His
65                  70                  75                  80

Leu Glu Asn Arg Val Thr Phe Asp Leu Ala Val Ile Phe His Gln His
                85                  90                  95

Ser Gly Gly Glu Arg Cys His Leu Arg Asp Leu His Phe Glu Val Leu
            100                 105                 110

Arg Asp Arg Leu Glu
        115

<210> SEQ ID NO 36
<211> LENGTH: 129
<212> TYPE: PRT
```

<213> ORGANISM: Chimpanzee adenovirus AdY25
<220> FEATURE:
<221> NAME/KEY: SOURCE
<222> LOCATION: 1..129
<223> OTHER INFORMATION: /mol_type="protein"
      /organism="Chimpanzee adenovirus AdY25"

<400> SEQUENCE: 36

Met Leu Glu Arg Thr Pro Cys Thr Tyr Ser Ile Val Val Pro Glu Ala
1               5                   10                  15

Leu Asn Leu His Leu Asp Asp Phe Ser Phe Val Asp Phe Leu Lys Asn
            20                  25                  30

Cys Leu Pro Asp Phe Leu Ser Ser Tyr Leu Glu Asp Ile Thr Gly Ser
        35                  40                  45

Ser Gln His Ala Tyr Phe Asn Leu Thr Phe Gly Asn Ala His Trp Gly
    50                  55                  60

Gly Leu Arg Phe Ile Cys Asn Val Ala Cys Pro Ala Leu Ile Pro Gly
65                  70                  75                  80

Gly Pro Met Ala Lys Asn Phe Gly Asp Asp Met Lys Asp Tyr Ile Gln
                85                  90                  95

Leu Leu Leu Arg Glu Glu Leu Arg Asp Arg Gly Arg Asp Phe Asp Ile
            100                 105                 110

Pro Ile Val Asn Leu Leu Gln Val Asn Gln Glu Gln Asn Leu Leu Glu
        115                 120                 125

Leu

<210> SEQ ID NO 37
<211> LENGTH: 124
<212> TYPE: PRT
<213> ORGANISM: Chimpanzee adenovirus AdY25
<220> FEATURE:
<221> NAME/KEY: SOURCE
<222> LOCATION: 1..124
<223> OTHER INFORMATION: /mol_type="protein"
      /organism="Chimpanzee adenovirus AdY25"

<400> SEQUENCE: 37

Met Asp Ala Glu Ala Leu Tyr Val Phe Leu Glu Gly Ala Gly Ala Leu
1               5                   10                  15

Leu Pro Val Gln Glu Gly Ser Asn Tyr Ile Phe Tyr Ala Pro Ala Asn
            20                  25                  30

Phe Val Leu His Pro His Gly Val Ala Leu Leu Glu Leu Arg Leu Ser
        35                  40                  45

Ile Val Val Pro Arg Gly Phe Ile Gly Arg Phe Phe Ser Leu Thr Asp
    50                  55                  60

Ala Asn Val Pro Gly Val Tyr Ala Ser Ser Arg Ile Ile His Ala Gly
65                  70                  75                  80

His Arg Glu Gly Leu Ser Val Met Leu Phe Asn His Gly Asp Ser Phe
                85                  90                  95

Tyr Glu Gly Arg Ala Gly Asp Pro Val Ala Cys Leu Val Leu Glu Arg
            100                 105                 110

Val Ile Tyr Pro Pro Val Arg Gln Ala Ser Met Val
        115                 120

<210> SEQ ID NO 38
<211> LENGTH: 30964
<212> TYPE: DNA
<213> ORGANISM: Artificial Sequence
<220> FEATURE:
<221> NAME/KEY: source
<222> LOCATION: 1..30964
<223> OTHER INFORMATION: /mol_type="DNA"
/note="Viral vector based on Chimpanzee adenovirus AdY25"
/organism="Artificial Sequence"

<400> SEQUENCE: 38

```
ttaatcgcgt ttaaacccat catcaataat atacctcaaa cttttttgtgc gcgttaatat     60
gcaaatgagg cgtttgaatt tgggaaggga ggaaggtgat tggccgagag aagggcgacc    120
gttaggggcg gggcgagtga cgttttgatg acgtgaccgc gaggaggagc cagtttgcaa    180
gttctcgtgg gaaaagtgac gtcaaacgag gtgtggtttg aacacggaaa tactcaattt    240
tcccgcgctc tctgacagga aatgaggtgt ttctaggcgg atgcaagtga aaacgggcca    300
ttttcgcgcg aaaactgaat gaggaagtga aaatctgagt aatttcgcgt ttatgacagg    360
gaggagtatt tgccgagggc cgagtagact ttgaccgatt acgtgggggt ttcgattacc    420
gtgtttttca cctaaatttc cgcgtacggt gtcaaagtcc ggtgttttta cgtaggtgtc    480
agctgatcgc cagggtattt aaacctgcgc tctccagtca agaggccact cttgagtgcc    540
agcgagaaga gttttctcct ccgcgcgcga gtcagatcta cactttgaaa ggcgatcgct    600
agcgacatcg atcacaagtt tgtacaaaaa agctgaacga gaaacgtaaa atgatataaa    660
tatcaatata ttaaattaga ttttgcataa aaaacagact acataatact gtaaaacaca    720
acatatccag tcactatggc ggccgccgat ttattcaaca aagccacgtt gtgtctcaaa    780
atctctgatg ttacattgca caagataaaa atatatcatc atgaacaata aaactgtctg    840
cttacataaa cagtaataca aggggtgtta tgagccatat tcaacgggaa acgtcttgct    900
cgaggccgcg attaaattcc aacatggatg ctgatttata tgggtataaa tgggctcgtg    960
ataatgtcgg gcaatcaggt gcgacaatct atcgattgta tgggaagccc gatgcgccag   1020
agttgtttct gaaacatggc aaaggtagcg ttgccaatga tgttacagat gagatggtca   1080
gactaaactg gctgacggaa tttatgcctc ttccgaccat caagcatttt atccgtactc   1140
ctgatgatgc atggttactc accactgcga tccccgggaa acagcattc caggtattag   1200
aagaatatcc tgattcaggt gaaaatattg ttgatgcgct ggcagtgttc ctgcgccgt    1260
tgcattcgat tcctgtttgt aattgtcctt ttaacagcga tcgcgtattt cgtctcgctc   1320
aggcgcaatc acgaatgaat aacggtttgg ttgatgcgag tgattttgat gacgagcgta   1380
atggctggcc tgttgaacaa gtctggaaag aaatgcataa gcttttgcca ttctcaccgg   1440
attcagtcgt cactcatggt gatttctcac ttgataacct tatttttgac gaggggaaat   1500
taataggttg tattgatgtt ggacgagtcg gaatcgcaga ccgataccag gatcttgcca   1560
tcctatggaa ctgcctcggt gagttttctc cttcattaca gaaacggctt tttcaaaaat   1620
atggtattga taatcctgat atgaataaat tgcagtttca tttgatgctc gatgagtttt   1680
tctaatcaga attggttaat tggttgtaac actggcacgc gtggatccgg cttactaaaa   1740
gccagataac agtatgcgta tttgcgcgct gattttgcg gtataagaat atatactgat   1800
atgtataccc gaagtatgtc aaaaagaggt atgctatgaa gcagcgtatt acagtgacag   1860
ttgacagcga cagctatcag ttgctcaagg catatatgat gtcaatatct ccggtctggt   1920
aagcacaacc atgcagaatg aagcccgtcg tctgcgtgcc gaacgctgga aagcggaaaa   1980
tcaggaaggg atggctgagg tcgcccggtt tattgaaatg aacggctctt tgctgacga    2040
gaacagggg tggtgaaatg cagtttaagg tttacaccta aaaagagag agccgttatc    2100
gtctgtttgt ggatgtacag agtgatatta ttgacacgcc cgggcgacgg atggtgatcc   2160
```

```
ccctggccag tgcacgtctg ctgtcagata aagtctcccg tgaactttac ccggtggtgc    2220
atatcgggga tgaaagctgg cgcatgatga ccaccgatat ggccagtgtg ccggtctccg    2280
ttatcgggga agaagtggct gatctcagcc accgcgaaaa tgacatcaaa aacgccatta    2340
acctgatgtt ctggggaata taaatgtcag gctcccttat acacagccag tctgcaggtc    2400
gaccatagtg actggatatg ttgtgtttta cagtattatg tagtctgttt tttatgcaaa    2460
atctaattta atatattgat atttatatca ttttacgttt ctcgttcagc tttcttgtac    2520
aaagtggtga tcgattcgac agatcgcgat cgcagtgagt agtgttctgg ggcggggggag    2580 gacctgcatg agggccagaa tgactgaaat ctgtgctttt ctgtgtgttg cagcatcatg    2640
agcggaagcg gctcctttga gggaggggta ttcagcccct atctgacggg gcgtctcccc    2700
tcctgggcgg gagtgcgtca gaatgtgatg gatccacgg tggacggccg gcccgtgcag    2760
cccgcgaact cttcaaccct gacctatgca accctgagct cttcgtcggt ggacgcagct    2820
gccgccgcag ctgctgcatc cgccgccagc gccgtgcgcg gaatggccat gggcgccggc    2880
tactacggca ctctggtggc caactcgagt tccaccaata atcccgccag cctgaacgag    2940
gagaagctgc tgctgctgat ggcccagctt gaggccttga cccagcgcct gggcgagctg    3000
acccagcagg tggctcagct gcaggagcag acgcgggccg cggttgccac ggtgaaatcc    3060
aaataaaaaa tgaatcaata ataaaacgga gacggttgtt gattttaaca cagagtctga    3120
atctttattt gattttttcgc gcgcggtagg ccctggacca ccggtctcga tcattgagca    3180
cccggtggat cttttccagg acccggtaga ggtgggcttg gatgttgagg tacatgggca    3240
tgagcccgtc ccgggggtgg aggtagctcc attgcagggc ctcgtgctcg ggggtggtgt    3300
tgtaaatcac ccagtcatag caggggcgca gggcgtggtg ttgcacaata tctttgagga    3360
ggagactgat ggccacgggc agcccttggt gtaggtgtt tacaaatctg ttgagctggg    3420
agggatgcat gcgggggag atgaggtgca tcttggcctg gatcttgaga ttggcgatgt    3480
taccgcccag atcccgcctg gggttcatgt tgtgcaggac caccagcacg gtgtatccgg    3540
tgcacttggg gaatttatca tgcaacttgg aagggaaggc gtgaaagaat tggcgacgc    3600 ccttgtgtcc gccaggtttt ccatgcact catccatgat gatggcaatg gcccgtgggg    3660
cggcggcctg gcaaagacg tttcgggggt cggacacatc atagttgtgg tcctgggtga    3720
ggtcatcata ggccattta atgaatttgg ggcggagggt gccggactgg gggacaaagg    3780
taccctcgat cccgggggcg tagttcccct cacagatctg catctcccag gctttgagct    3840 cagaggggggg gatcatgtcc acctgcgggg cgataaagaa cacggtttcc ggggcggggg    3900
agatgagctg ggccgaaagc aagttccgga gcagctggga cttgccgcag ccggtggggc    3960
cgtaaatgac cccgatgacc ggctgcaggt ggtagttgag ggagagacag ctgccgtcct    4020
cccggaggag gggggccacc tcgttcatca tctcgcgcac gtgcatgttc tcgcgcacca    4080
gttccgccag gaggcgctct ccccccagag ataggagctc ctggagcgag gcgaagtttt    4140
tcagcggctt gagtccgtcg gccatgggca ttttggagag ggtctgttgc aagagttcca    4200
agcggtccca gagctcggtg atgtgctcta cggcatctcg atccagcaga cctcctcgtt    4260
tcgcgggttg gacgactgc gggagtaggg caccagacga tggcgtcca gcgcagccag    4320 ggtccggtcc ttccagggcc gcagcgtccg cgtcagggtg gtctccgtca cggtgaaggg    4380
gtgcgcgccg ggctgggcgc ttgcgagggt gcgcttcagg ctcatccggc tggtcgaaaa    4440
ccgctcccga tcggcgccct gcgcgtcggc caggtagcaa ttgaccatga gttcgtagtt    4500
gagcgcctcg gccgcgtggc ctttggcgcg gagcttacct ttggaagtct gcccgcaggc    4560
```

```
gggacagagg agggacttga gggcgtagag cttgggggcg aggaagacgg aatcggggc     4620
gtaggcgtcc gcgccgcagt gggcgcagac ggtctcgcac tccacgagcc aggtgaggtc    4680
gggctggtcg gggtcaaaaa ccagtttccc gccgttcttt ttgatgcgtt tcttaccttt    4740
ggtctccatg agctcgtgtc cccgctgggt gacaaagagg ctgtccgtgt ccccgtagac    4800
cgactttatg ggccggtcct cgagcggtgt gccgcggtcc tcctcgtaga ggaaccccgc    4860
ccactccgag acgaaagccc gggtccaggc cagcacgaag gaggccacgt gggacgggta    4920
gcggtcgttg tccaccagcg ggtccacttt tccagggta tgcaaacaca tgtcccctc     4980
gtccacatcc aggaaggtga ttggcttgta agtgtaggcc acgtgaccgg ggtcccggc    5040
cggggggta taaaggggg cgggcccctg ctcgtcctca ctgtcttccg gatcgctgtc    5100
caggagcgcc agctgttggg gtaggtattc cctctcgaag gcgggcatga cctcggcact    5160
caggttgtca gtttctagaa acgaggagga tttgatattg acggtgccag cggagatgcc    5220
tttcaagagc ccctcgtcca tctggtcaga aaagacgatt tttttgttgt cgagcttggt    5280
ggcgaaggag ccgtagaggg cgttggaaag gagcttggcg atggagcgca tggtctggtt    5340
ttttccttg tcggcgcgct ccttggccgc gatgttgagc tgcacgtact cgcgcgccac    5400
gcacttccat tcggggaaga cggtggtcat ctcgtcgggc acgattctga cctgccaacc    5460
tcgattatgc agggtgatga ggtccacact ggtggccacc tcgccgcgca ggggctcgtt    5520
ggtccagcag aggcggccgc ccttgcgcga gcagaagggg ggcagagggt ccagcatgac    5580
ctcgtcgggg gggtcggcat cgatggtgaa gatgccgggc aggagatcgg ggtcgaagta    5640
gctgatggaa gtggccagat cgtccaggga agcttgccat tcgcgcacgg ccagcgcgcg    5700
ctcgtaggga ctgaggggcg tgccccaggg catggggtgg gtgagcgcgg aggcgtacat    5760
gccgcagatg tcgtagacgt agagggctc ctcgaggatg ccgatgtagg tggggtagca    5820
gcgcccccg cggatgctgg cgcgcacgta gtcatacagc tcgtgcgagg gcgcgaggag    5880
ccccgggccc aggttggtgc gactgggctt ttcggcgcgg tagacgatct ggcgaaagat    5940
ggcatgcgag ttggaggaga tggtgggcct ttggaagatg ttgaagtggg cgtggggag    6000
gccgaccgag tcgcggatga agtgggcgta ggagtcttgc agtttggcga cgagctcggc    6060
ggtgacgagg acgtccagag cgcagtagtc gagggtctcc tggatgatgt catacttgag    6120
ctggcccttt tgtttccaca gctcgcggtt gagaaggaac tcttcgcggt ccttccagta    6180
ctcttcgagg gggaacccgt cctgatctgc acggtaagag cctagcatgt agaactggtt    6240
gacggccttg taggcgcagc agcccttctc cacggggagg gcgtaggcct gggcggcctt    6300
gcgcagggag gtgtgcgtga gggcgaaggt gtccctgacc atgaccttga ggaactggtg    6360
cttgaaatcg atatcgtcgc agcccccctg ctcccagagc tggaagtccg tgcgcttctt    6420
gtaggcgggg ttgggcaaag cgaaagtaac atcgttgaaa aggatcttgc ccgcgcgggg    6480
cataaagttg cgagtgatgc ggaaaggctg gggcacctcg gcccggttgt tgatgacctg    6540
ggcggcgagc acgatctcgt cgaaaccgtt gatgttgtgg cccacgatgt agagttccac    6600
gaatcgcggg cggcccttga cgtggggcag cttcttgagc tcctcgtagg tgagctcgtc    6660
ggggtcgctg agaccgtgct gctcgagcgc ccagtcggcg agatgggggt tggcgcggag    6720
gaaggaagtc cagagatcca cggccagggc ggtttgcaga cggtcccggt actgacggaa    6780
ctgctgcccg acgccatttt tttcgggggt gacgcagtag aaggtgcggg ggtccccgtg    6840
ccagcggtcc catttgagct ggagggcgag atcgagggcg agctcgacga ggcggtcgtc    6900
```

```
ccctgagagt tcatgacca gcatgaaggg gacgagctgc ttgccgaagg accccatcca   6960
ggtgtaggtt tccacatcgt aggtgaggaa gagcctttcg gtgcgaggat gcgagccgat   7020
ggggaagaac tggatctcct gccaccaatt ggaggaatgg ctgttgatgt gatggaagta   7080
gaaatgccga cggcgcgccg aacactcgtg cttgtgttta tacaagcggc cacagtgctc   7140
gcaacgctgc acgggatgca cgtgctgcac gagctgtacc tgagttcctt tgacgaggaa   7200
tttcagtggg aagtggagtc gtggcgcctg catctcgtgc tgtactacgt cgtggtggtc   7260
ggcctggccc tcttctgcct cgatggtggt catgctgacg agcccgcgcg ggaggcaggt   7320
ccagacctcg gcgcgagcgg tcggagagc gaggacgagg gcgcgcaggc cggagctgtc   7380
cagggtcctg agacgctgcg gagtcaggtc agtgggcagc ggcggcgcgc ggttgacttg   7440
caggagtttt tccagggcgc gcgggaggtc cagatggtac ttgatctcca ccgcgccgtt   7500
ggtggcgacg tcgatggctt gcagggtccc gtgccctgg ggtgtgacca ccgtcccccg   7560
tttcttcttg ggcggctggg gcgacggggg cggtgcctct tccatggtta aagcggcgg   7620
cgaggacgcg cgccgggcgg cagaggcggc tcggggcccg gaggcagggg cggcaggggc   7680
acgtcggcgc cgcgcgcggg taggttctgg tactgcgccc ggagaagact ggcgtgagcg   7740
acgacgcgac ggttgacgtc ctggatctga cgcctctggg tgaaggccac gggacccgtg   7800
agtttgaacc tgaaagagag ttcgacagaa tcaatctcgg tatcgttgac ggcggcctgc   7860
cgcaggatct cttgcacgtc gcccgagttg tcctggtagg cgatctcggt catgaactgc   7920
tcgatctcct cctcctgaag gtctccgcga ccggcgcgct ccacggtggc cgcgaggtcg   7980
ttggagatgc ggcccatgag ctgcgagaag gcgttcatgc ccgcctcgtt ccagacgcgg   8040
ctgtagacca cgacgccctc gggatcgcgg gcgcgcatga ccacctgggc gaggttgagc   8100
tccacgtggc gcgtgaagac cgcgtagttg cagaggcgct ggtagaggta gttgagcgtg   8160
gtggcgatgt gctcggtgac gaagaaatac atgatccagc ggcggagcgg catctcgctg   8220
acgtcgccca gcgcctccaa gcgttccatg gcctcgtaaa agtccacggc gaagttgaaa   8280
aactgggagt tgcgcgccga gacggtcaac tcctcctcca gaagacggat gagctcggcg   8340
atggtggcgc gcacctcgcg ctcgaaggcc cccgggagtt cctccacttc ctcctcttct   8400
tcctcctcca ctaacatctc ttctacttcc tcctcaggcg gtggtggtgg cggggagg   8460
ggcctgcgtc gccggcggcg cacgggcaga cggtcgatga agcgctcgat ggtctcgccg   8520
cgccggcgtc gcatggtctc ggtgacggcg cgcccgtcct cgcggggccg cagcgtgaag   8580
acgccgccgc gcatctccag gtggccgggg gggtccccgt tgggcaggga gagggcgctg   8640
acgatgcatc ttatcaattg ccccgtaggg actccgcgca aggacctgag cgtctcgaga   8700
tccacgggat ctgaaaaccg ttgaacgaag gcttcgagcc agtcgcagtc gcaaggtagg   8760
ctgagcacgg tttcttctgc cgggtcatgt tggggagcgg ggcgggcgat gctgctggtg   8820
atgaagttga aataggcggt tctgagacgg cggatggtgg cgaggagcac caggtctttg   8880
ggcccggctt gctggatgcg cagacggtcg gccatgcccc aggcgtggtc ctgacacctg   8940
gccaggtcct tgtagtagtc ctgcatgagc cgctccacgg gcacctcctc ctcgcccgcg   9000
cggccgtgca tgcgcgtgag cccgaagccg cgctggggct ggacgagcgc caggtcggcg   9060
acgacgcgct cggcgaggat ggcctgctgg atctgggtga gggtggtctg gaagtcgtca   9120
aagtcgacga agcggtggta ggctccggtg ttgatggtgt aggagcagtt ggccatgacg   9180
gaccagttga cggtctggtg gcccggacgc acgagctcgt ggtacttgag gcgcgagtag   9240
gcgcgcgtgt cgaagatgta gtcgttgcag gtgcgcacca ggtactggta gccgatgagg   9300
```

```
aagtgcggcg gcggctggcg gtagagcggc catcgctcgg tggcggggc gccgggcgcg      9360 aggtcctcga gcatggtgcg gtggtagccg tagatgtacc tggacatcca ggtgatgcca      9420
gcggcggtgg tggaggcgcg cgggaactcg cggacgcggt tccagatgtt gcgcagcggc      9480
aggaagtagt tcatggtggg cacggtctgg cccgtgaggc gcgcgcagtc gtggatgctc      9540
tatacgggca aaaacgaaag cggtcagcgg ctcgactccg tggcctggag gctaagcgaa      9600
cgggttgggc tgcgcgtgta ccccggttcg aatctcgaat caggctggag ccgcagctaa      9660
cgtggtactg gcactcccgt ctcgacccaa gcctgcacca accctccagg atacggaggc      9720
gggtcgtttt gcaacttttt ttggaggccg gaaatgaaac tagtaagcgc ggaaagcggc      9780
cgaccgcgat ggctcgctgc cgtagtctgg agaagaatcg ccagggttgc gttgcggtgt      9840
gccccggttc gaggccggcc ggattccgcg gctaacgagg gcgtggctgc cccgtcgttt      9900
ccaagacccc atagccagcc gacttctcca gttacggagc gagcccctct tttgttttgt      9960 ttgttttgc cagatgcatc ccgtactgcg gcagatgcgc cccaccacc ctccaccgca      10020 acaacagccc cctcctccac agccggcgct tctgccccg cccagcagc agcagcaact      10080 tccagccacg accgccgcgg ccgccgtgag cggggctgga cagacttctc agtatgatca      10140
cctggccttg gaagagggcg aggggctggc gcgcctgggg gcgtcgtcgc cggagcggca      10200
cccgcgcgtg cagatgaaaa gggacgctcg cgaggcctac gtgcccaagc agaacctgtt      10260
cagagacagg agcggcgagg agcccgagga gatgcgcgcg gcccggttcc acgcggggcg      10320
ggagctgcgg cgcggcctgg accgaaagag ggtgctgagg gacgaggatt tcgaggcgga      10380
cgagctgacg gggatcagcc ccgcgcgcgc gcacgtggcc gcggccaacc tggtcacggc      10440
gtacgagcag accgtgaagg aggagagcaa cttccaaaaa tccttcaaca accacgtgcg      10500
caccctgatc gcgcgcgagg aggtgaccct gggcctgatg cacctgtggg acctgctgga      10560
ggccatcgtg cagaacccca ccagcaagcc gctgacggcg cagctgttcc tggtggtgca      10620
gcatagtcgg gacaacgagg cgttcaggga ggcgctgctg aatatcaccg agcccgaggg      10680
ccgctggctc ctggacctgg tgaacattct gcagagcatc gtggtgcagg agcgcgggct      10740
gccgctgtcc gagaagctgg cggccatcaa cttctcggtg ctgagtctgg gcaagtacta      10800
cgctaggaag atctacaaga ccccgtacgt gcccatagac aaggaggtga agatcgacgg      10860
gttttacatg cgcatgaccc tgaaagtgct gaccctgagc gacgatctgg gggtgtaccg      10920
caacgacagg atgcaccgcg cggtgagcgc cagcaggcgg cgcgagctga gcgaccagga      10980
gctgatgcac agcctgcagc gggccctgac cggggccggg accgagggg agagctactt      11040 tgacatgggc gcggacctgc actggcagcc cagccgccgg gccttggagg cggcaggcgg      11100 tccccctac atagaagagg tggacgatga ggtggacgag gagggcgagt acctggaaga      11160
ctgatggcgc gaccgtattt ttgctagatg caacaacagc cacctcctga tcccgcgatg      11220
cgggcggcgc tgcagagcca gccgtccggc attaactcct cggacgattg gacccaggcc      11280
atgcaacgca tcatggcgct gacgacccgc aaccccgaag cctttagaca gcagccccag      11340
gccaaccggc tctcggccat cctggaggcc gtggtgccct cgcgctccaa ccccacgcac      11400
gagaaggtcc tggccatcgt gaacgcgctg gtggagaaca aggccatccg cggcgacgag      11460
gccggcctgg tgtacaacgc gctgctggag cgcgtggccc gctacaacag caccaacgtg      11520
cagaccaacc tggaccgcat ggtgaccgac gtgcgcgagg ccgtgccca gcgcgagcgg      11580 ttccaccgcg agtccaacct gggatccatg gtggcgctga acgccttcct cagcacccag      11640
```

```
cccgccaacg tgccccgggg ccaggaggac tacaccaact tcatcagcgc cctgcgcctg   11700
atggtgaccg aggtgcccca gagcgaggtg taccagtccg ggccggacta cttcttccag   11760
accagtcgcc agggcttgca gaccgtgaac ctgagccagg cgttcaagaa cttgcagggc   11820
ctgtggggcg tgcaggcccc ggtcggggac cgcgcgacgg tgtcgagcct gctgacgccg   11880
aactcgcgcc tgctgctgct gctggtggcc cccttcacgg acagcggcag catcaaccgc   11940
aactcgtacc tgggctacct gattaacctg taccgcgagg ccatcggcca ggcgcacgtg   12000
gacgagcaga cctaccagga gatcacccac gtgagccgcg ccctgggcca ggacgacccg   12060
ggcaatctgg aagccaccct gaacttttg ctgaccaacc ggtcgcagaa gatcccgccc   12120
cagtacacgc tcagcgccga ggaggagcgc atcctgcgat acgtgcagca gagcgtgggc   12180
ctgttcctga tgcaggaggg ggccaccccc agcgccgcgc tcgacatgac cgcgcgcaac   12240
atggagccca gcatgtacgc cagcaaccgc ccgttcatca taaactgat ggactacttg   12300 catcgggcgg ccgccatgaa ctctgactat ttcaccaacg ccatcctgaa tccccactgg   12360
ctcccgccgc cggggttcta cacggcgag tacgacatgc ccgaccccaa tgacgggttc   12420
ctgtgggacg atgtggacag cagcgtgttc tcccccgac cgggtgctaa cgagcgcccc   12480
ttgtggaaga aggaaggcag cgaccgacgc ccgtcctcgg cgctgtccgg ccgcgagggt   12540
gctgccgcgg cggtgcccga ggccgccagt ccttccccga gcttgccctt ctcgctgaac   12600
agtattcgca gcagcgagct gggcaggatc acgcgcccgc gcttgctggg cgaggaggag   12660
tacttgaatg actcgctgtt gagacccgag cgggagaaga acttccccaa taacgggata   12720
gagagcctgg tggacaagat gagccgctgg aagacgtatg cgcaggagca cagggacgat   12780
ccgtcgcagg gggccacgag ccggggcagc gccgcccgta acgccggtg gcacgacagg   12840 cagcggggac tgatgtggga cgatgaggat tccgccgacg acagcagcgt gttggacttg   12900
ggtgggagtg gtaacccgtt cgctcacctg cgcccccgca tcgggcgcat gatgtaagag   12960
aaaccgaaaa taaatgatac tcaccaaggc catggcgacc agcgtgcgtt cgtttcttct   13020
ctgttgttgt atctagtatg atgaggcgtg cgtacccgga gggtcctcct ccctcgtacg   13080
agagcgtgat gcagcaggcg atggcggcgg cggcggcgat gcagcccccg ctggaggctc   13140
cttacgtgcc cccgcggtac ctggcgccta cggaggggcg gaacagcatt cgttactcgg   13200
agctggcacc cttgtacgat accacccggt tgtacctggt ggacaacaag tcggcggaca   13260
tcgcctcgct gaactaccag aacgaccaca gcaacttcct gaccaccgtg gtgcagaaca   13320
atgacttcac ccccacggag gccagcaccc agaccatcaa cttgacgag cgctcgcggt   13380 gggcgggtca gctgaaaacc atcatgcaca ccaacatgcc caacgtgaac gagttcatgt   13440
acagcaacaa gttcaaggcg cggggtgatgg tctcccgcaa gacccccaac ggggtgacag   13500
tgacagatgg tagtcaggat atcttggagt atgaatgggt ggagtttgag ctgcccgaag   13560
gcaacttctc ggtgaccatg accatcgacc tgatgaacaa cgccatcatc gacaattact   13620
tggcggtggg gcggcagaac ggggtcctgg agagcgatat cggcgtgaag ttcgacacta   13680
ggaacttcag gctgggctgg gaccccgtga ccgagctggt catgcccggg gtgtacacca   13740
acgaggcctt ccaccccgat attgtcttgc tgccggctg cggggtggac ttcaccgaga   13800
gccgcctcag caacctgctg gcattcgca agaggcagcc cttccaggag gcttccaga   13860 tcatgtacga ggatctggag gggggcaaca tccccgcgct cctggatgtc gacgcctatg   13920
agaaaagcaa ggaggagagc gccgccgcgg cgactgcagc tgtagccacc gcctctaccg   13980
aggtcagggg cgataattt gccagccctg cagcagtggc agcggccgag gcggctgaaa   14040
```

```
ccgaaagtaa gatagtcatt cagccggtgg agaaggatag caaggacagg agctacaacg    14100
tgctgccgga caagataaac accgcctacc gcagctggta cctggcctac aactatggcg    14160
accccgagaa gggcgtgcgc tcctggacgc tgctcaccac ctcggacgtc acctgcggcg    14220
tggagcaagt ctactggtcg ctgcccgaca tgatgcaaga cccggtcacc ttccgctcca    14280
cgcgtcaagt tagcaactac ccggtggtgg gcgccgagct cctgcccgtc tactccaaga    14340
gcttcttcaa cgagcaggcc gtctactcgc agcagctgcg cgccttcacc tcgctcacgc    14400
acgtcttcaa ccgcttcccc gagaaccaga tcctcgtccg cccgcccgcg cccaccatta    14460
ccaccgtcag tgaaaacgtt cctgctctca cagatcacgg gaccctgccg ctgcgcagca    14520
gtatccgggg agtccagcgc gtgaccgtta ctgacgccag acgccgcacc tgcccctacg    14580
tctacaaggc cctgggcata gtcgcgccgc gcgtcctctc gagccgcacc ttctaaaaaa    14640
tgtccattct catctcgccc agtaataaca ccggttgggg cctgcgcgcg cccagcaaga    14700
tgtacggagg cgctcgccaa cgctccacgc aacaccccgt gcgcgtgcgc gggcacttcc    14760
gcgctccctg gggcgccctc aagggccgcg tgcggtcgcg caccaccgtc gacgacgtga    14820
tcgaccaggt ggtggccgac gcgcgcaact acaccccgc cgccgcgccc gtctccaccg    14880
tggacgccgt catcgacagc gtggtggccg acgcgcgccg gtacgcccgc gccaagagcc    14940
ggcggcggcg catcgcccgg cggcaccgga gcaccccgc catgcgcgcg gcgcgagcct    15000
tgctgcgcag ggccaggcgc acgggacgca gggccatgct cagggcggcc agacgcgcgg    15060
cttcaggcgc cagcgccggc aggacccgga gacgcgcggc cacggcggcg gcagcggcca    15120
tcgccagcat gtcccgcccg cggcgaggga acgtgtactg ggtgcgcgac gccgccaccg    15180
gtgtgcgcgt gcccgtgcgc acccgccccc ctcgcacttg aagatgttca cttcgcgatg    15240
ttgatgtgtc ccagcggcga ggaggatgtc caagcgcaaa ttcaaggaag agatgctcca    15300
ggtcatcgcg cctgagatct acggccccgc ggtggtgaag gaggaaagaa agccccgcaa    15360
aatcaagcgg gtcaaaaagg acaaaaagga agaagatgac gatctggtgg agtttgtgcg    15420
cgagttcgcc ccccggcggc gcgtgcagtg gcgcgggcgg aaagtgcacc cggtgctgag    15480
acccggcacc accgtggtct tcacgcccgg cgagcgctcc ggcagcgctt ccaagcgctc    15540
ctacgacgag gtgtacgggg acgaggacat cctcgagcag gcggccgagc gcctgggcga    15600
gtttgcttac ggcaagcgca gccgccccgc cctgaaggaa gaggcggtgt ccatcccgct    15660
ggaccacggc aaccccacgc cgagcctcaa gcccgtgacc ctgcagcagg tgctgccgag    15720
cgcagcgccg cgccgggggt tcaagcgcga gggcgaggat ctgtaccccca ccatgcagct    15780 gatggtgccc aagcgccaga agctggaaga cgtgctggag accatgaagg tggacccgga    15840
cgtgcagccc gaggtcaagg tgcggcccat caagcaggtg gccccgggcc tgggcgtgca    15900
gaccgtggac atcaagatcc ccacggagcc catggaaacg cagaccgagc ccatgatcaa    15960
gcccagcacc agcaccatgg aggtgcagac ggatccctgg atgccatcgg ctcctagccg    16020
aagaccccgg cgcaagtacg gcgcggccag cctgctgatg cccaactacg cgctgcatcc    16080
ttccatcatc cccacgccgg gctaccgcgg cacgcgcttc taccgcggtc atacaaccag    16140
ccgccgccgc aagaccacca cccgccgccg ccgtcgccgc acagccgctg catctacccc    16200
tgccgccctg gtgcggagag tgtaccgccg cggccgcgcg cctctgaccc taccgcgcgc    16260
gcgctaccac ccgagcatcg ccatttaaac tttcgcctgc tttgcagatg gccctcacat    16320
gccgcctccg cgttcccatt acgggctacc gaggaagaaa accgcgccgt agaaggctgg    16380
```

```
cggggaacgg gatgcgtcgc caccaccatc ggcggcggcg cgccatcagc aagcggttgg   16440
ggggaggctt cctgcccgcg ctgatcccca tcatcgccgc ggcgatcggg gcgatcccg    16500 gcattgcttc cgtggcggtg caggcctctc agcgccactg agacacttgg aaaacatctt   16560
gtaataaacc aatggactct gacgctcctg gtcctgtgat gtgttttcgt agacagatgg   16620
aagacatcaa ttttcgtcc ctggctccgc gacacggcac gcggccgttc atgggcacct    16680
ggagcgacat cggcaccagc caactgaacg ggggcgcctt caattggagc agtctctgga   16740
gcgggcttaa gaatttcggg tccacgctta aacctatgg cagcaaggcg tggaacagca    16800
ccacagggca ggcgctgagg ataagctga aagagcagaa cttccagcag aaggtggtcg     16860
atgggctcgc ctcgggcatc aacggggtgg tggacctggc caaccaggcc gtgcagcggc   16920
agatcaacag ccgcctggac ccggtgccgc ccgccggctc cgtggagatg ccgcaggtgg   16980
aggaggagct gcctcccctg gacaagcggg gcgagaagcg accccgcccc gacgcggagg   17040
agacgctgct gacgcacacg gacgagccgc ccccgtacga ggaggcggtg aaactgggtc   17100
tgcccaccac gcggcccatc gcgcccctgg ccaccggggt gctgaaaccc gaaagtaata   17160
agcccgcgac cctggacttg cctcctcccg cttcccgccc ctctacagtg gctaagcccc   17220
tgccgccggt ggccgtggcc cgcgcgcgac ccggggggctc cgcccgccct catgcgaact   17280
ggcagagcac tctgaacagc atcgtgggtc tgggagtgca gagtgtgaag cgccgccgct   17340
gctattaaac ctaccgtagc gcttaacttg cttgtctgtg tgtgtatgta ttatgtcgcc   17400
gctgtccgcc agaaggagga gtgaagaggc gcgtcgccga gttgcaagat ggccacccca   17460
tcgatgctgc cccagtgggc gtacatgcac atcgccggac aggacgcttc ggagtacctg   17520
agtccgggtc tggtgcagtt cgcccgcgcc acagacacct acttcagtct ggggaacaag   17580
tttaggaacc ccacggtggc gcccacgcac gatgtgacca ccgaccgcag ccagcggctg   17640
acgctgcgct tcgtgcccgt ggaccgcgag gacaacacct actcgtacaa agtgcgctac   17700
acgctggccg tgggcgacaa ccgcgtgctg gacatggcca gcacctactt tgacatccgc   17760
ggcgtgctgg atcggggccc tagcttcaaa ccctactccg gcaccgccta caacagcctg   17820
gctcccaagg gagcgcccaa ttccagccag tgggagcaaa aaaaggcagg caatggtgac   17880
actatggaaa cacacacatt tggtgtggcc ccaatgggcg gtgagaatat tacaatcgac   17940
ggattacaaa ttggaactga cgctacagct gatcaggata aaccaattta tgctgacaaa   18000
acattccagc ctgaacctca agtaggagaa gaaaattggc aagaaactga aagcttttat   18060
ggcggtaggc ctcttaaaaa agacacaagc atgaaacctt gctatggctc ctatgctaga   18120
cccaccaatg taagggagg tcaagctaaa cttaagtgg gagctgatgg agttcctacc     18180
aaagaatttg acatagacct ggctttcttt gatactcccg gtggcacagt gaatggacaa   18240
gatgagtata aagcagacat tgtcatgtat accgaaaaca cgtatctgga aactccagac   18300
acgcatgtgg tatacaaacc aggcaaggat gatgcaagtt ctgaaattaa cctggttcag   18360
cagtccatgc caatagacc caactatatt gggttcagag acaactttat tgggctcatg   18420
tattacaaca gtactggcaa tatggggggtg ctggctggtc aggcctcaca gctgaatgct   18480
gtggtcgact gcaagacag aaacaccgag ctgtcatacc agctcttgct tgactctttg   18540
ggtgacagaa cccggtattt cagtatgtgg aatcaggcgg tggacagtta tgatcctgat   18600
gtgcgcatta ttgaaaacca tggtgtggaa gacgaacttc ccaactattg cttcccctg    18660 gatgggtctg gcactaatgc cgcttaccaa ggtgtgaaag taaaaaatgg taacgatggt   18720
gatgttgaga gcgaatggga aaatgatgat actgtcgcag ctcgaaatca attatgcaag   18780
```

```
ggcaacattt tgccatgga aattaacctc caagccaacc tgtggagaag tttcctctac   18840
tcgaacgtgg ccctgtacct gcccgactct tacaagtaca cgccagccaa catcaccctg   18900
cccaccaaca ccaacactta tgattacatg aacgggagag tggtgcctcc ctcgctggtg   18960
gacgcctaca tcaacatcgg ggcgcgctgg tcgctggacc ccatggacaa cgtcaatccc   19020
ttcaaccacc accgcaacgc gggcctgcgc taccgctcca tgctcctggg caacgggcgc   19080
tacgtgccct tccacatcca ggtgccccag aaattttcg ccatcaagag cctcctgctc   19140
ctgcccgggt cctacaccta cgagtggaac ttccgcaagg acgtcaacat gatcctgcag   19200
agctccctcg gcaacgacct cgcacggacg ggggcctcca tctccttcac cagcatcaac   19260
ctctacgcca ccttcttccc catggcgcac aacacggcct ccacgctcga ggccatgctg   19320
cgcaacgaca ccaacgacca gtccttcaac gactacctct cggcggccaa catgctctac   19380
cccatcccgg ccaacgccac caacgtgccc atctccatcc cctcgcgcaa ctgggccgcc   19440
ttccgcggct ggtccttcac gcgcctcaag accaaggaga cgccctcgct gggctccggg   19500
ttcgacccct acttcgtcta ctcgggctcc atcccctacc tcgacggcac cttctacctc   19560
aaccacacct tcaagaaggt ctccatcacc ttcgactcct ccgtcagctg gcccggcaac   19620
gaccggctcc tgacgcccaa cgagttcgaa atcaagcgca ccgtcgacgg cgagggatac   19680
aacgtggccc agtgcaacat gaccaaggac tggttcctgg tccagatgct ggcccactac   19740
aacatcggct accagggctt ctacgtgccc gagggctaca aggaccgcat gtactccttc   19800
ttccgcaact tccagcccat gagccgccag gtggtggacg aggtcaacta caaggactac   19860
caggccgtca ccctggccta ccagcacaac aactcgggct tcgtcggcta cctcgcgccc   19920
accatgcgcc agggccagcc ctaccccgcc aactacccgt accgctcat cggcaagagc   19980
gccgtcacca gcgtcaccca gaaaaagttc ctctgcgaca gggtcatgtg cgcatcccc   20040
ttctccagca acttcatgtc catgggcgcg ctcaccgacc tcggccagaa catgctctat   20100
gccaactccg cccacgcgct agacatgaat ttcgaagtcg accccatgga tgagtccacc   20160
cttctctatg ttgtcttcga agtcttcgac gtcgtccgag tgcaccagcc ccaccgcggc   20220
gtcatcgagg ccgtctacct gcgcaccccc ttctcggccg gtaacgccac cacctaaatt   20280
gctacttgca tgatggctga gcccacaggc tccggcgagc aggagctcag ggccatcatc   20340
cgcgacctgg gctgcgggcc ctacttcctg ggcaccttcg ataagcgctt cccgggattc   20400
atggccccgc acaagctggc ctgcgccatc gtcaacacgg ccggccgcga gaccgggggc   20460
gagcactggc tggccttcgc ctggaacccg cgctcgaaca cctgctacct cttcgacccc   20520
ttcgggttct cggacgagcg cctcaagcag atctaccagt tcgagtacga gggcctgctg   20580
cgccgtagcg ccctggccac cgaggaccgc tgcgtcaccc tggaaaagtc cacccagacc   20640
gtgcagggtc cgcgctcggc cgcctgcggg ctcttctgct gcatgttcct gcacgccttc   20700
gtgcactggc ccgaccgccc catggacaag aaccccacca tgaacttgct gacggggtg   20760
cccaacggca tgctccagtc gccccaggtg gaacccaccc tgcgccgcaa ccaggaggcg   20820
ctctaccgct tcctcaactc ccactccgcc tactttcgct cccaccgcgc gcgcatcgag   20880
aaggccaccg ccttcgaccg catgaacaat caagacatgt aaaccgtgtg tgtatgttta   20940
aaatatcttt taataaacag cactttaatg ttacacatgc atctgagatg attttatttt   21000
agaaatcgaa agggttctgc cgggtctcgg catggcccgc gggcagggac acgttgcgga   21060
actggtactt ggccagccac ttgaactcgg ggatcagcag tttgggcagc ggggtgtcgg   21120
```

```
ggaaggagtc ggtccacagc ttccgcgtca gctgcagggc gcccagcagg tcgggcgcgg    21180
agatcttgaa atcgcagttg ggacccgcgt tctgcgcgcg agagttgcgg tacacggggt    21240
tgcagcactg gaacaccatc agggccgggt gcttcacgct cgccagcacc gccgcgtcgg    21300
tgatgctctc cacgtcgagg tcctcggcgt tggccatccc gaaggggtc atcttgcagg     21360
tctgccttcc catggtgggc acgcacccgg gcttgtggtt gcaatcgcag tgcaggggga    21420
tcagcatcat ctgggcctgg tcggcgttca tccccgggta catggccttc atgaaagcct    21480
ccaattgcct gaacgcctgc tgggccttgg ctccctcggt gaagaagacc ccgcaggact    21540
tgctagagaa ctggttggtg gcacagccgg catcgtgcac gcagcagcgc gcgtcgttgt    21600
tggccagctg caccacgctg cgcccccagc ggttctgggt gatcttggcc cggtcggggt    21660
tctccttcag cgccgcgctg ccgttctcgc tcgccacatc catctcgatc atgtgctcct    21720
tctggatcat ggtggtcccg tgcaggcacc gcagtttgcc ctcggcctcg gtgcacccgt    21780
gcagccacag cgcgcacccg gtgcactccc agttcttgtg ggcgatctgg gaatgcgcgt    21840
gcacgaaccc ttgcaggaag cggcccatca tggtcgtcag ggtcttgttg ctagtgaagg    21900
tcaacgggat gccgcggtgc tcctcgttga tgtacaggtg gcagatgcgg cggtacacct    21960
cgccctgctc gggcatcagt tggaagttgg cttcaggtc ggtctccacg cggtagcggt     22020
ccatcagcat agtcatgatt tccatgccct ctcccaggc cgagacgatg ggcaggctca     22080
tagggttctt caccatcatc ttagcactag cagccgcggc caggggggtcg ctctcatcca   22140
gggtctcaaa gctccgcttg ccgtccttct cggtgatccg caccggggggg tagctgaagc   22200
ccacggccgc cagctcctcc tcggcctgtc tttcgtcctc gctgtcctgg ctgacgtcct    22260
gcatgaccac atgcttggtc ttgcggggtt tcttcttggg cggcagtggc ggcggagatg    22320
cttgtggcga gggggagcgc gagttctcgc tcaccactac tatctcttcc tcttcttggt    22380
ccgaggccac gcggcggtag gtatgtctct tcgggggcag aggcggaggc gacgggctct    22440
cgccgccgcg acttggcgga tggctggcag agccccttcc gcgttcgggg gtgcgctccc    22500
ggcggcgctc tgactgactt cctccgcggc cggccattgt gttctcctag ggaggaacaa    22560
caagcatgga gactcagcca tcgccaacct cgccatctgc ccccaccgcc ggcgacgaga    22620
agcagcagca gcagaatgaa agcttaaccg ccccgccgcc cagccccgcc tccgacgcag    22680
ccgcggtccc agacatgcaa gagatggagg aatccatcga gattgacctg ggctatgtga    22740
cgcccgcgga gcatgaggag gagctggcag tgcgctttca atcgtcaagc caggaagata    22800
aagaacagcc agagcaggaa gcagagaacg agcagagtca ggctgggctc gagcatggcg    22860
actacctcca cctgagcggg gaggaggacg cgctcatcaa gcatctggcc cggcaggcca    22920
ccatcgtcaa ggacgcgctg ctcgaccgca ccgaggtgcc cctcagcgtg gaggagctca    22980
gccgcgccta cgagctcaac ctcttctcgc cgcgcgtgcc cccaagcgc cagcccaacg     23040
gcacctgcga gccaaccccc cgcctcaact tctacccggt cttcgcggtg cccgaggccc    23100
tggccaccta ccacatcttt ttcaagaacc aaaagatccc cgtctcctgc cgcgccaacc    23160
gcacccgcgc cgacgccctc ttcaacctgg gtcccggcgc ccgcctacct gatatcgcct    23220
ccttggaaga ggttcccaag atcttcgagg gtctgggcag cgacgagact cgggccgcga    23280
acgctctgca aggagaagga ggaggagagc atgagcacca cagcgccctg gtcgagttgg    23340
aaggcgacaa cgcgcggctg gcggtgctca aacgcacggt cgagctgacc catttcgcct    23400
acccggctct gaacctgccc ccgaaagtca tgagcgcggt catggaccag gtgctcatca    23460
agcgcgcgtc gcccatctcc gaggacgagg gcatgcaaga ctccgaggag ggcaagcccg    23520
```

```
tggtcagcga cgagcagctg gcccggtggc tgggtcctaa tgctaccct caaagtttgg   23580 aagagcggcg caagctcatg atggccgtgg tcctggtgac cgtggagctg gagtgcctgc   23640
gccgcttctt cgccgacgcg gagaccctgc gcaaggtcga ggagaacctg cactacctct   23700
tcaggcacgg gttcgtgcgc caggcctgca agatctccaa cgtggagctg accaacctgg   23760
tctcctacat gggcatcttg cacgagaacc gcctggggca gaacgtgctg cacaccaccc   23820
tgcgcgggga ggcccgccgc gactacatcc gcgactgcgt ctacctctac ctctgccaca   23880
cctggcagac gggcatgggc gtgtggcagc agtgtctgga ggagcagaac ctgaaagagc   23940
tctgcaagct cctgcaaaag aacctcaagg gtctgtggac cgggttcgac gagcggacca   24000
ccgcctcgga cctggccgac ctcatcttcc ccgagcgcct caggctgacg ctgcgcaacg   24060
gcctgcccga ctttatgagc caaagcatgt tgcaaaactt cgctctttc atcctcgaac   24120 gctccggaat cctgcccgcc acctgctccg cgctgccctc ggacttcgtg ccgctgacct   24180
tccgcgagtg ccccccgccg ctgtggagcc actgctacct gctgcgcctg ccaactacc   24240 tggcctacca ctcggacgtg atcgaggacg tcagcggcga gggcctgctc gagtgccact   24300
gccgctgcaa cctctgcacg ccgcaccgct ccctggcctg caacccccag ctgctgagcg   24360
agacccagat catcggcacc ttcgagttgc aagggcccag cgagggcgag ggagccaagg   24420
ggggtctgaa actcaccccg gggctgtgga cctcggccta cttgcgcaag ttcgtgcccg   24480
aggattacca tcccttcgag atcaggttct acgaggacca atcccagccg cccaaggccg   24540
agctgtcggc ctgcgtcatc acccaggggg cgatcctggc ccaattgcaa gccatccaga   24600
aatcccgcca agaattcttg ctgaaaaagg gccgcggggt ctacctcgac ccccagaccg   24660
gtgaggagct caaccccggc ttcccccagg atgccccgag gaaacaagaa gctgaaagtg   24720
gagctgccgc ccgtggagga tttggaggaa gactgggaga cagcagtca ggcagaggag   24780 atggaggaag actgggacag cactcaggca gaggaggaca gcctgcaaga cagtctggag   24840
gaagacgagg aggaggcaga ggaggaggtg gaagaagcag ccgccgccag accgtcgtcc   24900
tcggcggggg agaaagcaag cagcacggat accatctccg ctccgggtcg gggtcccgct   24960 cggcccccaca gtagatggga cgagaccggg cgattcccga accccaccac ccagaccggt   25020
aagaaggagc ggcagggata caagtcctgg cggggggcaca aaaacgccat cgtctcctgc   25080
ttgcaggcct gcggggggcaa catctccttc acccggcgct acctgctctt ccaccgcggg   25140
gtgaacttcc cccgcaacat cttgcattac taccgtcacc tccacagccc ctactacttc   25200
caagaagagg cagcagcagc agaaaaagac cagaaaacca gctagaaaat ccacagcggc   25260
ggcagcggca ggtggactga ggatcgcggc gaacgagccg gcgcagaccc gggagctgag   25320
gaaccggatc tttcccaccc tctatgccat cttccagcag agtcggggc aggagcagga   25380 actgaaagtc aagaaccgtt ctctgcgctc gctcacccgc agttgtctgt atcacaagag   25440
cgaagaccaa cttcagcgca ctctcgagga cgccgaggct ctcttcaaca agtactgcgc   25500
gctcactctt aaagagtagc ccgcgcccgc ccagtcgcag aaaaaggcgg gaattacgtc   25560
acctgtgccc ttcgccctag ccgcctccac ccagcaccgc catgagcaaa gagattccca   25620
cgccttacat gtggagctac cagccccaga tgggcctggc cgccggcgcc gcccaggact   25680
actccacccg catgaattgg ctcagcgccg ggcccgcgat gatctcacgg gtgaatgaca   25740
tccgcgccca ccgaaaccag atactcctag aacagtcagc gctcaccgcc acgcccgca   25800 atcacctcaa tccgcgtaat tggcccgccg ccctggtgta ccaggaaatt ccccagccca   25860
```

```
cgaccgtact acttccgcga gacgcccagg ccgaagtcca gctgactaac tcaggtgtcc  25920
agctggcggg cggcgccacc ctgtgtcgtc accgccccgc tcagggtata aagcggctgg  25980
tgatccgggg cagaggcaca cagctcaacg acgaggtggt gagctcttcg ctgggtctgc  26040
gacctgacgg agtcttccaa ctcgccggat cggggagatc ttccttcacg cctcgtcagg  26100
cggtcctgac tttggagagt tcgtcctcgc agccccgctc gggcggcatc ggcactctcc  26160
agttcgtgga ggagttcact ccctcggtct acttcaaccc cttctccggc tcccccggcc  26220
actacccgga cgagttcatc ccgaactttg acgccatcag cgagtcggtg gacggctacg  26280
attgattaat taatcaacta acccccttacc cctttacctt ccagtaaaaa taaagattaa  26340
aaatgattga attgatcaat aaagaatcac ttacttgaaa tctgaaacca ggtctctgtc  26400
catgttttct gtcagcagca cttcactccc ctcttcccaa ctctggtact gcaggccccg  26460
gcgggctgca aacttcctcc acactctgaa ggggatgtca aattcctcct gtccctcaat  26520
cttcattttt atcttctatc agatgtccaa aaagcgcgcg cgggtggatg atggcttcga  26580
ccccgtgtac ccctacgatg cagacaacgc accgactgtg cccttcatca accctcccct  26640
cgtctcttca gatggattcc aagaaaagcc cctgggggtg ttgtccctgc gactggccga  26700
ccccgtcacc accaagaatg gggctgtcac cctcaagctg ggggaggggg tggacctcga  26760
cgactcggga aaactcatct ccaaaaatgc caccaaggcc actgcccctc tcagtatttc  26820
caacggcacc atttccctta acatggctgc ccctttttac aacaacaatg gaacgttaag  26880
tctcaatgtt tctacaccat tagcagtatt tcccactttt aacactttag gtatcagtct  26940
tggaaacggt cttcaaactt ctaataagtt gctgactgta cagttaactc atcctcttac  27000
attcagctca aatagcatca cagtaaaaac agacaaagga ctctatatta attctagtgg  27060
aaacagaggc cttgaggcta acataagcct aaaaagagga ctgattttttg atggtaatgc  27120 tattgcaaca taccttggaa gtggtttaga ctatggatcc tatgatagcg atgggaaaac  27180
aagacccatc atcaccaaaa ttggagcagg tttgaatttt gatgctaata atgccatggc  27240
tgtgaagcta ggcacaggtt taagttttga ctctgccggt gccttaacag ctggaaacaa  27300
agaggatgac aagctaacac tttggactac acctgaccca agccctaatt gtcaattact  27360
ttcagacaga gatgccaaat ttaccctatg tcttacaaaa tgcggtagtc aaatactagg  27420
cactgttgca gtagctgctg ttactgtagg ttcagcacta aatccaatta atgacacagt  27480
aaaaagcgcc atagtattcc ttagatttga ctctgacggt gtgctcatgt caaactcatc  27540
aatggtaggt gattactgga actttaggga aggacagacc acccaaagtg tggcctatac  27600
aaatgctgtg ggattcatgc ccaatctagg tgcatatcct aaaacccaaa gcaaaacacc  27660
aaaaaatagt atagtaagtc aggtatattt aaatggagaa actactatgc caatgacact  27720
gacaataact ttcaatggca ctgatgaaaa agacacaaca cctgtgagca cttactccat  27780
gacttttaca tggcagtgga ctggagacta taaggacaag aatattacct ttgctaccaa  27840
ctcctttact ttctcctaca tggcccaaga ataaaccctg catgccaacc ccattgttcc  27900
caccactatg aaaactctg aagcagaaaa aaataaagtt caagtgtttt attgattcaa  27960
cagttttcac agaattcgag tagttatttt ccctcctccc tcccaactca tggaatacac  28020
caccctctcc ccacgcacag ccttaaacat ctgaatgcca ttggtaatgg acatggtttt  28080
ggtctccaca ttccacacag tttcagagcg agccagtctc gggtcggtca gggagatgaa  28140
accctccggg cactcctgca tctgcacctc aaagttcagt agctgagggc tgtcctcggt  28200
ggtcgggatc acagttatct ggaagaagag cggtgagagt cataatccgc gaacgggatc  28260
```

```
gggcggttgt ggcgcatcag gccccgcagc agtcgctgtc tgcgccgctc cgtcaagctg   28320
ctgctcaagg ggtctgggtc cagggactcc ctgcgcatga tgccgatggc cctgagcatc   28380
agtcgcctgg tgcggcgggc gcagcagcgg atgcggatct cactcaggtc ggagcagtac   28440
gtgcagcaca gcactaccaa gttgttcaac agtccatagt tcaacgtgct ccagccaaaa   28500
ctcatctgtg gaactatgct gcccacatgt ccatcgtacc agatcctgat gtaaatcagg   28560
tggcgccccc tccagaacac actgcccatg tacatgatct ccttgggcat gtgcaggttc   28620
accacctccc ggtaccacat cacccgctgg ttgaacatgc agccctggat aatcctgcgg   28680
aaccagatgg ccagcaccgc cccgcccgcc atgcagcgca gggaccccgg gtcctggcaa   28740
tggcagtgga gcacccaccg ctcacggccg tggattaact gggagctgaa caagtctatg   28800
ttggcacagc acaggcacac gctcatgcat gtcttcagca ctctcagttc tcgggggtc    28860 aggaccatgt cccagggcac ggggaactct gcaggacag tgaacccggc agaacagggc    28920
agccctcgca cacaacttac attgtgcatg gacagggtat cgcaatcagg cagcaccgga   28980
tgatcctcca ccagagaagc gcgggtctcg gtctcctcac agcgaggtaa ggggggccggc   29040 ggttggtacg gatgatggcg ggatgacgct aatcgtgttc tggatcgtgt catgatggag   29100
ctgtttcctg acattttcgt acttcacgaa gcagaacctg gtacgggcac tgcacaccgc   29160
tcgccggcga cggtctcggc gcttcgagcg ctcggtgttg aagttataga acagccactc   29220
cctcagagcg tgcagtatct cctgagcctc ttgggtgatg aaaatcccat ccgctctgat   29280
ggctctgatc acatcggcca cggtggaatg ggccagaccc agccagatga tgcaattttg   29340
ttgggtttcg gtgacggagg gagagggaag aacaggaaga accatgatta actttattcc   29400
aaacggtctc ggagcacttc aaaatgcagg tccggaggt ggcacctctc gcccccactg    29460
tgttggtgga aataacagc caggtcaaag gtgacacggt tctcgagatg ttccacggtg    29520
gcttccagca aagcctccac gcgcacatcc agaaacaaga ggacagcgaa agcgggagcg   29580
ttttctaatt cctcaatcat catattacac tcctgcacca tccccagata atttttcattt   29640 ttccagcctt gaatgattcg tattagttcc tgaggtaaat ccaagccagc catgataaaa   29700
agctcgcgca gagcgccctc caccggcatt cttaagcaca ccctcataat tccaagagat   29760
tctgctcctg gttcacctgc agcagattaa caatgggaat atcaaaatct ctgccgcgat   29820
ccctaagctc ctccctcaac aataactgta tgtaatcttt catatcatct ccgaaatttt   29880
tagccatagg gccgccagga ataagagcag ggcaagccac attacagata aagcgaagtc   29940
ctccccagtg agcattgcca aatgtaagat tgaaataagc atgctggcta gaccctgtga   30000
tatcttccag ataactggac agaaaatcag gcaagcaatt tttaagaaaa tcaacaaaag   30060
aaaagtcgtc caggtgcagg tttagagcct caggaacaac gatggaataa gtgcaaggag   30120
tgcgttccag catggttagt gttttttgg tgatctgtag aacaaaaaat aaacatgcaa     30180
tattaaacca tgctagcctg gcgaacaggt gggtaaatca ctctttccag caccaggcag   30240
gctacggggt ctccggcgcg accctcgtag aagctgtcgc catgattgaa aagcatcacc   30300
gagagacctt cccggtggcc ggcatggatg attcgagaag aagcatacac tccgggaaca   30360
ttggcatccg tgagtgaaaa aaagcgacct ataaagcctc ggggcactac aatgctcaat   30420
ctcaattcca gcaaagccac cccatgcgga tggagcacaa aattggcagg tgcgtaaaaa   30480
atgtaattac tcccctcctg cacaggcagc aaagcccccg ctccctccag aaacacatac   30540
aaagcctcag cgtccatagc ttaccgagca cggcaggcgc aagagtcaga gaaaaggctg   30600
```

-continued

```
agctctaacc tgactgcccg ctcctgtgct caatatatag ccctaaccta cactgacgta    30660
aaggccaaag tctaaaaata cccgccaaaa tgacacacac gcccagcaca cgcccagaaa    30720
ccggtgacac actcaaaaaa atacgtgcgc ttcctcaaac gcccaaaccg gcgtcatttc    30780
cgggttccca cgctacgtca ccgctcagcg actttcaaat tccgtcgacc gttaaaaacg    30840
tcactcgccc cgcccctaac ggtcgccctt ctctcggcca atcaccttcc tcccttccca    30900
aattcaaacg cctcatttgc atattaacgc gcacaaaaag tttgaggtat atatttgaat    30960
gatg                                                                30964
```

<210> SEQ ID NO 39
<211> LENGTH: 150
<212> TYPE: PRT
<213> ORGANISM: Human adenovirus AdHu5
<220> FEATURE:
<221> NAME/KEY: SOURCE
<222> LOCATION: 1..150
<223> OTHER INFORMATION: /mol_type="protein"
      /organism="Human adenovirus AdHu5"

<400> SEQUENCE: 39

```
Met Thr Thr Ser Gly Val Pro Phe Gly Met Thr Leu Arg Pro Thr Arg
1               5                   10                  15

Ser Arg Leu Ser Arg Arg Thr Pro Tyr Ser Arg Asp Arg Leu Pro Pro
            20                  25                  30

Phe Glu Thr Glu Thr Arg Ala Thr Ile Leu Glu Asp His Pro Leu Leu
        35                  40                  45

Pro Glu Cys Asn Thr Leu Thr Met His Asn Ala Trp Thr Ser Pro Ser
    50                  55                  60

Pro Pro Val Lys Gln Pro Gln Val Gly Gln Gln Pro Val Ala Gln Gln
65                  70                  75                  80

Leu Asp Ser Asp Met Asn Leu Ser Glu Leu Pro Gly Glu Phe Ile Asn
                85                  90                  95

Ile Thr Asp Glu Arg Leu Ala Arg Gln Glu Thr Val Trp Asn Ile Thr
            100                 105                 110

Pro Lys Asn Met Ser Val Thr His Asp Met Met Leu Phe Lys Ala Ser
        115                 120                 125

Arg Gly Glu Arg Thr Val Tyr Ser Val Cys Trp Glu Gly Gly Gly Arg
    130                 135                 140

Leu Asn Thr Arg Val Leu
145                 150
```

<210> SEQ ID NO 40
<211> LENGTH: 294
<212> TYPE: PRT
<213> ORGANISM: Human adenovirus AdHu5
<220> FEATURE:
<221> NAME/KEY: SOURCE
<222> LOCATION: 1..294
<223> OTHER INFORMATION: /mol_type="protein"
      /organism="Human adenovirus AdHu5"

<400> SEQUENCE: 40

```
Met Thr Thr Ser Gly Val Pro Phe Gly Met Thr Leu Arg Pro Thr Arg
1               5                   10                  15

Ser Arg Leu Ser Arg Arg Thr Pro Tyr Ser Arg Asp Arg Leu Pro Pro
            20                  25                  30

Phe Glu Thr Glu Thr Arg Ala Thr Ile Leu Glu Asp His Pro Leu Leu
        35                  40                  45
```

```
Pro Glu Cys Asn Thr Leu Thr Met His Asn Val Ser Tyr Val Arg Gly
 50                  55                  60

Leu Pro Cys Ser Val Gly Phe Thr Leu Ile Gln Glu Trp Val Val Pro
 65                  70                  75                  80

Trp Asp Met Val Leu Thr Arg Glu Glu Leu Val Ile Leu Arg Lys Cys
                 85                  90                  95

Met His Val Cys Leu Cys Cys Ala Asn Ile Asp Ile Met Thr Ser Met
                100                 105                 110

Met Ile His Gly Tyr Glu Ser Trp Ala Leu His Cys His Cys Ser Ser
                115                 120                 125

Pro Gly Ser Leu Gln Cys Ile Ala Gly Gly Gln Val Leu Ala Ser Trp
130                 135                 140

Phe Arg Met Val Val Asp Gly Ala Met Phe Asn Gln Arg Phe Ile Trp
145                 150                 155                 160

Tyr Arg Glu Val Val Asn Tyr Asn Met Pro Lys Glu Val Met Phe Met
                165                 170                 175

Ser Ser Val Phe Met Arg Gly Arg His Leu Ile Tyr Leu Arg Leu Trp
                180                 185                 190

Tyr Asp Gly His Val Gly Ser Val Val Pro Ala Met Ser Phe Gly Tyr
                195                 200                 205

Ser Ala Leu His Cys Gly Ile Leu Asn Asn Ile Val Val Leu Cys Cys
210                 215                 220

Ser Tyr Cys Ala Asp Leu Ser Glu Ile Arg Val Arg Cys Cys Ala Arg
225                 230                 235                 240

Arg Thr Arg Arg Leu Met Leu Arg Ala Val Arg Ile Ile Ala Glu Glu
                245                 250                 255

Thr Thr Ala Met Leu Tyr Ser Cys Arg Thr Glu Arg Arg Arg Gln Gln
                260                 265                 270

Phe Ile Arg Ala Leu Leu Gln His His Arg Pro Ile Leu Met His Asp
                275                 280                 285

Tyr Asp Ser Thr Pro Met
                290

<210> SEQ ID NO 41
<211> LENGTH: 114
<212> TYPE: PRT
<213> ORGANISM: Human adenovirus AdHu5
<220> FEATURE:
<221> NAME/KEY: SOURCE
<222> LOCATION: 1..114
<223> OTHER INFORMATION: /mol_type="protein"
      /organism="Human adenovirus AdHu5"

<400> SEQUENCE: 41

Met Val Leu Pro Ala Leu Pro Ala Pro Val Cys Asp Ser Gln Asn
  1               5                  10                  15

Glu Cys Val Gly Trp Leu Gly Val Ala Tyr Ser Ala Val Val Asp Val
                 20                  25                  30

Ile Arg Ala Ala Ala His Glu Gly Val Tyr Ile Glu Pro Glu Ala Arg
                 35                  40                  45

Gly Arg Leu Asp Ala Leu Arg Glu Trp Ile Tyr Tyr Asn Tyr Tyr Thr
 50                  55                  60

Glu Arg Ser Lys Arg Arg Asp Arg Arg Arg Ser Val Cys His Ala
 65                  70                  75                  80

Arg Thr Trp Phe Cys Phe Arg Lys Tyr Asp Tyr Val Arg Ser Ile
                 85                  90                  95
```

```
Trp His Asp Thr Thr Thr Asn Thr Ile Ser Val Val Ser Ala His Ser
            100                 105                 110

Val Gln

<210> SEQ ID NO 42
<211> LENGTH: 1107
<212> TYPE: DNA
<213> ORGANISM: Mycobacterium tuberculosis
<220> FEATURE:
<221> NAME/KEY: source
<222> LOCATION: 1..1107
<223> OTHER INFORMATION: /mol_type="DNA"
      /note="Ag85A"
      /organism="Mycobacterium tuberculosis"
<220> FEATURE:
<221> NAME/KEY: CDS
<222> LOCATION: 1..1107
<220> FEATURE:
<221> NAME/KEY: sig_peptide
<222> LOCATION: 1..102
<223> OTHER INFORMATION: /note="signal peptide from human tissue
      plasminogen activator (tPA)"
<220> FEATURE:
<221> NAME/KEY: misc_feature
<222> LOCATION: 1072..1104
<223> OTHER INFORMATION: /note="PK tag"

<400> SEQUENCE: 42
atggacgcca tgaagagggg cctgtgctgc gtgctgctgc tgtgtggcgc cgtgttcgtg     60
tcccccagcc aggaaatcca cgcccggttc agacggggca gcatgcagct ggtggacaga    120
gtcagaggcg ccgtgaccgg catgagcaga cggctggtcg tgggagctgt cggagccgct    180
ctggtgtctg gactcgtggg agccgtgggc ggaacagcta cagccggcgc tttcagcaga    240
cccggcctgc ccgtggaata tctgcaggtc cccagcccca gcatgggccg ggacatcaag    300
gtgcagttcc agtctggcgg agccaacagc cctgctctgt acctgctgga cggcctgaga    360
gcccaggacg acttcagcgg ctgggacatc aacacccccg ccttcgagtg gtacgaccag    420
agcggcctgt ctgtggtcat gcctgtgggc ggccagagca gcttctacag cgactggtat    480
cagcccgctt gtggcaaggc cggctgccag acctacaagt gggagacatt cctgaccagc    540
gagctgcccg gctggctgca ggccaacaga cacgtgaagc ccaccggctc tgccgtcgtg    600
ggcctgtcta tggctgccag ctctgccctg accctggcca tctaccaccc ccagcagttc    660
gtgtacgctg gcgccatgtc tggcctgctg gatccttctc aggccatggg acccaccctg    720
atcggactgg ctatgggaga tgccggcgga tacaaggcca gcgacatgtg gggccctaaa    780
gaggaccccg cctggcagag aaacgacccc ctgctgaacg tgggcaagct gatcgccaac    840
aacaccagag tgtgggtgta ctgcggcaac ggcaagctga gcgacctggg cggcaacaac    900
ctgcccgcca agttcctgga aggcttcgtg cggaccagca acatcaagtt ccaggacgcc    960
tacaacgctg gcggcggaca caacggcgtg ttcgacttcc ccgacagcgg cacccacagc   1020
tgggagtatt ggggagccca gctgaatgcc atgaagcccg acctgcagag aggcagcatc   1080
cctaatcctc tgctgggcct ggactga                                       1107

<210> SEQ ID NO 43
<211> LENGTH: 368
<212> TYPE: PRT
<213> ORGANISM: Mycobacterium tuberculosis
<220> FEATURE:
<221> NAME/KEY: SOURCE
<222> LOCATION: 1..368
<223> OTHER INFORMATION: /mol_type="protein"
      /note="Ag85A"
```

-continued

/organism="Mycobacterium tuberculosis"

<400> SEQUENCE: 43

```
Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
            20                  25                  30

Gly Ser Met Gln Leu Val Asp Arg Val Arg Gly Ala Val Thr Gly Met
        35                  40                  45

Ser Arg Arg Leu Val Val Gly Ala Val Gly Ala Ala Leu Val Ser Gly
    50                  55                  60

Leu Val Gly Ala Val Gly Gly Thr Ala Thr Ala Gly Ala Phe Ser Arg
65                  70                  75                  80

Pro Gly Leu Pro Val Glu Tyr Leu Gln Val Pro Ser Pro Ser Met Gly
                85                  90                  95

Arg Asp Ile Lys Val Gln Phe Gln Ser Gly Gly Ala Asn Ser Pro Ala
            100                 105                 110

Leu Tyr Leu Leu Asp Gly Leu Arg Ala Gln Asp Asp Phe Ser Gly Trp
        115                 120                 125

Asp Ile Asn Thr Pro Ala Phe Glu Trp Tyr Asp Gln Ser Gly Leu Ser
    130                 135                 140

Val Val Met Pro Val Gly Gly Gln Ser Ser Phe Tyr Ser Asp Trp Tyr
145                 150                 155                 160

Gln Pro Ala Cys Gly Lys Ala Gly Cys Gln Thr Tyr Lys Trp Glu Thr
                165                 170                 175

Phe Leu Thr Ser Glu Leu Pro Gly Trp Leu Gln Ala Asn Arg His Val
            180                 185                 190

Lys Pro Thr Gly Ser Ala Val Val Gly Leu Ser Met Ala Ala Ser Ser
        195                 200                 205

Ala Leu Thr Leu Ala Ile Tyr His Pro Gln Gln Phe Val Tyr Ala Gly
    210                 215                 220

Ala Met Ser Gly Leu Leu Asp Pro Ser Gln Ala Met Gly Pro Thr Leu
225                 230                 235                 240

Ile Gly Leu Ala Met Gly Asp Ala Gly Gly Tyr Lys Ala Ser Asp Met
                245                 250                 255

Trp Gly Pro Lys Glu Asp Pro Ala Trp Gln Arg Asn Asp Pro Leu Leu
            260                 265                 270

Asn Val Gly Lys Leu Ile Ala Asn Asn Thr Arg Val Trp Val Tyr Cys
        275                 280                 285

Gly Asn Gly Lys Leu Ser Asp Leu Gly Gly Asn Asn Leu Pro Ala Lys
    290                 295                 300

Phe Leu Glu Gly Phe Val Arg Thr Ser Asn Ile Lys Phe Gln Asp Ala
305                 310                 315                 320

Tyr Asn Ala Gly Gly Gly His Asn Gly Val Phe Asp Phe Pro Asp Ser
                325                 330                 335

Gly Thr His Ser Trp Glu Tyr Trp Gly Ala Gln Leu Asn Ala Met Lys
            340                 345                 350

Pro Asp Leu Gln Arg Gly Ser Ile Pro Asn Pro Leu Leu Gly Leu Asp
        355                 360                 365
```

<210> SEQ ID NO 44
<211> LENGTH: 9
<212> TYPE: PRT
<213> ORGANISM: Artificial Sequence
<220> FEATURE:

```
<221> NAME/KEY: SOURCE
<222> LOCATION: 1..9
<223> OTHER INFORMATION: /mol_type="protein"
      /note="Synthetic peptide corresponding to known immunodominant CD
      8+ T cell H-2d restricted epitopes in Ag85A"
      /organism="Artificial Sequence"

<400> SEQUENCE: 44

Trp Tyr Asp Gln Ser Gly Leu Ser Val
1               5

<210> SEQ ID NO 45
<211> LENGTH: 20
<212> TYPE: PRT
<213> ORGANISM: Artificial Sequence
<220> FEATURE:
<221> NAME/KEY: SOURCE
<222> LOCATION: 1..20
<223> OTHER INFORMATION: /mol_type="protein"
      /note="Synthetic peptide corresponding to the known immunodominant
      CD4+ T cell H-2d restricted epitopes in Ag85A"
      /organism="Artificial Sequence"

<400> SEQUENCE: 45

Thr Phe Leu Thr Ser Glu Leu Pro Gly Trp Leu Gln Ala Asn Arg His
1               5                   10                  15

Val Lys Pro Thr
            20

<210> SEQ ID NO 46
<211> LENGTH: 2274
<212> TYPE: DNA
<213> ORGANISM: Unknown
<220> FEATURE:
<221> NAME/KEY: source
<222> LOCATION: 1..2274
<223> OTHER INFORMATION: /mol_type="DNA"
      /note="Influenza A virus nucleoprotein and matrix protein 1"
      /organism="Unknown"
<220> FEATURE:
<221> NAME/KEY: CDS
<222> LOCATION: 1..2274
<220> FEATURE:
<221> NAME/KEY: misc_feature
<222> LOCATION: 1495..1515
<223> OTHER INFORMATION: /function="Linker"
<220> FEATURE:
<221> NAME/KEY: misc_feature
<222> LOCATION: 1..1494
<223> OTHER INFORMATION: /note="Nucleoprotein sequence"
<220> FEATURE:
<221> NAME/KEY: misc_feature
<222> LOCATION: 1516..2274
<223> OTHER INFORMATION: /note="Matrix protein 1 sequence"

<400> SEQUENCE: 46
atggccagcc agggcaccaa gcggagctac gagcagatgg aaaccgacgg cgaccggcag     60
aacgccaccg agatccgggc cagcgtgggc aagatgatcg acggcatcgg ccggttctac    120
atccagatgt gcaccgagct gaagctgtcc gactacgagg ccggctgat ccagaacagc     180 ctgaccatcg agaagatggt gctgtccgcc ttcgacgagc ggcggaacag atacctggaa    240
gagcacccca cgccggcaa ggaccccaag aaaaccggcg acccatcta ccggcgggtg      300 gacggcaagt ggatgcggga gctggtgctg tacgacaaag aggaaatccg gcggatctgg    360
cggcaggcca acaacggcga ggacgccaca gccggcctga cccacatgat gatctggcac    420
agcaacctga acgacaccac ctaccagcgg accaggccc tcgtgcggac cggcatggac    480
ccccggatgt gcagcctgat gcagggcagc acactgccca agaagcgg agctgccgga     540
```

```
gccgccgtga agggcatcgg caccatggtg atggaactga tccggatggt gaagcggggc    600
atcaacgacc ggaattttg gaggggcgag aacggcagaa agactagaag cgcctacgag    660
cggatgtgca acatcctgaa gggcaagttc cagacagccg cccagcgggc catggtggac    720
caggtccggg agagccggaa ccccggcaac gccgagatcg aggacctgat cttcctggcc    780
cggtccgccc tgatcctgcg gggcagcgtg gcccacaaga gctgcctgcc cgcctgcgtg    840
tacggccctg ccgtgagcag cggctacgac ttcgagaaag agggctacag cctggtcggc    900
atcgacccct tcaagctgct gcagaacagc caggtgtaca gcctgatccg gcccaacgag    960
aaccccgccc acaagtccca gctggtctgg atggcctgcc acagcgccgc cttcgaggat   1020
ctgcggctgc tgtccttcat ccggggcacc aaggtgtccc caggggcaa gctgtccacc   1080 agaggcgtgc agatcgccag caacgagaac atggacaaca tgggcagcag caccctggaa   1140
ctgcggagcg gctactgggc catccggacc cggtccggcg gcaacaccaa ccagcagcgg   1200
gccagcgccg gacagatcag cgtgcagccc accttctccg tgcagcggaa cctgcccttc   1260
gagaagagca ccgtgatggc cgccttcacc ggcaacaccg agggccggac cagcgacatg   1320
cgggccgaga ttatccggat gatggaaggc gccaagcccg aggaagtgag cttccggggc   1380 agggggcgtgt tcgagctgtc cgatgagaag gccaccaacc ccatcgtgcc cagcttcgag   1440
atgagcaacg agggcagcta cttcttcggc gacaacgccg aggaatacga caatggcggc   1500
ggaccaggcg gcggaatgag cctgctgacc gaggtggaga cctacgtgct gtccatcgtg   1560
cctagcggcc ctctgaaggc cgagatcgcc cagcggctgg aagatgtgtt cgccggcaag   1620
aacaccgacc tggaagccct gatggaatgg ctgaaaaccc ggcccatcct gagccccctg   1680
accaagggca tcctgggctt cgtgttcacc ctgaccgtgc ccagcgagcg gggcctgcag   1740
cggcggagat tcgtgcagaa cgccctgaac ggcaacggcg accccaacaa catggataag   1800
gccgtgaagc tgtaccggaa gctgaagcgg gagatcacct tccacggcgc caaagagatc   1860
gccctgagct acagcgccgg agccctggcc agctgcatgg gcctgatcta aaccggatg   1920 ggcgccgtga ccaccgaggt ggccttcggc ctggtctgcg ccacctgcga gcagatcgcc   1980
gacagccagc acagatccca ccggcagatg gtggccacaa ccaaccctct gatcaagcac   2040
gagaaccgga tggtgctggc tagcaccacc gccaaggcca tggaacagat ggccggcagc   2100
agcgagcagg ccgccgaagc catggaaatc gccagccagg ccagacagat ggtgcaggcc   2160
atgcggaccg tgggcacccc ccccagcagc tccaccggcc tgcgggacga cctgctggaa   2220
aacctgcaga cctaccagaa acggatgggg gtgcagatgc agcggttcaa gtga         2274
```

<210> SEQ ID NO 47
<211> LENGTH: 757
<212> TYPE: PRT
<213> ORGANISM: Unknown
<220> FEATURE:
<221> NAME/KEY: SOURCE
<222> LOCATION: 1..757
<223> OTHER INFORMATION: /mol_type="protein"
    /note="Influenza A virus nucleoprotein and matrix protein 1"
    /organism="Unknown"

<400> SEQUENCE: 47

Met Ala Ser Gln Gly Thr Lys Arg Ser Tyr Glu Gln Met Glu Thr Asp
1               5                   10                  15

Gly Asp Arg Gln Asn Ala Thr Glu Ile Arg Ala Ser Val Gly Lys Met
            20                  25                  30

```
Ile Asp Gly Ile Gly Arg Phe Tyr Ile Gln Met Cys Thr Glu Leu Lys
         35                  40                  45

Leu Ser Asp Tyr Glu Gly Arg Leu Ile Gln Asn Ser Leu Thr Ile Glu
 50                  55                  60

Lys Met Val Leu Ser Ala Phe Asp Glu Arg Arg Asn Arg Tyr Leu Glu
 65                  70                  75                  80

Glu His Pro Ser Ala Gly Lys Asp Pro Lys Lys Thr Gly Gly Pro Ile
                 85                  90                  95

Tyr Arg Arg Val Asp Gly Lys Trp Met Arg Glu Leu Val Leu Tyr Asp
                100                 105                 110

Lys Glu Glu Ile Arg Arg Ile Trp Arg Gln Ala Asn Asn Gly Glu Asp
            115                 120                 125

Ala Thr Ala Gly Leu Thr His Met Met Ile Trp His Ser Asn Leu Asn
130                 135                 140

Asp Thr Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Ile Gly Thr Met Val Met Glu
                180                 185                 190

Leu Ile Arg Met Val Lys Arg Gly Ile Asn Asp Arg Asn Phe Trp Arg
            195                 200                 205

Gly Glu Asn Gly Arg Lys Thr Arg Ser Ala Tyr Glu Arg Met Cys Asn
            210                 215                 220

Ile Leu Lys Gly Lys Phe Gln Thr Ala Ala Gln Arg Ala Met Val Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
                260                 265                 270

Lys Ser Cys Leu Pro Ala Cys Val Tyr Gly Pro Ala Val Ser Ser Gly
            275                 280                 285

Tyr Asp Phe Glu Lys Glu Gly Tyr Ser Leu Val Gly Ile Asp Pro Phe
290                 295                 300

Lys Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Leu Leu Ser Phe Ile Arg Gly Thr Lys Val
            340                 345                 350

Ser Pro Arg Gly Lys Leu Ser Thr Arg Gly Val Gln Ile Ala Ser Asn
            355                 360                 365

Glu Asn Met Asp Asn Met Gly Ser Ser Thr Leu Glu Leu Arg Ser Gly
            370                 375                 380

Tyr Trp Ala Ile Arg Thr Arg Ser Gly Asn Thr Asn Gln Gln Arg
385                 390                 395                 400

Ala Ser Ala Gly Gln Ile Ser Val Gln Pro Thr Phe Ser Val Gln Arg
                405                 410                 415

Asn Leu Pro Phe Glu Lys Ser Thr Val Met Ala Ala Phe Thr Gly Asn
                420                 425                 430

Thr Glu Gly Arg Thr Ser Asp Met Arg Ala Glu Ile Ile Arg Met Met
            435                 440                 445

Glu Gly Ala Lys Pro Glu Glu Val Ser Phe Arg Gly Arg Gly Val Phe
```

```
            450                 455                 460
Glu Leu Ser Asp Glu Lys Ala Thr Asn Pro Ile Val Pro Ser Phe Glu
465                 470                 475                 480

Met Ser Asn Glu Gly Ser Tyr Phe Phe Gly Asp Asn Ala Glu Glu Tyr
                485                 490                 495

Asp Asn Gly Gly Gly Pro Gly Gly Gly Met Ser Leu Leu Thr Glu Val
            500                 505                 510

Glu Thr Tyr Val Leu Ser Ile Val Pro Ser Gly Pro Leu Lys Ala Glu
        515                 520                 525

Ile Ala Gln Arg Leu Glu Asp Val Phe Ala Gly Lys Asn Thr Asp Leu
    530                 535                 540

Glu Ala Leu Met Glu Trp Leu Lys Thr Arg Pro Ile Leu Ser Pro Leu
545                 550                 555                 560

Thr Lys Gly Ile Leu Gly Phe Val Phe Thr Leu Thr Val Pro Ser Glu
                565                 570                 575

Arg Gly Leu Gln Arg Arg Arg Phe Val Gln Asn Ala Leu Asn Gly Asn
            580                 585                 590

Gly Asp Pro Asn Asn Met Asp Lys Ala Val Lys Leu Tyr Arg Lys Leu
        595                 600                 605

Lys Arg Glu Ile Thr Phe His Gly Ala Lys Glu Ile Ala Leu Ser Tyr
    610                 615                 620

Ser Ala Gly Ala Leu Ala Ser Cys Met Gly Leu Ile Tyr Asn Arg Met
625                 630                 635                 640

Gly Ala Val Thr Thr Glu Val Ala Phe Gly Leu Val Cys Ala Thr Cys
                645                 650                 655

Glu Gln Ile Ala Asp Ser Gln His Arg Ser His Arg Gln Met Val Ala
            660                 665                 670

Thr Thr Asn Pro Leu Ile Lys His Glu Asn Arg Met Val Leu Ala Ser
        675                 680                 685

Thr Thr Ala Lys Ala Met Glu Gln Met Ala Gly Ser Ser Glu Gln Ala
    690                 695                 700

Ala Glu Ala Met Glu Ile Ala Ser Gln Ala Arg Gln Met Val Gln Ala
705                 710                 715                 720

Met Arg Thr Val Gly Thr His Pro Ser Ser Ser Thr Gly Leu Arg Asp
                725                 730                 735

Asp Leu Leu Glu Asn Leu Gln Thr Tyr Gln Lys Arg Met Gly Val Gln
            740                 745                 750

Met Gln Arg Phe Lys
        755

<210> SEQ ID NO 48
<211> LENGTH: 9
<212> TYPE: PRT
<213> ORGANISM: Artificial Sequence
<220> FEATURE:
<221> NAME/KEY: SOURCE
<222> LOCATION: 1..9
<223> OTHER INFORMATION: /mol_type="protein"
      /note="Synthetic peptide corresponding to known immunodominant CD
      8+ T cell H-2d restricted epitope in NP"
      /organism="Artificial Sequence"

<400> SEQUENCE: 48

Thr Tyr Gln Arg Thr Arg Ala Leu Val
1               5

<210> SEQ ID NO 49
```

```
<211> LENGTH: 9
<212> TYPE: PRT
<213> ORGANISM: Artificial Sequence
<220> FEATURE:
<221> NAME/KEY: SOURCE
<222> LOCATION: 1..9
<223> OTHER INFORMATION: /mol_type="protein"
      /note="Linker"
      /organism="Artificial Sequence"

<400> SEQUENCE: 49

Ile Pro Asn Pro Leu Leu Gly Leu Asp
1               5
```

SIMIAN ADENOVIRUS AND HYBRID ADENOVIRAL VECTORS

The present invention relates to novel adenoviral vectors derived from a chimpanzee adenovirus, immunogenic compositions thereof and their use in medicine.

All publications, patents and patent applications cited herein are incorporated in full by reference.

BACKGROUND

Traditionally, vaccines have been based on whole inactivated or attenuated pathogens. However, for many infectious diseases such as malaria, this approach is impractical and the focus of research has changed to the development of 'subunit vaccines' expressing only those pathogen-derived antigens that induce immune correlates of protection.

Subunit vaccines present an antigen to the immune system without introducing a whole infectious organism. One such method involves the administration of a specific, isolated protein from an infectious organism. However, this technique often induces only a weak immune response and the isolated proteins may have a different three-dimensional structure than the protein in its normal context, resulting in the production of antibodies that may not recognize the infectious organism.

An alternative method has therefore been developed which utilizes viral vectors for the delivery of antigens. Viruses are obligate intracellular parasites which replicate by transfecting their DNA into a host cell, and inducing the host cell to express the viral genome. This reproductive strategy has been harnessed to create vectored vaccines by creating recombinant, non-replicating viral vectors which carry one or more heterologous transgenes. Transfection or transduction of the recombinant viral genome into the host cell results in the expression of the heterologous transgene in the host cell. When the heterologous transgene encodes an antigen, for example, expression of the antigen within the host cell can elicit a protective or therapeutic immune response by the host immune system. As such, the viral vectors may function as effective vaccines. Alternatively, the heterologous transgene may encode a functional allele of a gene, expression of which can be used to counteract the effects of a deleterious mutant allele of the gene, in a process known as gene therapy.

Particularly suitable for use as viral vectors are adenoviruses. Adenoviruses are non-enveloped viruses, approximately 90-100 nm in diameter, comprising a nucleocapsid and a linear double stranded DNA genome. The viral nucleocapsid comprises penton and hexon capsomers. A unique fibre is associated with each penton base and aids in the attachment of the virus to the host cell via the Coxsackie-adenovirus receptor on the surface of the host cell. Over 50 serotype strains of adenoviruses have been identified, most of which cause respiratory tract infections, conjunctivitis and gastroentiritus in humans. Rather than integrating into the host genome, adenoviruses normally replicate as episomal elements in the nucleus of the host cell. The genome of adenoviruses comprises 4 early transcriptional units (E1, E2, E3 and E4), which have mainly regulatory functions and prepare the host cell for viral replication. The genome also comprises 5 late transcriptional units (L1, L2, L3, L4 and L5), which encode structural proteins including the penton (L2), the hexon (L3), the scaffolding protein (L4) and the fiber protein (L5), which are under the control of a single promoter. Each extremity of the genome comprises an Inverted Terminal Repeat (ITR) which is necessary for viral replication.

Recombinant adenoviruses were originally developed for gene therapy, but the strong and sustained transgene-specific immune responses elicited by these gene delivery agents prompted their use as vaccine carriers. In addition to being highly immunogenic, adenoviruses offer many other advantages for clinical vaccine development. The adenoviral genome is relatively small (between 26 and 45 kbp), well characterised and easy to manipulate. The deletion of a single transcriptional unit, E1, renders the virus replication-incompetent which increases its predictability and reduces side effects in clinical applications. Recombinant adenoviruses can accommodate relatively large transgenes, in some cases up to 8 kb, allowing flexibility in subunit design, and have a relatively broad tropism facilitating transgene delivery to a wide variety of cells and tissues. Importantly for clinical applications, methods for scaled-up production and purification of recombinant adenoviruses to high titre are well established. Thus far, subgroup C serotypes AdHu2 or AdHu5 have predominantly been used as vectors.

However, the first generation of vaccine vectors based on the archetypal human adenovirus AdHu5 showed poor efficacy in clinical trials, despite encouraging pre-clinical data[1]. It was subsequently discovered that a large proportion of human adults harbour significant titres of neutralising antibodies to common human serotypes such as AdHu2 and AdHu5, as a result of natural infection. Neutralising antibodies could reduce the potency of viral vector vaccines by blocking viral entry into host cells and hence delivery of the target transgene.

The occurrence of pre-existing anti-vector immunity is being addressed through the development of new adenoviral vectors based on serotypes to which the human population is less likely to have been exposed, including those of chimpanzee origin[2,3]. However, some such chimpanzee adenoviral vectors have limited efficacy on the grounds of unexplained immunity in human populations, varying levels of cross-reactivity with human adenoviruses, and sub-optimal growth in transformed cell lines. In addition, it is advantageous to have a range of different adenoviral vectors available for use in immunising against different diseases, on the grounds that induction of neutralising antibodies against a vector may prevent its re-administration for another indication.

Thus, there continues to be a need in the art for highly immunogenic, non-human adenoviral vectors which effectively deliver the target transgene, minimize the effect of pre-existing immunity to adenovirus serotypes and replicate efficiently in transformed cell lines.

SUMMARY OF INVENTION

In a first aspect, the present invention provides the complete genomic sequence of a chimpanzee adenovirus referred to herein as AdY25.

In a second aspect, the present invention provides an adenovirus vector comprising a capsid derived from chimpanzee adenovirus AdY25, wherein said capsid encapsidates a nucleic acid molecule comprising an exogenous nucleotide sequence of interest operably linked to expression control sequences which direct the translation, transcription and/or expression thereof in an animal cell and an adenoviral packaging signal sequence.

A third aspect provides immunogenic compositions comprising the adenoviral vector according to the second aspect, optionally in combination with one or more additional active ingredients, a pharmaceutically acceptable carrier, diluent, excipient or adjuvant.

A fourth aspect provides the use of the adenoviral vector according to the second aspect or the immunogenic composition according to the third aspect in medicine. In particular, the adenoviral vector and immunogenic compositions are provided for delivery of a transgene into a host cell, elicitation of an immune response in an animal, boosting an immune response in an animal, treating or preventing at least one disease, inducing an immune response in an animal that will break tolerance to a self antigen and gene therapy.

A fifth aspect of the present invention provides a polynucleotide sequence encoding the adenoviral vector according to the second aspect of the present invention.

A sixth aspect of the present invention provides a host cell transduced with the viral vector according to the second aspect of the present invention.

A seventh aspect of the present invention provides a method of producing the viral vector according to the second aspect of the present invention, preferably by generating a molecular clone of AdY25 in a Bacterial Artificial Chromosome (BAC).

An eighth aspect of the present invention therefore provides a Bacterial Artificial Chromosome (BAC) clone comprising the polynucleotide sequence according to the fifth aspect of the present invention.

A ninth aspect of the present invention provides a packaging cell line producing the viral vector according to the second aspect of the present invention.

A tenth aspect of the present invention provides an adenoviral vector other than AdHu5 having a nucleic acid molecule comprising the E4Orf4, E4Orf6 and E4Orf6/7 coding regions from AdHu5.

FIGURES

The present invention is described with reference to the following figures in which.

Figure 3:
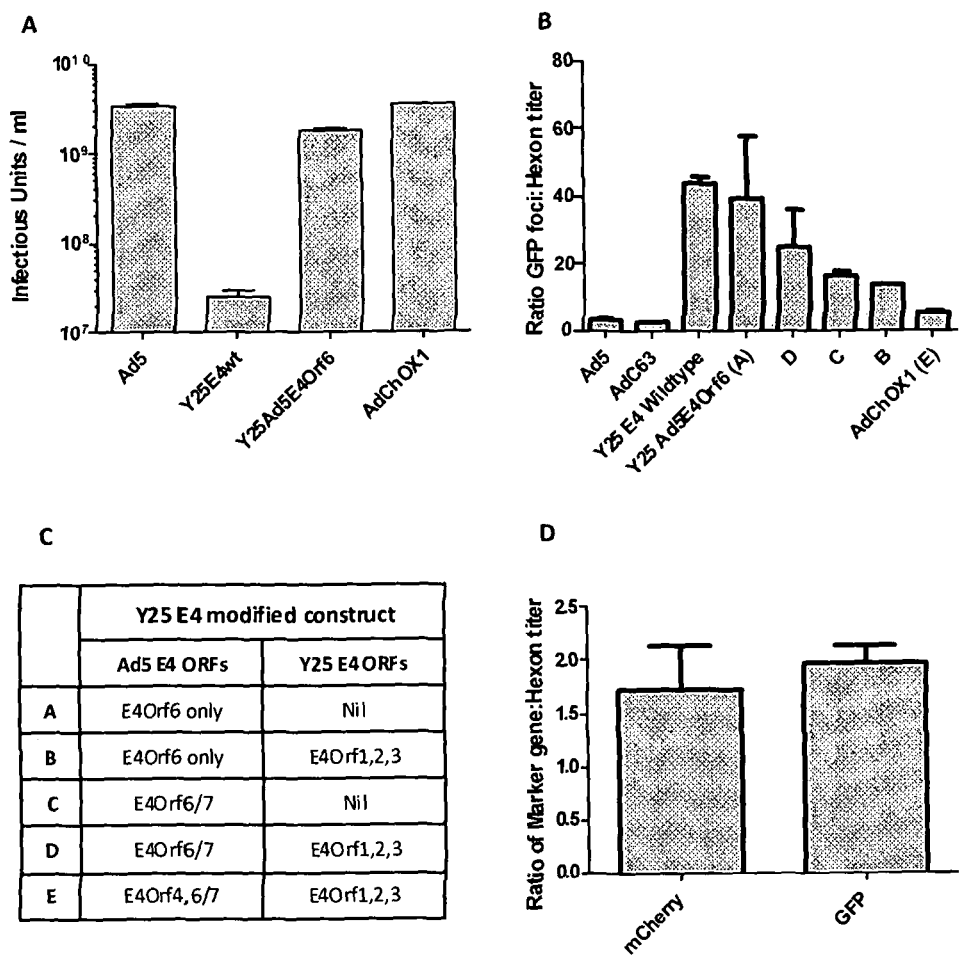
FIG. 3A is a histogram of the viral yield (infectious units/ml) of AdHu5 and three AdY25-based vectors expressing Green Fluorescent Protein (GFP): i) AdY25 E4 wildtype ("Y25E4 wt"); ii) AdY25 E4 AdHu5 Orf6 ("Y25Ad5E4Orf6") and iii) AdY25 AdHu5 E4Orf4/6/7 ("AdChOX1").
FIG. 3B is a histogram of the ratio of GFP foci to anti-hexon titer for AdHu5, AdCh63, AdY25 E4 wildtype and the constructs A-E as described in FIG. 3C, all expressing the TIPeGFP antigen.
FIG. 3C is a table detailing the construction of the E4-modified AdY25 vector constructs A, B, C, D and E.

FIG. 3D is a histogram of the ratio of marker gene: hexon titer for AdChOX1-based vectors expressing TIPeGFP, having either GFP or mCherry fluorescent transgenes. All data is representative of at least two independent experiments. Error bars show mean and SEM.

Figure 4:
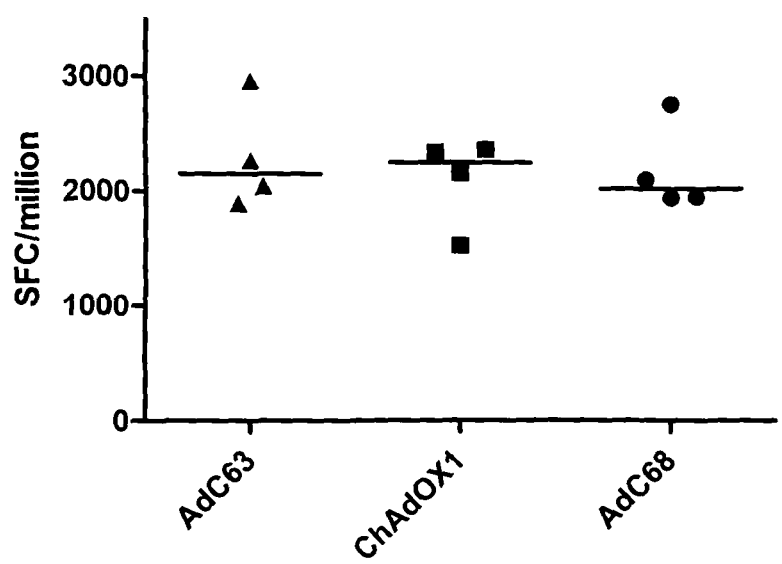

FIG. 4 is a graphical representation of cellular immunogenicity (spot forming cells (SFC)/million) of ChAdOX1 as compared to AdCh63 and AdCh68.

Figure 5:
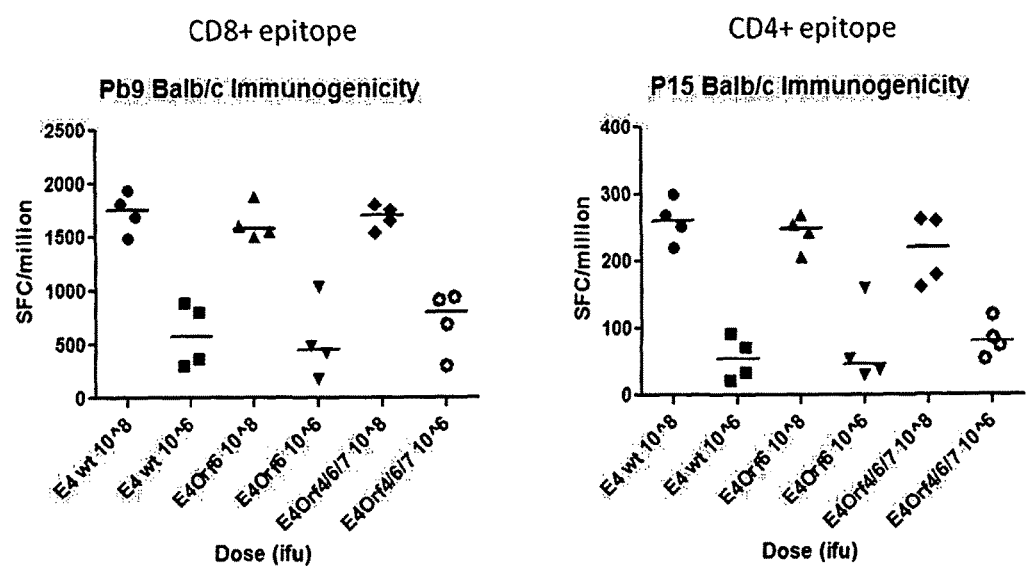

FIG. 5 is a graphical representation of the effect of E4 modification on IFN-γ, spleen ELISpot responses (SFC/million) to two epitopes, Pb9 and P15, two weeks after intramuscular immunisation of Balb/c mice (4/group) with either $10^8$ or $10^6$ infectious units (ifu) of AdY25-based vectors with the following E4 regions: i) wildtype E4 region ("E4 wt"); ii) E4Orf6 from AdHu5 ("E4Orf6"); or iii) E4Orf4, 6 and 7 from AdHu5 ("E4Orf4/6/7").

Figure 6:
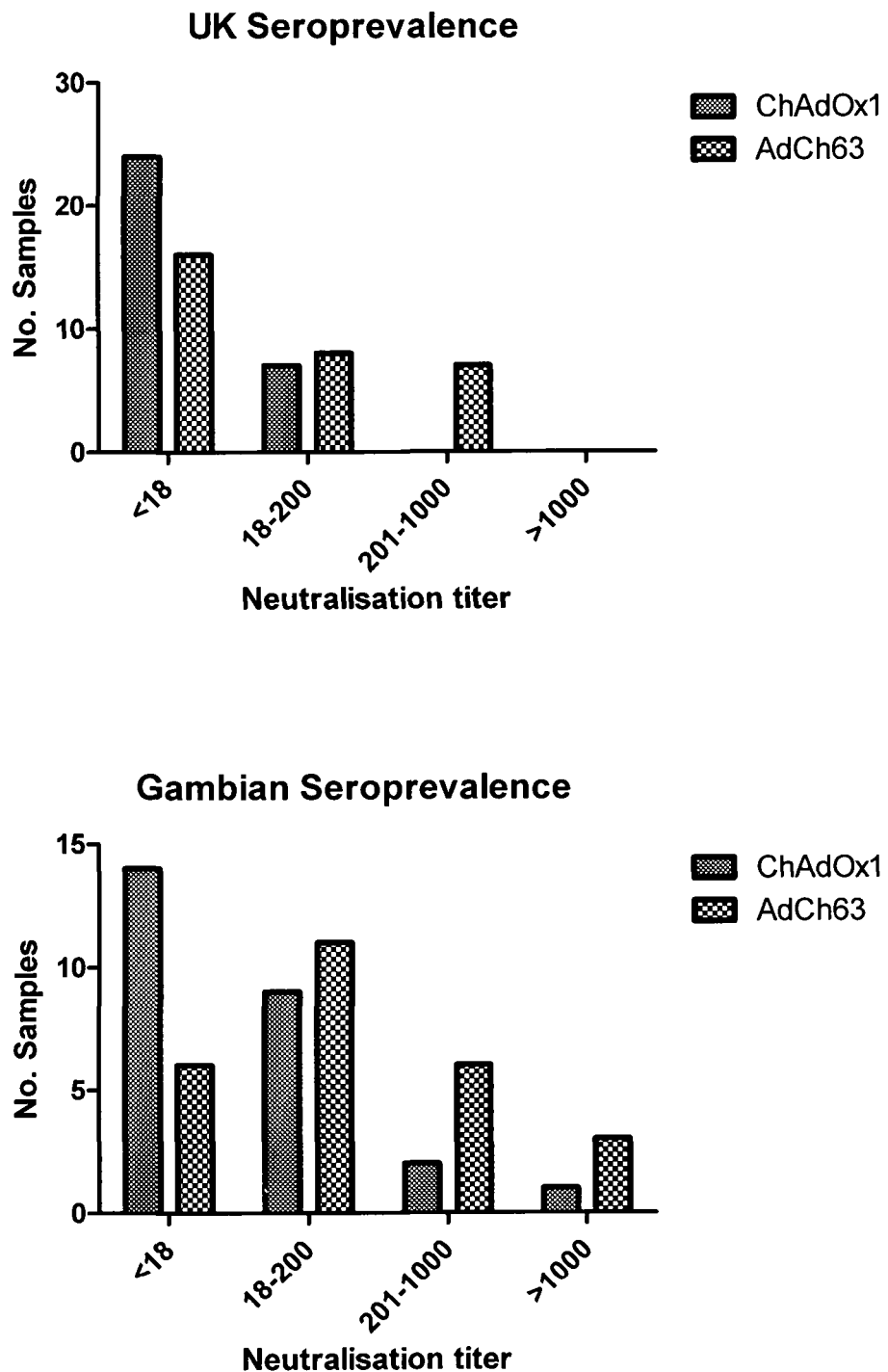

FIG. 6 is a histogram showing the prevalence of vector-neutralising antibodies in human sera from (A) the UK and (B) the Gambia, against Y25Ad5E4Orf6 (referred to in FIG. 6 as "ChAdOX1") and AdCh63.

Figure 7:
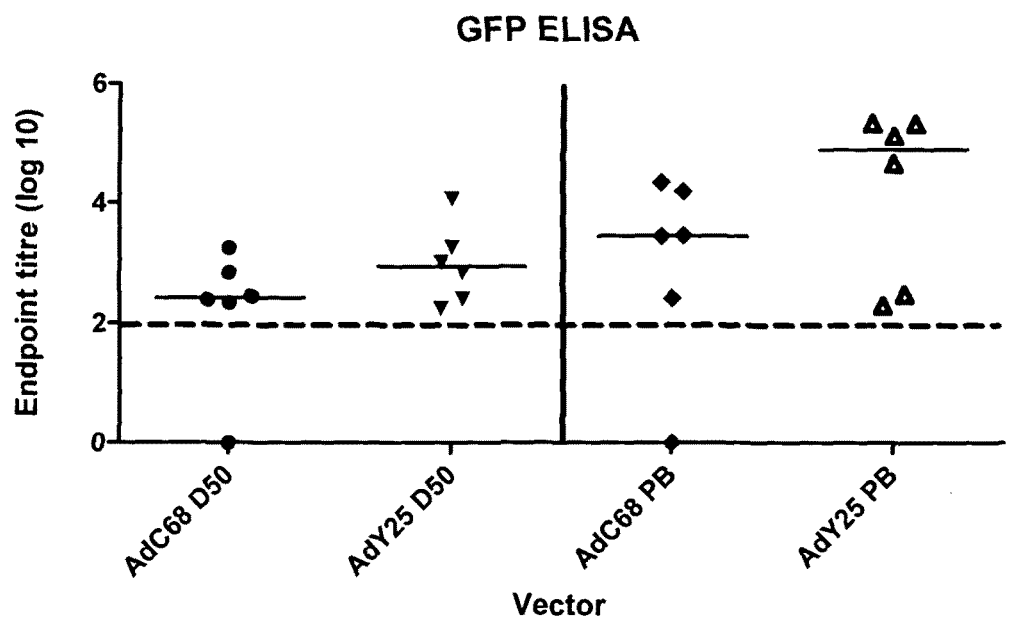

FIG. 7 is a graphical representation of the humoral immunogenicity of ChAdOX1 and AdCh68-based vectors carrying TIPeGFP antigen. After 56 days post prime, mice were boosted with $10^6$ pfu MVA-TIPeGFP Serum was collected and responses measured by endpoint ELISA a) 50 days post prime and b) 10 days post boost. Mean and significance indicated. Statistical analyses performed by one way ANOVA. Dotted line indicates limit of detection of the assay.

Figure 8:
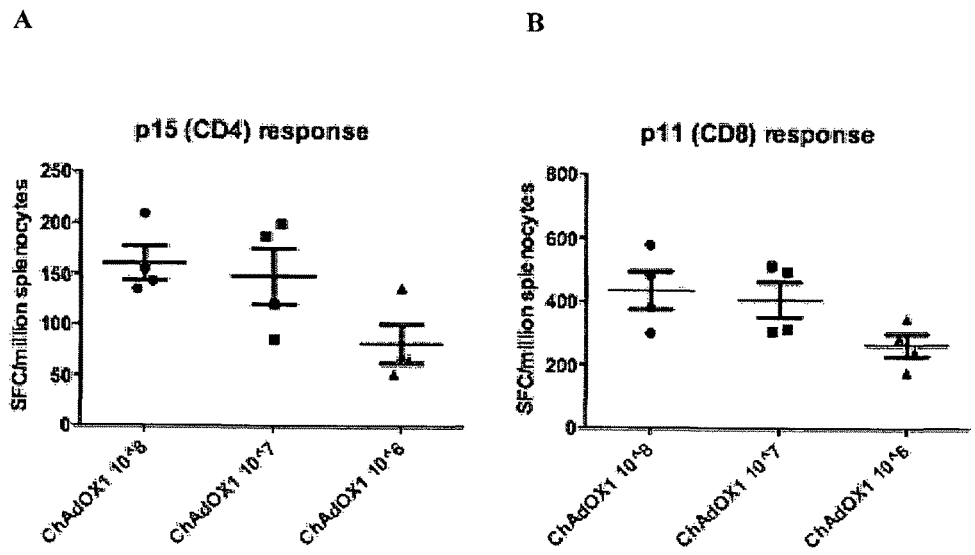

FIG. 8A is a graphical representation of cellular immunogenicity (spot forming cells (SFC)/million splenocyltes) of ChAdOX1 vector carrying the *Mycobacterium tuberculosis* Ag85A antigen, at three different doses. Cellular immune responses to Ag85A were determined by IFN-γ ELIspot assay using splenocytes stimulated with synthetic peptides corresponding to the known immunodominant CD4+ T cell H-$2^d$ restricted epitope in Ag85A (p15).

FIG. 8B is a graphical representation of cellular immunogenicity (spot forming cells (SFC)/million splenocyltes) of ChAdOX1 carrying the *Mycobacterium tuberculosis* Ag85A antigen, at three different doses. Cellular immune responses to Ag85A were determined by IFN-γ ELIspot assay using splenocytes stimulated with synthetic peptides corresponding to the known immunodominant CD8+ T cell H-$2^d$ restricted epitope in Ag85A (p11).

Figure 9:
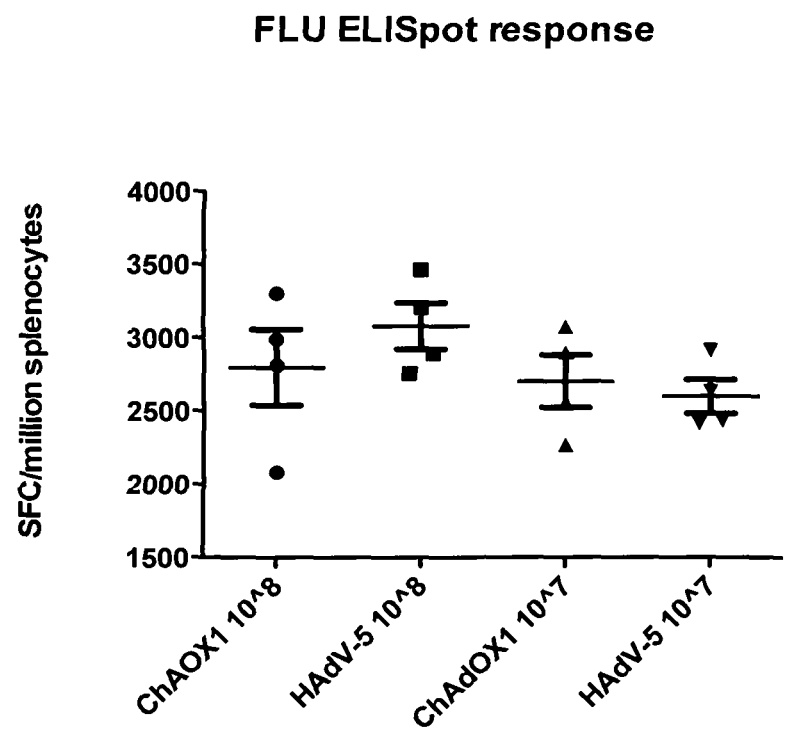

FIG. 9 is a graphical representation of cellular immunogenicity (spot forming cells (SFC)/million splenocyltes) of ChAdOX1 and HAdV-5 carrying the nucleoprotein (NP) and matrix protein 1 (M1) of Influenza A virus, at two different doses. Cellular immune responses to nucleoprotein (NP) were determined by IFN-γ ELIspot assay using splenocytes stimulated with synthetic peptides corresponding to the known immunodominant CD8+ T cell H-$2_d$ restricted epitope in NP.

DETAILED DESCRIPTION

The present invention relates to novel adenoviral vectors derived from a chimpanzee adenovirus, AdY25, immunogenic compositions thereof and their use in medicine.

AdY25 is a chimpanzee adenovirus which has been sequenced for the first time by the present inventors. The nucleotide sequence is provided in SEQ ID NO. 1.

A first aspect of the present invention therefore provides a nucleic acid molecule having the sequence of SEQ ID NO. 1. In one embodiment, the nucleic acid molecule is isolated.

The person skilled in the art will appreciate that there are homologues, equivalents and derivatives of all of the nucleic acid sequences described herein. Thus, the invention also encompasses nucleic acid molecules having a sequence substantially identical to the nucleic acid sequences described herein over their entire length.

One of skill in the art will appreciate that the present invention can also include variants of those particular nucleic acid molecules which are exemplified herein. These may occur in nature, for example because of strain variation. For example, additions, substitutions and/or deletions are included. One of skill in the art will also appreciate that variation from the particular nucleic acid molecules exemplified herein will be possible in view of the degeneracy of the genetic code. Preferably, the variants have substantial identity to the nucleic acid sequences described herein over their entire length.

As used herein, nucleic acid sequences which have "substantial identity" preferably have at least 80%, 90%, 91%, 92%, 93%, 94%, 95% 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4% 99.5%, 99.6%, 99.7%, 99.8% or 99.9% identity with said sequences. Desirably, the term "substantial identity" indicates that said sequence has a greater degree of identity with any of the sequences described herein than with prior art nucleic acid sequences.

When comparing nucleic acid sequences for the purposes of determining the degree of homology or identity one can use programs such as BESTFIT and GAP (both from the Wisconsin Genetics Computer Group (GCG) software package). BESTFIT, for example, compares two sequences and produces an optimal alignment of the most similar segments. GAP enables sequences to be aligned along their whole length and finds the optimal alignment by inserting spaces in either sequence as appropriate. Suitably, in the context of the present invention, when discussing identity of nucleic acid sequences, the comparison is made by alignment of the sequences along their whole length. The above applied mutatis mutandis to all nucleic acid sequences disclosed in the present application.

Preferably, the nucleic acid molecule according to the first aspect has a sequence at least 98% identical to SEQ ID NO. 1, more preferably at least 98.6% identical to SEQ ID NO. 1.

Preferably, the nucleic acid molecule according to the first aspect comprises one or more nucleotide sequences selected from the group consisting of;
(a) nucleotides 18302 to 21130 of SEQ ID NO. 1 or a sequence substantially identical thereto;
(b) nucleotides 13891 to 15486 of SEQ ID NO. 1 or a sequence substantially identical thereto; and
(c) nucleotides 32290 to 33621 of SEQ ID NO. 1 or a sequence substantially identical thereto.

These nucleotide sequences encode the (a) hexon, (b) penton and (c) fibre capsid proteins of AdY25, the exterior regions of which determine the properties of the viral vector, including serotype.

The nucleic acid molecule according to the first aspect may also comprise one or more nucleotide sequences selected from the group consisting of:
(a) a nucleotide sequence encoding a hexon protein comprising the amino acid sequence of SEQ ID NO. 2, or a sequence at least 98.2% identical thereto; or a nucleotide sequence encoding a hexon protein having a sequence at least 98.2% identical to the protein encoded by nucleotides 18302 to 21130 of SEQ ID NO. 1;
(b) a nucleotide sequence encoding a penton protein comprising the amino acid sequence of SEQ ID NO. 3, or a sequence at least 98.3% identical thereto; or a nucleotide sequence encoding a penton protein having a sequence at least 98.3% identical to the protein encoded by nucleotides 13891 to 15486 of SEQ ID NO. 1; and
(c) a nucleotide sequence encoding a fiber protein comprising the amino acid sequence of SEQ ID NO. 4 or a sequence at least 99.1% identical thereto; or a nucleotide sequence encoding a fiber protein having a sequence at least 99.1% identical to the protein encoded by nucleotides 32290 to 33621 of SEQ ID NO. 1.

Nucleic acid molecules comprising a sequence complementary to the nucleic acid molecule according to the first aspect of the present invention are within the scope of the present invention.

Nucleic acid molecules which hybridize only to the nucleic acid molecule according to the first aspect of the present invention are also encompassed by the present application. Thus, the conditions used for hybridisation are sufficiently stringent that only such nucleic acid sequences would remain hybridised. The person skilled in the art would easily be able to determine such conditions.

The nucleic acid can be DNA, including cDNA, RNA including mRNA or PNA (peptide nucleic acid) or a mixture thereof.

Table 1 provides an overview of the wildtype AdY25 sequences disclosed herein:

TABLE 1

| SEQ ID NO. | Description | Corresponding nucleotides in SEQ ID NO. 1 |
| --- | --- | --- |
| 1 | Genome (nucleotide sequence) | N/A |
| 2 | Hexon protein | Nucleotides 18302 to 21130 (L3) |
| 3 | Penton protein | Nucleotides 13891 to 15486 (L2) |
| 4 | Fibre protein | Nucleotides 32290 to 33621 (L5) |
| 5 | E1A | Nucleotides 577 to 1143 and 1237 to 1443 |
| 6 | E1B 19 KDa | Nucleotides 1602 to 2165 |
| 7 | E1B 55 KDa | Nucleotides 1907 to 3406 |
| 8 | pIX | Nucleotides 3491 to 3919 |
| 9 | IVa2 | Nucleotides 5587 to 5602 and 3978 to 5311 (E2) |
| 10 | Polymerase | Nucleotides 13838 to 13846 and 5081 to 8662 (E2) |
| 11 | pTP | Nucleotides 13838 to 13846 and 8463 to 10392 (E2) |
| 12 | 52/55 kDa | Nucleotides 10827 to 12017 (L1) |
| 13 | IIIa | Nucleotides 12041 to 13807 (L1) |
| 14 | VII | Nucleotides 15493 to 16074 |
| 15 | V | Nucleotides 16119 to 17141 |
| 16 | Mu | Nucleotides 17161 to 17394 |
| 17 | VI | Nucleotides 17470 to 18201 |
| 18 | Endoprotease | Nucleotides 21146 to 21775 |
| 19 | DNA binding protein | Nucleotides 21852 to 23390 |
| 20 | 100 kDa | Nucleotides 23419 to 25827 (L4) |
| 21 | 22 KDa | Nucleotides 25544 to 26098 |
| 22 | 33 KDa | Nucleotides 25544 to 25871 and 26041 to 26372 (L4) |
| 23 | pVIII | Nucleotides 25602 to 26285 (L4) |
| 24 | E3 12.5 KDa | Nucleotides 27139 to 27459 |
| 25 | E3 CR1aI | Nucleotides 27413 to 28051 |
| 26 | E3 gp19 KDa | Nucleotides 28033 to 28563 |
| 27 | E3 22.3 KDa | Nucleotides 29350 to 29979 |
| 28 | E3 31 KDa | Nucleotides 29999 to 30907 |
| 29 | E3 10.4 KDa | Nucleotides 30916 to 31191 |
| 30 | E3 15.2 KDa | Nucleotides 31200 to 31643 |
| 31 | E3 14.7 KDa | Nucleotides 31636 to 32040 |
| 32 | E4 Orf 6/7 | Nucleotides 34688 to 34861 and 33716 to 33965 |
| 33 | E4 Orf 6 | Nucleotides 33965 to 34861 |
| 34 | E4 Orf 4 | Nucleotides 34764 to 35132 |
| 35 | E4 Orf 3 | Nucleotides 35141 to 35494 |
| 36 | E4 Orf 2 | Nucleotides 35491 to 35880 |
| 37 | E4 Orf 1 | Nucleotides 35930 to 36304 |

Figure 1:
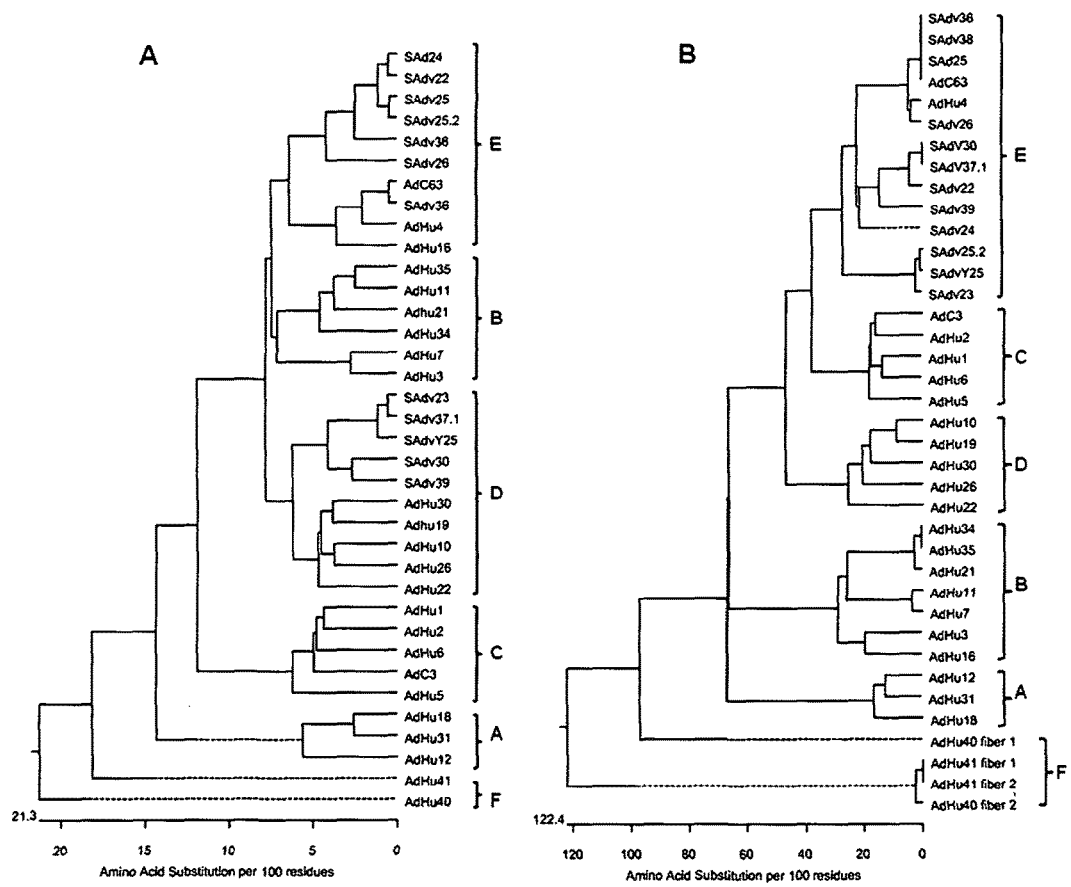
FIG. 1 shows a phylogenetic sequence alignment of the amino acid sequences of (A) the hexon protein and (B) the fiber protein of different adenovirus serotypes. Sequences are clustered into the six adenovirus groups A-F.
Figure 2:
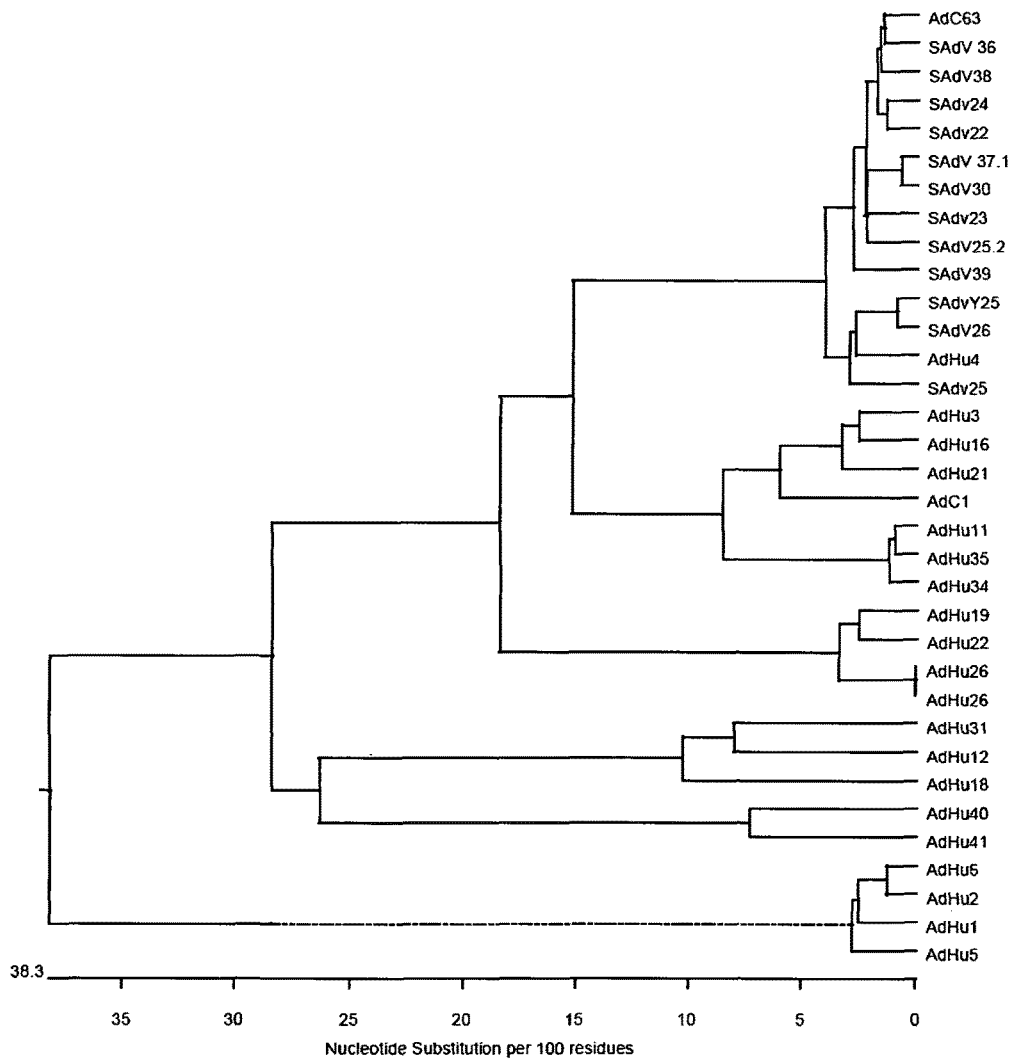
FIG. 2 shows a phylogenetic sequence alignment based on the whole genomic nucleotide sequence of wild type adenoviruses of different species. Sequences are clustered into the six adenovirus groups A-F.

The genome sequence data has confirmed early serological studies that simian AdY25 is closely related to human group E adenovirus, AdHu4[4]. Alignment of the amino acid sequences of hexon and fibre proteins from different adenoviral serotypes have been used to create the phylogenetic trees in FIG. 1. These are the major surface-exposed capsid components and are believed to be the primary determinants of vector tropism. Alignment of whole genomic nucleotide sequences of different adenoviral species have been used to create the phylogenetic tree in FIG. 2. The genome and the fibre proteins align AdY25 with the group E adenoviruses. However, the hexon proteins align AdY25 with the group D adenoviruses.

Merely for the convenience of those of skill in the art, a sample of E. coli strain DH10B containing bacterial artificial chromosomes (BACs) containing the cloned genome of chimpanzee adenovirus Y25 (pBACe3.6 Y25, cell line name "Y25") was deposited by Isis Innovation Limited on 24 May 2012 with the European Collection of Cell Cultures (ECACC) at the Health Protection Agency Culture Collections, Health Protection Agency, Porton Down, Salisbury SP4 0JG, United Kingdom under the Budapest Treaty and designated by provisional accession no. 12052401.

The E. coli containing the BAC is a class I genetically modified organism. The genotype of E. coli strain DH is: F-mcrA Δ(mrr-hsdRMS-mcrBC) Φ80dlacZΔM15 ΔlacX74 endA1 recA1 deoR Δ(ara, leu) 7697 araD139 gal U galK nupG rpsL λ-. Chimpanzee adenovirus Y25 is provisionally classified within the species Human adenovirus E based on the nucleotide sequence of the viral DNA polymerase.

The BAC propagates within the bacteria during replication and can be maintained by selection with chloramphenicol. The E. coli strain DH10B containing the BAC into which the genome is cloned can be propagated in Luria-Bertani broth or agar containing 12.5 µg/mL chloramphenicol at 37° C.

Converting the BAC clones of the viral genomes into viruses ("rescue") can be carried out by the following steps. The E. coli host is propagated and the BAC DNA is purified from the bacteria according to standard methods. The DNA is linearised with the restriction endonuclease PmeI and transfected into any cell line supporting growth of human adenoviruses (e.g. A549 cells). The resulting adenovirus can then be propagated and purified for use as a vaccine, for example. All of these reagents and cells are publicly available. If the deposition were rescued, the resulting virus would be a wild-type adenovirus.

In respect of all designated states to which such action is possible and to the extent that it is legally permissible under the law of the designated state, it is requested that a sample of the deposited material be made available only by the issue thereof to an independent expert, in accordance with the relevant patent legislation, e.g. Rule 32(1) EPC, Rule 13(1) and Schedule 1 of the UK Patent Rules 2007, Regulation 3.25(3) of the Australian Patent Regulations and generally similar provisions mutatis mutandis for any other designated state.

Furthermore, merely for the convenience of those of skill in the art, a sample of E. coli strain DH10B containing bacterial artificial chromosomes (BACs) containing the cloned genome of chimpanzee adenovirus Y25 with deletion of the E1 region (pBACe3.6 Y25delE1, cell line name "Y25delE1") was deposited by Isis Innovation Limited on 24 May 2012 with the European Collection of Cell Cultures (ECACC) at the Health Protection Agency Culture Collections, Health Protection Agency, Porton Down, Salisbury SP4 0JG, United Kingdom under the Budapest Treaty and designated by provisional accession no. 12052402.

The E. coli containing the BAC is a class I genetically modified organism. The genotype of E. coli strain DH10B is: F-mcrA Δ(mrr-hsdRMS-mcrBC) Φ80dlacZΔM15 ΔlacX74 endA1 recA1 deoR Δ(ara,leu) 7697 araD139 galU galK nupG rpsL λ-. Chimpanzee adenovirus Y25 is provisionally classified within the species Human adenovirus E based on the nucleotide sequence of the viral DNA polymerase.

The BAC propagates within the bacteria during replication and can be maintained by selection with chloramphenicol. The E. coli strain DH10B containing the bacterial artificial chromosomes into which the genomes are cloned can be propagated in Luria-Bertani broth or agar containing 12.5 µg/mL chloramphenicol at 37° C.

Converting the BAC clones of the viral genomes into viruses ("rescue") can be carried out by the following steps. The E. coli host is propagated and the BAC DNA is purified from the bacteria according to standard methods. The DNA is linearised with the restriction endonuclease PmeI and transfected into HEK293 cells (or a similar E1 complementing cell line). The resulting adenovirus can then be propagated and purified for use as a vaccine for example. All of these reagents and cells are publicly available. If the deposition were rescued, the resulting virus would be a class I genetically modified organism.

In respect of all designated states to which such action is possible and to the extent that it is legally permissible under the law of the designated state, it is requested that a sample of the deposited material be made available only by the issue thereof to an independent expert, in accordance with the relevant patent legislation, e.g. Rule 32(1) EPC, Rule 13(1) and Schedule 1 of the UK Patent Rules 2007, Regulation 3.25(3) of the Australian Patent Regulations and generally similar provisions mutatis mutandis for any other designated state.

A specific embodiment of the first aspect of the present invention provides the complete genomic sequence of a chimpanzee adenovirus referred to herein as AdY25, wherein said genomic sequence comprises or consists of the genomic sequence deposited in a BAC in E. coli strain DH10B by Isis Innovation Limited on 24 May 2012 with the European Collection of Cell Cultures (ECACC) at the Health Protection Agency Culture Collections, Health Protection Agency, Porton Down, Salisbury SP4 0JG, United Kingdom under the Budapest Treaty and designated by provisional accession no. 12052401, or the genomic sequence deposited in a BAC in E. coli strain DH10B by Isis Innovation Limited on 24 May 2012 with the European Collection of Cell Cultures (ECACC) at the Health Protection Agency Culture Collections, Health Protection Agency, Porton Down, Salisbury SP4 0JG, United Kingdom under the Budapest Treaty and designated by provisional accession no. 12052402.

The inventors have discovered that viral vectors based on the newly sequenced AdY25 can be highly effective. A second aspect of the present invention therefore provides an adenovirus vector comprising a capsid derived from chimpanzee adenovirus AdY25, wherein said capsid encapsidates a nucleic acid molecule comprising an exogeneous nucleotide sequence of interest operably linked to expression control sequences which direct the translation, transcription and/or expression thereof in an animal cell and an adenoviral packaging signal sequence.

As used herein, the phrase "viral vector" refers to a recombinant virus or a derivative thereof which is capable of introducing genetic material, including recombinant DNA, into a host cell or host organism by means of transduction or non-productive infection. For example, the vector of the present invention may be a gene delivery vector, a vaccine vector, an antisense delivery vector or a gene therapy vector.

As used herein, "AdY25" and "Y25" refer to the chimpanzee adenovirus AdY25 or vectors derived therefrom or based thereon. Shorthand terms are used to indicate modifications made to the wildtype virus. For example, "ΔE1" or "delE1" indicates deletion or functional deletion of the E1 locus. The phrase "Ad5E4Orf6" indicates that the viral vector comprises heterologous E4 open reading frame 6 from the Ad5 virus.

The vector of the present invention comprises a capsid derived from chimpanzee adenovirus AdY25. Preferably, the capsid comprises the native or wildtype AdY25 capsid proteins, including penton proteins, hexon proteins, fiber proteins and/or scaffolding proteins. However, one of skill in the art will readily appreciate that small modifications can be made to the capsid proteins without adversely altering vector tropism. In a particularly preferred embodiment, the vector capsid comprises one or more capsid proteins selected from the group consisting of:

(a) a hexon protein comprising the amino acid sequence of SEQ ID NO. 2 or a sequence substantially identical thereto;
(b) a penton protein comprising amino acid sequence of SEQ ID NO. 3 or a sequence substantially identical thereto; and
(c) a fibre protein comprising the amino acid sequence of SEQ ID NO. 4 or a sequence substantially identical thereto.

One of skill in the art will appreciate that the present invention can include variants of those particular amino acid sequences which are exemplified herein. Particularly preferred are variants having an amino acid sequence similar to that of the parent protein, in which one or more amino acid residues are substituted, deleted or added in any combination. Especially preferred are silent substitutions, additions and deletions, which do not alter the properties and activities of the protein of the present invention. Various amino acids have similar properties, and one or more such amino acids of a substance can often be substituted by one or more other such amino acids without eliminating a desired activity of that substance. Thus, the amino acids glycine, alanine, valine, leucine and isoleucine can often be substituted for one another (amino acids having aliphatic side chains). Of these possible substitutions it is preferred that glycine and alanine are used to substitute for one another (since they have relatively short side chains) and that valine, leucine and isoleucine are used to substitute for one another (since they have larger aliphatic side chains which are hydrophobic). Other amino acids which can often be substituted for one another include: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains); and cysteine and methionine (amino acids having sulphur containing side chains). Variants include naturally occurring and artificial variants. Artificial variants may be generated using mutagenesis techniques, including those applied to nucleic acid molecules, cells or organisms. Preferably, the variants have substantial identity to the amino acid sequences exemplified herein.

As used herein, amino acid sequences which have "substantial identity" preferably have at least 80%, 90%, 91%, 92%, 93%, 94%, 95% 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8% or 99.9% identity with said sequences. Desirably, the term "substantial identity" indicates that said sequence has a greater degree of identity with any of the sequences described herein than with prior art amino acid sequences.

One can use a program such as the CLUSTAL program to compare amino acid sequences. This program compares amino acid sequences and finds the optimal alignment by inserting spaces in either sequence as appropriate. It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. The above applied mutatis mutandis to all amino acid sequences disclosed in the present application.

Preferably, the hexon protein comprises an amino acid sequence at least 98.2% identical to SEQ ID NO. 2. Preferably, the penton protein comprises an amino acid sequence at least 98.3% identical to SEQ ID NO. 3. Preferably, the fiber protein comprises an amino acid sequence at least 99.1% identical to SEQ ID NO. 4.

The nucleotide sequences for the AdY25 hexon, penton and fibre proteins are set out in nucleotides 18302 to 21130 of SEQ ID NO. 1 (hexon protein), nucleotides 13891 to 15486 of SEQ ID NO. 1 (penton protein) and nucleotides 32290-33621 of SEQ ID NO. 1 (fibre protein). The vector capsid may comprise one or more AdY25 capsid proteins encoded by these nucleotide sequences or sequences substantially identical thereto.

The vector according to the second aspect of the present invention may comprise one of the hexon, penton and fibre proteins as described above, any combination of two of said proteins, or all three of said proteins.

The vector of the present invention also comprises a nucleic acid molecule. As a minimum, the nucleic acid molecule comprises an exogenous nucleotide sequence of interest, operably linked to expression control sequences which direct the translation, transcription and/or expression thereof in an animal cell and an adenoviral packaging signal sequence.

Preferably, the exogenous nucleotide sequence encodes a molecule of interest. The molecule of interest may be a protein, polypeptide or nucleic acid molecule of interest. The exogenous nucleotide sequence may encode one or more, two or more or three or more molecules of interest.

Proteins and polypeptides of interest include antigens, molecular adjuvants, immunostimulatory proteins and recombinases.

Preferably, the protein or polypeptide of interest is an antigen. In one embodiment, the antigen is a pathogen-derived antigen. Preferably, the pathogen is selected from the group consisting of bacteria, viruses, prions, fungi, protists and helminthes. Preferably, the antigen is derived from the group consisting of *M. tuberculosis, Plasomodium* sp, influenza virus, HIV, Hepatitis C virus, Cytomegalovirus, Human papilloma virus, malaria parasites, leishmania parasites or any mycobacterial species. Preferred antigens include TRAP, MSP-1, AMA-1 and CSP from *Plasmodium*, influenza virus antigens and ESAT6, TB10.4 85A and 85B antigens from *Mycobacterium tuberculosis*. Particularly preferred antigens include Ag85A from *Mycobacterium tuberculosis* and nucleoprotein (NP) and matrix protein 1 (M1) from influenza A virus, preferably Influenza A virus.

In an alternative embodiment, the antigen is a self-antigen. Suitable self-antigens include antigens expressed by tumour cells which allow the immune system to differentiate between tumour cells and other cell types. Suitable self-antigens include antigens that are either inappropriate for the cell type and/or its environment, or are only normally present during the organisms' development (e.g. foetal antigens). For example, GD2 is normally only expressed at a significant level on the outer surface membranes of neuronal cells, where its exposure to the immune system is limited by the blood-brain barrier. However, GD2 is expressed on the surfaces of a wide range of tumour cells including small-cell lung cancer, neuroblastoma, melanomas and osteosarcomas. Other suitable self-antigens include cell-surface receptors that are found on tumour cells but are rare or absent on the surface of healthy cells. Such receptors may be responsible for activating cellular signalling pathways that result in the unregulated growth and division of the tumour cell. For example, ErbB2 is produced at abnormally high levels on the surface of breast cancer tumour cells. Preferably, the self antigen comprises a tumour-associated antigen (TAA).

As used herein, the term 'antigen' encompasses one or more epitopes from an antigen and includes the parent antigen, and fragments and variants thereof. These fragments and variants retain essentially the same biological activity or function as the parent antigen. Preferably, they retain or improve upon the antigenicity and/or immunogenicity of the parent antigen. Generally, "antigenic" is taken to mean that the protein or polypeptide is capable of being used to raise antibodies or T cells or indeed is capable of inducing an antibody or T cell response in a subject. "Immunogenic" is taken to mean that the protein or polypeptide is capable of eliciting a potent and preferably a protective immune response in a subject. Thus, in the latter case, the protein or polypeptide may be capable of generating an antibody response and a non-antibody based immune response.

Preferably, fragments of the antigens comprise at least n consecutive amino acids from the sequence of the parent antigen, wherein n is preferably at least, or more than, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 57, 58, 59, 60, 70, 80, 90 or 100. The fragments preferably include one or more epitopic regions from the parent antigen. Indeed, the fragment may comprise or consist of an epitope from the parent antigen. Alternatively, the fragment may be sufficiently similar to such regions to retain their antigenic/immunogenic properties.

The antigens of the present invention include variants such as derivatives, analogues, homologues or functional equivalents of the parent antigen. Particularly preferred are derivatives, analogues, homologues or functional equivalents having an amino acid sequence similar to that of the parent antigen, in which one or more amino acid residues are substituted, deleted or added in any combination. Preferably, these variants retain an antigenic determinant or epitope in common with the parent antigen.

Preferably, the derivatives, analogues, homologues, and functional equivalents have an amino acid sequence substantially identical to amino acid sequence of the parent antigen.

The exogeneous nucleotide sequence may encode more than one antigen. The viral vector may be designed to express the one or more antigen genes as an epitope string. Preferably, the epitopes in a string of multiple epitopes are linked together without intervening sequences such that unnecessary nucleic acid and/or amino acid material is avoided. The creation of the epitope string is preferably achieved using a recombinant DNA construct that encodes the amino acid sequence of the epitope string, with the DNA encoding the one or more epitopes in the same reading frame. An exemplary antigen, TIPeGFP, comprises an epitope string which includes the following epitopes: E6FP, SIV-gag, PyCD4 and Py3. Alternatively, the antigens may be expressed as separate polypeptides.

One or more of the antigens or antigen genes may be truncated at the C-terminus and/or the N-terminus. This may facilitate cloning and construction of the vectored vaccine and/or enhance the immunogenicity or antigenicity of the antigen. Methods for truncation will be known to those of skill in the art. For example, various well-known techniques of genetic engineering can be used to selectively delete the encoding nucleic acid sequence at either end of the antigen gene, and then insert the desired coding sequence into the viral vector. For example, truncations of the candidate protein are created using 3' and/or 5' exonuclease strategies selectively to erode the 3' and/or 5' ends of the encoding nucleic acid, respectively. Preferably, the wild type gene sequence is truncated such that the expressed antigen is truncated by 1, 2, 3, 4, 5, 6, 7, 8, 9, 10, 11, 12, 13, 14, 15, 16, 17, 18, 19, 20 or more amino acids relative to the parent antigen. Preferably, the antigen gene is truncated by 10-20 amino acids at the C-terminus relative to the wild type antigen. More preferably, the antigen gene is truncated by 13-18 amino acids, most preferably by 15 amino acids at the C-terminus relative to the wild type antigen. Preferably, the Ag85A antigen is C-terminally truncated in this manner.

One or more of the antigen genes may also comprise a leader sequence. The leader sequence may affect processing of the primary transcript to mRNA, translation efficiency, mRNA stability, and may enhance expression and/or immunogenicity of the antigen. Preferably, the leader sequence is tissue plasminogen activator (tPA). Preferably, the tPA leader sequence is positioned N-terminal to the one or more antigens.

The leader sequence such as the tPA leaders sequence may be linked to the sequence of the antigen via a peptide linker. Peptide linkers are generally from 2 to about 50 amino acids in length, and can have any sequence, provided that it does not form a secondary structure that would interfere with domain folding of the fusion protein.

One or more of the antigen genes may comprise a marker such as the Green Fluorescent Protein (GFP) marker to facilitate detection of the expressed product of the inserted gene sequence.

One or more of the antigen genes may comprise a nucleic acid sequence encoding a tag polypeptide that is covalently linked to the antigen upon translation. Preferably the tag polypeptide is selected from the group consisting of a PK tag, a FLAG tag, a MYC tag, a polyhistidine tag or any tag that can be detected by a monoclonal antibody. The nucleic acid sequence encoding the tag polypeptide may be positioned such that, following translation, the tag is located at the C-terminus or the N-terminus of the expressed antigen or may be internal to the expressed antigen. Preferably, the tag is located at the C-terminus of the expressed antigen. In a preferred embodiment, one or more of the antigen genes encode a PK tag. A tag of this type may facilitate detection of antigen expression and clones expressing the antigen, and/or enhance the immunogenicity or antigenicity of the antigen.

If a tag polypeptide is used, nucleotides encoding a linker sequence are preferably inserted between the nucleic acid encoding the tag polypeptide and the nucleic acid encoding the expressed antigen. An exemplary linker is IPNPLLGLD (SEQ ID NO. 49).

In an alternative embodiment, the exogeneous sequence of interest may be non-protein encoding. For example, the exogeneous nucleotide sequence may be an miRNA or immunostimulatory RNA sequence.

The adenoviral vector may comprise one or more exogeneous nucleotide sequences, for example 1, 2 or 3 or more exogeneous nucleotide sequences. Preferably, each exogeneous nucleotide sequence embodies a transgene. The exogeneous nucleotide sequence embodying the transgene can be a gene or a functional part of the gene. The adenoviral vector may comprise one nucleotide sequence encoding a single molecule of interest. Alternatively, the adenoviral vector may comprise one nucleotide sequence or more than one nucleotide sequence encoding more than one molecule of interest.

Preferably, the exogeneous nucleotide sequence is located in a nucleic acid molecule that contains other, adenoviral sequences. The exogeneous nucleotide sequence may be inserted into the site of a partially or fully deleted AdY25 gene, for example into the site of an E1 deletion or an E3 deletion. The exogeneous nucleotide sequence may be inserted into an existing AdY25 gene region to disrupt the function of that region. Alternatively, the exogeneous nucleotide sequence may be inserted into a region of the AdY25 genome with no alteration to the function or seqeuence of the surrounding genes.

The exogeneous nucleotide sequence or transgene is preferably operably linked to regulatory sequences necessary to drive translation, transcription and/or expression of the exogeneous nucleotide sequence/transgene in a host cell, for example a mammalian cell. As used herein, the phrase "operably linked" means that the regulatory sequences are contiguous with the nucleic acid sequences they regulate or that said regulatory sequences act in trans, or at a distance, to control the regulated nucleic acid sequence. Such regulatory sequences include appropriate expression control sequences such as transcription initiation, termination, enhancer and promoter sequences, efficient RNA processing signals, such as splicing and polyadenylation signals, sequences that enhance translation efficiency and protein stability and sequences promote protein secretion. Additionally they may contain sequences for repression of transgene expression, for example during production in cell lines expression a transactivating receptor. Promoters and other regulatory sequences which control expression of a nucleic acid have been identified and are known in the art. Preferably, the promoter is selected from the group consisting of human CMV promoters, simian CMV promoters, murine CMV promoters, ubiquitin, the EF1 promoter, frog EF1 promoter, actin and other mammalian promoters. Most preferred are human CMV promoters and in particular the human CMV major immediate early promoter.

The exogeneous nucleotide sequence(s) of interest may be introduced into the viral vector as part of a cassette. As used herein, the term "cassette" refers to a nucleic acid molecule comprising at least one nucleotide sequence to be expressed, along with its transcriptional and translational control sequences to allow the expression of the nucleotide sequence(s) in a host cell, and optionally restriction sites at the 5' and 3' ends of the cassette. Because of the restriction endonuclease sites, the cassettes can easily be inserted, removed or replaced with another cassette. Changing the cassette will result in the expression of different sequence(s) by the vector into which the cassette is incorporated. Alternatively, any method known to one of skill in the art could be used to construct, modify or derive said cassette, for example PCR mutagenesis, In-Fusion®, recombineering, Gateway® cloning, site-specific recombination or topoisomerase cloning.

The expression control sequences preferably include the adenovirus elements necessary for replication and virion encapsidation. Preferably, the elements flank the exogeneous nucleotide sequence. Preferably, the Y25 vector comprises the 5' inverted terminal repeat (ITR) sequences of Y25, which function as origins of replication, and 3' ITR sequences.

The packaging signal sequence functions to direct the assembly of the viral vector.

As one of skill in the art will appreciate, there are minimum and maximum contraints upon the length of the nucleic acid molecule that can be encapsidated in the viral vector. Therefore, if required, the nucleic acid molecule may also comprise "stuffing", i.e. extra nucleotide sequence to bring the final vector genome up to the required size. Preferably, the nucleic acid molecule comprises sufficient "stuffing" to ensure that the nucleic acid molecule is about 80% to about 108% of the length of the wild-type nucleic acid molecule.

The nucleic acid molecule may also comprise one or more genes or loci from the AdY25 genome. The wildtype AdY25 genome comprises 4 early transcriptional units (E1, E2, E3 and E4), which have mainly regulatory functions and prepare the host cell for viral replication. The genome also comprises 5 late transcriptional units (L1, L2, L3, L4 and L5), which encode structural proteins including the penton (L2), the hexon (L3), the scaffolding protein (L4) and the fiber protein (L5), which are under the control of a single promoter. Each extremity of the genome comprises an Inverted Terminal Repeat (ITR) which is necessary for viral replication. The viral vector of the present invention may comprise the complete native AdY25 genome, into which the exogeneous nucleotide sequence has been inserted. However, one of skill in the art will appreciate that various modifications to the native AdY25 genome are possible, and indeed desirable, when creating a viral vector.

One or more native AdY25 genes may be deleted, functionally deleted or modified to optimise the viral vector. As used herein, the phrase "deleted" refers to total deletion of a gene, whilst "functional deletion" refers to a partial deletion of a gene/locus, or some other modification such as a frame shift mutation, which destroys the ability of the adenovirus to express the gene/locus or renders the gene product non-functional. The AdY25 genome may be modified to increase the insert capacity or hinder replication in host cells and/or increase growth and yield of the viral vector in transformed packaging cell lines. One of skill in the art will appreciate that any number of early or late genes can be functionally deleted. Replication of such modified viral vectors will still be possible in transformed cell lines which comprise a complement of the deleted genes. For example, the viral proteins necessary for replication and assembly can be provided in trans by engineered packaging cell lines or by a helper virus.

Therefore, in addition to the exogeneous nucleotide sequence, the vector of the present invention may comprise the minimal adenoviral sequences, the adenoviral genome with one or more deletions or functional deletions of particular genes, or the complete native adenoviral genome, into which has been inserted the exogeneous nucleotide sequence.

Preferably, the vector of the present invention comprises the native Y25 late transcriptional units (L1-L5) and/or the native Y25 Inverted Terminal Repeats (ITR) or sequences substantially identical thereto. The amino acid sequences of the native L1, L2, L3, L4, L5 loci, and the corresponding nucleic sequences, are set out in Table 1, above.

Preferably, one or more of the early transcriptional units are modified, deleted or functionally deleted.

In one embodiment, the viral vector is non-replicating or replication-impaired. As used herein, the term "non-replicating" or "replication-impaired" means not capable of replicating to any significant extent in the majority of normal mammalian cells, preferably normal human cells. It is preferred that the viral vector is incapable of causing a productive infection or disease in the human patient. However, the viral vector is preferably capable of stimulating an immune response. Viruses which are non-replicating or replication-impaired may have become so naturally, i.e. they may be isolated as such from nature. Alternatively, the viruses may be rendered non-replicating or replication-impaired artificially, e.g. by breeding in vitro or by genetic manipulation. For example, a gene which is critical for replication may be functionally deleted. Preferably, the adenoviral vector replication is rendered incompetent by functional deletion of a single transcriptional unit which is essential for viral replication. Preferably, the E1 gene/locus is deleted or functionally deleted. The E1 gene/locus may be replaced with a heterologous transgene, for example a nucleotide sequence or expression cassette encoding a protein or polypeptide of interest.

The wildtype AdY25 E1 amino acid sequence, and the corresponding nucleic acid sequence, are set out in Table 1, above.

As discussed herein, the recombinant adenovirus may be created by generating a molecular clone of AdY25 in a Bacterial Artificial Chromosome (BAC), and the E1 locus is preferably deleted by including an extra homology flank downstream of the adenovirus E1 region to enable simultaneous deletion of E1 during homologous recombination between the AdY25 viral DNA and a linearised BAC "rescue vector", as described in Example 1.

Preferably, the viral vector according to the present invention comprises one or more recombination sites to enable the insertion of one or more transgenes or cassettes comprising the exogeneous nucleotide sequence. Preferably, the recombination sites comprise phage lambda site specific recombination sites. These recombination sites may be introduced at any suitable locus, but are preferably introduced at the Ad E1 locus. Thus, the non-replicating or replication-impaired vector may be prepared by replacing the E1 gene with a nucleotide sequence encoding the protein or polypeptide of interest. Preferably, the recombination sites attR1 and attR2 are introduced at the Ad E1 locus as part of an Invitrogen Gateway® destination cassette as described in Example 1.

Preferably, the vector lacks an adenovirus E3 gene/locus. Deletion of the adenovirus E3 region increases the insert capacity of the new vector by approximately 5 kb. Deletion of E3 has little consequence to viral vector yield since this region is not required for virus replication and therefore does not need to be provided in trans in the packaging cell line. The E3 locus may be deleted using GalK recombineering as described in Example 2.

The wildtype AdY25 E3 amino acid sequence, and the corresponding nucleic acid sequence, are set out in Table 1, above.

In a particularly preferred embodiment of the present invention, both the E1 and E3 loci are deleted from the AdY25 genome.

Preferably, the vector of the present invention comprises the native E2 locus. E2 is a transcriptional unit comprising the open reading frames encoding the Polymerase, PTP and IVa2 proteins. The wildtype AdY25 E4 amino acid sequence, and the corresponding nucleotide sequence, are set out in Table 1, above. Preferably, the vector of the present invention comprises a nucleotide sequence encoding E2 or a sequence substantially identical thereto.

As stated above, the viral vectors of the present invention may be produced in engineered cell lines containing a complement of any deleted genes required for viral replication. However, replication of viral vectors according to the present invention may be sub-optimal in cells designed to facilitate replication of other serotypes. For example, as shown in FIG. 3A, the first generation of AdY25-based vectors comprising the wildtype E4 locus were found to grow inefficiently in HEK293 cells and yield was approximately two logs lower than for comparable AdHu5-based vectors. It is hypothesized that the low yield resulted from suboptimal interaction between the cell-expressed E1 proteins (designed to support propagation of AdHu5 viruses) and vector-encoded E4 gene products. Therefore, the adenoviral vectors according to the present invention preferably further comprise one or more modifications designed to optimise vector growth and yield in transformed cell lines, such as HEK293, expressing the genes functionally deleted in the adenoviral vector according to the present invention.

In one embodiment, the native E4 region may be replaced in its entirety with a heterologous E4 region from other serotype(s), which heterologous E4 region preferably increases vector yield and growth in a transformed cell line. For example, the native E4 region may be replaced with the E4 region from AdHu5 to increase vector yield and growth in HEK293.

The adenovirus E4 region comprises at least 6 Open Reading Frames (ORFs or Orfs). Thus, in an alternative embodiment, one or more of the ORFs in the E4 region may be replaced with one or more heterologous ORFs from the E4 region of other adenoviral serotype(s), which heterologous ORF(s) preferably increase(s) vector yield and growth in a transformed cell line. Preferably, 1, 2, 3, 4, 5 or 6 ORFs in the E4 region may be replaced 1, 2, 3, 4, 5 or 6 heterologous ORFs from the E4 region of other serotype(s), e.g. AdHu5.

Of particular importance for viral replication in HEK293 cells is the gene product of E4Orf6, a multifunctional protein implicated in late viral mRNA splicing and selective export of viral mRNA, viral DNA synthesis and inhibition of apoptosis. Suboptimal interaction between E4Orf6 and the cell-expressed E1B-55K is believed to reduce the yield of AdChOX1 vectors in HEK293 cells. Therefore, the native E4Orf6 region may be replaced with a heterologous E4Orf6 region. For example, the entire native E4 locus may be replaced with the E4Orf6 gene from AdHu5, as described in Example 3. The amino acid sequence of E4Orf6 from AdHu5 is found in SEQ ID NO. 40. A corresponding nucleotide sequence is found at nucleotides 28248 to 29132 of SEQ ID NO. 38. In one embodiment, the vector of the present invention comprises the nucleotide sequence of AdHu5E4Orf6 or a sequence substantially identical thereto. As described in Example 3 and shown in FIG. 3A, this modification was found to improve viral yield and growth.

In a preferred embodiment, more than one ORF in the E4 region is replaced with more than one heterologous ORF from the E4 region of other serotype(s). For example, native E4Orf4, E4Orf6 and E4Orf7 may be replaced with the E4Orf4, E4Orf6 and E4Orf6/7 coding regions from AdHu5. In a particularly preferred embodiment, the recombinant E4 region comprises the E4Orf1, E4Orf2 and E4Orf3 coding regions from AdY25 and the E4Orf4, E4Orf6 and E4Orf6/7 coding regions from AdHu5. The amino acid sequence of E4Orf4 from AdHu5 is found in SEQ ID NO. 41. A corresponding nucleotide sequence is found at nucleotides 29053 to 29397 of SEQ ID NO. 38. The amino acid sequence of the E4Orf6 from AdHu5 is found in SEQ ID NO. 40. A corresponding nucleotide sequence is found at nucleotides 28248 to 29132 of SEQ ID NO. 38. The amino acid sequence of the E4Orf6/7 from AdHu5 is found in SEQ ID NO. 39. A corresponding nucleotide sequence is found at nucleotides 28959 to 29132 and 27969 to 28247 of SEQ ID NO. 38. In one embodiment, the vector of the present invention comprises the nucleotide sequences of AdHu5 E4Orf4, E4Orf6 and E4Orf6/7 or sequences substantially identical thereto.

In a particularly preferred embodiment of the present invention, the genome of the viral vector according to the present invention lacks the nucleotide sequences which encode the adenovirus E1 and E3 regions, and has the native E4 locus replaced with E4Orf4, E4Orf6 and E4Orf6/7 coding regions from AdHu5, and the E4Orf1, E4Orf2 and E4Orf3 coding regions from AdY25. This particularly preferred embodiment is referred to herein interchangeably as "ChAdOX1" or "AdChOX1". As described in Example 3, and shown in FIG. 3A, the modification of the vector in this way was surprisingly found to increase the rate of hexon production and the growth and replication of the virus.

An exemplary nucleotide sequence encoding ChAdOX1 is set out in SEQ ID NO. 38. In this embodiment, E1A, E1B 19 kDa and E1B 55 kDa are deleted and replaced with a Gateway® Destination Cassette (nucleotides 592 to 2550 of SEQ ID NO. 38). E3 CR1a1, E3 gp19 kDa, E3 22.3 kDa, E3 31 kDa, E3 10.4 kDa, E3 15.2 kDa and E3 14.7 kDa are deleted and replaced with a PacI site (nucleotides 26286 to 26293 of SEQ ID NO. 38). The native E4 region is deleted and replaced with E4Orf4, E4Orf6 and E4Orf6/7 coding regions from AdHu5, and the E4Orf1, E4Orf2 and E4Orf3 coding regions from AdY25, as described above. The viral vector encoded by SEQ ID NO. 38 also comprises a number of wild-type AdY25 proteins, the nucleotide sequences of which are set out in Table 2, below:

TABLE 2

| Protein | Corresponding nucleotides in SEQ ID NO. 38 |
|---|---|
| pIX | 2638 to 3066 |
| IVa2 | 4734 to 4749 and 3125 to 4458 |
| Polymerase | 12985 to 12993 and 4228 to 7809 |
| pTP | 12985 to 12993 and 7610 to 9539 |
| 52/55 kD | 9974 to 11164 |
| IIIa | 11188 to 12954 |
| Penton | 13038 to 14633 |
| VII | 14640 to 15221 |
| V | 15266 to 16288 |
| Mu | 16308 to 16541 |
| VI | 16617 to 17348 |
| Hexon | 17449 to 20277 |
| Endoprotease | 20293 to 20922 |
| DNA Binding Protein | 20999 to 22537 |
| 100 kDa | 22566 to 24974 |
| 22K | 24691 to 25245 |
| 33K | 24691 to 25018, 25188 . . . 25519 |
| VIII | 25602 to 26285 |
| Fiber | 26543 to 27874 |
| E4Orf3 | 29406 to 29759 |
| E4Orf2 | 29756 to 30145 |
| E4Orf1 | 30195 to 30569 |

Preferably, the genome of the viral vector according to the present invention comprises the nucleotide sequence of SEQ ID NO. 38 or a sequence substantially identical thereto, into which is inserted the exogenous nucleotide sequence encoding the protein of interest.

As described in Example 5 and shown in FIG. 5, modification of the E4 region was found to have little impact on immunogenicity of the viral vector, but did improve the rate of viral growth and replication. Therefore, such E4 modifications can be used to enhance the rate of production of the viral vectors, but will not have a negative impact on the immunogenicity of the vectors.

Example 4 and FIG. 4 demonstrate that the immune responses elicited by the AdY25-based vector ChAdOX1 are robust and comparable to those elicited by AdCh63 (also known as ChAd63) and AdCh68 (also known as AdC68, ChAd68, C9 or SAdV-25). However, the humoral immunogenicity of ChAdOX1 was found to be superior to that of AdCh68, as described in Example 7 and FIG. 7. One of skill in the art would expect T-cell responses and antibody responses to correlate fully with one another. The superiority of the humoral responses to ChAdOX1 is therefore surprising.

The prevalence of vector neutralising antibodies in human sera from the UK and the Gambia was also surprisingly found to be much lower for the AdY25-based vectors than for another chimpanzee adenoviral vector, AdCh63 (see Example 6 and FIG. 6). This data suggest that vectors based on AdY25 may encounter less pre-existing immunity within the human population, not only in comparison to vectors based on human adenoviruses, but also in comparison to other existing vectors based on chimpanzee adenoviruses.

Example 8 and FIGS. 8A and 8B demonstrate that ChAdOX1 is capable of inducing immune responses against *Mycobacterium tuberculosis*, whilst Example 9 and FIG. 9 demonstrate that ChAdOX1 is capable of inducing immune responses against Influenza A.

A third aspect of the present invention provides a pharmaceutical or immunogenic composition comprising the viral vector according to the second aspect of the present invention optionally in combination with one or more additional active ingredients, a pharmaceutically acceptable carrier, diluent, excipient or adjuvant.

Preferably, the composition is an immunogenic and/or antigenic composition. The immunogenic and/or antigenic compositions according to the present invention may be prophylactic (to prevent infection), post-exposure (to treat after infection but before disease) or therapeutic (to treat disease). Preferably, the composition is prophylactic or post-exposure. Preferably, the composition is a vaccine.

Where the immunogenic composition is for prophylactic use, the subject is preferably an infant, young child, older child or teenager. Where the immunogenic composition is for therapeutic use, the subject is preferably an adult.

The composition may comprise one or more additional active agents, such as an anti-inflammatory agent (for example a p38 inhibitor, glutamate receptor antagonist, or a calcium channel antagonist), AMPA receptor antagonist, a chemotherapeutic agent and/or an antiproliferative agent. The composition may also comprise one or more antimicrobial compounds. Examples of suitable antimicrobial compounds include antituberculous chemotherapeutics such as rifampicin, isoniazid, ethambutol and pyrizinamide.

Suitable carriers and/or diluents are well known in the art and include pharmaceutical grade starch, mannitol, lactose, magnesium stearate, sodium saccharin, talcum, cellulose, glucose, sucrose, (or other sugar), magnesium carbonate, gelatin, oil, alcohol, detergents, emulsifiers or water (preferably sterile). The composition may be a mixed preparation of a composition or may be a combined preparation for simultaneous, separate or sequential use (including administration).

Suitable adjuvants are well known in the art and include incomplete Freund's adjuvant, complete Freund's adjuvant, Freund's adjuvant with MDP (muramyldipeptide), alum (aluminium hydroxide), alum plus *Bordatella pertussis* and immune stimulatory complexes (ISCOMs, typically a matrix of Quil A containing viral proteins).

The composition according to the invention for use in the aforementioned indications may be administered by any convenient method, for example by oral (including by inhalation), parenteral, mucosal (e.g. buccal, sublingual, nasal), rectal or transdermal administration and the compositions adapted accordingly.

For oral administration, the composition can be formulated as liquids or solids, for example solutions, syrups, suspensions or emulsions, tablets, capsules and lozenges.

A liquid formulation will generally consist of a suspension or solution of the compound or physiologically acceptable salt in a suitable aqueous or non-aqueous liquid carrier(s) for example water, ethanol, glycerine, polyethylene glycol or oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and microcrystalline cellulose.

A composition in the form of a capsule can be prepared using routine encapsulation procedures. For example, powders, granules or pellets containing the active ingredient can be prepared using standard carriers and then filled into a hard gelatine capsule; alternatively, a dispersion or suspension can be prepared using any suitable pharmaceutical carrier(s), for example aqueous gums, celluloses, silicates or oils and the dispersion or suspension then filled into a soft gelatine capsule.

Compositions for oral administration may be designed to protect the active ingredient against degradation as it passes through the alimentary tract, for example by an outer coating of the formulation on a tablet or capsule.

Typical parenteral compositions consist of a solution or suspension of the compound or physiologically acceptable salt in a sterile aqueous or non-aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal or oral administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve, which is intended for disposal once the contents of the container have been exhausted. Where the dosage form comprises an aerosol dispenser, it will contain a pharmaceutically acceptable propellant. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal or vaginal administration are conveniently in the form of suppositories (containing a conventional suppository base such as cocoa butter), pessaries, vaginal tabs, foams or enemas.

Compositions suitable for transdermal administration include ointments, gels, patches and injections including powder injections.

Conveniently the composition is in unit dose form such as a tablet, capsule or ampoule.

The pharmaceutical composition is preferably sterile. It is preferably pyrogen-free. It is preferably buffered e.g. at between pH 6 and pH 8, generally around pH 7. Preferably, the composition is substantially isotonic with humans.

Preferably, the pharmaceutical compositions of the present invention deliver an immunogenically or pharmaceutically effective amount of the viral vector to a patient.

As used herein 'immunogenically or pharmaceutically effective amount' means that the administration of that amount to an individual, either as a single dose or as a series of doses, is effective for prevention or treatment of a disease or condition. In particular, this phrase means that a sufficient amount of the viral vector is delivered to the patient over a suitable timeframe such that a sufficient amount of the antigen is produced by the patient's cells to stimulate an immune response which is effective for prevention or treatment of a disease or condition. This amount varies depending on the health and physical condition of the individual to be treated, age, the capacity of the individual's immune system, the degree of protection desired, the formulation of the vaccine, the doctor's assessment of the medical situation and other relevant factors.

In general, a pharmaceutically effective dose comprises $1\times10^7$ to $1\times10^{12}$ viral particles, preferably $1\times10^{10}$ to $1\times10^{11}$ particles.

The immunogenic composition of the present invention may also comprise one or more other viral vectors, preferably other adenoviral vectors.

A fourth aspect of the present invention provides the use of the viral vector according to the second aspect of the present invention or the immunogenic composition according to the third aspect of the present invention. In particular, the fourth aspect provides the use of the viral vector or the immunogenic composition of the present invention in medicine.

This aspect also provides: i) the viral vector or the immunogenic composition according to the present invention for use in medicine and ii) the use of the viral vector or the immunogenic composition according to the present invention in the manufacture of a medicament for use in medicine. Some exemplary medical uses are described in further detail below.

In one embodiment, the viral vector according to the second aspect of the present invention or the immunogenic composition according to the third aspect of the present invention may be used to deliver a transgene into a host cell.

This method preferably comprises the step of administering to said host cell a viral vector according to the second aspect of the present invention or the immunogenic composition according to the third aspect of the present invention.

Preferably, the host cell is an animal cell, more preferably a mammalian cell. Preferred mammals include chickens, other poultry, cows, sheep, goats, pigs, wild boar, buffalo, bison, horses, camelids, deer, elephants, badgers, possums, cats, lions, monkeys and humans. Preferably, the host cell is a somatic cell. The host cell may be selected from the group consisting of an antigen-presenting dendritic cell, langerhans cell, macrophage, B cell, lymphocyte, leukocyte, myocyte and fibroblast.

This method may be carried out in vitro or in vivo. Where the method is carried out in vitro, the viral vector or immunogenic composition is brought into contact with the host cell under suitable conditions such that transduction or non-productive infection of the host cell with the viral vector is facilitated. In this embodiment, the host cell may comprise an isolated host cell or a sample from an animal subject. Where the method is carried out in vivo, the viral vector or immunogenic composition is preferably administered to the animal subject such that transduction of one or more cells of the subject with the viral vector is facilitated. Preferably, the viral vector or immunogenic composition is administered to the subject by oral (including by inhalation), parenteral, mucosal (e.g. buccal, sublingual, nasal), rectal or transdermal administration.

Preferably, the transduction of the host cell with the viral vector of the present invention results in the stable delivery of the exogeneous nucleotide sequence of interest into the host cell.

Therefore, in another embodiment, the viral vector according to the second aspect of the present invention or the immunogenic composition according to the third aspect of the present invention may be used to elicit an immune response in an animal. This method preferably comprises the step of administering to said animal a viral vector according to the second aspect of the present invention or the immunogenic composition according to the third aspect of the present invention.

Where the protein or polypeptide of interest is an antigen, expression of the protein or polypeptide in an animal will result in the elicitation of a primary immune response to that antigen, leading to the development of an immunological memory which will provide an enhanced response in the event of a secondary encounter, for example upon infection by the pathogen from which the antigen was derived.

Preferably, the animal is a naïve animal, i.e. an animal that has not previously been exposed to the pathogen or antigens in question.

As well as eliciting an immune response in an animal, the viral vector of the present invention or the immunogenic composition thereof can be used to boost the immune response of an animal previously exposed to the antigen.

Therefore, in a further embodiment, the viral vector according to the second aspect of the present invention or the immunogenic composition according to the third aspect of the present invention may be used to boost an immune response in an animal. This method preferably comprises the step of administering to said animal a viral vector according to the second aspect of the present invention or the immunogenic composition according to the third aspect of the present invention.

Preferably, the animal subject has been previously exposed to the antigen in question, or "primed". For example, the subject may have previously been inoculated or vaccinated with a composition comprising the antigen, or may have previously been infected with the pathogen from which the antigen was derived. The subject may be latently infected with the pathogen from which the antigen was derived.

In another embodiment, the vector according to the second aspect of the present invention or the immunogenic composition according to the third aspect of the present invention may be used to treat or prevent at least one disease in a patient. This method preferably comprising the step of administering to said patient a viral vector according to the second aspect of the present invention or the immunogenic composition according to the third aspect of the present invention.

Preferably, the disease is selected from the group consisting of Tuberculosis and other mycobacterial infections, malaria, influenza, HIV/AIDS, Hepatitis C, Cytomegalovirus infection, Human papilloma virus infection, adenoviral infection, leishmaniasis, *streptococcus* spp., *staphylococcus* spp., *meningococcus* spp., infection, rift valley fever, foot and mouth disease and chikungunya virus infection.

As well as inducing an immune response against the pathogenic organism from which the heterologous antigen is derived, the adenoviral vector of the present invention may also induce an immune response against the adenovirus from which the viral vector is derived. As such, an immune response against AdY25 may be elicited. The immune response induced against AdY25 may also be cross-reactive with other adenoviral serotypes, and as such an immune response against more than one adenovirus may be elicited. The viral vector according to the second aspect of the present invention or the immunogenic composition according to the third aspect of the present invention can therefore also be used for treating or preventing an adenoviral disease.

This embodiment of the present invention therefore also provides the treatment or prevention of at least one adenoviral disease and at least one non-adenoviral disease in a patient.

In a further embodiment, the viral vector according to the second aspect of the present invention or the immunogenic composition according to the third aspect of the present invention may be used to induce an immune response in an animal that will break tolerance to a self antigen. This method preferably comprises the step of administering to said animal a viral vector according to the second aspect of the present invention or the immunogenic composition according to the third aspect of the present invention.

Many tumour cells are tolerated by the patient's immune system, on the grounds that tumour cells are essentially the patient's own cells that are growing, dividing and spreading without proper regulatory control. Thus, cancerous tumours are able to grow unchecked within the patient's body. However, the viral vector of the present invention can be used to stimulate a patient's immune system to attack the tumour cells in a process known as "cancer immunotherapy". Specifically, the vector of the present invention can be used to 'train' the patient's immune system to recognise tumour cells as targets to be destroyed. This can be achieved by including within the viral vector an exogeneous nucleotide sequence encoding a suitable self-antigen. As described previously, suitable self-antigens include antigens expressed by tumour cells which allow the immune system to differentiate between tumour cells and other cell types. Suitable self-antigens include antigens that are either inappropriate for the cell type and/or its environment, or are only normally present during the organisms' development (e.g. foetal antigens). For example, GD2 is normally only expressed at a significant level on the outer surface membranes of neuronal cells, where its exposure to the immune system is limited by the blood-brain barrier. However, GD2 is expressed on the surfaces of a wide range of tumour cells including small-cell lung cancer, neuroblastoma, melanomas and osteosarcomas. Other suitable self-antigens include cell-surface receptors that are found on tumour cells but are rare or absent on the surface of healthy cells. Such receptors may be responsible for activating cellular signalling pathways that result in the unregulated growth and division of the tumour cell. For example, ErbB2 is produced at abnormally high levels on the surface of breast cancer tumour cells. Thus, the adenoviral vector of the present invention may be used to induce an immune response against a tumour cell, and can therefore be used in the treatment of cancer.

The following details apply mutatis mutandis to all of the above uses of the vector and immunogenic composition of the present invention.

The treatment and prevention of many diseases, including liver stage malaria, tuberculosis and influenza, are associated with the maintenance of a strong cell-mediated response to infection involving both CD4+ and CD8+ T cells and the ability to respond with Th1-type cytokines, particularly IFN-γ, TNF-α, IL-2 and IL-17. Although many subunit vaccine platforms effectively generate human immunity, the generation of robust cell-mediated immune responses, particularly CD4+ and CD8+ T cell immune responses, has been much more challenging. The viral vector of the present invention preferably stimulates both cellular and humoral immune responses against the encoded antigen.

It is also desirable to induce a memory immune response. Memory immune responses are classically attributed to the reactivation of long-lived, antigen-specific T lymphocytes that arise directly from differentiated effector T cells and persist in a uniformly quiescent state. Memory T cells have been shown to be heterogeneous and to comprise at least two subsets, endowed with different migratory capacity and effector function; effector memory T cells (TEM) and central memory T cells (CTM). TEM resemble the effector cells generated in the primary response in that they lack the lymph node-homing receptors L-selectin and CCR7 and express receptors for migration into inflamed tissues. Upon re-encounter with antigen, these TEM can rapidly produce IFN-γ or IL-4 or release pre-stored perform. TCM express L-selectin and CCR7 and lack immediate effector function. These cells have a low activation threshold and, upon restimulation in secondary lymphoid organs, proliferate and differentiate to effectors.

Preferably, the viral vector according to the second aspect of the present invention or the immunogenic composition according to the third aspect of the present invention is capable of eliciting, inducing or boosting an antigen-specific immune response. Preferably, the immune response is a strong T cell immune response, for example a strong CD8+ and CD4+ T cell response. Preferably, the T cell immune response is a protective T cell immune response. Preferably, the T cell immune response is long lasting and persists for at least 1, 2, 5, 10, 15, 20, 25 or more years. Preferably, the immune response induced is a memory T cell immune response.

The viral vector of the second aspect of the present invention or immunogenic composition according to the third aspect of the present invention may be administered to the host cell or subject either as a single immunisation or multiple immunisations. Preferably, the viral vector or immunogenic composition thereof are administered as part of a single, double or triple vaccination strategy. They may also be administered as part of a homologous or heterologous prime-boost immunisation regime.

The vaccination strategy or immunisation regime may include second or subsequent administrations of the viral vector or immunogenic composition of the present invention. The second administration can be administered over a short time period or over a long time period. The doses may be administered over a period of hours, days, weeks, months or years, for example up to or at least 1, 2, 3, 4, 5, 6, 7, 8, 9, or 10 or more weeks or 0.25, 0.5, 0.75, 1, 5, 10, 15, 20, 25, 30, 35 or 40 or more years after the first administration. Preferably, the second administration occurs at least 2 months after the first administration. Preferably, the second administration occurs up to 10 years after the first administration. These time intervals preferably apply mutatis mutandis to the period between any subsequent doses.

The viral vector and/or immunogenic composition may be administered alone or in combination with other viral or non-viral DNA/protein vaccines. Preferred examples include MVA, FP9 and other adenoviral vector vaccines.

The viral vector and/or immunogenic composition may be administered to the subject by oral (including by inhalation), parenteral, mucosal (e.g. buccal, sublingual, nasal), rectal or transdermal administration. Alternatively, the viral vector and/or immunogenic composition may be administered to an isolated host cell or sample from a subject by contacting the cell(s) with the viral vector or immunogenic composition in vitro under conditions that facilitate the transduction of the host cell with the viral vector.

The viral vector and immunogenic composition of the present invention are not limited to the delivery of nucleic acid sequences encoding antigens. Many diseases, including cancer, are associated with one or more deleterious mutant alleles in a patient's genome. Gene therapy is a process involving the insertion of genes into the patient's cells or tissues to replace the deleterious mutant or non-functional allele(s) with 'normal' or functional allele(s). Commonly, a functional allele is inserted into a non-specific location within the genome to replace the non-functional allele. Alternatively, the non-functional allele may be swapped for the functional allele through homologous recombination. Subsequent expression of the functional allele within the target cell restores the target cell to a normal state and thus provides a treatment for the disease. The 'normal' or functional allele(s) may be inserted into a patient's genome using a viral vector. The present invention therefore also provides the use of the viral vector according to the second aspect of the present invention or the immunogenic composition according to the third aspect of the present invention in gene therapy.

This method preferably comprises the step of administering to said animal a viral vector according to the second aspect of the present invention or the immunogenic composition according to the third aspect of the present invention.

The vector of the present invention may comprise an exogeneous nucleotide sequence encoding the functional or 'normal' protein, the non-functional or 'Mutant' version of which is associated with a disease or condition.

Preferably, the target cell is a somatic cell. The subject to be treated is preferably mammalian. Preferred mammals include chickens, other poultry, cows, sheep, goats, pigs, wild boar, buffalo, bison, horses, camelids, deer, elephants, badgers, possums, cats, lions, monkeys and humans.

A fifth aspect of the present invention provides a polynucleotide sequence encoding the viral vector according to the second aspect of the present invention. Preferably, the polynucleotide sequence comprises the sequence of SEQ ID NO. 38 or a sequence substantially identical thereto. The polynucleotide may additionally comprise the exogeneous nucleotide sequence of interest.

A sixth aspect of the present invention provides a host cell transduced or infected with the viral vector according to the second aspect of the present invention. Following transduction or infection, the host cell will express the exogeneous nucleotide sequence in the nucleic acid molecule to produce the molecule of interest, in addition to any other adenoviral proteins encoded by the nucleic acid molecule. Preferably, the host cell is stably transduced and suitable for viral propagation.

The host cell may be an isolated host cell, part of a tissue sample from an organism, or part of a multicellular organism or organ or tissue thereof.

Preferably, the host cell is a somatic cell. Preferably, the host cell is not a stem cell, more particularly an embryonic stem cell, more particularly a human embryonic stem cell.

The host cell may be selected from the group consisting of an antigen-presenting dendritic cell, langerhans cell, macrophage, B cell, lymphocyte, leukocyte, myocyte and fibroblast.

Preferably, the host cell is an animal cell, more preferably a mammalian cell.

Preferred mammals include chickens, other poultry, cows, sheep, goats, pigs, wild boar, buffalo, bison, horses, camelids, deer, elephants, badgers, possums, cats, lions, monkeys and humans.

The fifth aspect of the present invention also encompasses an animal transduced or infected with the viral vector according to the second aspect of the present invention. Preferably, the animal comprises one or more cells transformed or transfected with the viral vector according to the second aspect of the present invention. Preferably, the animal is a mammal. Preferred mammals include chickens, other poultry, cows, sheep, goats, pigs, wild boar, buffalo, bison, horses, camelids, deer, elephants, badgers, possums, cats, lions, monkeys and humans.

In a seventh aspect, the present invention provides a method of producing the viral vector according to the second aspect of the present invention. Preferably, the method comprises the step of incorporating a nucleotide sequence derived from AdY25 into a Bacterial Artificial Chromosome (BAC) to produce an Ad-BAC vector.

Unlike plasmid vectors, BACs are present within *E. Coli* in single copy conferring increased genetic stability. In addition, the single copy BAC vectors permit very precise modifications to be made to the viral genome by recombineering (recombination mediated genetic engineering).

Preferably, incorporation of the nucleotide sequence derived from AdY25 into a Bacterial Artificial Chromosome (BAC) comprises the steps of:
i) constructing a BAC rescue vector comprising regions of homology to the left and right flanks of the viral nucleotide sequence;
ii) linearising the BAC rescue vector; and
iii) performing homologous recombination in a host cell between the viral nucleotide sequence and the linearised BAC rescue vector to incorporate the viral nucleotide sequence into the BAC rescue vector.

Preferably, the nucleotide sequence incorporated into the BAC rescue vector comprises the sequence of SEQ ID NO. 1 or SEQ ID NO. 38 or a sequence substantially identical thereto.

Preferably, the method additionally comprises the step of further modifying the Ad-BAC vector genome. These further modifications may be carried out by GalK recombineering. This technique, pioneered by Soren Warming and colleagues, utilises the GalK gene for both positive and negative selection of recombinant clones[6]. SW102 *E. Coli* cells, in which recombination may be performed, have been specifically engineered to lack the GalK gene which is required for the utilisation of galactose as the sole carbon source. Gene deletion is performed by recombination between the vector genome and a PCR amplified GalK cassette, flanked by 50 bp regions of homology either side of the gene targeted for deletion. Selection on minimal media containing only galactose should ensure that only recombinants containing the GalK gene (in place of the target gene) should grow. Replacement of GalK with a different gene sequence can be performed in a similar fashion, this time using GalK for negative selection. The addition of 2-deoxygalactose (DOG) to selection media will select clones in which GalK has been replaced since the product of GalK, galactokinase, metabolises DOG into a product that is highly toxic to *E. Coli*. Preferably, the host cell is BJ5183 *E. Coli* for steps i) to iii) above and SW102 for further modifications.

Preferably, an extra homology flank is included downstream of the adenovirus E1 region to enable simultaneous deletion of E1, as described in Example 1.

Preferably, the method further includes deletion of the E3 region of the Ad-BAC vector genome. Deletion of the E3 region may be carried out by GalK recombineering, as described in Example 2.

Preferably, the method further includes modifying the E4 region to optimise vector growth and yield. In one embodiment, the entire native E4 locus is replaced with the E4Orf6 gene from AdHu5. In a second embodiment, the native E4 locus is replaced with E4Orf4, E4Orf6 and E4Orf6/7 coding regions from AdHu5, and the E4Orf1, E4Orf2 and E4Orf3 coding regions from AdY25, as described in Example 3.

Preferably, the method further includes introducing phage lambda site specific recombination sites attR1 and attR2 at the Ad E1 locus as part of an Invitrogen Gateway® destination cassette. Such a modification enables the efficient directional insertion of vaccine transgenes. Transgenes could also be inserted by recombineering, In-Fusion®, conventional ligation or gap repair.

An eighth aspect of the present invention provides a Bacterial Artificial Chromosome (BAC) clone comprising a polynucleotide sequence encoding the viral vector according to the second aspect of the present invention.

Preferably, the BAC clone comprises:
(a) a BAC backbone;
(b) the polynucleotide sequence according to the fifth aspect of the present invention.

As described above, the viral vector according to the second aspect of the present invention may be replicated in a transformed cell line or helper virus (gutless vector system) which, if necessary, comprises the complement of any genes deleted from the virus. Such genes may be deleted from the virus in order to hinder replication in host cells, but are of course required in order to replicate the viral vector to produce immunogenic compositions according to the second aspect of the present invention. One can make use of any cell line permissive of wild type adenovirus replication that has been modified to express the functionally deleted genes, or a cell line which is not permissive of wild-type virus replication which has additionally or alternatively been modified to express CAR or integrins in addition to the functionally deleted genes.

The present invention provides host cells comprising a Bacterial Artificial Chromosome (BAC) in accordance with the eighth aspect of the present invention, and suitable for propagation thereof. Preferably such host cells are bacteria, most preferably *E. coli*. Suitable examples include *E. coli* strains DH10B and SW102[9].

A ninth aspect of the present invention therefore provides a packaging cell or cell line producing or capable of producing the viral vector according to the second aspect of the present invention. The packaging cell or cell line comprises one or more nucleotide sequences which encode the viral vector of the second aspect of the present invention. Expression of these sequences results in the production of the viral vector. Some of the required genes may be provided by infection of the cell or cell line with a viral vector according to the second aspect. Preferably, the cell comprises the complement of any genes deleted or functionally deleted from the viral vector. Preferably, the cell comprises the complement of the AdY25 E1 gene. Preferably, the cell is an HEK293 cell or a PER.C6® cell.

As described above, modification of the E4 locus of the adenoviral vector to include the E4Orf4, E4Orf6 and E4Orf6/7 coding regions from AdHu5 increased the rate of hexon production, increasing the sensitivity of anti-hexon titre to allow quantification of the infectious titre of the viral vector, in particular those viral vectors developed for clinical use which do not contain a fluorescent marker gene. In addition, this modification was surprisingly found to increase the yield and rate of growth of the vector. One of skill in the art would appreciate that such a modification is expected to have a beneficial effect on a wide variety of adenoviruses, and not simply those derived from AdY25.

A tenth aspect of the present invention therefore provides an adenoviral vector other than AdHu5 comprising a nucleic acid molecule, wherein said nucleic acid molecule comprises heterologous E4Orf4, E4Orf6 and E4Orf6/7 coding regions from AdHu5.

In one embodiment, the native E4 locus is deleted and replaced with heterologous E4Orf4, E4Orf6 and E4Orf6/7 coding regions from AdHu5. Alternatively, nucleic acid molecule may comprise the native coding regions in addition to heterologous E4Orf4, E4Orf6 and E4Orf6/7 coding regions from AdHu5. Preferably, the native coding regions are E4Orf1, E4Orf2 and E4Orf3.

Preferred adenoviral vectors are selected from the group consisting of AdY25 and AdY68.

Preferably, the adenoviral vector according to the tenth aspect lacks and E1 and an E3 locus.

Merely for the convenience of those of skill in the art, a sample of E. coli strain SW102[9] (a derivative of DH10B) containing bacterial artificial chromosomes (BACs) containing the cloned genome of AdChOX1 (pBACe3.6 AdChOx1 (E4 modified) TIPeGFP, cell line name "AdChOx1 (E4 modified) TIPeGFP") was deposited by Isis Innovation Limited on 24 May 2012 with the European Collection of Cell Cultures (ECACC) at the Health Protection Agency Culture Collections, Health Protection Agency, Porton Down, Salisbury SP4 0JG, United Kingdom under the Budapest Treaty and designated by provisional accession no. 12052403.

As described herein, the vector AdChOx1 is derived from chimpanzee adenovirus Y25, with deletion of E1 region, E3 region, modification of E4 region and insertion of TIPeGFP model antigen into E1 locus. The E. coli containing the BAC is a class I genetically modified organism.

The BAC propagates within the bacteria during replication and can be maintained by selection with chloramphenicol. The E. coli strain SW102 containing the bacterial artificial chromosomes into which the genomes are cloned can be propagated in Luria-Bertani broth or agar containing 12.5 μg/mL chloramphenicol at 32° C. The genome may be modified by genetic engineering in E. coli according to standard methods, as described in the specification, e.g. to insert an alternative recombinant antigen in place of TIPeGFP.

Converting the BAC clones of the viral genomes into viruses ("rescue") can be carried out by the following steps. The E. coli host is propagated and the BAC DNA is purified from the bacteria according to standard methods. The DNA is linearised with the restriction endonuclease PmeI and transfected into HEK293 cells (or a similar E1 complementing cell line). The resulting adenovirus can then be propagated and purified for use as a vaccine, for example. All of these reagents and cells are publicly available. If the deposition were rescued, the resulting virus would be a class I genetically modified organism.

In respect of all designated states to which such action is possible and to the extent that it is legally permissible under the law of the designated state, it is requested that a sample of the deposited material be made available only by the issue thereof to an independent expert, in accordance with the relevant patent legislation, e.g. Rule 32(1) EPC, Rule 13(1) and Schedule 1 of the UK Patent Rules 2007, Regulation 3.25(3) of the Australian Patent Regulations and generally similar provisions mutatis mutandis for any other designated state.

A specific embodiment of the fifth aspect of the present invention provides a polynucleotide sequence encoding an adenoviral vector according to the second aspect of the present invention, wherein said polynucleotide sequence comprises or consists of the polynucleotide sequence of the viral vector AdChOX1, deposited in a BAC contained in E. coli strain SW102[9] by Isis Innovation Limited on 24 May 2012 with the European Collection of Cell Cultures (ECACC) at the Health Protection Agency Culture Collections, Health Protection Agency, Porton Down, Salisbury SP4 0JG, United Kingdom under the Budapest Treaty and designated by provisional accession no. 12052403. The deposited BAC additionally comprises a transgene encoding the antigen TIPeGFP. In this aspect of the present invention, the polynucleotide sequence for AdChOX1 preferably does not include the sequence encoding the TIPeGFP antigen.

A further embodiment of the present invention provides a host cell transduced with the viral vector according to the second aspect of the present invention, wherein said host cell is preferably a bacterium, more preferably E. coli strain SW102[9] containing a bacterial artificial chromosome (BAC) containing the cloned genome of AdChOX1 deposited by Isis Innovation Limited on 24 May 2012 with the European Collection of Cell Cultures (ECACC) at the Health Protection Agency Culture Collections, Health Protection Agency, Porton Down, Salisbury SP4 0JG, United Kingdom under the Budapest Treaty and designated by provisional accession no. 12052403. The deposited BAC additionally comprises a transgene encoding the antigen TIPeGFP. In this aspect of the present invention, the polynucleotide sequence for AdChOX1 preferably does not include the sequence encoding the TIPeGFP antigen. Such a host cell may be used for BAC propagation.

A specific embodiment of the seventh aspect of the present invention provides a method of producing the viral vector according to the second aspect of the present invention by generating a molecular clone of AdY25 in a Bacterial Artificial Chromosome (BAC), wherein said BAC is the BAC containing the cloned genome of AdChOX1, deposited in E. coli strain SW102[9] by Isis Innovation Limited on 24 May 2012 with the European Collection of Cell Cultures (ECACC) at the Health Protection Agency Culture Collections, Health Protection Agency, Porton Down, Salisbury SP4 0JG, United Kingdom under the Budapest Treaty and designated by provisional accession no. 12052403. The deposited BAC additionally comprises a transgene encoding the antigen TIPeGFP. In this aspect of the present invention, the polynucleotide sequence for AdChOX1 preferably does not include the sequence encoding the TIPeGFP antigen.

A specific embodiment of the eighth aspect of the present invention provides a Bacterial Artificial Chromosome (BAC) clone comprising the polynucleotide sequence according to the fifth aspect of the present invention, wherein said BAC is the BAC containing the cloned genome of AdChOX1, deposited in *E. coli* strain SW102[9] by Isis Innovation Limited on 24 May 2012 with the European Collection of Cell Cultures (ECACC) at the Health Protection Agency Culture Collections, Health Protection Agency, Porton Down, Salisbury SP4 0JG, United Kingdom under the Budapest Treaty and designated by provisional accession no. 12052403. The deposited BAC additionally comprises a transgene encoding the antigen TIPeGFP. In this aspect of the present invention, the polynucleotide sequence for AdChOX1 preferably does not include the sequence encoding the TIPeGFP antigen.

For the avoidance of doubt, it is hereby expressly stated that features described herein as 'preferred', 'preferable', "alternative" or the like may be present in the invention in isolation or in any combination with any one or more other features so described (unless the context dictates otherwise) and this constitutes and explicit disclosure of such combinations of features.

All the features of each embodiment described above apply mutatis mutandis to all other embodiments of the present invention.

EXAMPLES

Example 1: Generation of a Molecular Clone of AdY25 in a Bacterial Artificial Chromosome Wild type chimpanzee adenovirus AdY25 was obtained from Goran Wadell of Umea University, Sweden. The virus was propagated to high titer in HEK293 cells and the viral DNA phenol extracted and sequenced. The nucleotide sequence of the wild type AdY25 virus is found in SEQ ID NO. 1. Based on the sequencing data, a BAC 'rescue vector' was constructed containing regions of homology to the left and right flanks of the viral genome (homology flanks were PCR amplified from viral DNA). Homologous recombination was then performed in BJ5183 *E. Coli* cells between viral DNA and the linearised rescue vector to incorporate the viral genome into the BAC vector.

An extra homology flank downstream of the adenovirus E1 region was included to enable simultaneous deletion of E1 in order to render the new vector immediately replication incompetent.

Phage lambda site specific recombination sites attR1 and attR2 were introduced at the Ad E1 locus as part of an Invitrogen Gateway® destination cassette to enable the efficient directional insertion of vaccine transgenes. A modified destination cassette was ligated into the AsiSI restriction site introduced at the E1 locus during isolation of the genomic clone.

The resulting ΔE1 Ad-BAC vector was screened by both PCR and restriction digest before replication incompetent clones were transfected into E1 complementing HEK293 cells, where the new vector demonstrated the ability to produce infectious virions capable of replication and cytopathic effect in HEK293 cells.

Example 2: Deletion of the Adenoviral E3 Region

The ΔE1 Ad-BAC vector genome produced in accordance with Example 1 was further modified using GalK recombineering to delete the adenoviral E3 region and thus increase the insert capacity of the new vector by approximately 5 kb.

The E3 region was deleted by recombination between the vector genome and a PCR amplified GalK cassette, flanked by 50 bp regions of homology either side of the E3 gene. Recombination was performed in SW102 *E. coli* cells, which have been specifically engineered to lack the GalK gene which is required for the utilisation of galactose as the sole carbon source. Recombinant cells were selected using minimal media containing only galactose, in which only recombinants containing the GalK gene in place of the E3 locus were able to grow[6].

Example 3: Modification of the E4 Region and Effects Thereof i) Modification of E4 Region The E4 locus of the ΔE1 ΔE3 Ad-BAC vector genome produced in accordance with Example 2 was then modified. The E4 region was deleted by recombination in SW102 *E. Coli* cells between the vector genome and a PCR-amplified GalK cassette, flanked by 50 bp regions of homology either side of the E4 gene. Recombinant cells were selected using minimal media containing only galactose. The GalK gene was then replaced with the required E4 open reading frames from AdHu5 and AdY25 in a similar manner to provide the 5 constructs listed in FIG. 3C. Recombinant cells comprising the gene in place of the GalK gene were then selected using media comprising 2-deoxygalactose (DOG)[6].

ii) Effect of E4 Modification on Viral Yield

HEK293 cells were infected with the following viral vectors at a multiplicity of infention of 9 and incubated at 37° C. for 48 hours before harvesting:
 i) AdHu5 ("Ad5")
 ii) AdY25 E4 wildtype ("Y25E4 wt")
 iii) AdY25 E4 AdHu5 E4Orf6 ("Y25Ad5E4Orf")
 iv) AdY25 E4 AdHu5 E4Orf4, 6, 6/7 ("AdChOX1")

Infectious titre of the harvested material was measured by quantifying GFP positive foci 48 hours post infection.

As can be seen in FIG. 3A, the infectious titre of the AdY25-based viral vector comprising the wildtype E4 locus was significantly lower than that of AdHu5. Modification of the viral vector to replace the wildtype E4 locus with the E4Orf6 gene from AdHu5 signficantly increased the infectious titre. Replacement of the wildtype E4 locus with the E4Orf4, E4Orf6 and E4Orf6/7 coding regions from AdHu5, and the E4Orf1, E4Orf2 and E4Orf3 coding regions from AdY25 (to create ChAdOX1) surprisingly further increased the infectious titre.

Iii) GFP Vs. Anti-Hexon Titre

In order to assess vaccine vector immunogenicity and efficacy it is essential to develop a reliable method of quantifying the infectious titer of the virus. Traditionally, plaque assays in HEK293 cells have been the method of choice, but these require a long incubation period and titers are often inconsistent. Furthermore the plaque assay is inherently insensitive, not all infectious virions will induce plaque formation. One method is the single cell infectivity assay which simply involves quantifying the number of virally infected cells. The first recombinant AdY25-derived viral vectors expressed green fluorescent protein (GFP), enabling viruses that had initiated recombinant transgene expression within a cell to be visualised directly by fluorescence microscopy. However, an alternative method of assessing cell infectivity must be used where the vaccine antigen constructs do not contain a fluorescent marker gene, for example where the vaccine antigen constructs are for clinical use.

An anti-hexon immunostaining assay has now been developed that enables visualisation of infected cells in which the viral hexon protein is being expressed. This assay uses a polyclonal anti-hexon antibody so can be used to titer virtually any adenovirus vaccine vector and we have found the assay to be reliable and consistent for both AdHu5 and AdCh63 based vectors. It does of course rely on the assumption that the rate of hexon production relative to transgene expression is consistent between vectors. The titers of GFP-expressing AdY25-derived viral vectors were compared by GFP and anti-hexon based assays. Titers were assessed at 48 hours post infection for AdHu5, AdC63, AdY25 E4 wild-type, and constructs A-E as described in FIG. 3C, all expressing the TIPeGFP antigen.

TIP is essentially an epitope string consisting of a number of strong murine T cell epitopes including Pb9 (a dominant CD8+ epitope from malarial antigen PbCSP) and P15 (a strong CD4+ epitope from *M. tuberculosis* antigen 85A). The TIP epitope string is fused to the 5' end of eGFP which enables transgene expression to be visualised directly and simplifies vaccine titration.

FIG. 3B illustrates the ratio of GFP foci to anti-hexon titer. For Ad5- and AdC63-based vectors, GFP titers were approximately twice as sensitive as anti-hexon titers. However, for AdY25-based vectors, the sensitivity of the anti-hexon assay varied considerably with E4 modification. For the AdY25 E4 wildtype vector, anti-hexon titers were over 40 fold less sensitive than GFP titers after 48 hrs, suggesting that the rate of hexon production is considerably slower than for AdHu5 and AdCh63 vectors. This was to be expected, given the poor yield of AdY25 E4 wildtype vector. Surprisingly, however, the construct A ("Y25Ad5E4Orf6") was still 30 fold less sensitive by anti-hexon than by GFP. The best results were obtained with construct E ("ChAdOX1"), in which the wildtype E4 locus was replaced with the E4Orf4, E4Orf6 and E4Orf6/7 coding regions from AdHu5, and the E4Orf1, E4Orf2 and E4Orf3 coding regions from AdY25.

iii) Hexon Expression

The ratio of marker gene to hexon titre for ChAdOX1 viral vectors expressing TIPeGFP was measured using GFP and mCherry fluorescent transgenes in order to control for the sensitivity of the fluorescent detection.

The results are provided in FIG. 3D. In both cases, the marker gene:hexon titre ratio was approximately twofold, and thus the particular marker gene used did not affect the resulting marker gene:hexon titre ratio. The marker gene: hexon titre ratio for the ChAdOX1 vector is the same as that for HAdV-5, indicating that the E4 modification to the ChAdOX1 vector has been optimised.

Example 4: Immunogenicity of AdY25-Based Vectors

Immunogenicity was assessed using the model antigen TIPeGFP in order to determine whether comparable immunogenicity to AdC63 and AdC68 could be obtained in mice using an AdY25-based vector.

Balb/c mice (4/group) were immunised intramuscularly with $10^9$ infectious units (ifu) of each of the following viral vectors, all expressing the TIPeGFP antigen:
i) AdCh63;
ii) ΔE1 ΔE3 AdCh68; and
iii) ChAdOX1.

After 14 days post-prime, spleen immunogenicity against a strong CD8+ epitope (Pb9) was assessed by IFN-γ ELISpot The IFN-γ spleen ELISpot responses are shown in FIG. 4. Responses elicited by ChAdOX1 were robust and comparable to those seen using AdCh63 and the AdCh68-based vector. These data support the continued development of AdY25-based vectors for clinical application.

Example 5: Effect of E4 Modification on Immunogenicity of AdY25-Based Vectors

The impact of two different E4 modifications on the immunogenicity of AdY25-based vectors was assessed using the following constructs:
(i) AdY25 E4 wildtype ("E4 wt")
(ii) AdY25 E4AdHu5Orf6 ("E4Orf6"); and
(iii) AdY25 E4AdHu5Orf4/6/7("E4Orf4/6/7").

Balb/c mice (4/group) were immunised intramuscularly with either $10^6$ ifu or $10^8$ ifu of each vector. Responses to Pb9 and P15 epitopes were assayed two weeks post immunisation. Titers calculated once again on GFP to remove the effect of hexon production rates on vaccine titer.

The effect of E4 modification on IFN-γ spleen ELISpot responses is shown in FIG. 5. The data indicate that E4 modification has no effect on vector immunogenicity. Therefore, such modifications can be used to enhance the rate of production of the viral vectors, without having a negative impact on the immunogenicity of the vectors.

Example 6: Prevalence of Vector-Neutralising Antibodies

The prevalence of vector neutralising antibodies in human sera from the UK and The Gambia against AdY25-based vectors and AdCh63-based vectors was assessed.

HEK293 cells were infected with Y25Ad5E4Orf6-SEAP or AdCh63-SEAP (SEAP=Secreted Placental Alkaline Phosphatase). Recombinant adenoviruses were incubated with five serial dilutions of serum in FBS-DMEM before infection. The final serum dilutions were 1:18, 1:72, 1:288, 1:1152, 1:4608; each serum sample was tested in duplicate. Supernatants were collected and assayed for SEAP concentration using CSPD (Tropix) according to the manufacturer's instructions. Luminescence intensity was measured using a Varioskan flash luminometer (Thermo Scientific). Neutralization titers were defined as the serum dilution required to reduce SEAP concentration by 50% compared to wells infected with virus alone. Neutralization titer was calculated by linear interpolation of adjacent values.

As shown in FIG. 6, the seroprevalence of neutralising antibodies against Y25Ad5E4Orf6 was surprisingly found to be much lower than that for AdCh63 in both the UK and The Gambia.

Example 7: Humoral Immunogenicity of AdY25-Based Vectors

Balb/c mice (6/group) were immunised with $10^8$ infectious units of either of the following vectors, both expressing TIPeGFP:
i) ΔE1 ΔE3 AdCh68; or
ii) ChAdOX1.

After 56 days post prime, mice were boosted with $10^6$ pfu MVA-TIPeGFP. Serum was collected 50 days post-prime and 10 days post-boost to compare pre- and post-boost anti-GFP antibody responses. Responses were measured by endpoint ELISA. Statistical analyses were performed by one way ANOVA.

As shown in FIG. 7, humoral immunogenicity of the AdY25-based vector ChAdOX1 is superior to current chimpanzee adenovirus vector AdCh68, indicating an enhanced antibody response elicited by the AdY25-based vector in comparison to the AdCh68-based vector.

Example 8: Induction of Immune Response Against *Mycobacterium tuberculosis*

A transgene encoding the *Mycobacterium tuberculosis* protein Ag85A was inserted into the E1 locus of ChAdOX1 under control of the human cytomegalovirus immediate early promoter, using the BAC technology as described in Example 1. The nucleotide sequence of the transgene (SEQ ID NO. 42) encodes residues 1 to 323 of the antigen, encoded by a sequence optimised to human codon usage (nucleotides 103 to 1071), fused at the N-terminus to tPA (the signal peptide from human tissue plasminogen activator)(nucleotides 1 to 102) and at the C-terminus to a PK tag (nucleotides 1072 to 1104). The amino acid sequence of the Ag85A antigen is provided in SEQ ID NO. 43.

The BAC clone was transfected into HEK293 cells and the virus vector was amplified, purified and titred using the anti-hexon immunostaining assay described in Example 3.

The immunogenicity of the vector was assessed in Balb/c mice immunized with varying doses, expressed in infectious units, of the vaccine, administered intramuscularly. After 14 days cellular immune responses to Ag85A were determined by IFN-γ ELIspot assay using splenocytes stimulated with synthetic peptides corresponding to the known immunodominant CD8+ (p11; WYDQSGLSV (SEQ ID NO. 44)) and CD4+ T cell (p15; TFLTSELPGWLQANRHVKPT (SEQ ID NO. 45)) H-2$^d$ restricted epitopes in Ag85A.

The results are shown in FIGS. 8A and 8B. These results indicate that the ChAdOX1 vector is capable of inducing immune responses against *Mycobacterium tuberculosis*. The magnitude of these responses is similar to that induced by vectors based on other adenoviruses.

Example 9: Induction of Immune Response Against Influenza A

A transgene encoding the nucleoprotein (NP) and matrix protein 1 (M1) of influenza A virus was inserted into the E1 locus of ChAdOX1 under control of the human cytomegalovirus major immediate early promoter, using the BAC technology as described in Example 1. The nucleotide sequence of the transgene (SEQ ID NO. 46) encodes the influenza A nucleoprotein (nucleotides 1 to 1494) fused to the matrix protein 1 (nucleotides 1516 to 2274) and separated by a linker (nucleotides 1495 to 1515). The amino acid sequence of the NPM1 fusion protein is provided in SEQ ID NO. 47.

The BAC clone was transfected into HEK293 cells and the virus vector was amplified, purified and titred using the anti-hexon immunostaining assay described in Example 3. A similar vector based on human adenovirus type 5 (HAdV-5) was similarly generated and titred for comparative purposes.

The immunogenicity of the vector was assessed in Balb/c mice immunized with varying doses, expressed in infectious units, of the vaccine, administered intramuscularly. After 14 days cellular immune responses to NP were determined by IFN-γ ELIspot assay using splenocytes stimulated with synthetic peptides corresponding to the known immunodominant CD8+ T cell H-2$^d$ restricted epitope in NP ((TYQRTRALV) (SEQ ID NO. 48)).

The results are shown in FIG. 9. These results indicate that the ChAdOX1 vector is capable of inducing immune responses against influenza A virus and that, at the doses tested, these are similar to those induced by a HAdV-5 vector.

The ChAdOX1-NPM1 vaccine has recently been produced for human clinical trials according to current good manufacturing practice at the University of Oxford Clinical Biomanufacturing Facility. This indicates the suitability of the vector for deployment as a medical product.

REFERENCES

1. Buchbinder et al, Lancet, Vol 372, November 2008
2. Farina et al, J. Virol, December 2001, p11603-11613
3. Dudareva et al, Vaccine 27, 2009, 3501-3504
4. R. Wigand et al, Intervirology, Vo130; 1 1989
5. Roy et al, Hum. Gen. Ther., 2004, 15:519-530
6. Warming et al. Nuc. Acid. Res, 2005, Vol 33; 4
7. http://www.invitrogen.com/gateway
8. Havenga et al, J.G.V., 2006, 87, 2135-214
9. Warming, S. et al. Nucleic Acids Res, 2005 Feb. 24; 33(4): e36

```
                                         Sequences (Chimpanzee Adenovirus AdY25 genome)
                                                                      SEQ ID NO. 1
CCATCATCAATAATATACCTCAAACTTTTTGTGCGCGTTAATATGCAAATGAGGCGTTTGAATTTGGGA
AGGGAGGAAGGTGATTGGCCGAGAGAAGGGCGACCGTTAGGGGCGGGGCGAGTGACGTTTTGATGACGT
GACCGCGAGGAGGAGCCAGTTTGCAAGTTCTCGTGGGAAAAGTGACGTCAAACGAGGTGTGGTTTGAAC
ACGGAAATACTCAATTTTCCCGCGCTCTCTGACAGGAAATGAGGTGTTTCTAGGCGGATGCAAGTGAAA
ACGGGCCATTTTCGCGCGAAAACTGAATGAGGAAGTGAAAATCTGAGTAATTTCGCGTTTATGACAGGG
AGGAGTATTTGCCGAGGGCCGAGTAGACTTTGACCGATTACGTGGGGGTTTCGATTACCGTGTTTTTCA
CCTAAATTTCCGCGTACGGTGTCAAAGTCCGGTGTTTTTACGTAGGTGTCAGCTGATCGCCAGGGTATT
TAAACCTGCGCTCTCCAGTCAAGAGGCCACTCTTGAGTGCCAGCGAGAAGAGTTTTCTCCTCCGCGCCG
CGAGTCAGATCTACACTTTGAAAGATGAGGCACCTGAGAGACCTGCCCGATGAGAAAATCATCATCGCT
TCCGGGAACGAGATTCTGGAACTGGTGGTAAATGCCATGATGGGCGACGACCCTCCGGAGCCCCCCACC
CCATTTGAGGCACCTTCGCTACACGATTTGTATGATCTGGAGGTGGATGTGCCCGAGGACGACCCCAAC
GAGGAGGCGGTAAATGATTTATTTAGCGATGCCGCGCTGCTAGCTGCCGAGGAGGCTTCGAGCCCTAGC
TCAGACAGCGACTCTTCACTGCATACCCCTAGACCCGGCAGAGGTGAGAAAAAGATCCCCGAGCTTAAA
GGGGAAGAGATGGACTTGCGCTGCTATGAGGAATGCTTGCCCCCGAGCGATGATGAGGACGAGCAGGCG
ATCCAGAACGCAGCGAGCCAGGGAATGCAAGCCGCCAGCGAGAGTTTTGCGCTGGACTGCCCGCCTCTG
CCCGGACACGGCTGTAAGTCTTGTGAATTTCATCGCTTGAATACTGGAGATAAAGCTGTGTTATGTGCA
CTTTGCTATATGAGAGCTTACAACCATTGTGTTTACAGTAAGTGTGATTAAGTTGAACTTTAGAGGGAG
GCAGAGAGCAGGGTGACTGGGCGATGACTGGTTTATTTATGTATATATGTTCTTTATATAGGTCCCGTC
TCTGACGCAGATGATGAGACCCCCACTACAGAGTCCACTTCGTCACCCCCAGAAATTGGCACATCTCCA
```

| Sequences |
|---|
| CCTGAGAATATTGTTAGACCAGTTCCTGTTAGAGCCACTGGGAGGAGAGCAGCTGTGGAATGTTTGGAT |
| GACTTGCTACAGGCTGGGGATGAACCTTTGGACTTGTGTACCCGGAAACGCCCCAGGCACTAAGTGCCA |
| CACATGTGTGTTTACTTGAGGTGATGTCAGTATTTATAGGGTGTGGAGTGCAATAAAAAATGTGTTGAC |
| TTTAAGTGCGTGGTTTATGACTCAGGGGTGGGGACTGTGGGTATATAAGCAGGTGCAGACCTGTGTGGT |
| TAGCTCAGAGCGGCATGGAGATTTGGACGATCTTGGAAGATCTTCACAAGACTAGACAGCTGCTAGAGA |
| ACGCCTCGAACGGAGTCTCTCACCTGTGGAGATTCTGCTTCGGTGGCGACCTAGCTAAGCTAGTCTATA |
| GGGCCAAACAGGATTATAGCGAACAATTTGAGGTTATTTTGAGAGAGTGTCCGGGTCTTTTTGACGCTC |
| TTAATTTGGGTCATCAGACTCACTTTAACCAGAGGATTGTAAGAGCCCTTGATTTTACTACTCCCGGCA |
| GATCCACTGCGGCAGTAGCCTTTTTTGCTTTTCTTCTTGACAAATGGAGTCAAGAAACCCATTTCAGCA |
| GGGATTACCAGCTGGATTTCTTAGCAGTAGCTTTGTGGAGAACATGGAAATCCCAGCGCCTGAATGCAA |
| TCTCAGGCTACTTGCCGGTACAGCCACTAGACACTCTGAAGATCCTGAATCTCCAGGAGAGTCCCAGGG |
| CACGCCAACGTCGCCGGCAGCAGCAGCGGCAGCAGGAGGAGGATCAAGAAGAGAACCCGAGAGCCGGCC |
| TGGACCCTCCGGCGGAGGAGGAGTAGCTGACCTGTTTCCTGAACTGCGCCGGGTGCTGACTAGGTCTTC |
| GAGTGGTCGGGAGAGGGGGATTAAGCGGGAGAGGCATGATGAGACTAATCACAGAACTGAACTGACTGT |
| GGGTCTGATGAGCCGCAAGCGTCCAGAAACAGTGTGGTGGCATGAGGTGCAGTCGACTGGCACAGATGA |
| GGTGTCAGTGATGCATGAGAGGTTTTCCCTAGAACAAGTCAAGACTTGTTGGTTAGAGCCTGAGGATGA |
| TTGGGAGGTAGCCATCAGGAATTATGCCAAGCTGGCTCTGAGGCCAGACAAGAAGTACAAGATTACTAA |
| GCTGATAAATATCAGAAATGCCTGCTACATCTCAGGGAATGGGGCTGAAGTGGAGATCTGTCTTCAGGA |
| AAGGGTGGCTTTCAGATGCTGCATGATGAATATGTACCCGGGAGTGGTGGGCATGGATGGGGTCACCTT |
| TATGAGGTTCAGGGGAGATGGGTATAATGGCACGGTCTTTATGGCCAATACCAAGCTGACAGT |
| TCATGGCTGCTCCTTCTTTGGGTTTAATAACACCTGCATTGAGGCCTGGGGTCAGGTTGGTGTGAGGGG |
| CTGTAGTTTTTCAGCCAACTGGATGGGGTCGTGGGCAGGACCAAGAGTATGCTGTCCGTGAAGAAATG |
| CTTGTTCGAGAGGTGCCACCTGGGGGTGATGAGCGAGGGCGAAGCCAGAATCCGCCACTGCGCCTCTAC |
| CGAGACGGGCTGTTTTGTGCTGTGCAAGGGCAATGCTAAGATCAAGCATAATATGATCTGTGGAGCCTC |
| GGACGAGCGCGGCTACCAGATGCTGACCTGCGCCGGTGGGAACAGCCATATGCTGGCCACCGTGCATGT |
| GGCCTCCCATGCCCGCAAGCCCTGGCCCGAGTTCGAGCACAATGTCATGACCAGGTGCAATATGCATCT |
| GGGGTCCCGCCGAGGCATGTTCATGCCCTATCAGTGCAACCTGAATTATGTGAAGGTGCTGCTGGAGCC |
| CGATGCCATGTCCAGAGTGAGCCTGACGGGGGTGTTTGACATGAATGTGGAGGTGTGGAAGATTCTGAG |
| ATATGATGAATCCAAGACCAGGTGCCGAGCCTGCGAGTGCGGAGGGAAGCATGCCAGGTTCCAGCCCGT |
| GTGTGTGGAGGTGACGGAGGACCTGCGACCCGATCATTTGGTGTTGTCCTGCACCGGGACGGAGTTCGG |
| TTCCAGCGGGGAAGAATCTGACTAGAGTGAGTAGTGTTCTGGGGCGGGGAGGACCTGCATGAGGGCCA |
| GAATGACTGAAATCTGTCCTTTTCTGTGTGTTGCAGCATCATGAGCGGAAGCGGCTCCTTTGAGGGAGG |
| GGTATTCAGCCCTTATCTGACGGGGCGTCTCCCCTCCTGGGCGGGAGTGCGTCAGAATGTGATGGGATC |
| CACGGTGGACGGCCGGCCCGTGCAGCCCGCGAACTCTTCAACCCTGACCTATGCAACCCTGAGCTCTTC |
| GTCGGTGGACGCAGCTGCCGCCGCAGCTGCTGCATCCGCCGCCAGCGCCGTGCGCGGAATGGCCATGGG |
| CGCCGGCTACTACGGCACTCTGGTGGCCAACTCGAGTTCCACCAATAATCCCGCCAGCCTGAACGAGGA |
| GAAGCTGCTGCTGCTGATGGCCCAGCTTGAGGCCTTGACCCAGCGCCTGGGCGAGCTGACCCAGCAGGT |
| GGCTCAGCTGCAGGAGCAGACGCGGGCGCGGTTGCCACGGTGAAATCCAAATAAAAAATGAATCAATA |
| AATAAACGGAGACGGTTGTTGATTTTAACACAGAGTCTGAATCTTTATTTGATTTTTCGCGCGCGGTAG |
| GCCCTGGACCACCGGTCTCGATCATTGAGCACCCGGTGGATCTTTTCCAGGACCCGGTAGAGGTGGGCT |
| TGGATGTTGAGGTACATGGGCATGAGCCCGTCCCGGGGGTGGAGGTAGCTCCATTGCAGGGCCTCGTGC |
| TCGGGGGTGGTGTTGTAAATCACCCAGTCATAGCAGGGGCGCAGGGCGTGGTGTTGCACAATATCTTTG |
| AGGAGGAGACTGATGGCCACGGGCAGCCCTTTGGTGTAGGTGTTTACAAATCTGTTGAGCTGGGAGGGA |
| TGCATGCGGGGGAGATGAGGTGCATCTTGGCCTGGATCTTGAGATTGGCGATGTTACCGCCCAGATCC |
| CGCCTCGGGGTTCATGTTGTGCAGGACCACCAGCACGGTGTATCCGGTGCACTTGGGAATTTATCATGC |
| AACTTGGAAGGGAAGGCGTGAAAGAATTTGGCGACGCCCTTGTGTCCGCCCAGGTTTTCCATGCACTCA |
| TCCATGATGATGGCAATGGGCCCGTGGGCGGCGGCCTGGCAAAGACGTTTCGGGGGTCGGACACATCA |
| TAGTTGTGGTCCTGGGTGAGGTCATCATAGGCCATTTTAATGAATTTGGGCGGAGGGTGCCGGACTGG |
| GGGACAAAGGTACCCTCGATCCCGGGGGCGTAGTTCCCCTCACAGATCTGCATCTCCCAGGCTTTGAGC |
| TCAGAGGGGGGGATCATGTCCACCTGCGGGGCGATAAAGAACACGGTTTCCGGGGCGGGGGAGATGAGC |
| TGGGCCGAAAGCAAGTTCCGGAGCAGCTGGGACTTGCCGCAGCCGGTGGGGCCGTAAATGACCCCGATG |
| ACCGGCTGCAGGTGGTAGTTGAGGGAGAGACAGCTGCCGTCCTCCCGGAGGAGGGGGGCCACCTCGTTC |
| ATCATCTCGCGCACGTGCATGTTCTGCGCACCAGTTCCGCCAGGAGGCGCTCTCCCCCCAGAGATAGG |
| AGCTCCTGGAGCGAGGCGAAGTTTTTCAGCGGCTTGAGTCCGTCGGCCATGGGCATTTTGGAGAGGGTC |
| TGTTGCAAGAGTTCCAAGCGGTCCCAGAGCTCGGTGATGTGCTACGGCATCTCGATCCAGCAGACCT |
| CCTCGTTTCGCGGGTTGGGACGACTGCGGGAGTAGGGCACCAGACGATGGGCGTCCAGCGCAGCCAGGG |
| TCCGGTCCTTCCAGGGCCGCAGCGTCCGCGTCAGGGTGGTCTCCGTCACGGTGAAGGGGTGCGCGCCGG |
| GCTGGGCGCTTGCGAGGGTGCGCTTCAGGCTCATCCGGCTGGTCGAAAACCGCTCCCGATCGGCGCCCT |
| GCGCGTCGGCCAGGTAGCAATTGACCATGAGTTCGTAGTTGAGCGCCTCGGCCGCGTGGCCTTTGGCGC |
| GGAGCTTACCTTTGGAAGTCTGCCCGCAGGCGGGACAGAGGAGGGACTTGAGGGCGTAGAGCTTGGGGG |
| CGAGGAAGACGGAATCGGGGGCGTAGGCGTCCGCGCCGCAGTGGGCGCAGACGTCTCGCACTCCACGA |
| GCCAGGTGAGGTCGGGCTGGTCGGGGTCAAAAACCAGTTTCCCGCCGTTCTTTTTGATGCGTTTCTTAC |
| CTTTGGTCTCCATGAGCTCGTGTCCCGCTGGGTGACAAAGAGGCTGTCCGTGTCCCGTAGACCGACT |
| TTATGGGCCGGTCCTCGAGCGGTGTGCCGCGGTCCTCCTCGTAGAGGAACCCGCCCACTCCGAGACGA |
| AAGCCCGGGTCCAGGCCAGCACGAAGGAGGCCACGTGGGACGGGTAGCGGTCGTTGTCCACCAGCGGGT |
| CCACTTTTTCCAGGGTATGCAAACACATGTCCCCCTCGTCCACATCCAGGAAGGTGATTGGCTTGTAAG |
| TGTAGGCCACGTGACCGGGGGTCCCGGCCGGGGGGGGTATAAAAGGGGCGGGCCCCTGCTCGTCCTCAC |
| TGTCTTCCGGATCGCTGTCCAGGAGCGCCAGCTGTTGGGTAGGTATTCCCTCTCGAAGGCGGGCATGA |
| CCTCGGCACTCAGGTTGTCAGTTTCTAGAAACGAGGAGGATTTGATATTGACGGTGCCAGCGGAGATGC |
| CTTTCAAGAGCCCCTCGTCCATCTGGTCAGAAAAGACGATTTTTTGTTGTCGAGCTTGGTGGCGAAGG |
| AGCCGTAGAGGGCGTTGGAAAGGAGCTTGGCGATGAGCGCATTGTTGGGGTCTGGTTTTTTCCTTGTCGGCGC |
| GCTCCTTGGCCGCGATGTTGAGCTGCACGTACTCGCGCGCCACGCACTTCCATTCGGGGAAGACGGTGG |
| TCATCTCGTCGGGCACGATTCTGACCTGCCAACCTCGATTATGCAGGGTGATGAGGTCCACACTGGTGG |
| CCACCTCGCCGCGCAGGGGCTCGTTGGTCAGCAGAGGCGGCCGCCCTTGCGCGAGCAGAAGGGGGCA |
| GAGGGTCCAGCATGACCTCGTCGGGGGGTCGGCATCGATGGTGAAGATGCCGGGCAGGAGATCGGGGT |
| CGAAGTAGCTGATGGAAGTGGCCAGATCGTCCAGGGAAGCTTGCCATTCGCGCACGGCCAGCGCGCGCT |
| CGTAGGGACTGAGGGGCGTGCCCCAGGGCATGGGGTGGGTGAGCGCGGAGGCGTACATGCCGCAGATGT |

-continued

| Sequences |
|---|
| CGTAGACGTAGAGGGGCTCCTCGAGGATGCCGATGTAGGTGGGGTAGCAGCGCCCCCGCGGATGCTGG |
| CGCGCACGTAGTCATACAGCTCGTGCGAGGGCGCGAGGAGCCCCGGGCCCAGGTTGGTGCGACTGGGCT |
| TTTCGGCGCGGTAGACGATCTGGCGAAAGATGGCATGCGAGTTGGAGGAGATGGTGGGCGTTTGGAAGA |
| TGTTGAAGTGGGCGTGGGGGAGGCCGACCGAGTCGCGGATGAAGTGGGCGTAGGAGTCTTGCAGTTTGG |
| CGACGAGCTCGGCGGTGACGAGGACGTCCAGAGCGCAGTAGTCGAGGGTCTCCTGGATGATGTCATACT |
| TGAGCTGGCCCTTTTGTTTCCACAGCTCGCGGTTGAGAAGGAACTCTTCGCGGTCCTTCCAGTACTCTT |
| CGAGGGGGAACCCGTCCTGATCTGCACGGTAAGAGCCTAGCATGTAGAACTGGTTGACGGCCTTGTAGG |
| CGCAGCAGCCCTTCTCCACGGGGAGGGCGTAGGCCTGGGCGGCCTTGCGCAGGGAGGTGTGCGTGAGGG |
| CGAAGGTGTCCCTGACCATGACCTTGAGGAACTGGTGCTTGAAATCGATATCGTCGCAGCCCCCCTGCT |
| CCCAGAGCTGGAAGTCCGTGCGCTTCTTGTAGGCGGGGTTGGGCAAAGCGAAAGTAACATCGTTGAAAA |
| GGATCTTGCCCGCGCGGGGCATAAAGTTGCGAGTGATGCGGAAAGGCTGGGGCACCTCGGCCCGGTTGT |
| TGATGACCTGGGCGGCGAGCACGATCTCGTCGAAACCGTTGATGTTGTGGCCCACGATGTAGAGTTCCA |
| CGAATCGCGGGCGGCCCTTGACGTGGGGCAGCTTCTTGAGCTCCTCGTAGGTGAGCTCGTCGGGGTCGC |
| TGAGACCGTGCTGCTCGAGCGCCCAGTCGGCGAGATGGGGGTTGGCGCGGAGGAAGGAAGTCCAGAGAT |
| CCACGGCCAGGGCGGTTTGCAGACGGTCCCGGTACTGACGGAACTGCTGCCCGACGGCCATTTTTTCGG |
| GGGTGACGCAGTAGAAGGTGCGGGGGTCCCCGTGCCAGCGGTCCCATTTGAGCTGGAGGGCGAGATCGA |
| GGGCGAGCTCGACGAGGCGGTCGTCCCCTGAGAGTTTCATGACCAGCATGAAGGGGACGAGCTGCTTGC |
| CGAAGGACCCCATCCAGGTGTAGGTTTCCACATCGTAGGTGAGGAAGAGCCTTTCGGTGCGAGGATGCG |
| AGCCGATGGGGAAGAACTGGATCTCCTGCCACCAATTGGAGGAATGGCTGTTGATGTGATGGAAGTAGA |
| AATGCCGACGGCGCGCCGAACACTCGTGCTTGTGTTTATACAAGCGGCCACAGTGCTCGCAACGCTGCA |
| CGGGATGCACGTGCTGCACGAGCTGTACCTGAGTTCCTTTGACGAGGAATTTCAGTGGGAAGTGGAGTC |
| GTGGCGCCTGCATCTCGTGCTGTACTACGTCGTGGTGGTCGGCCTGGCCCTCTTCTGCCTCGATGGTGG |
| TCATGCTGACGAGCCCGCGCGGGAGGCAGGTCCAGACCTCGGCGCGAGCGGGTCGGAGAGCGAGGACGA |
| GGGCGCGCAGGCCGGAGCTGTCCAGGGTCCTGAGCACGCTGCGGAGTCAGTGGGCAGCGGCGGCG |
| CGCGGTTGACTTGCAGGAGTTTTTCCAGGGCGCGCGGGAGGTCCAGATGGTACTTGATCTCCACCGCGC |
| CGTTGGTGGCGACGTCGATGGCTTGCAGGGTCCCGTGCCCCTGGGGTGTGACCACCGTCCCCCGTTTCT |
| TCTTGGGCGGCTGGGCGACGGGGGCGGTGCCTCTTCCATGGTTAGAAGCGGCGGCGAGGACGCGCGCC |
| GGGCGGCAGAGGCGGCTCGGGGCCCGAGGCAGGGGCGGCAGGGGCACGTCGGCGCCGCGCGCGCGGGTAG |
| GTTCTGGTACTGCGCCCGGAGAAGACTGGCGTGAGCGACGACGCGACGGTTGACGTCCTGGATCTGACG |
| CCTCTGGGTGAAGGCCACGGGACCCGTGAGTTTGAACCTGAAAGAGAGTTCGACAGAATCAATCTCGGT |
| ATCGTTGACGGCGGCCTGCCGCAGGATCTCTTGCACGTCGCCCGAGTTGTCCTGGTAGGCGATCTCGGT |
| CATGAACTGCTCGATCTCCTCCTCCTGAAGGTCTCCGCGACCGGCGCGCTCCACGGTGGCCGCGAGGTC |
| GTTGGAGATGCGGCCCATGAGCTGCGAGAAGGCGTTCATGCCCGCCTCGTTCCAGACGCGGCTGTAGAC |
| CACGACGCCCTCGGGATCGCGGGCGCGCATGACCACCTGGGCGAGGTTGAGCTCCACGTGGCGCGTGAA |
| GACCGCGTAGTTGCAGAGGCGCTGGTAGAGGTAGTTGAGCGTGGTGGCGATGTGCTCGGTGACGAAGAA |
| ATACATGATCCAGCGGCGGAGCGGCATCTCGCTGACGTCGCCCAGCGCCTCCAAGCGTTCCATGGCCTC |
| GTAAAAGTCCACGGCGAAGTTGAAAAACTGGGAGTTGCGCGCCGAGACGGTCAACTCCTCCTCCAGAAG |
| ACGGATGAGCTCGGCGATGGTGGCGCGCACCTCGCGCTCGAAGGCCCCCGGGAGTTCCTCCACTTCCTC |
| CTCTTCTTCCTCCTCCACTAACATCTCTTCTACTTCCTCCTCAGGCGGTGGTGGTGGCGGGGAGGGGG |
| CCTGCGTCGCCGGCGGCGCACGGGCAGACGGTCGATGAAGCGCTCGATGGTTCTCGCCGCGCCGGCGTCG |
| CATGGTTCGGTGACGGCGCGCCCGTCCTCGCGGGGCCGCAGCGTGAAGACGCCGCCGCGCATCTCCAG |
| GTGGCCGGGGGGTCCCCGTTGGGCAGGGAGAGGGCGCTGACGATGCATCTTATCAATTGCCCCGTAGG |
| GACTCCGCGCAAGGACCTGAGCGTCTCGAGATCCACGGGATCTGAAAACCGTTGAACGAAGGCTTCGAG |
| CCAGTCGCAGTCGCAAGGTAGGCTGAGCACGGTTTCTTCGCCGGGTCATGTTGGGGAGCGGGGCGGGC |
| GATGCTGCTGGTGATGAAGTTGAAATAGGCGGTTCTGAGACGGCGGATGGTGGCGAGGAGCACCAGGTC |
| TTTGGGCCCGGCTTGCTGGATGCGCAGACGGTCGGCCATGCCCCAGGCGTGGTCCTGACACCTGGCCAG |
| GTCCTTGTAGTAGTCCTGCATGAGCCGCTCCACGGGCACCTCCTCCTCGCCCGCGCGGCCGTGCATGCG |
| CGTGAGCCCGAAGCCGCGCTGGGGCTGGACGAGCGCCAGGTCGGCGACGACGCGCTCGGCGAGGATGGC |
| CTGCTGGATCTGGGTGAGGGTGGTCTGGAAGTCGTCAAAGTCGACGAAGCGGTGGTAGGCTCCGGTGTT |
| GATGGTGTAGGAGCAGTTGGCCATGACGGACCAGTTGACGGTCTGGTGGCCCGGACGCACGAGCTCGTG |
| GTACTTGAGGCGCGAGTAGGCGCGCGTGTCGAAGATGTAGTCGTTGCAGGTGCGCACCAGGTACTGGTA |
| GCCGATGAGGAAGTGCGGCGGCGGCTGGCGGTAGAGCGGCCATCGCTCGGTGGCGGGGGCGCCGGGCGC |
| GAGGTCCTCGAGCATGGTGCGGTGGTAGCCGTAGATGTACCTGGACATCCAGGTGATGCCGGCGGCGGT |
| GGTGGAGGCGCGCGGGAACTCGCGGACGCGGTTCCAGATGTTGCGCAGCGGCAGGAAGTAGTTCATGGT |
| GGGCACGGTCTGGCCCGTGAGGCGCGCAGTCGTGGATGCTCTATACGGGCAAAAACGAAAGCGGTCA |
| GCGGCTCGACTCCGTGCCTGGAGGCTAAGCAACGGGTTGGGCTGCGCGTGTACCCCGGTTCGAATCT |
| CGAATCAGGCTGGAGCCGCAGCTAACGTGGTACTGGCACTCCGTCTCGACCCAAGCCTGCACCAACCC |
| TCCAGGATACGGAGGCGGGTCGTTTTGCAACTTTTTTTGGAGGCCGGAAATGAAACTAGTAAGCGCGGA |
| AAGCGGCCGACCGCGATGGCTCGCTGCCGTAGTCTGGAGAAGAATCGCCAGGGTTGCGTTGCGGTGTGC |
| CCCGGTTCGAGGCCGGCCGGATTCCGCGGCTAACGAGGGCGTGGCTGCCCCGTCGTTTCCAAGACCCCA |
| TAGCCAGCCGACTTCTCCAGTTACGGAGCGAGCCCCTCTTTTGTTTTGTTTGTTTTCCAGATGCATC |
| CCGTACTGCGGCAGATGCGCCCCCACCACCCTCCACCGCAACAACAGCCCCCTCCTCCACAGCCGGCGC |
| TTCTGCCCCGCCCCAGCAGCAGCAGCAACTTCCAGCCACGACCGCCGCGGCCGCCGTGAGCGGGGCTG |
| GACAGACTTCTCAGTATGATCACCTGGCCTTGGAAGAGGGCGAGGGGCTGGCGCGCCTGGGGCGTCGT |
| CGCCGGAGCGGCACCCGCGCGTGCAGATGAAAAGGGACGCTCGCGAGGCCTACGTGCCCAAGCAGAACC |
| TGTTCAGAGACAGGAGCGGCGAGGAGCCCGAGGAGATGCGCGTCCGTTCCACGCGGGGCGGGAGC |
| TGCGGCGCGGCCTGGACCGAAAGAGGGTGCTGAGGGACGAGGATTTCGAGGCGGACGAGCTGACGGGGA |
| TCAGCCCCGCGCGCGCACGTGGCCGCGGCCAACCTGGTCACGGCGTACGAGCAGACCGTGAAGGAGG |
| AGAGCAACTTCCAAAAATCCTTCAACAACCACGTGCGCACCCTGATCGCGCGCGAGGAGGTGACCCTGG |
| GCCTGATGCACCTGTGGGACCTGCTGGAGGCCATCGTGCAGAACCCCACCAGCAAGCGCTGACGGCGC |
| AGCTGTTCCTGGTGGTGCAGCATAGTCGGGACAACGAGGCGTTCAGGGAGGCGCTGCTGAATATCACCG |
| AGCCCGAGGGCCGCTGGCCTCCTGGACCTGGTGAACATTCTGCAGAGCATCGTGGTGCAGGAGCGCGGAC |
| TGCCGCTGTCCGAGAAGCTGGCGGCCATCAACTTCTCGGTGCTGAGTCTGGGCAAGTACTACGCTAGGA |
| AGATCTACAAGACCCCGTACGTGCCCATAGACAAGGAGGTGAAGATCGACGGTTTTACATGCGCATGA |
| CCCTGAAAGTGCTGACCCTGAGCGACGATCTGGGGGTGTACCGCAACGACAGGATGCACCGCGCGGTGA |
| GCGCCAGCAGGCGGCGCGAGCTGAGCGACCAGGAGCTGATGCACAGCCTGCAGCGGGCCCTGACCGGGG |
| CCGGGACCGAGGGGGAGAGCTACTTTGACATGGGCGCGGACCTGCACTGGCAGCCCAGCCGCCGGGCCT |

| Sequences |
| --- |
| TGGAGGCGGCAGGCGGTCCCCCCTACATAGAAGAGGTGGACGATGAGGTGGACGAGGAGGGCGAGTACC |
| TGGAAGACTGATGGCGCGACCGTATTTTTGCTAGATGCAACAACAGCCACCTCCTGATCCCGCGATGCG |
| GGCGGCGCTGCAGAGCCAGCCGTCCGGCATTAACTCCTCGGACGATTGGACCCAGGCCATGCAACGCAT |
| CATGGCGCTGACGACCCGCAACCCCGAAGCCTTTAGACAGCAGCCCCAGGCCAACCGGCTCTCGGCCAT |
| CCTGGAGGCCGTGGTGCCCTCGCGCTCCAACCCCACGCACGAGAAGGTCCTGGCCATCGTGAACGCGCT |
| GGTGGAGAACAAGGCCATCCGCGGCGACGAGGCCGGCCTGGTGTACAACGCGCTGCTGGAGCGCGTGGC |
| CCGCTACAACAGCACCAACGTGCAGAACAACCTGGACCGACATGGTGACCGACGTGCGCGAGGCCGTGGC |
| CCAGCGCGAGCGGTTCCACCGCGAGTCCAACCTGGGATCCATGGTGGCGCTGAACGCCTTCCTCAGCAC |
| CCAGCCCGCCAACGTGCCCCGGGGCCAGGAGGACTACACCAACTTCATCAGCGCCCTGCGCCTGATGGT |
| GACCGAGGTGCCCCAGAGCGAGGTGTACCAGTCCGGGCCGGACTACTTCTTCCAGACCAGTCGCCAGGG |
| CTTGCAGACCGTGAACCTGAGCCAGGCGTTCAAGAACTTGCAGGGCCTGTGGGGCGTGCAGGCCCCGGT |
| CGGGGACCGCGCGACGGTGTCGAGCCTGCTGACGCCGAACTCGCGCCTGCTGCTGCTGCTGGTGGCCCC |
| CTTCACGGACAGCGGCAGCATCAACCGCAACTCGTACCTGGGCTACCTGATTAACCTGTACCGCGAGGC |
| CATCGGCCAGGCGCACGTGGACGAGCAGACCTACCAGGAGATCACCCACGTGAGCCGCGCCCTGGGCCA |
| GGACGACCCGGGCAATCTGGAAGCCACCCTGAACTTTTTGCTGACCAACCGGTCGCAGAAGATCCCGCC |
| CCAGTACACGCTCAGCGCCGAGGAGGAGCGCATCCTGCGATACGTGCAGCAGAGCGTGGGCCTGTTCCT |
| GATGCAGGAGGGGGCCACCCCCAGCGCCGCGCTCGACATGACCGCGCGCAACATGGAGCCCAGCATGTA |
| CGCCAGCAACCGCCCGTTCATCAATAAACTGATGGACTACTTGCATCGGGCGGCCGCCATGAACTCTGA |
| CTATTTCACCAACGCCATCCTGAATCCCCACTGGCTCCCGCCGCCGGGGTTCTACACGGGCGAGTACGA |
| CATGCCCGACCCCAATGACGGGTTCCTGTGGGACGATGTGGACAGCAGCGTGTTCTCCCCCGACCGGG |
| TGCTAACGAGCGCCCCTTGTGGAAGAAGGAAGGCAGCGACCGACGCCCGTCCTCGGCGCTGTCCGGCCG |
| CGAGGGTGCTGCCGCGGCGGTGCCCGAGGCCGCCAGTCCTTTCCCGAGCTTGCCCTTCTCGCTGAACAG |
| TATTCGCAGCAGCGAGCTGGGCAGGATCACGCGCCCGCGCTTGCTGGGCGAGGAGGAGTACTTGAATGA |
| CTCGCTGTTGAGACCCGAGCGGGAGAAGAACTTCCCAATAACGGATAGAGAGCCTGGTGGACAAGAT |
| GAGCCGCTGGAAGACGTATGCGCAGGAGCACAGGGACGATCCGTCGCAGGGGGCCACGAGCCGGGGCAG |
| CGCCGCCCGTAAACGCCGGTGGCACGACAGGCAGCGGGGACTGATGTGGGACGATGAGGATTCCGCCGA |
| CGACAGCAGCGTGTTGGACTTGGGTGGGAGTGGTAACCCGTTCGCTCACCTGCGCCCCCGCATCGGGCG |
| CATGATGTAAGAGAAACCGAAAATAAATGATACTCACCAAGGCCATGGCGACCAGCGTGCGTTCGTTTC |
| TTCTCTGTTGTTGTATCTAGTATGATGAGGCGTGCGTACCCGGAGGGTCCTCCTCCCTCGTACGAGAGC |
| GTGATGCAGCAGGCGATGGCGGCGGCGGCGGCGATGCAGCCCCCGCTGGAGGCTCCTTACGTGCCCCCG |
| CGGTACCTGGCGCCTACGGAGGGGCGGAACAGCATTCGTTACTCGGAGCTGGCACCCTTGTACGATACC |
| ACCCGGTTGTACCTGGTGGACAACAAGTCGGCGGACATCGCCTCGCTGAACTACCAGAACGACCACAGC |
| AACTTCCTGACCACCGTGGTGCAGAACAATGACTTCACCCCACGGAGGCCAGCACCCAGACCATCAAC |
| TTTGACGAGCGCTCGCGGTGGGCGGTCAGCTGAAAACCATCATGCACACCAACATGCCCAACGTGAAC |
| GAGTTCATGTACAGCAACAAGTTCAAGGCGCGGGTGATGGTCTCCCGCAAGACCCCCAACGGGGTGACA |
| GTGACAGATGGTAGTCAGGATATCTTGGAGTATGAATGGGTGGAGTTTGAGCTGCCCGAAGGCAACTTC |
| TCGGTGACCATGACCATCGACCTGATGAACAACGCCATCATCGACAATTACTTGGCGGTGGGGCGGCAG |
| AACGGGGTCCTGGAGAGCGATATCGGCGTGAAGTTCGACACTAGGAACTTCAGGCTGGGCTGGGACCCC |
| GTGACCGAGCTGGTCATGCCCGGGGTGTACACCAACGAGGCCTTCCACCCCGATATTGTCTTGCTGCCC |
| GGCTGCGGGGTGGACTTCACCGAGAGCCGCCTCAGCAACCTGCTGGCGCATTCGCAAGAGGCAGCCCTTC |
| CAGGAGGGCTTCCAGATCATGTACGAGGATCTGGAGGGGGGCAACATCCCCGCGCTCCTGGATGTCGAC |
| GCCTATGAGAAAAGCAAGGAGGAGAGCGCCGCCGCGGCGACTGCAGCTGTAGCCACCGCCTCTACCGAG |
| GTCAGGGGCGATAATTTTGCCAGCCCTGCAGCAGTGGCAGCGGCCGAGGCGGCTGAAACCGAAAGTAAG |
| ATAGTCATTCAGCCGGTGGAGAAGGATAGCAAGGACAGGAGCTACAACGTGCTGCCGGACAAGATAAAC |
| ACCGCCTACCGCAGCTGGTACCTGGCCTACAACTATGGCGACCCCGAGAAGGGCGTGCCTCCTGGACG |
| CTGCTCACCACCTCGGACGTCACCTGCGCGTGGAGCAAGTCTACTGGTCGCTGCCCGACATGATGCAA |
| GACCCGGTCACCTTCCGCTCCACGCGTCAAGTTAGCAACTACCCGGTGGTGGGCGCCGAGCTCCTGCCC |
| GTCTACTCCAAGAGCTTCTTCAACGAGCAGGCCGTCTACTCGCAGCAGCTGCGCGCCTTCACCTCGCTC |
| ACGCACGTCTTCAACCGCTTCCCCGAGAACCAGATCCTCGTCCGCCGCCGCCCACCATTACCACC |
| GTCAGTGAAAACGTTCCTGCTCTCACAGATCACGGGACCCTGCCGCTGCGCAGCAGTATCCGGGGAGTC |
| CAGCGCGTGACCGTTACTGACGCCAGACGCCGCACCTGCCCCTACGTCTACAAGGCCCTGGGCATAGTC |
| GCGCCGCGCGTCCTCTCGAGCCGCACCTTCTAAAAAATGTCCATTCTCATCTCGCCCAGTAATAACACC |
| GGTTGGGGCCTGCGCGCGCCCAGCAAGATGTACGGAGGCGCTCGGCCAACGCTCCACGCAACACCCCGTG |
| CGCGTGCGCGGGCACTTCCGCGCTCCCTGGGGCGCCCTCAAGGGCCGCGTGCGGTCGCGCACCACCGTC |
| GACGACGTGATCGACCAGGTGGTGGCCGACGCGCGCAACTACACCCCCGCCGCCGCGCCCGTCTCCACC |
| GTGGACGCCGTCATCGACAGCGTGGTGGCCGACGCGCGCCGGTACGCCCGCGCCAAGAGCCGGCGGCGG |
| CGCATCCCGGCGGCACCGGAGCACCCCCGCCATGCGCGCAGCCTGCGGCCTTGCTGCGCAGGGCCAGG |
| CGCACGGGACGCAGGGCCATGCTCAGGGCGGCCAGACGCGCGGCTTCAGGCGCCAGCGCCGGCAGGACC |
| CGGAGACGCGCGGCCACGGCGGCGGCAGCGGCCATCGCCAGCATGTCCGCCCGCGGCGAGGGAACGTG |
| TACTGGGTGCGCGACGCCGCCACCGGTGTGCGCGTGCCCGTGCGCACCCGCCCCCTCGCACTTGAAGA |
| TGTTCACTTCGCGATGTTGATGTGTCCCAGCGGCGAGGAGGATGTCCAAGCGCAAATTCAAGGAAGAGA |
| TGCTCCAGGTCATCGCGCCTGAGATCTACGGCCCCGCGGTGGTGAAGGAGGAAAGAAAGCCCCGCAAAA |
| TCAAGCGGGTCAAAAAGGACAAAAAGGAAGAAGATGACGATCTGGTGGAGTTTGTGCGCGAGTTCGCCC |
| CCCGGCGGCGCGTGCAGTGGCGCGGGCGGAAAGTGCACCCGGTGCTGAGACCCGGCACCACCGTGGTCT |
| TCACGCCCGGCGAGCGCTCCGGCAGCGCTTCCAAGCGCTCCTACGACGAGGTGTACGGGACGAGGACA |
| TCCTCGAGCAGGCGGCCGAGCGCCTGGGCGAGTTTGCTTACGGCAAGCGCAGCGCCGCCCGCCCTGAAGG |
| AAGAGGCGGTGTCCATCCCGCTGGACCACGGCAACCCCACGCCGAGCCTCAAGCCCGTGACCCTGCAGC |
| AGGTGCTGCCGAGCGCAGCGCCGCGCCGGGGGTTCAAGCGCGAGGGCGAGGATCTGTACCCCACCATGC |
| AGCTGATGGTGCCCAAGCGCCAGAAGCTGGAAGACGTGCTGGAGACCATGAAGGTGGACCGGACGTGC |
| AGCCCGAGGTCAAGGTGCGGCCCATCAAGCAGGTGGCCCCGGGCCTGGGCGTGCAGACCGTGGACATCA |
| AGATCCCCACGGAGCCCATGGAAACGCAGACCGAGCCCATGATCAAGCCCAGCACCAGCACCATGGAGG |
| TGCAGACGGATCCCTGGATGCCATCGGCTCCTAGCCGAAGACCCCGGCGAAGTACGCGCGGCCAGCC |
| TGCTGATGCCCAACTACGCGCTGCATCCTTCCATCATCCCCACGCCGGGCTACCGCGGCACGCGCTTCT |
| ACCGCGGTCATACAACCAGCGCCGCCGCGCAAGACCACCACCCGCCGCCGCCGTCGCCGCACAGCCGCTG |
| CATCTACCCCTGCCGCCCTGGTGCGGAGAGTGTACCGCCGCGGCCGCGCGCCTCTGACCCTACCGCGCG |
| CGCGCTACCACCCGAGCATCGCCATTTAAACTTTCGCCTGCTTTGCAGATGCCCTCACATGCCGCCTC |
| CGCGTTCCCATTACGGGCTACCGAGGAAGAAAACCGCGCCGTAGAAGGCTGGCGGGGAACGGGATGCGT |

-continued

| Sequences |
|---|
| CGCCACCACCATCGGCGGCGGCGCGCCATCAGCAAGCGGTTGGGGGGAGGCTTCCTGCCCGCGCTGATC |
| CCCATCATCGCCGCGGCGATCGGGGCGATCCCCGGCATTGCTTCCGTGGCGGTGCAGGCCTCTCAGCGC |
| CACTGAGACACTTGGAAAACATCTTGTAATAAACCAATGGACTCTGACTCCTGGTCCTGTGATGTGT |
| TTTCGTAGACAGATGGAAGACATCAATTTTTCGTCCCTGGCTCCGCGACACGGCACGCGGCCGTTCATG |
| GGCACCTGGAGCGACATCGGCACCAGCCAACTGAACGGGGCGCCTTCAATTGGAGCAGTCTCTGGAGC |
| GGGCTTAAGAATTTCGGGTCCACGCTTAAAACCTATGGCAGCAAGGCGTGGAACAGCACCACAGGGCAG |
| GCGCTGAGGGATAAGCTGAAAGAGCAGAACTTCCAGCAGAAGGTGGTCGATGGGCTCGCCTCGGGCATC |
| AACGGGGTGGTGGACCTGGCCAACCAGGCCGTGCAGCGGCAGATCAACAGCCGCCTGGACCCGGTGCCA |
| CCCGCCGGCTCCGTGGAGATGCCGCAGGTGGAGGAGGAGCTGCCTCCCCTGGACAAGCGGGGCGAGAAG |
| CGACCCCGCCCCGACGCGGAGGAGACGCTGCTGACGCACACGGACGAGCCGCCCCCGTACGAGGAGGCG |
| GTGAAACTGGGTCTGCCCACCACGCGGCCCATCGCGCCCCTGGCCACCGGGGTGCTGAAACCCGAAAGT |
| AATAAGCCCGCGACCCTGGACTTGCCTCCTCCCGCTTCCCGCCCCTCTACAGTGGCTAAGCCCCTGCCG |
| CCGGTGGCCGTGGCCCGCGCGCGACCCGGGGGCTCCGCCCGCCCTCATGCGAACTGGCAGAGCACTCTG |
| AACAGCATCGTGGGTCTGGGAGTGCAGAGTGTGAAGCGCCGCCGCTGCTATTAAACCTACCGTAGCGCT |
| TAACTTGCTTGTCTGTGTGTGTATGTATTATGTCGCCGCTGTCGCCAGAAGGAGGAGTGAAGAGGCGC |
| GTCGCCGAGTTGCAAGATGGCCACCCCATCGATGCTGCCCCAGTGGGCGTACATGCACATCGCCGGACA |
| GGACGCTTCGGAGTACCTGAGTCCGGGTCTGGTGCAGTTCGCCCGCGCCACAGACACCTACTTCAGTCT |
| GGGGAACAAGTTTAGGAACCCCACGGTGGCGCCCACGCACGATGTGACCACCGACCGCAGCCAGCGGCT |
| GACGCTGCGCTTCGTGCCCGTGGACCGCGAGGACAACACCTACTCGTACAAAGTGCGCTACACGCTGGC |
| CGTGGGCGACAACCGCGTGCTGGACATGGCCAGCACTTACTTTGACATCCGCGGCGTGCTGGATCGGGG |
| CCCTAGCTTCAAACCCTACTCCGGCACCGCCTACAACAGCCTGGCTCCCAAGGGAGCGCCCAATTCCAG |
| CCAGTGGGAGCAAAAAAGGCAGGCAATGGTGACACTATGGAAACACACATTTGGTGTGGCCCCAAT |
| GGGCGGTGAGAATATTACAATCGACGGATTACAAATTGGAACTGACGCTACAGCTGATCAGGATAAACC |
| AATTTATGCTGACAAAACATTCCAGCCTGAACCTCAAGTAGGAAGAGAAGAAATTGGCAAGAAACTGAAAG |
| CTTTTATGGCGGTAGGGCTCTTAAAAAAGACACAAGCATGAAACCTTGCTATGGCTCCTATGCTAGACC |
| CACCAATGTAAAGGGAGGTCAAGCTAAACTTAAAGTTGGAGCTGATGGAGTTCCTACCAAAGAATTTGA |
| CATAGACCTGGCTTTCTTTGATACTCCCGGTGGCACAGTGAATGGACAAGATGAGTATAAAGCAGACAT |
| TGTCATGTATACCGAAAACACGTATCTGGAAACTCCAGACACGCATGTGGTATACAAACCAGGCAAGGA |
| TGATGCAAGTTCTGAAATTAACCTGGTTCAGCAGTCCATGCCCAATAGACCCAACTATATTGGGTTCAG |
| AGACAACTTTATTGGGCTCATGTATTACAACAGTACTGGCAATATGGGGGTGCTGGCTGGTCAGGCCTC |
| ACAGCTGAATGCTGTGGTCGACTTGCAAGACAGAAACACCGAGCTGTCATACCAGCTCTTGCTTGACTC |
| TTTGGGTGACAGAACCCGGTATTTCAGTATGTGGAATCAGGCGGTGGACAGTTATGATCCTGATGTGCG |
| CATTATTGAAAACCATGGTGTGGAAGACGAACTTCCCAACTATTGCTTCCCCCTGGATGGGTCTGGCAC |
| TAATGCCGCTTACCAAGGTGTGAAAGTAAAAAATGGTAACGATGGTGATGTTGAGAGCGAATGGGAAAA |
| TGATGATACTGTCGCAGCTCGAAATCAATTATGCAAGGGCAACATTTTTGCCATGGAAATTAACCTCCA |
| AGCCAACCTGTGGAGAAGTTTCCTCTACTCGAACGTGGCCCTGTACCTGCCCGACTCTTACAAGTACAC |
| GCCAGCCAACATCACCCTGCCCCACCAACACCAACACTTATGATTACATGAACGGGAGAGTGGTGCCTCC |
| CTCGCTGGTGGACGCCTACATCAACATCGGGGCGCGCTGGTCGCTGGACCCCATGGACAACGTCAATCC |
| CTTCAACCACCACCGCAACGCGGGCCTGCGCTACCGCTCCATGCTCCTGGGCAACGGGCGCTACGTGCC |
| CTTCCACATCCAGGTGCCCCAGAAATTTTTCGCCATCAAGCCTCCTGCTCCTGCCCGGGTCCTGCAC |
| CTACGAGTGGAACTTCCGCAAGGACGTCAACATGATCCTGCAGAGCTCCCTCGGCAACGACCTGCGCAC |
| GGACGGGGCCTCCATCTCCTTCACCAGCATCAACCTCTACGCCACCTTCTTCCCCATGGCGCACAACAC |
| GGCCTCCACGCTCGAGGCCATGCTGCGCAACGACACCAACGACCAGTCCTTCAACGACTACCTCTCGGC |
| GGCCAACATGCTCTACCCCATCCCGGCCAACGCCACCAACGTGCCCATCTCCATCCCCTCGCGCAACTG |
| GGCCGCCTTCCGCGGCTGGTCCTTCACGCGCGCCTCAAGACCAAGGAGACGCCCCTCGCTGGGCTTCCGGGTT |
| CGACCCCTACTTCGTCTACTCGGGCTCCATCCCCTACCTCGACGGCACCTTCTACCTCAACCACACCTT |
| CAAGAAGGTCTCCATCACCTTCGACTCCTCCGTCAGCTGGCCCGGCAACGACCGGCTCCTGACGCCCAA |
| CGAGTTCGAAATCAAGCGCACCGTCGACGGCGAGGGATACAACGTGGCCCAGTGCAACATGACCAAGGA |
| CTGGTTCCTGGTCCAGATGCTGGCCCACTACAACATCGGCTACCAGGCTCCGGCGGCTTCTACGTGCCCGAGGGCTA |
| CAAGGACCGCATGTACTCCTTCTTCCGCAACTTCCAGCCCATGAGCCGCCAGGTGGTGGACGAGGTCAA |
| CTACAAGGACTACCAGGCCGTCACCCTGGCCTACCAGCACAACAACTCGGGCTTCGTCGGCTACCTCGC |
| GCCCACCATGCGCCAGGGCCAGCCCTACCCCGCCAACTACCCGTACCCGCTCATCGGCAAGAGCGCCGT |
| CACCAGCGTCACCCAGAAAAAGTTCCTCTGCGACAGGGTCATGTGGCGCATCCCCTTCTCCAGCAACTT |
| CATGTCCATGGGCGCGCTCACCGACCTCGGCCAGAACATGCTCTATGCCAACTCCGCCCACGCGCTAGA |
| CATGAATTTCGAAGTCGACCCCATGGATGAGTCCACCCTTCTCTATGTTGTCTTCGAAGTCTTCGACGT |
| CGTCCGAGTGCACCAGCCCCACCGCGGCGTCATCGAGGCCGTCTACCTGCGCACCCCCTTCTCGGCCGG |
| TAACGCCACCACCTAAATTGCTACTTGCATGATGGCTGAGCCCACAGGCTCCGGCAGCAGGAGCTCAG |
| GGCCATCATCCGCGACCTGGGCTGCGGGCCCTACTTCCTGGGCACCTTCGATAAGCGCTTCCCGGGATT |
| CATGGCCCCGCACAAGCTGGCCTGCGCCATCGTCAACACGGCCGGCCGCGAGACCGGGGCGAGCACTG |
| GCTGGCCTTCGCCTGGAACCCGCGCTCGAACACCTGCTACCTCTTCGACCCCTTCGGGTTCTCGGACGA |
| GCGCCTCAAGCAGATCTACCAGTTCGAGTACGAGGGCCTGCTGCGCCGTAGCGCCCTGGCCACCGAGGA |
| CCGCTGCGTCACCCTGGAAAAGTCCACCCAGACCGTGCAGGGTCCGCGCTCGGCCGCTCGCGGGCTCTT |
| CTGCTGCATGTTCCTGCACGCCTTCGTGCACTGGCCCGACCGCCCATGGACAAGAACCCCACCATGAA |
| CTTGCTGACGGGGGTGCCCAACGGCATGCTCCAGTCGCCCCAGGTGGAACCCACCCTGCCGCGCAACCA |
| GGAGGCGCTCTACCGCTTCCTCAACTCCCACTCCGCCTACTTTCGCTCCCACCGCGCGCGCATCGAGAA |
| GGCCACCGCCTTCGACGCATGAACAATCAAGACATGTAAACCGTGTGTATGTTTAAAATATCTTTT |
| AATAAACAGCACTTTAATGTTACACATGCATCTGAGATGATTTTATTTTAGAAATCGAAAGGGTTCTGC |
| CGGGTCTCGGCATGGCCCGCGGGCAGGGACACGTTGCGGAACTGGTACTTGGCCAGCCACTTGAACTCG |
| GGGATCAGCAGTTTGGGCAGCGGGGTGTCGGGGAAGGAGTCGGTCCACAGCTTCCGCGTCAGCTGCAGG |
| GCGCCCAGCAGGTCGGGCGCGGAGATCTTGAAATCGCAGTTGGGACCCGCGTTCTGCGCGCGAGAGTTG |
| CGGTACACGGGGTTGCAGCACTGGAACACCATCAGGGGCGGGTGCTTCACGCTCGCAGCACCGCCGCGG |
| TCGGTGATGCTCTCCACGTCGAGGTCCTCGGCGTTGGCCATCCCGAAGGGGGTCATCTTGCAGGTCTGC |
| CTTCCCATGGTGGGCACGCACCCGGGCTTGTGGTTGCAATCGCAGTGCAGGGGATCAGCATCATCTGG |
| GCCTGGTCGGCGTTCATCCCCGGGTACATGGCCTTCATGAAAGCCTCCAATTGCCTGAACGCCTGCTGG |
| GCCTTGGCTCCCTCGGTGAAGAAGACCCCGCAGGACTTGCTAGAGAACTGGTTGGTGGCACAGCCGGCA |
| TCGTGCACGCAGCAGCGCGCGTCGTTGTTGGCCAGCTGCACCACGCTGCGCCCCAGCGGTTCTGGGTG |
| ATCTTGGCCCGGTCGGGGTTCTCCTTCAGCGCGCGCTGCCCGTTCTCGCTCGCCACATCCATCTCGATC |

| Sequences |
| --- |
| ATGTGCTCCTTCTGGATCATGGTGGTCCCGTGCAGGCACCGCAGTTTGCCCTCGGCCTCGGTGCACCCG
TGCAGCCACAGCGCGCACCCGGTGCACTCCCAGTTCTTGTGGGCGATCTGGGAATGCGCGTGCACGAAC
CCTTGCAGGAAGCGGCCCATCATGGTCGTCAGGGTCTTGTTGCTAGTGAAGGTCAACGGGATGCCGCGG
TGCTCCTCGTTGATGTACAGGTGGCAGATGCGGCGGTACACCTCGCCCTGCTCGGGCATCAGTTGGAAG
TTGGCTTTCAGGTCGGTCTCCACGCGGTAGCGGTCCATCAGCATAGTCATGATTTCCATGCCCTTCTCC
CAGGCCGAGACGATGGGCAGGCTCATAGGGTTCTTCACCATCATCTTAGCACTAGCAGCCGCGGCCAGG
GGGTCGCTCTCATCCAGGGTCTCAAAGCTCCGCTTGCCGTCCTTCTCGGTGATCCGCACCGGGGGGTAG
CTGAAGCCCACGGCCGCCAGCTCCTCCTCGGCCTGTCTTTCGTCCTCGCTGTCCTGGCTGACGTCCTGC
ATGACCACATGCTTGGTCTTGCGGGGTTTCTTCTTGGGCGGCAGTGGCGGCGGAGATGCTTGTGGCGAG
GGGGAGCGCGAGTTCTCGCTCACCACTACTATCTCTTCCTCTTCTTGGTCCGAGGCCACGCGGCGGTAG
GTATGTCTCTTCGGGGGCAGAGGCGGAGGCGACGGGCTCTCGCCGCCGCGACTTGGCGGATGGCTGGCA
GAGCCCCTTCCGCGTTCGGGGTGCGCTCCCGGCGGCGCTCTGACTGACTTCCTCCGCGGCCGGCCATT
GTGTTCTCCTAGGGAGGAACAACAAGCATGGAGACTCAGCCATCGCCAACCTCGCCATCTGCCCCCACC
GCCGGCGACGAGAAGCAGCAGCAGCAGAATGAAAGCTTAACCGCCCCGCCGCCCAGCCCCGCCTCCGAC
GCAGCCGCGGTCCCAGACATGCAAGAGATGGAGGAATCCATCGAGATTGACCTGGGCTATGTGACGCCC
GCGGAGCATGGAGGAGCTGGCAGTGCGCTTTCAATCGTCAAGCCAGGAAGATAAAGAACAGCCAGAG
CAGGAAGCAGAGAACGAGCAGAGTCAGGCTGGGCTCGAGCATGGCGACTACCTCCACCTGAGCGGGGAG
GAGGACGCGCTCATCAAGCATCTGGCCCGGCAGGCCACCATCGTCAAGGACGCGCTGCTCGACCGCACC
GAGGTGCCCCTCAGCGTGGAGGAGCTCAGCCGCGCCTACGAGCTCAACCTCTTCTCGCCGCGCGTGCCC
CCCAAGCGCCAGCCCAACGGCACCTGCGAGCCCAACCCCCGCCTCAACTTCTACCCGGTCTTCGCGGTG
CCCGAGGCCCTGGCCACCTACCACATCTTTTTCAAGAACAAAAGATCCCCGTCTCCTGCCGCGCCAAC
CGCACCCGCGCCGACGCCCTCTTCAACCTGGGTCCCGGCGCCCGCCTACCTGATATCGCCTCCTTGGAA
GAGGTTCCCAAGATCTTCGAGGGTCTGGGCAGCGACGAGACTCGGGCGCGAACGCTCTGCAAGGAGAA
GGAGGAGGAGAGCATGAGCACCACAGCGCCCTGGTCGAGTTGGAAGGCGACAACGCGCGGCTGGCGGTG
CTCAAACGCACGGTCGAGCTGACCCATTTCGCCTACCCGGCTCTGAACCTGCCCCCGAAAGTCATGAGC
GCGGTCATGGACCAGGTGCTCATCAAGCGCGCGTCGCCCATCTCCGAGGACGAGGGCATGCAAGACTCC
GAGGAGGGCAAGCCCGTGGTCAGCGACGAGCAGCTGGCCCGGTGGCTGGGTCCTAATGCTACCCCTCAA
AGTTTGGAAGAGCGGCGCAAGCTCATGATGGCCGTGGTCCTGGTGACCGTGGAGCTGGAGTGCCTGCCC
CGCTTCTTCGCCGACGCGGAGACCCTGCGCAAGGTCGAGGAGAACCTGCACTACCTCTTCAGGCACGGG
TTCGTGCGCCAGGCCTGCAAGATCTCCAACGTGGAGCTGACCAACCTGGTCTCCTACATGGGCATCTTG
CACGAGAACCGCCTGGGGCAGAACGTGCTGCACACCACCCTGCGCGGGGAGGCCCGCCGCGACTACATC
CGCGACTGCGTCTACCTCTACCTCTGCCACACCTGGCAGACGGGCATGGGCGTGTGGCAGCAGTGTCTG
GAGGAGCAGAACCTGAAAGAGCTCTGCAAGCTCCTGCAAAAGAACCTCAAGGGTCTGTGGACCGGGTTC
GACGAGCGGACCACCGCCTCGGACCTGGCCGACCTCATCTTCCCCGAGCGCCTCAGGCTGACGCTGCGC
AACGGCCTGCCCGACTTTATGAGCCAAAGCATGTTGCAAAACTTTCGCTCTTTCATCCTCGAACGCTCC
GGAATCCTGCCCGCCACCTGCTCCGCGCTGCCCTCGGACTTCGTGCCGCTGACCTTCCGCGAGTGCCCC
CCGCCGCTGTGGAGCCACTGCTACCTGCTGCGCCTGGCCAACTACCTGGCCTACCACTCGGACGTGATC
GAGGACGTCAGCGGCGAGGGCCTGCTCGAGTGCCACTGCCGCTGCAACCTCTGCACGCCGCACCGCTCC
CTGGCCTGCAACCCCCAGCTGCTGAGCGAGACCCAGATCATCGGCACCTTCGAGTTGCAAGGGCCCAGC
GAGGGCGAGGGAGCCAAGGGGGGTCTGAAACTCACCCCGGGGCTGTGGACCTCGGCCTACTTGCGCAAG
TTCGTGCCCGAGGATTACCATCCCTTCGAGATCAGGTTCTACGAGGACCAATCCCAGCCGCCCAAGGCC
GAGCTGTCGGCCTGCGTCATCACCCAGGGGGCGATCCTGGCCCAATTGCAAGCCATCCAGAAATCCCGC
CAAGAATTCTTGCTGAAAAAGGGCCGCGGGGTCTACCTCGACCCCCAGACCGGTGAGGAGCTCAACCCC
GGCTTCCCCCAGGATGCCCCGAGGAAACAAGAAGCTGAAAGTGGAGCTGCCGCCCGTGGAGGATTTGGA
GGAAGACTGGGAGAACAGCAGTCAGGCAGAGGAGATGGAGGAAGACTGGGACAGCACTCAGGCAGAGGA
GGACAGCCTGCAAGACAGTCTGGAGGAAGACGAGGAGGAGGCAGAGGAGGAGGTGGAAGAAGCAGCCGC
CGCCAGACCGTCGTCCTCGGCGGGGAGAAAGCAAGCAGCACGGATACCATCTCCGCTCCGGGTCGGGG
TCCCGCTCGGCCCCACAGTAGATGGGACGAGACCGGGCGATTCCCGAACCCCACCACCCAGACCGGTAA
GAAGGAGCGGCAGGGATACAAGTCCTGGCGGGGGCACAAAAACGCCATCGTCTCCTGCTTGCAGGCCTG
CGGGGGCAACATCTCCTTCACCCGGCGCTACCTGCTCTTCCACCGCGGGGTGAACTTCCCCCGCAACAT
CTTGCATTACTACCGTCACCTCCACAGCCCCTACTACTTCCAAGAAGAGGCAGCAGCAGCAGAAAAAGA
CCAGAAAACCAGCTAGAAAATCCACAGCGGCGGCAGCGGCAGGTGGACTGAGGATCGCGGCGAACGAGC
CGGCGCAGACCCGGGAGCTGAGGAACCGGATCTTTCCCACCCTCTATGCCATCTTCCAGCAGAGTCGGG
GGCAGGAGCAGGAACTGAAAGTCAAGAACCGTTCTCTGCGCTCGCTCACCCGCAGTTGTCTGTATCACA
AGAGCGAAGACCAACTTCAGCGCACTCTCGAGGACGCCGAGGCTCTCTTCAACAAGTACTGCGCGCTCA
CTCTTAAAGAGTAGCCCGCGCCCGCCCAGTCGCAGAAAAGGCGGGAATTACGTCACCTGTGCCCTTCG
CCCTAGCCGCCTCCACCCAGCACCGCCATGAGCAAAGAGATTCCCACGCCTTACATGTGGAGCTACCAG
CCCCAGATGGGCCTGGCCGCCGGCGCCGCCCAGGACTACTCCACCCGCATGAATTGGCTCAGCGCCGGG
CCCGCGATGATCTCACGGGTGAATGACATCCGCGCCCACCGAAACAGATACTCCTAGAACAGTCAGCG
CTCACCGCCACGCCCCGCAATCACCTCAATCCGCGTAATTGGCCCGCCGCCCTGGTGTACCAGGAAATT
CCCCAGCCCACGACCGTACTACTTCCGCGAGACGCCCAGGCCGAAGTCCAGCTGACTAACTCAGGTGTC
CAGCTGGCGGGCGGCGCCACCCTGTGTCGTCACCGCCCCGCTCAGGGTATAAAGCGGCTGGTGATCCGG
GGCAGAGGCACACAGCTCAACGACGAGGTGGTGAGCTCTTCGCTGGGTCTGCGACCTGACGGAGTCTTC
CAACTCGCCGGATCGGGGAGATCTTCCTTCACGCCTCGTCAGGCGGTCCTGACTTTGGAGAGTTCGTCC
TCGCAGCCCCGCTCGGGCGGCATCGGCACTCTCCAGTTCGTGGAGGAGTTCACTCCCTCGGTCTACTTC
AACCCCTTCTCCGGCTCCCCCGGCCACTACCCGGACGAGTTCATCCCGAACTTTGACGCCCATCAGCAG
TCGGTGGACGGCTACGATTGAATGTCCCATGGTGGCGCGGCTGACCTAGTCTCGGCTTCGACACCTGGAC
CACTGCCGCCGCTTTCGCTGCTTCGCTCGGGACCTCGCCGAGTTCACCTACTTTGAGCTGCCCGAGGAG
CATCCTCAGGGCCCGGCCCACGGAGTGCGGATCGTCGTGAAGGGGCCTAGACTCCCACCTGCTTCGG
ATCTTCAGCCAGCGCCCGATCCTGGTCAGCGCCAACAGGGCAACACCCTCCTGACCCTCTACTGCATC
TGCGACCACCCCGGCCTGCATGAAAGTCTTTGTTGTCTGCTGTGTACTGAGTATAATAAAAGCTGAGAT
CAGCGACTACTCCGGACTCAACTGTGGTGTTTCTGCATCCATCAATCGGTCTCTGACCTTCACCGGGAA
CGAGACCGAGCTCCAGGTCAGTGTAAGCCCCACAAGAAGTACCTCACCTGGCTGTACCAGGGCTCCCC
GATCGCCGTTGTTAACCACTGCGACGACGACGGAGTCCTGCTGAACGGCCCCGCCAACCTTACTTTTTC
CACCCGCAGAAGCAAGCTACTGCTCTTCCGACCCTTCCTCCCCGGCACCTATCAGTGCATCTCGGGACC
CTGCCATCACACCTTCCACCTGATCCCGAATACCACCTCTTCCCCAGCACCGCTCCCCACTAACAACCA
AACTAACCACCACCAACGCTACCGACGCGACCTCGTTTCTGAATCTAATACCACCCACACCGGAGGTGA |

| Sequences |
| --- |
| GCTCCGAGGTCGCAAACCCTCTGGGATTTATTACGGCCCCTGGGAGGTGGTGGGGTTAATAGCTTTAGG |
| CTTAGTGGCGGGTGGGCTTTTGGCTCTCTGCTACCTATACCTCCCTTGCTTTTCCTACTTAGTGGTGCT |
| TTGTTGCTGGTTTAAGAAATGGGGAAGATCACCCTAGTGTGCGGTGTGCTGGTGACGGTGGTGCTTTCG |
| ATTCTGGGAGGGGGAAGCGCGGCTGTAGTGACGGAGAAGAAGGCCGATCCCTGCTTGACTTTCAACCCC |
| GATAAATGCCGGCTGAGTTTTCAGCCCGATGGCAATCGGTGCGCGGTGTTGATCAAGTGCGGATGGGAA |
| TGCGAGAGCGTGTTGGTCCAGTATAAAAACAAGACCTGGAACAATACTCTCGCGTCCACATGGCAGCCC |
| GGGGACCCCGAGTGGTACACCGTCTCTGTCCCTGGTGCTGACGGCTCCCTCCGCACGGTGAACAACACT |
| TTCATTTTTGAGCACATGTGCGAGACCGCCATGTTCATGAGCAAGCAGTACGGTATGTGGCCCCACGT |
| AAAGAGAATATCGTGGTCTTCTCCATCGCTTACAGCGCGTGCACGGTGCTAATCACCGCGATCGTGTGC |
| CTGAGCATTCACATGCTCATCGCTATTCGCCCCAGAAATAATGCCGAGAAAGAGAAACAGCCATAACAC |
| ACTTTTCACATACCTTTTTCAGACCATGGCCTCTGTTACAATCCTTATTTATTTTTTGGGACTTGTGGG |
| CACTAGCAGCACTTTTCAGCATATAAACAAAACTGTTTATGCTGGTTCAAATTCTGTGTTAGCTGGACA |
| TCAGTCATACCAGAAAGTTTCATGGTACTGGTATGATAAAAATCAAACACCCGTTACACTCTGCAAGGG |
| TCCACAACAGCCCGTAAACCGTAGTGGGATTTTTTTTAGCTGTAATCATAATAATATCACACTACTTTC |
| AATTACAAAGCACTATGCTGGAACTTACTATGGAACCAATTTCAATATCAAACATGACACTTACTATAG |
| TGTCAGAGTATTGGATCCAACTACCCCTAGAACAACTACAAAGCCCACCACAACTAAGAAGCCCACTAC |
| ACCTAAGAAGCCTACCACGCCCAAAACCACTAAGACAACTACTAAGACCACTACCACAGAGCCAACCAC |
| AACCAGCACCCACACTTGCTATAACTACACACACACACACACACAcTGAGCTGACCTCACAGGCAACTACT |
| GAAAATGGTTTTGCCCTGTTACAAAAGGGGGAAAACAGTAGCAGCAGTCCTCTGCCTACCACCCCCAGT |
| GAGGAAATACCTAAATCATGGTTGGCATTATCGCTGCTGTAGTGGTGTGTATGCTGATTATCATCTTG |
| TGCATGATGTACTATGCCTGCTACTACAGAAAACACAGGCTGAACAACAAGCTGGACCCCCTACTGAAT |
| GTTGATTTTAATTTTTAGAACCATGAAGATCCTAAGCCTTTTTTGTTTTTCTATAATTATTACCTCT |
| GCTATTTGTAACTCAGTGGATAAGGACGTTACTGTCACCACTGGCTCTAATTATACACTGAAAGGACCT |
| CCCTCAGGTATGCTTTCGTGGTATTGCTATTTTGGAACTGATGTTTCACAAACTGAATTGTGTAATTTT |
| CAAAAAGGCAAAACCCAAAATCCTAAAATTCATAACTATCAATGCAATGGTACTGATTTAGTACTGTTC |
| AATATCACGAAAACATATGCTGGAAGTTATTACTGCCCGGGAGATAATGTTGACAATATGATTTTTTAC |
| GAATTACAAGTAGTTGATCCCACTACTCCAGCACCACCCACCACAACTACCAAGGCACATAGCACAGAC |
| ACACAGGAAACCACTCCAGAGGCAGAAGTAGCAGAGTTAGCAAAGCAGATTCATGAAGATTCCTTTGTT |
| GCCAATACCCCCACACACCCCGGACCGCAATGTCCAGGGCCATTAGTCAGCGGCATTGTCGGTGTGCTT |
| TGCGGGTTAGCAGTTATAATCATCTGCATGTTCATTTTTGCTTGCTGCTACAGAAGGCTTCACCGACAA |
| AAATCAGACCCACTGCTGAACCTCTATGTTTAATTTTTGATTTTCCAGAGCCATGAAGGCACTTAGCAC |
| TTTAGTTTTTTTGACCTTGATTGGCATTGTTTTTAATAGTAAAATTACCAGGGTTAGCTTTCTCAAACA |
| TGTTAATGTTACTGAAGGAAATAATATCACACTAGTAGGTGTAGAAGGTGCTCAAAACACCACTGGAC |
| AAAATACCATCTCGGGTGGAAAGATATTTGCACCTGGAATGTCACTTATTTTGCATAGGAGTTAATCT |
| TACCATTGTTAATGCTAATCAATCTCAGAATGGATTAATTAAAGGGCAGAGCGTGAGTGTTACCAGTGA |
| TGGGTACTATACCCAGCATAATTTCAACTACAACATTACTGTTATACCACTGCCAACACCTAGCCCACC |
| TAGCACTACTCAGACCACACAAACAACTCACACTACACAGAGCTCCACAACTACCATGCAGACCACTCA |
| GACAACCACATACACTACTTCCCCTCAGCCCACCACCACTACAGCAGAGGCGAGTAGCTCACCCACCAT |
| CAAAGTGGCATTTTTAATGCTGGCCCCATCTAGCAGTCCCACTGCTAGTACCAATGAGCAGACTACTGA |
| ATTTTTGTCCACTATTCAGAGCAGCACCACAGCTACCTCGAGTGGCCTTCTCTAGCACCGCCAATCTCAC |
| CTCGCTTTCCTCTATGCCAATCAGTAATGCTACTACCTCCCCCGCTCCTCTTCCCACTCCTCCTGAAGCA |
| ATCCGAGTCCAGCACGCAGCTGCAGATCACCCTGCTCATTGTGATCGGGGTGGTCATCCTGGCAGTGCT |
| GCTCTACTTTATCTTCTGCCGTCGCATCCCCAACGCAAAGCCGGCCTACAAGCCCATTGTTATCGGGAC |
| GCCGGAGCCGCTTCAGGTGGAGGGAGGTCTAAGGAATCTTCTCTTCTCTTTTACAGTATGGTGATTTGA |
| ACTATGATTCCTAGACATTTCATTATCACTTCTCTAATCTGTGTGCTCCAAGTCTGTGCCACCCTCGCT |
| CTCGTGGCTAACGCGAGTCCAGACTGCATTGGAGCGTTCGCCTCCTACGTGCTCTTTGCCTTCATCACC |
| TGCATCTGCTGCTGTAGCATAGTCTGCCTGCTTATCACCTTCTTCCAGTTCGTTGACTGGGTCTTTGTG |
| CGCATCGCCTACCTGCGCCACCACCCCCAGTACCGCGACCAGAGAGTGGCGCAACTGTTGAGACTCATC |
| TGATGATAAGCATGCGGGCTCTGCTACTACTTCTCGCGCTTCTGCTAGCTCCCCTCGCCGCCCCCTAT |
| CCCTCAAATCCCCCACCCAGTCCCCTGAAGAGGTTCGAAAATGTAAATTCCAAGAACCCTGGAAATTCC |
| TTTCATGCTACAAACTCAAATCAGAAATGCACCCCAGCTGGATCATGATCGTTGGAATCGTGAACATCC |
| TTGCCTGTACCCTCTTCTCCTTTGTGATTTACCCCCGCTTTGACTTTGGGTGGAACGCACCCGAGGCGC |
| TCTGGCTCCCGCCTGATCCCGACACACCACCACAGCAGCAGCAGCAAAATCAGGCACAGGCACACGCAC |
| CACCACAGCCTAGGCCACAATACATGCCCATCTTAAACTATGAGGCCGAGGCACAGCGAGCCATGCTTC |
| CTGCTATTAGTTACTTCAATCTAACCGGCGGAGATGACTGACCCCATGGCCAACAACACCGTCAACGAC |
| CTCCTGGACATGGACGCCGCGCCTCGGAGCAGCGACTCGCCCAACTCCGCATCCGCCAGCAGCAGGAG |
| AGAGCCGTCAAGGAGCTGCAGGATGCGGTGGCCATCCACCAGTGCAAGAGGCATCTTCTGCCTGGTG |
| AAGCAGGCCAAGATCTCCTTCGAGGTCACGTCCACCGACCATCGCCTCTCCTACGAGTCCTGCAGCAG |
| CGCCAGAAGTTCACCTGCCTGGTCGGAGTCAACCCCATCGTCATCACCCAGCAGTCTGGCGATACCAAG |
| GGTTGCATCCACTGCTCCTGCGACTCCCCGAGTGCGTTCACACCCTGATCAAGACCCTCTGCGGCCTC |
| CGCGACCTTCCTCCCCATGAACTAATCAACTAACCCCCTACCCCTTTACCCTCCATGAAAAATAAAGATT |
| AAAAATGATTGAATTGATCAATAAAGAATCACTTACTTGAAATCTGAAACCAGGTCTCTGTCCATGTTT |
| TCTGTCAGCAGCACTTCACTCCCCTCTTCCCAACTCTGGTACTGCAGGCCCCGGCGGGCTGCAAACTTC |
| CTCCACACTCTGAAGGGGATGTCAAATTCCTCCTGTCCCTCAATCTTCATTTTTATCTTCTATCAGATG |
| TCCAAAAAGCGCGCGGGTGGATGATGGCTTCGACCCCGTGTACCCCTACGATGCAGACAACGCACCG |
| ACTGTGCCCTTCATCAACCCTCCCTTCGTCTCTTCAGATGGATTCCAAGAAAAGCCCCTGGGGGTGTTG |
| TCCCTGCGACTGGCCGACCCCGTCACCACCAAGAATGGGGCTGTCACCCTCAAGCTGGGGGAGGGGGTG |
| GACCTCGACGACTCGGGAAAACTCATCTCCAAAAATGCCACCAAGGCCACTGCCCCTCTCAGTATTTCC |
| AACGGCACCATTTCCCTTAACATGGCTGCCCCTTTTTACAACAACAATGGAACGTTAAGTCTCAATGTT |
| TCTACACCATTAGCAGTATTTCCCACTTTTAACACTTTAGGTATCAGTCTTGGAAACGGTCTTCAAACT |
| TCTAATAAGTTGCTGACTGTACAGTTAACTCATCCTCTTACATTCAGCTCAAATAGCATCACAGTAAAA |
| ACAGACAAAGGACTCTATATTAATTCTAGTGGAAACAGAGGGCTTGAGGCTAACATAAGCCTAAAAGA |
| GGACTGATTTTTGATGGTAATGCTATTGCAACATACCTTGGAAGTGGTTTAGACTATGGATCCTATGAT |
| AGCGATGGGAAACAAGACCCATCATCACCAAAATTGGAGCAGGTTTGAATTTTGATGCTAATAATGCC |
| ATGGCTGTGAAGCTAGGCACAGGTTTAAGTTTTGACTCTGCCGGTGCCTTAACAGCTGGAAACAAAGAG |
| GATGACAAGCTAACACTTTGGACTACACCTGACCCAAGCCCTAATTGTCAATTACTTTCAGACAGAGAT |
| GCCAAATTTACCCTATGTCTTACAAAATGCGGTAGTCAAATACTAGGCACTGTTGCAGTAGCTGCTGTT |

| Sequences |
| --- |
| ACTGTAGGTTCAGCACTAAATCCAATTAATGACACAGTAAAAAGCGCCATAGTATTCCTTAGATTTGAC
TCTGACGGTGTGCTCATGTCAAACTCATCAATGGTAGGTGATTACTGGAACTTTAGGGAAGGACAGACC
ACCCAAAGTGTGGCCTATACAAATGCTGTGGGATTCATGCCCAATCTAGGTGCATATCCTAAAACCCAA
AGCAAAACACCAAAAAATAGTATAGTAAGTCAGGTATATTTAAATGGAGAAACTACTATGCCAATGACA
CTGACAATAACTTTCAATGGCACTGATGAAAAAGACACAACACCTGTGAGCACTTACTCCATGACTTTT
ACATGGCAGTGGACTGGAGACTATAAGGACAAGAATATTACCTTTGCTACCAACTCCTTTACTTTCTCC
TACATGGCCCAAGAATAAACCCTGCATGCCAACCCCATTGTTCCCACCACTATGGAAAACTCTGAAGCA
GAAAAAAATAAAGTTCAAGTGTTTTATTGATTCAACAGTTTTCACAGAATTCGAGTAGTTATTTTCCCT
CCTCCCTCCCAACTCATGGAATACACCACCCTCTCCCCACGCACAGCCTTAAACATCTGAATGCCATTG
GTAATGGACATGGTTTTGGTCTCCACATTCCACACAGTTTCAGAGCGAGCCAGTCTCGGGTCGGTCAGG
GAGATGAAACCCTCCGGGCACTCCTGCATCTGCACCTCAAAGTTCAGTAGCTGAGGGCTGTCCTCGGTG
GTCGGGATCACAGTTATCTGGAAGAAGAGCGGTGAGAGTCATAATCCGCGAACGGGATCGGCGGTTGT
GGCGCATCAGGCCCCGCAGCAGTCGCTGTCTGCGCCGCTCCGTCAAGCTGCTGCTCAAGGGGTCTGGGT
CCAGGGACTCCCTGCGCATGATGCCGATGGCCCTGAGCATCAGTCGCCTGGTGCGGCGGGCGCAGCAGC
GGATGCGGATCTCACTCAGGTCGGAGCAGTACGTGCAGCACAGCACTACCAAGTTGTTCAACAGTCCAT
AGTTCAACGTGCTCCAGCCAAAACTCATCTGTGGAACTATGCTGCCCACATGTCCATCGTACCAGATCC
TGATGTAAATCAGGTGGCGCCCCCTCCAGAACACACTGCCCATGTACATGATCTCCTTGGGCATGTGCA
GGTTCACCACCTCCCGGTACCACATCACCCGCTGGTTGAACATGCAGCCCTGGATAATCCTGCGGAACC
AGATGGCCAGCACCGCCCCGCCCGCCATGCAGCGCAGGGACCCCGGGTCCTGGCAATGGCAGTGGAGCA
CCCACCGCTCACGGCCGTGGATTAACTGGGAGCTGAACAAGTCTATGTTGGCACAGCACAGGCACACGC
TCATGCATGTCTTCAGCACTCTCAGTTCCTCGGGGGTCAGGACCATGTCCCAGGGCACGGGGAACTCTT
GCAGGACAGTGAACCCGGCAGAACAGGGCAGCCCTCGCACACAACTTACATTGTGCATGGACAGGGTAT
CGCAATCAGGCAGCACCGGATGATCCTCCACCAGAGAAGCGCGGGTCTCGGTCTCCTCACAGCGAGGTA
AGGGGGCCGGCGGTTGGTACGGATGATGGCGGGATGACGCTAATCGTGTTCTGGATCGTGTCATGATGG
AGCTGTTTCCTGACATTTTCGTACTTCACGAAGCAGAACCTGGTACGGGCACTGCACACCGCTCGCCGG
CGACGGTCTCGGCGCTTCGAGCGCTCGGTGTTGAAGTTATAGAACAGCCACTCCCTCAGAGCGTGCAGT
ATCTCCTGAGCCTCTTGGGTGATGAAAATCCCATCCGCTCTGATGGCTCTGATCACATCGGCCACGGTG
GAATGGGCCAGACCCAGCCAGATGATGCAATTTTGTTGGGTTTCGGTGACGGAGGGAGAGGGAAGAACA
GGAAGAACCATGATTAACTTTATTCCAAACGGTCTCGGAGCACTTCAAAATGCAGGTCCCGGAGGTGGC
ACCTCTCGCCCCACTGTGtTGGTGGAAAATAACAGCCAGGTCAAAGGTGACACGGTTCTCGAGATGTT
CCACGGTGGCTTCCAGCAAAGCCTCCACGCGCACATCCAGAAACAAGAGGACAGCGAAAGCGGGAGCGT
TTTCTAATTCCTCAATCATCATATTACACTCCTGCACCATCCCCAGATAATTTTCATTTTTCCAGCCTT
GAATGATTCGTATTAGTTCCTGAGGTAAATCCAAGCCAGCCATGATAAAAAGCTCGCGCAGAGCGCCCT
CCACCGGCATTCTTAAGCACACCCTCATAATTCCAAGAGATTCTGCTCCTGGTTCACCTGCAGCAGATT
AACAATGGGAATATCAAAATCTCTGCCGCGATCCCTAAGCTCCTCCCTCAACAATAACTGTATGTAATC
TTTCATATCATCTCCGAAATTTTTAGCCATAGGGCCGCCAGGAATAAGAGCAGGGCAAGCCACATTACA
GATAAAGCGAAGTCCTCCCCAGTGAGCATTGCCAAATGTAAGATTGAAATAAGCATGCTGGCTAGACCC
TGTGATATCTTCCAGATAACTGGACAGAAATCAGGCAAGCAATTTTTAAGAAAATCAACAAAAGAAAA
GTCGTCCAGGTGCAGGTTTAGAGCCTCAGGAACAACGATGGAATAAGTGCAAGGAGTGCGTTCCAGCAT
GGTTAGTGTTTTTTGGTGATCTGTAGAACAAAAAATAAACATGCAATATTAAACCATGCTAGCCTGGC
GAACAGGTGGGTAAATCACTCTTTCCAGCACCAGGCAGGCTACGGGGTCTCCGGCGCGACCCTCGTAGA
AGCTGTCGCCATGATTGAAAGCATCACCGAGAGACCTTCCCGGTGGCCGGCATGGATGATTCGAGAAG
AAGCATACACTCCGGGAACATTGGCATCCGTGAGTGAAAAAAAGCGACCTATAAAGCCTCGGGGCACTA
CAATGCTCAATCTCAATTCCAGCAAAGCCACCCCATGCGGATGGAGCACAAAATTGGCAGGTGCGTAAA
AATGTAATTACTCCCCTCCTGCACAGGCAGCAAAGCCCCCGCTCCCTCCAGAAACACATACAAAGCCT
CAGCGTCCATAGCTTACCGAGCACGGCAGGCGCAAGAGTCAGAGAAAAGGCTGAGCTCTAACCTGACTG
CCCGCTCCTGTGCTCAATATATAGCCCTAACCTACACTGACGTAAAGGCCAAAGTCTAAAAATACCCGC
CAAAATGACACACACGCCCAGCACACGCCCAGAAACCGGTGACACACTCAAAAAAATACGTGCGCTTCC
TCAAACGCCCAAACCGGCGTCATTTCCGGGTTCCCACGCTACGTCACCGCTCAGCGACTTTCAAATTCC
GTCGACCGTTAAAAACGTCACTCGCCCCGCCCCTAACGGTCGCCCTTCTCTCGGCCAATCACCTTCCTC
CCTTCCCAAATTCAAACGCCTCATTTGCATATTAACGCGCACAAAAGTTTGAGGTATATATTTGAATG
ATG |

(AdY25 Hexon protein (L3))

SEQ ID NO. 2

MATPSMLPQWAYMHIAGQDASEYLSPGLVQFARATDTYFSLGNKFRNPTVAPTHDVTTDRSQRLTLRFV
PVDREDNTYSYKVRYTLAVGDNRVLDMASTYFDIRGVLDRGPSFKPYSGTAYNSLAPKGAPNSSQWEQK
KAGNGDTMETHTFGVAPMGGENITIDGLQIGTDATADQDKPIYADKTFQPEPQVGEENWQETESFYGGR
ALKKDTSMKPCYGSYARPTNVKGGQAKLKVGADGVPTKEFDIDLAFFDTPGGTVNGQDEYKADIVMYTE
NNTYLETPDTHVVYKPGKDDASSEINLVQQSMPNRPNYIGFRDNFIGLMYYNSTGNMGVLAGQASQLNAV
VDLQDRNTELSYQLLLDSLGDRTRYFSMWNQAVDSYDPDVRIIENHGVEDELPNYCFPLDGSGTNAAYQ
GVKVKNGNDGDVESEWENDDTVAARNQLCKGNIFAMEINLQANLWRSFLYSNVALYLPDSYKYTPANIT
LPTNTNTYDYMNGRVVPPSLVDAYINIGARWSLDPMDNVNPFNHHRNAGLRYRSMLLGNGRYVPFHIQV
PQKFFAIKSLLLLPGSYTYEWNFRKDVNMILQSSLGNDLRTDGASISFTSINLYATFFPMAHNTASTLE
AMLRNDINDQSFNDYLSAANMLYPIPANATNVPISIPSRNWAAFRGWSFTRLKTKETPSLGSGFDPYFV
YSGSIPYLDGTFYLNHTFKKVSITFDSSVSWPGNDRLLTPNEFEIKRTVDGEGYNVAQCNMTKDWFLVQ
MLAHYNIGYQGFYVPEGYKDRMYSFFRNFQPMSRQVVDEVNYKDYQAVTLAYQHNNSGFVGYLAPTMRQ
GQPYPANYPYPLIGKSAVTSVTQKKFLCDRVMWRIPFSSNFMSMGALTDLGQNMLYANSAHALDMNFEV
DPMDESTLLYVVFEVFDVVRVHQPHRGVIEAVYLRTPFSAGNATT (AdY25 Penton protein (L2))

SEQ ID NO. 3

MMRRAYPEGPPPSYESVMQQAMAAAAMQPPLEAPYVPPRYLAPTEGRNSIRYSELAPLYDTTRLYLVD
NKSADIASLNYQNDHSNFLTTVVQNNDFTPTEASTQTINFDERSRWGGQLKTIMHTNMPVNEFMYSNK
FKARVMVSRKTPNGVTVTDGSQDILEYEWVEFELPEGNFSVTMTIDLMNNAIIDNYLAVGRQNGVLESD
IGVKFDTRNFRLGWDPVTELVMPGVYTNEAFHPDIVLLPGCGVDFTESRLSNLLGIRKRQPFQEGFQIM
YEDLEGGNIPALLDVDAYEKSKEESAAAATAAVATASTEVRGDNFASPAAVAAAEAAETESKIVIQPVE

| Sequences |
|---|
| KDSKDRSYNVLPDKINTAYRSWYLAYNYGDPEKGVRSWTLLTTSDVTCGVEQVYWSLPDMMQDPVTFRS<br>TRQVSNYPVVGAELLPVYSKSFFNEQAVYSQQLRAFTSLTHVFNRFPENQILVRPPAPTITTVSENVPA<br>LTDHGTLPLRSSIRGVQRVTVTDARRRTCPYVYKALGIVAPRVLSSRTF |

(AdY25 Fibre Protein (L5))

SEQ ID NO. 4

MSKKRARVDDGFDPVYPYDADNAPTVPFINPPFVSSDGFQEKPLGVLSLRLADPVTTKNGAVTLKLGEG
VDLDDSGKLISKNATKATAPLSISNGTISLNMAAPFYNNNGTLSLNVSTPLAVFPTFNTLGISLGNGLQ
TSNKLLTVQLTHPLTFSSNSITVKTDKGLYINSSGNRGLEANISLKRGLIFDGNAIATYLGSGLDYGSY
DSDGKTRPIITKIGAGLNFDANNAMAVKLGTGLSFDSAGALTAGNKEDDKLTLWTTPDPSPNCQLLSDR
DAKFTLCLTKCGSQILGTVAVAAVTVGSALNPINDTVKSAIVFLRFDSDGVLMSNSSMVGDYWNFREGQ
TTQSVAYTNAVGFMPNLGAYPKTQSKTPKNSIVSQVYLNGETTMPMTLTITFNGTDEKDTTPVSTYSMT
FTWQWTGDYKDKNITFATNSFTFSYMAQE (AdY25 E1A)

SEQ ID NO. 5

MRHLRDLPDEKIIIASGNEILELVVNAMMGDDPPEPPTPFEAPSLHDLYDLEVDVPEDDPNEEAVNDLF
SDAALLAAEEASSPSSDSDSSLHTPRPGRGEKKIPELKGEEMDLRCYEECLPPSDDEDEQAIQNAASQG
MQAASESFALDCPPLPGHGCKSCEFHRLNTGDKAVLCALCYMRAYNHCVYSPVSDADDETPTTESTSSP
PEIGTSPPENIVRPVPVRATGRRAAVECLDDLLQAGDEPLDLCTRKRPRH (AdY25 E1B 19 KDa)

SEQ ID NO. 6

MEIWTILEDLHKTRQLLENASNGVSHLWRFCFGGDLAKLVYRAKQDYSEQFEVILRECPGLFDALNLGH
QTHFNQRIVRALDFTTPGRSTAAVAFFAFLLDKWSQETHFSRDYQLDFLAVALWRTWKSQRLNAISGYL
PVQPLDTLKILNLQESPRARQRRRQQQRQQEEDQEENPRAGLDPPAEEE (AdY25 E1B 55 KDa)

SEQ ID NO. 7

MESRNPFQQGLPAGFLSSSFVENMEIPAPECNLRLLAGTATRHSEDPESPGESQGTPTSPAAAAAGGG
SRREPESRPGPSGGGGVADLFPELRRVLTRSSSGRERGIKRERHDETNHRTELTVGLMSRKRPETVWWH
EVQSTGTDEVSVMHERFSLEQVKTCWLEPEDDWEVAIRNYAKLALRPDKKYKITKLINIRNACYISGNG
AEVEICLQERVAFRCCMMNMYPGVVGMDGVTFMNMRFRGDGYNGTVFMANTKLTVHGCSFFGFNNTCIE
AWGQVGVRGCSFSANWMGVVGRTKSMLSVKKCLFERCHLGVMSEGEARIRHCASTETGCFVLCKGNAKI
KHNMICGASDERGYQMLTCAGGNSHMLATVHVASHARKPWPEFEHNVMTRCNMHLGSRRGMFMPYQCNL
NYVKVLLEPDAMSRVSLTGVFDMNVEVWKILRYDESKTRCRACECGGKHARFQPVCVEVTEDLRPDHLV
LSCTGTEFGSSGEESD (AdY25 pIX)

SEQ ID NO. 8

MSGSGSFEGGVFSPYLTGRLPSWAGVRQNVMGSTVDGRPVQPANSSTLTYATLSSSSVDAAAAAAAASA
ASAVRGMAMGAGYYGTLVANSSSTNNPASLNEEKLLLLMAQLEALTQRLGELTQQVAQLQEQTRAAVAT
VKSK (AdY25 IVa2 (E2))

SEQ ID NO. 9

METKGRRRSGAVFDQPDEPEAHPRKRPARRAPLHRDGDHPDADAAALEGPDPGCAGRPSSGALLPQSSQ
PAKRGGLLDRDAVEHITELWDRLELLQQTLSKMPMADGLKPLKNFASLQELLSLGGLLPQSSQERLLAE
LVRENMHVREMMNEVAPLLREDGSCLSLNYHLQPVIGVIYGPTGCGKSQLLRNLLSAQLISPAPETVFF
IAPQVDMIPPSELKAWEMQICEGNYAPGIEGTFVPQSGTLRPKFIKMAYDDLTQDHNYDVSDPRNVFAQ
AAAHGPIAIIMDECMENLGGHKGVAKFFHAFPSKLHDKFPKCIGYTVLVVLHNMNPARDLGGNIANLKI
QAKMBLISPRMHPSQLNRFVNTYTKGLPVAISLLLKDIVQHHALRPCYDWVIYNTTPEHEALQWSYLHP
RDGLMPMYLNIQAHLYRVLEKIHRVLNDRDRWSRAYRARKIK (AdY25 Polymerase (E2))

SEQ ID NO. 10

MALVQTHGSRGLHPEASDPGRQPSRRRSRQSSPGAVPEPTRARRRRAPAAPASGPRAASAARRASSPPL
LTMEEAPPPSPQPPKKKRGTVVTPQGHGTLQAIDVATNGAVEIKYHLDLPRALEKLLQVNRAPPLPTDL
TPQRLRILDSSGLRALVLALRPARAEVWTCLPRGLVSMTTIEAEEGQADITHDVVQHEMQAPRLHFPLK
FLVKGTQVQLVQHVHPVQRCEHCGRINKHKHECSARRRHFYPHHINSHSSNWWQEIQFFPIGSHPRTER
LFLTYDVETYTWMGSFGKQLVPFMLVMKLSGDDRLVELALDLALQLKWDRWHGDPRTFYCVTPEKMAVG
QQFRQYRDRLQTALAVDLWTSFLRANPHLADWALEQHGLSDPDELTYEELKKLPHVKGRPRFVELYIVG
HNINGFDEIVLAAQVINNRAEVPQPFRITRNFMPRAGKILFNDTVFALPNPAYKKRTDFQLWEQGGCGG
IDFKHQFLKVMVRDTFALTHTSLRKAAQAYALPVEKGCCAYKAVNQFYMLGSYRADQDGFPLEEYWKDR
EEFLLNRELWKQKGQLKYDIIQETLDYCALDVLVTAELVAKLQDSYAHFIRDSVGLPHAHFNIFQRPTI
SSNSHAIFRQIVYRAEKPSRTNLGPGLLAPSHELYDYVRASIRGGRCYPTYIGILEEPLYVYDICGMYA
SALTHPMPWGTPLSPYERALAVREWQASLDDLATSISYFDPDLLPGIFTIDADPPDEVMLDPLPPFCSR
KGGRLCWTNEPLRGEVATSVDLITLHNRGWQVRIVPDEMTTVFPEWKCVAREYVQLNIAAKERADKEKN
QTMRSIAKLLSNALYGSFATKLDNKKIVFSDQMDEGLLKGISAGTVNIKSSSFLETDNLSAEVMPAFER
EYLPQQLALLDSDPEDSEDEQGPAPFYTPPAGTPGHVAYTYKPITFLDVDEGDMCLHTLEKVDPLVDND
RYPSHVASFVLAWTRAPVSEWAGFLYEEDRGTPLEDRPIKSVYGDTSLFVTQRGHELMETKGKKRIKK
NGGKLVFDPDQPDLTWLVECETVCAHCGADAYAPDSVFLAPKLYALKSLLCPACGQTSKGKLRAKGHAA
EALNYELMVNCYLADAQGADRERFSTSRMSLKRTLASAQPGAHPFTVTETTLTRTLRPWKDRTLAALDA
HRLVPYSRSRPNPRNEEVCWIEMP

-continued

Sequences (AdY25 pTP (E2))
SEQ ID NO. 11
MALSIHDCARLTGQTVPTMNYFLPLRNIWNRVREFPRASTTAAGITWMSRYIYGYHRTMLEDLAPGAPA
TERWPLYRQPPPHFLIGYQYLVRTCNDYIFDTRAYSRLKYHELVRPGHQTVNWSVMANCSYTINTGAYH
RFVDFDDFQTTLTQIQQAILAERVVADLALVQPQRGFGLTRMHGRAGEEEVPVERLMQDYYKDLARCQD
HAWGMADRLRIQQAGPKDLVLLATIRRLRTAYFNFITSSIARPAPQHDPAEETVLSLPCDCDWLEAFVQ
RFSDPVDLETLRSLRGVPTGQLIRCIVSALSLPNGDPPGHLEMRGGVFTLRPREDGRAVTETMRRRRGE
TIERFIDRLPVRRRRRRPPPPPPPPEEEVEEWILVEEEEEEVEELPGAFEREVRATIAELIRLLEEE
LTVSARNSQFFNFAVDFYEAMERLEALGDVSEMPLRRWIMYFFVTEHIATTLNYLYQRLCNYAVFTRHV
ELNLAQVVMRARDPEGVVVYSRVWNEAGMNAFSQLMGRISNDLAATVERAGRGDLQEEEIEQFMTEIAY
QDNSGDVQEILRQAAVNDTEIDSVELSFRFKLTGPVAFTQRRQIQDVNRRVVAHASLLRAQYQNLPARG
ADVPLPPLPPGPEPPLPPGARPRRRF (AdY25 52/55 kDa (L1))
SEQ ID NO. 12
MHPVLRQMRPHHPPPQQQPPPPQPALLPPPQQQQQLPATTAAAAVSGAGQTSQYDRLALEEGEGLARLG
ASSPERHPRVQMKRDAREAYVPKQNLFRDRSGEEPEEMRAARFHAGRELRRGLDRKVLRDEDFEADEL
TGISPARAHVAAANLVTAYEQTVKEESNFQKSFNNHVRTLIAREEVTLGLMHLWDLLEAIVQNPTSKPL
TAQLFLVVQHSRDNEAFREALLNITEPEGRWLLDLVNILQSIVVQERGLPLSEKLAAINFSVLSLGKYY
ARKIYKTPYVPIDKEVKIDGFYMRMTLKVLTLSDDLGVYRNDRMBRAVSASRRRELSDQELMHSLQRAL
TGAGTEGESYFDMGADLHWQPSRRALEAAGGPPYIEEVDDEVDEEGEYLED (AdY25 IIIa (L1))
SEQ ID NO. 13
MQQQPPPDPAMRAALQSQPSGINSSDDWTQAMQRIMALTTRNPEAFRQQPQANRLSAILEAVVPSRSNP
THEKVLAIVNALVENKAIRGDEAGLVYNALLERVARYNSTNVQTNLDRMVTDVREAVAQRERFHRESNL
GSMVALNAFLSTQPANVPRGQEDYTNFISALRLMVTEVPQSEVQSGPDYFFQTSRQGLQTVNLSQAFK
NLQGLWGVQAPVGDRATVSSLLTPNSRLLLLLVAPFTDSGSINRNSYLGYLINLYREAIGQAHVDEQTY
QEITHVSRALGQDDPGNLEATLNFLLTNRSQKIPPQYTLSAEEERILRYVQQSVGLFLMQEGATPSAAL
DMTARNMEPSMYASNRPFINKLMDYLHRAAAMNSDYFTNAILNPHWLPPPGFYTGEYDMPDPNDGFLWD
DVDSSVFSPRPGANERPLWICKEGSDRRPSSALSGREGAAAAVPEAASPFPSLPFSLNSIRSSELGRIT
RPRLLGEEEYLNDSLLRPEREKNFPNNGIESLVDKMSRWKTYAQEHRDDPSQGATSRGSAARKRRWEDR
QRGLMWDDEDSADDSSVLDLGGSGNPFAHLRPRIGRMM (AdY25 VII)
SEQ ID NO. 14
MSILISPSNNTGWGLRAPSKMYGGARQRSTQHPVRVRGHFRAPWGALKGRVRSRTTVDDVIDQVVADAR
NYTPAAAPVSTVDAVIDSVVADARRYARAKSRRRRIARRHRSTPAMRAARALLRRARRTGRRAMLRAAR
RAASGASAGRTRRRAATAAAAAIASMSRPRRGNVYWVRDAATGVRVPVRTRPPRT (AdY25 V)
SEQ ID NO. 15
MSKRKFKEEMLQVIAPEIYGPAVVKEERKPRKIKRVKKDKKEEDDDLVEFVREFAPRRRVQWRGRKVIT
PVLRPGTTVVFTPGERSGSASKRSYDEVYGDEDILEQAAERLGEFAYGKRSRPALKEEAVSIPLDHGNP
TPSLKPVTLQQVLPSAAPRRGFKREGEDLYPTMQLMVPKRQKLEDVLETMKVDPDVQPEVKVRPIKQVA
PGLGVQTVDIKIPTEPMETQTEPMIKPSTSTMEVQTDPWMPSAPSRRPRRKYGAASLLMPNYALHPSII
PTPGYRGTRFYRGHTTSRRRKTTTRRRRRTAAASTPAALVRRVYRRGRAPLTLPRARYHPSIAI (AdY25 Mu)
SEQ ID NO. 16
MALTCRLRVPITGYRGRKPRRRRLAGNGMRRHEHRRRRAISKRLGGGFLPALIPIIAAAIGAIPGIASV
AVQASQRH (AdY25 VI)
SEQ ID NO. 17
MEDINFSSLAPRHGTRPFMGTWSDIGTSQLNGGAFNWSSLWSGLKNEGSTLKTYGSKAWNSTTGQALRD
KLKEQNFQQKVVDGLASGINGVVDLANQAVQRQINSRLDPVPPAGSVEMPQVEEELPPLDKRGEKRPRP
DAEETLLTHTDEPPPYEEAVKLGLPTTRPIAPLATGVLKPESNKPATLDLPPPASRPSTVAKPLPPVAV
ARARPGGSARPHANWQSTLNSIVGLGVQSVKRRRCY (AdY25 Endoprotease)
SEQ ID NO. 18
MAEPTGSGEQELRAIIRDLGCGPYFLGTEDKRFPGFMAPHKLACAIVNTAGRETGGEHWLAFAWNPRSN
TCYLFDPFGFSDERLKQIYQFEYEGLLRRSALATEDRCVTLEKSTQTVQGPRSAACGLFCCMFLHAFVH
WPDRPMDKNPTMNLLTGVPNGMLQSPQVEPTLRRNQEALYRFLNSHSAYFRSHRARIEKATAFDRMNNQ
DM (AdY25 DNA Binding Protein)
SEQ ID NO. 19
MAGRGGSQSERRRERTPERGRGSASHPPSRGGESPSPPPLPPKRHTYRRVASDQEEEEIVVVSENSRSP
SPQASPPPLPPICKICPRICTKHVVMQDVSQDSEDERQAEEELAAVGESYPPVRITEKDGKRSFETLDE
SDPLAAAASAKMMVKNPMSLPIVSAWEKGMEIMTMLMDRYRVETDLKANFQLMPEQGEVYRRICHLYIN
EEHRGIPLTFTSNKTLTIMMGRFLQGFVHAHSQIAHKNWECTGCALWLHGCTEAEGKLRCLHGTTMIQK
EHMIEMDVASENGQRALKENPDRAKITQNRWGRSVVQLANNDARCCVHDAGCATNQESSKSCGVFFTEG

| Sequences |
|---|
| AKAQQAFRQLEAFMKAMYPGMNADQAQMMLIPLHCDCNHKPGCVPTMGRQTCKMTPFGMANAEDLDVES<br>ITDAAVLASVKITPALMVFQCCNPVYRNSRAQNAGPNCDFKISAPDLLGALQLTRKLWTDSFPDTPLPK<br>LLIPEFKWLAKYQFRNVSLPAGHAETRQNPFDF<br><br>(AdY25 100 kDa (L4))                                                                          SEQ ID NO. 20<br>METQPSPTSPSAPTAGDEKQQQQNESLTAPPPSPASDAAAVPDMQEMEESIEIDLGYVTPAEHEEELAV<br>REQSSSQEDICEQPEQEAENEQSQAGLEHGDYLHLSGEEDALIKHLARQATIVKDALLDRTEVPLSVEE<br>LSRAYELNLFSPRVPPKRQPNGTCEPNPRLNEYPVFAVPEALATYHIFFKNQKIPVSCRANRTRADALF<br>NLGPGARLPDIASLEEVPKIFEGLGSDETRAANALQGEGGGEHEHHSALVELEGDNARLAVLKRTVELT<br>HFAYPALNLPPKVMSAVMDQVLIKRASPISEDEGMQDSEEGKPVVSDEQLARWLGPNATPQSLEERRKL<br>MMAVVLVTVELECLARFFADAETLRKVEENLHYLFRHGEVRQACKISNVELTNLVSYMGILHENRLGQN<br>VLHTTLRGEARRDYIRDCVYLYLCHTWQTGMGVWQQCLEEQNLKELCKLLQKNLKGLWTGFDERTTASD<br>LADLIFPERLRLTLRNGLPDFMSQSMLQNFRSFILERSGILPATCSALPSDEVPLTFRECPPPLWSHCY<br>LLRLANYLAYHSDVIEDVSGEGLLECHCRCNLCTPITRSLACNPQLLSETQIIGTFELQGPSEGEGAKG<br>GLKLTPGLWTSAYLRKFVPEDYHPFEIRFYEDQSQPPKAELSACVITQGAILAQLQAIQKSRQEFLLKK<br>GRGVYLDPQTGEELNPGFPQDAPRKQEAESGAAARGGEGGRLGEQQSGRGDGGRLGQHSGRGGQPARQS<br>GGRRGGGRGGGGRSSRRQTVVLGGGESKQHGYHLRSGSGSRSAPQ<br><br>(AdY25 22 kDa)                                                                                 SEQ ID NO. 21<br>MPRGNKKLKVELPPVEDLEEDWENSSQAEEMEEDWDSTQAEEDSLQDSLEEDEEEAEEEVEEAAAARPS<br>SSAGEKASSTDTISAPGRGPARPHSRWDETGRFPNPTTQTGKKERQGYKSWRGHKNAIVSCLQACGGNI<br>SFTRRYLLEHRGVNFPRNILHYYRHLSPYYFQEEAAAAEKDQKTS<br><br>(AdY25 33 kDa (L4))                                                             SEQ ID NO. 22<br>MPRGNKKLKVELPPVEDLEEDWENSSQAEEMEEDWDSTQAEEDSLQDSLEEDEEEAEEEVEEAAAARPS<br>SSAGEKASSTDTISAPGRGPARPHSRWDETGRFPNPTTQTAPTTSKKRQQQQICKTRKPARKSTAAAAA<br>GGLRIAANEPAQTRELRNRIEPTLYAIFQQSRGQEQELKVKNRSLRSLTRSCLYHKSEDQLQRTLEDAE<br>ALFNKYCALTLKE<br><br>(AdY25 pVIII (L4))                                                            SEQ ID NO. 23<br>MSKEIPTPYMWSYQPQMGLAAGAAQDYSTRMNWLSAGPAMISRVNDIRAHRNQILLEQSALTATPRNHL<br>NPRNWPAALVYQEIPQPTTVLLPRDAQAEVQLTNSGVQLAGGATLCRHRPAQGIKRLVIRGRGTQLNDE<br>VVSSSLGLRPDGVFQLAGSGRSSFTPRQAVLTLESSSSQPRSGGIGTLQFVEEFTPSVYFNPFSGSPGH<br>YPDEFIPNFDAISESVDGYD<br><br>(AdY25 E3 12.5 kDa)                                                      SEQ ID NO. 24<br>MSHGGAADLARLRELDHCRRFRCFARDLAEFTYFELPEEHPQGPAHGVRIVVEGGLDSHLLRIFSQRPI<br>LVERQQGNTLLTLYCICDHPGLHESLCCLLCTEYNKS<br><br>(AdY25 E3 CRIaI)                                                        SEQ ID NO. 25<br>MKVFVVCCVLSIIKAEISDYSGLNCGVSASINRSLTFTGNETELQVQCKPRECKYLTWLYQGSPIAVVN<br>HCDDDGVLLNGPANLIFSTRRSKLLLFRPFLPGTYQCISGPCHHTFHLIPNTTSSPAPLPTNNQTNHHQ<br>RYRRDLVSESNTTHTGGELRGRICPSGIYYGPWEVVGLIALGLVAGGLLALCYLYLPCFSYLVVLCCWF<br>KKWGRSP<br><br>(AdY25 E3 gp19 kDa)                                            SEQ ID NO. 26<br>MGKITLVCGVLVTVVLSILGGGSAAVVTEKKADPCLTFNPDKCRLSFQPDGNRCAVLIKCGWECESVLV<br>QYKNKTWNNTLASTWQPGDPEWYTVSVPGADGSLRTVNNTFIFEHMCETAMFMSKQYGMWPPRKENIVV<br>FSIAYSACTVLITAIVCLSIHMLIAIRPRNNAEKEKQP<br><br>(AdY25 E3 22.3 kDa)                                       SEQ ID NO. 27<br>MICILSLFCFSIIITSAICNSVDICDVTVTTGSNYTLKGPPSGMLSWYCYFGTDVSQTELCNFQKGKTQ<br>NPKIHNYQCNGTDLVLFNITKTYAGSYYCPGDNVDNMIFYELQVVDPTTPAPPTTTTKAHSTDTQEETP<br>EAEVAELAKQIIIEDSFVANTPTHPGPQCPGPLVSGIVGVLCGLAVIIICMFIFACCYRRLHRQKSDPL<br>LNLYV<br><br>(AdY25 E3 31 kDa)                                                 SEQ ID NO. 28<br>MKALSTLVFLTLIGIVFNSKITRVSFLKHVNVTEGNNITLVGVEGAQNTTWTKYHLGWKDICTWNVTYF<br>CIGVNLTIVNANQSQNGLIKGQSVSVTSDGYYTQHNFNYNITVIPLPTPSPPSTTQTTQTTHTTQSSIT<br>TMQTTQTTYTTSPQPITTTAEASSSPTIKVAFLMLAPSSSPTASTNEQTTEFLSTIQSSTTATSSAFS<br>STANLTSLSSMPISNATTSPAPLPTPLKQSESSTQLQITLLIVIGVVILAVLLYFIFCRRIPNAKPAYK<br>PIVIGTPEPLQVEGGLRNLLFSFTVW<br><br>(AdY25 E3 10.4 kDa)                                      SEQ ID NO. 29<br>MIPRHFIITSLICVLQVCATLALVANASPDCIGAFASYVLFAFITCICCCSIVCLLITFFQFVDWVFVR<br>IAYLRHHPQYRDQRVAQLLRLI |

| Sequences |
|---|
| (AdY25 E3 15.2 kDa)<br>SEQ ID NO. 30<br>MRALLLLLALLLAPLAAPLSLKSPTQSPEEVRKCKFQEPWKFLSCYKLKSEMHPSWIMIVGIVNILACT<br>LFSFVIYPRFDFGWNAPEALWLPPDPDTPPQQQQQNQAQAHAPPQPRPQYMPILNYEAEAQRAMLPAIS<br>YFNLTGGDD |
| (AdY25 E3 14.7 kDa)<br>SEQ ID NO. 31<br>MTDPMANNTVNDLLDMDGRASEQRLAQLRIRQQQERAVKELQDAVAIHQCKRGIFCLVKQAKISFEVIS<br>TDHRLSYELLQQRQKFTCLVGVNPIVITQQSGDTKGCIHCSCDSPECVHTLIKTLCGLRDLLPMN |
| (AdY25 E4 Orf 6/7)<br>SEQ ID NO. 32<br>MSGNSSIMIRSRTRLASSRHHPYQPPAPLPRCEETETRASLVEDHPVLPDCDTLSMHNITVIPTTEDSP<br>QLLNFEVQMQECPEGFISLTDPRLARSETVWNVETKTMSIINGIQMFKAVRGERVVYSMSWEGGGKITT<br>RIL |
| (AdY25 E4 Orf 6)<br>SEQ ID NO. 33<br>MSGNSSIMTRSRTRLASSRHHPYQPPAPLPRCEETETRASLVEDHPVLPDCDTLSMHNVSCVRGLPCSA<br>GFTVLQEFPVPWDMVLTPEELRVLKTCMSVCLCCANIDLFSSQLIHGRERWVLHCHCQDPGSLRCMAGG<br>AVLAIWFRRIIQGCMFNQRVMWYREVVNLHMPKEIMYMGSVFWRGRHLIYIRIWYDGHVGSIVPQMSFG<br>WSTLNYGLLNNLVVLCCTYCSDLSEIRIRCCARRTRRLMLRAIGIMRRESLDPDPLSSSLTERRRQRLL<br>RGLMRHNRPIPFADYDSHRSSSR |
| (AdY25 E4 Orf 4)<br>SEQ ID NO. 34<br>MVLPVLPSPSVTETQQNCIIWLGLAHSTVADVIRAIRADGIFITQEAQEILHALREWLFYNFNTERSKR<br>RDRRRRAVCSARTRFCFVKYENVRKQLHFIDTIQNTISVIPPSSVPTAGPLTSL |
| (AdY25 E4 Orf 3)<br>SEQ ID NO. 35<br>MRVCLRMPVEGALRELFIMAGLDLPQELIRIIQGWKNENYLGMVQECNMMIEELENAPAFAVLLFLDVR<br>VEALLEATVEHLENRVTFDLAVIFHQHSGGERCHLRDLHFEVLRDRLE |
| (AdY25 E4 Orf 2)<br>SEQ ID NO. 36<br>MLERTPCTYSIVVPEALNLHLDDFSFVDFLKNCLPDFLSSYLEDITGSSQHAYFNLIFGNAHWGGLRFI<br>CNVACPALIPGGPMAKNFGDDMKDYIQLLLREELRDRGRDFDIPIVNLLQVNQEQNLLEL |
| (AdY25 E4 Orf 1)<br>SEQ ID NO. 37<br>MDAEALYVFLEGAGALLPVQEGSNYIFYAPANFVLHPHGVALLELRLSIVVPRGFIGRFFSLTDANVPG<br>VYASSRIIHAGHREGLSVMLFNHGDSFYEGRAGDPVACLVLERVIYPPVRQASMV |
| (ChAdOX1 vector sequence excluding BAC sequence)<br>SEQ ID NO. 38<br>TTAATCGCGTTTAAACCCATCATCAATAATATACCTCAAACTTTTTGTGCGCGTTAATATGCAAATGAG<br>GCGTTTGAATTTGGGAAGGGAGGAAGGTGATTGGCCGAGAGAAGGGCGACCGTTAGGGCGGGGCGAGT<br>GACGTTTTGATGACGTGACCGCGAGGAGGAGCCAGTTTGCAAGTTCTCGTGGGAAAAGTGACGTCAAAC<br>GAGGTGTGGTTTGAACACGGAAATACTCAATTTTCCCGCGCTCTCTGACAGGAAATGAGGTGTTTCTAG<br>GCGGATGCAAGTGAAAACGGGCCATTTTCGCGCGAAAACTGAATGAGGAAGTGAAAATCTGAGTAATTT<br>CGCGTTTATGACAGGGAGGAGTATTTGCCGAGGGCCGAGTAGACTTTGACCGATTACGTGGGGGTTTCG<br>ATTACCGTGTTTTTCACCTAAATTTCCGCGTACGGTGTCAAAGTCCGGTGTTTTTACGTAGGTGTCAGC<br>TGATCGCCAGGGTATTTAAACCTGCGCTCTCCAGTCAAGAGGCCACTCTTGAGTGCCAGCGAGAAGAGT<br>TTTCTCCTCCGCGCGCGAGTCGAGATCTACACTTTGAAAGGCGATCGCTAGCGACATCGATCACAAGTTT<br>GTACAAAAAAGCTGAACGAGAAACGTAAAATGATATAAATATCAATATATTTAAATTAGATTTTGCATaA<br>AAAACAGACTACATAATACTGTAAAACACAACATATCCAGTCACTATGGCGGCCGCCGATTTATTCAAC<br>AAAGCCACGTTGTGTCTCAAAATCTCTGATGTTACATTGCACAAGATAAAAATATATCATCATGAACAA<br>TAAAACTGTCTGCTTACATAAACAGTAATACAAGGGGTGTTATGAGCCATATTCAACGGGAAACGTCTT<br>GCTCGAGGCCGCGATTAAATTCCAACATGGATGCTGATTTATATGGGTATAAATGGGCTCGTGATAATG<br>TCGGGCAATCAGGTGCGACAATCTATCGATTGTATGGGAAGCCCGATGCGCCAGAGTTGTTTCTGAAAC<br>ATGGCAAAGGTAGCGTTGCCAATGATGTTACAGATGAGATGGTCAGACTAAACTGGCTGACGGAATTTA<br>TGCCTCTTCCGACCATCAAGCATTTTATCCGTACTCCTGATGATGCATGGTTACTCACCACTGCGATCC<br>CCGGGAAAACAGCATTCCAGGTATTAGAAGAATATCCTGATTCAGGTGAAAATATTGTTGATGCGCTGG<br>CAGTGTTCCTGCGCCGGTTGCATTCGATTCCTGTTTGTAATTGTCCTTTTAACAGCGATCGCGTATTTC<br>GTCTCGCTCAGGCGCAATCACGAATGAATAACGGTTTGGTTGATGCGAGTGATTTTGATGACGAGCGTA<br>ATGGCTGGCCTGTTGAACAAGTCTGGAAAGAAATGCATAAGCTTTTGCCATTCTCACCGGATTCAGTCG<br>TCACTCATGGTGATTTCTCACTTGATAACCTTATTTTTGACGAGGGGAAATTAATAGGTTGTATTGATG<br>TTGGACGAGTCGGAATCGCAGACCGATACCAGGATCTTGCCATCCTATGGAACTGCCTCGGTGAGTTTT<br>CTCCTTCATTACAGAAACGGCTTTTTCAAAAATATGGTATTGATAATCCTGATATGAATAAATTGCAGT<br>TTCATTTGATGCTCGATGAGTTTTTCTAATCAGAATTGGTTAATTGGTTGTAACACTGGCACGCGTGGA<br>TCCGGCTTACTAAAAGCCAGATAACAGTATGCGTATTTGCGCGCTGATTTTTGCGGTATAAGAATATAT<br>ACTGATATGTATACCCGAAGTATGTCAAAAGAGGTATGCTATGAAGCAGCGTATTACAGTGACAGTTG<br>ACAGCGACAGCTATCAGTTGCTCAAGGCATATATGATGTCAATATCTCCGGTCTGGTAAGCACAACCAT<br>GCAGAATGAAGCCCGTCGTCTGCGTGCCGAACGCTGGAAAGCGGAAAATCAGGAAGGGATGGCTGAGGT<br>CGCCCGGTTTATTGAAATGAACGGCTCTTTTGCTGACGAGAACAGGGGCTGGTGAAATGCAGTTTAAGG |

| Sequences |
|---|
| TTTACACCTATAAAAGAGAGAGCCGTTATCGTCTGTTTGTGGATGTACAGAGTGATATTATTGACACGC |
| CCGGGCGACGGATGGTGATCCCCCTGGCCAGTGCACGTCTGCTGTCAGATAAAGTCTCCCGTGAACTTT |
| ACCCGGTGGTGCATATCGGGGATGAAAGCTGGCGCATGATGACCACCGATATGGCCAGTGTGCCGGTCT |
| CCGTTATCGGGGAAGAAGTGGCTGATCTCAGCCACCGCGAAAATGACATCAAAAACGCCATTAACCTGA |
| TGTTCTGGGGAATATAAATGTCAGGCTCCCTTATACACAGCCAGTCTGCAGGTCGACCATAGTGACTGG |
| ATATGTTGTGTTTTACAGTATTATGTAGTCTGTTTTTTATGCAAAATCTAATTTAATATATTGATATTT |
| ATATCATTTTACGTTTCTCGTTCAGCTTTCTTGTACAAAGTGGTGATCGATTCGACAGATCGCGATCGC |
| AGTGAGTAGTGTTCTGGGGCGGGGAGGACCTGCATGAGGGCCAGAATGACTGAAATCTGTGCTTTTCT |
| GTGTGTTGCAGCATCATGAGCGGAAGCGGCTCCTTTGAGGGAGGGGTATTCAGCCCTTATCTGACGGGG |
| CGTCTCCCCTCCTGGGCGGGAGTGCGTCAGAATGTGATGGGATCCACGGTGGACGGCCGGCCCGTGCAG |
| CCCGCGAACTCTTCAACCCTGACCTATGCAACCCTGAGCTCTTCGTCGGTGGACGCAGCTGCCGCCGCA |
| GCTGCTGCATCCGCCGCCAGCGCCGTGCGCGGAATGGCCATGGGCGCCGGCTACTACGGCACTCTGGTG |
| GCCAACTCGAGTTCCACCAATAATCCCGCCAGCCTGAACGAGGAGAAGCTGCTGCTGCTGATGGCCCAG |
| CTTGAGGCCTTGACCCAGCGCCTGGGCGAGCTGACCCAGCAGGTGGCTCAGCTGCAGGAGCAGACGCGG |
| GCCGCGGTTGCCACGGTGAAATCCAAATAAAAAATGAATCAATAAATAAACGGAGACGGTTGTTGATTT |
| TAACACAGAGTCTGAATCTTTATTTGATTTTTCGCGCGCGGTAGGCCCTGGACCACCGGTCTCGATCAT |
| TGAGCACCCGGTGGATCTTTTCCAGGACCCGGTAGAGGTGGGCTTGGATGTTGAGGTACATGGGCATGA |
| GCCCGTCCCGGGGTGGAGGTAGCTCCATTGCAGGGCCTCGTGCTCGGGGGTGGTGTTGTAAATCACCC |
| AGTCATAGCAGGGGCGCAGGGCGTGGTGTTGCACAATATCTTTGAGGAGGAGACTGATGGCCACGGGCA |
| GCCCTTTGGTGTAGGTGTTTACAAATCTGTTGAGCTGGGAGGGGATGCATGCGGGGGGAGATGAGGTGCA |
| TCTTGGCCTGGATCTTGAGATTGGCGATGTTACCGCCCAGATCCCGCCTGGGGTTCATGTTGTGCAGGA |
| CCACCAGCACGGTGTATCCGGTGCACTTGGGGAATTTATCATGCAACTTGGAAGGGAAGGCGTGAAAGA |
| ATTTGGCGACGCCCTTGTGTCCGCCCAGGTTTTCCATGCACTCATCCATGATGATGGCAATGGGCCCGT |
| GGGCGGCGGCCTGGGCAAAGACGTTTCGGGGGTCGGACACATCATAGTTGTGGTCCTGGGTGAGGTCAT |
| CATAGGCCATTTTAATGAATTTGGGGCGGAGGGTGCCGGACTGGGGGACAAAGGTACCCTCGATCCCGG |
| GGGCGTAGTTCCCCTCACAGATCTGCATCTCCCAGGCTTTGAGCTCAGAGGGGGGGATCATGTCCACCT |
| GCGGGGCGATAAAGAACACGGTTTCCGGGGCGGGGGAGATGAGCTGGGCCGAAAGCAAGTTCCGGAGCA |
| GCTGGGACTTGCCGCAGCCGGTGGGGCCGTAAATGACCCCGATGACCGGCTGCAGGTGGTAGTTGAGGG |
| AGAGACAGCTGCCGTCCTCCCGGAGGAGGGGGGCCACCTCGTTCATCATCTCGCGCACGTGCATGTTCT |
| CGCGCACCAGTTCCGCCAGGAGGCGCTCTCCCCCCAGAGATAGGAGCTCCTGGAGCGAGGCGAAGTTTT |
| TCAGCGGCTTGAGTCCGTCGGCCATGGGCATTTTGGAGAGGGTCTGTTGCAAGAGTTCCAAGCGGTCCC |
| AGAGCTCGGTGATGTGCTCTACGCATCTCGATCCAGCAGACCTCCTCGTTTCGCGGGTTGGGACGACT |
| GCGGGAGTAGGGCACCAGACGATGGGCGTCCAGCGCAGCCAGGGTCCGGTCCTTCCAGGGCCGCAGCGT |
| CCGCGTCAGGGTGGTCTCCGTCACGGTGAAGGGGTGCGCGCCGGGCTGGGCGCTTGCGAGGGTGCGCTT |
| CAGGCTCATCCGGCTGGTCGAAAACCGCTCCCGATCGGCGCCCTGCGCGTCGGCCAGGTAGCAATTGAC |
| CATGAGTTCGTAGTTGAGCGCCTCGGCCGCGTGGCCTTTGGCGCGGAGCTTACCTTTGGAAGTCTGCCC |
| GCAGGCGGGACAGAGGAGGGACTTGAGGGCGTAGAGCTTGGGGGCGAGGAAGACGGAATCGGGGGCGTA |
| GGCGTCCGCGCCGCAGTGGGCGCAGACGGTCTCGCACTCCACGAGCCAGGTGAGGTCGGGCTGGTCGGG |
| GTCAAAAACCAGTTTCCCGCCGTTCTTTTTGATGCGTTTCTTACCTTTGGTCTCCATGAGCTCGTGTCC |
| CCGCTGGGTGACAAAGAGGCTGTCCGTGTCCCCGTAGACCGACTTTATGGCCGGTCCTCGAGCGGTGT |
| GCCGCGGTCCTCCTCGTAGAGGAACCCCGCCCACTCCGAGACGAAAGCCCGGGTCCAGGCCAGCACGAA |
| GGAGGCCACGTGGGACGGGTAGCGGTCGTTGTCCACCAGCGGGTCCACTTTTTCCAGGGTATGCAAACA |
| CATGTCCCCCTCGTCCACATCCAGGAAGGTGATTGGCTTGTAAGTGTAGGCACGTGACCGGGGGTCCC |
| GGCCGGGGGGTATAAAAGGGGGCGGGCCCCTGCTCGTCCTCACTGTCTTCCGGATCGCTGTCCAGGAG |
| CGCCAGCTGTTGGGGTAGGTATTCCCTCTCGAAGGCGGGCATGACCTCGGCACTCAGGTTGTCAGTTTC |
| TAGAAACGAGGAGGATTTGATATTGACGGTGCCAGCGGAGATGCCTTTCAAGAGCCCCTCGTCCATCTG |
| GTCAGAAAAGACGAtTTTTTTTGTTGTCGAGCTTGGTGGCGAAGGAGCCGTAGAGGGCGTTGGAAAGGAG |
| CTTGGCGATGGAGCGCATGGTCTGGTTTTTTCCTtGTCGGCGCGCTCCTTGGCCGCGATGTTGAGCTG |
| CACGTACTCGCGCGCCACGCACTTCCATTCGGGGAAGAGATTGGTGGTCATCTCGTCGGGCACGATTCTGAC |
| CTGCCAACCTCGATTATGCAGGGTGATGAGGTCCACACTGGTGGCCACCTCGCCGCGCAGGGGCTCGTT |
| GGTCCAGCAGAGGCGGCCGCCCTTGCGCGAGCAGAAGGGGGCAGAGGGTCCAGCATGACCTCGTCGGG |
| GGGGTCGGCATCGATGGTGAAGATGCCGGGCAGGAGATCGGGGTCGAAGTAGCTGATGGAAGTGGCCAG |
| ATCGTCCAGGGAAGCTTGCCATTCGCGCACGGCCAGCGCGCGCTCGTAGGGGACTGAAGGGCGTGCCCCA |
| GGGCATGGGGTGGGTGAGCGCGGAGGCGTACATGCCGCAGATGTCGTAGACGTAGAGGGGCTCCTCGAG |
| GATGCCGATGTAGGTGGGGTAGCAGCGCCCCCGCGGATGCTGGCGCGCACGTAGTCATACAGCTCGTG |
| CGAGGGCGCGAGGAGCCCCGGGCCCAGGTTGGTGCGACTGGGCTTTTCGGCGCGGTAGACGATCTGGCG |
| AAAGATGGCATGCGAGTTGGAGGAGATGGTGGGCCTTTGGAAGATGTTGAAGTGGGCGTGGGGGGAGGCC |
| GACCGAGTCGCGGATGAAGTGGGCGTAGGAGTCTTGCAGTTTGGCGACGAGCTCGGCGGTGACGAGGAC |
| GTCCAGAGCGCAGTAGTCGAGGGTCTCCTGGATGATGTCATACTTGAGCTGGCCCTTTTGTTTCCACAG |
| CTCGCGGTTGAGAAGGAACTCTTCGCGGTCCTTCCAGTACTCTTCGAGGGGGAACCCGTCCTGATCTGC |
| ACGGTAAGAGCCTAGCATGTAGAACTGGTTGACGGCCTTGTAGGCGCAGCAGCCCTTCTCCACGGGGAG |
| GGCGTAGGCCTGGGCGGCCTTGCGCAGGGAGGTGTGCGTGAGGGCGAAGGTGTCCCTGACCATGACCTT |
| GAGGAACTGGTGCTTGAAATCGATATCGTCGCAGcCCCCTGCTCCCAGAGCTGGAAGTCCGTGCGCTT |
| CTTGTAGGCGGGGTTGGGCAAAGCGAAAGTAACATCGTTGAAAAGGATCTTGCCCGCGCGGGGCATAAA |
| GTTGCGAGTGATGCGGAAAGGCTGGGGCACCTCGGCCCGGTTGTTGATGACCTGGGCGGCGAGCACGAT |
| CTCGTCGAAACCGTTGATGTTGTGGCCCACGATGTAGAGTTCCACGAATCGCGGGCGGCCCTTGACGTG |
| GGGCAGCTTCTTGAGCTCCTCGTAGGTGAGCTCGTCGGGGTCGCTGAGACCGTGCTGCTCGAGCGCCCA |
| GTCGGCGAGATGGGGGTTGGCGCGGAGGAAGGAAGTCCAGAGATCCACGGCCAGGGCGGTTTGCAGACG |
| GTCCCGGTACTGACGGAACTGCTGCCCGACGGCCATTTTTTCGGGGTGACGCAGTAGAAGGTGCGGGG |
| GTCCCCGTGCCAGCGGTCCCATTTGAGCTGGAGGGCGAGATCGAGGGCGAGCTCGACGAGGCGGTCGTC |
| CCTGAGAGTTTCATGACCAGCATGAAGGGGACGAGCTGCTTGCCGAAGGACCCCATCCAGGTGTAGGT |
| TTCCACATCGTAGGTGAGGAAGAGCCTTTCGGTGCGAGGATGCGAGCCGATGGGGAAGAACTGGATCTC |
| CTGCCACCAATTGGAGGAATGGCTGTTGATGTGATGAAGTAGAAATGCCGACGGCGCGCCGAACACTC |
| GTGCTTGTGTTTATACAAGCGGCCACAGTGCTCGCAACGCTGCACGGGATGCACGTGCTGCACGAGCTG |
| TACCTGAGTTCCTTTGACGAGGAATTTCAGTGGGAAGTGGAGTCGTGGCGCCTGCATCTCGTGCTGTAC |
| TACGTCGTGGTGGTCGGCCTGCCCCTCTTCTGCCTCGATGGTGGTCATGCTGACGAGCCCGCGCGGGAG |
| GCAGGTCCAGACCTCGGCGCGAGCGGGTCGGAGAGCGAGGACGAGGGCGCGCAGGCCGGAGCTGTCCAG |

| Sequences |
|---|
| GGTCCTGAGACGCTGCGGAGTCAGGTCAGTGGGCAGCGGCGGCGCGCGGTTGACTTGCAGGAGTTTTTC |
| CAGGGCGCGCGGGAGGTCCAGATGGTACTTGATCTCCACCGCGCCGTTGGTGGCGACGTCGATGGCTTG |
| CAGGGTCCCGTGCCCCTGGGGTGTGACCACCGTCCCCCGTTTCTTCTTGGGCGGCTGGGGCGACGGGGG |
| CGGTGCCTCTTCCATGGTTAGAAGCGGCGGCGAGGACGCGCGCCGGGCGGCAGAGGCGGCTCGGGGCCC |
| GGAGGCAGGGGCGGCAGGGGCACGTCGGCGCCGCGCGCGGGTAGGTTCTGGTACTGCGCCCGGAGAAGA |
| CTGGCGTGAGCGACGACGCGACGGTTGACGTCCTGGATCTGACGCCTCTGGGTGAAGGCCACGGGACCC |
| GTGAGTTTGAACCTGAAAGAGAGTTCGACAGAATCAATCTCGGTATCGTTGACGGCGGCCTGCCGCAGG |
| ATCTCTTGCACGTCGCCCGAGTTGTCCTGGTAGGCGATCTCGGTCATGAACTGCTCGATCTCCTCCTCC |
| TGAAGGTCTCCGCGACCGGCGCGCTCCACGGTGGCCGCGAGGTCGTTGGAGATGCGGCCCATGAGCTGC |
| GAGAAGGCGTTCATGCCCGCCTCGTTCCAGACGCGGCTGTAGACCACGACGCCCTCGGGATCGCGGGCG |
| CGCATGACCACCTGGGCGAGGTTGAGCTCCACGTGGCGCGTGAAGACCGCGTAGTTGCAGAGGCGCTGG |
| TAGAGGTAGTTGAGCGTGGTGGCGATGTGCTCGGTGACGAAGAAATACATGATCCAGCGGCGGAGCGGC |
| ATCTCGCTGACGTCGCCCAGCGCCTCCAAGCGTTCCATGGCCTCGTAAAGTCCACGGCGAAGTTGAAA |
| AACTGGGAGTTGCGCGCCGAGACGGTCAACTCCTCCTCCAGAAGACGGATGAGCTCGGCGATGGTGGCG |
| CGCACCTCGCGCTCGAAGGCCCCGGGAGTTCCTCCACTTCCTCCTCTTTCTTCCTCCTCCACTAACATC |
| TCTTCTACTTCCTCCTCAGGCGGTGGTGGTGGCGGGGGAGGGGGCCTGCGTCGCCGGCGGCGCACGGGC |
| AGACGGTCGATGAAGCGCTCGATGGTCTCGCCGCGCCGGCGTCGCATGGTCTCGGTGACGGCGCGCCCG |
| TCCTCGCGGGGCCGCAGCGTGAAGACGCCGCCGCGCATCTCCAGGTGGCCGGGGGGGTCCCCGTTGGGC |
| AGGGAGAGGGCGCTGACGATGCATCTTATCAATTGCCCCGTAGGGACTCCGCGCAAGGACCTGAGCGTC |
| TCGAGATCCACGGGATCTGAAAACCGTTGAACGAAGGCTTCAGCCAGTCGCAGTCGCAAGGTAGGCTG |
| AGCACGGTTTCTTCTGCCGGGTCATGTTGGGGAGCGGGGCGGGCGATGCTGCTGGTGATGAAGTTGAAA |
| TAGGCGGTTCTGAGACGGCGGATGGTGGCGAGGAGCACCAGGTCTTTGGGCCCGGCTTGCTGGATGCGC |
| AGACGGTCGGCCATGCCCCAGGCGTGGTCCTGACACCTGGCCAGGTCCTTGTAGTAGTCCTGCATGAGC |
| CGCTCCACGGGCACCTCCTCCTCGCCCGCGCGGCCGTGCATGCGCGTGAGCCCGAAGCCGCGCTGGGGC |
| TGGACGAGCGCCAGGTCGGCGACGACGCGCTCGGCGAGGATGGCCTGCTGGATCGGGTGAGGGTGGTC |
| TGGAAGTCGTCAAAGTCGACGAAGCGGTGGTAGGCTCCGGTGTTGATGGTGTAGGAGCAGTTGGCCATG |
| ACGGACCAGTTGACGGTCTGGTGGCCCGGACGCACGAGCTCGTGGTACTTGAGGCGCGAGTAGGCGCGC |
| GTGTCGAAGATGTAGTCGTTGCAGGTGCGCACCAGGTACTGGTAGCCGATGAGGAAGTGCGGCGGCGGC |
| TGGCGGTAGAGCGGCCATCGCTCGGTGGCGGGGGCGCCGGGCGCGAGGTCCTCGAGCATGGTGCGGTGG |
| TAGCCGTAGATGTACCTGGACATCCAGGTGATGCCGGCGGCGGTGGTGGAGGCGCGCGGGAACTCGCGG |
| ACGCGGTTCCAGATGTTGCGCAGCGGCAGGAAGTAGTTCATGGTGGGCACGGTCTGGCCCGTGAGGCGC |
| GCGCAGTCGTGGATGCTCTATACGGGCAAAAACGAAAGCGGTCAGCGGCTCGAGTCCGTGGCCTGGAGG |
| CTAAGCGAACGGGTTGGGCTGCGCGTGTACCCCGGTTCGAATCTCGAATCAGGCTGGAGCCGCAGCTAA |
| CGTGGTACTGGCACTCCCGTCTCGACCCAAGCCTGCACCAACCCTCCAGGATACGGAGGCGGGTCGTTT |
| TGCAACTTTTTTtGGAGGCCGGAAATGAAACTAGTAAGCGCGGAAAGCGGCCGACCGCGATGGCTCGCT |
| GCCGTAGTCTGGAGAAGAATCGCCAGGGTTGCGTTGCGGTGTGCCCCGGTTCGAGGCCGGCCGGATTCC |
| GCGGCTAACGAGGGCGTGGCTGCCCCGTCGTTTCCAAGACCCCATAGCCAGCGACTTCTCCAGTTACG |
| GAGCGAGCCCCTCTTTTGTTTTGTTTGTTTTTGCCAGATGCATCCCGTACTGCGGCAGATGCGCCCCCA |
| CCACCCTCCACCGCAACAACAGCCCCCTCCTCCACAGCCGGCGCTTCTGCCCCCGCCCCAGCAGCAGCA |
| GCAACTTCCAGCCACGACCGCCGCGGCCGCGCGTGAGCGGGGCTGGACAGACTTCTCAGTATGATCACCT |
| GGCCTTGGAAGAGGGCGAGGGGCTGGCGCGCCTGGGGGCGTCGTCGCCGGAGCGGCACCCGCGCGTGCA |
| GATGAAAAGGGACGCTCGCGAGGCCTACGTGCCCAAGCAGAACCTGTTCAGAGACAGGAGCGGCGAGGA |
| GCCCGAGGAGATGCGCGCGGCCCGGTTCCACGCGGGGCGGGAGCTGCGGCGCGGCCTGGACCGAAAGAG |
| GGTGCTGAGGGACGAGGATTTCGAGGCGGACGAGCTGACGGGGATCAGCCCCGCGCGCGCGCACGTGGC |
| CGCGGCCAACCTGGTCACGGCGTACGAGCAGACCGTGAAGGAGGAGGACAACTTCCAAAAATCCTTCAA |
| CAACCACGTGCGCACCCTGATCGCGCGCGAGGAGGTGACCCTGGGCCTGATGCACCTGTGGGACCTGCT |
| GGAGGCCATCGTGCAGAACCCCACCAGCAAGCCGCTGACGGCGCAGCTGTTCCTGGTGGTGCAGCATAG |
| TCGGGACAACGAGGCGTTCAGGGAGGCGCTGCTGAATATCACCGAGCCCGAGGGCCGCTGGCTCCTGGA |
| CCTGGTGAACATTCTGCAGAGCATCGTGGTGCAGGAGCGCGGGCTGCCGCTGCTGTCCGAAGCTGGCGGC |
| CATCAACTTCTCGGTGCTGAGTCTGGGCAAGTACTACGCTAGGAAGATCTACAAGACCCCGTACGTGCC |
| CATAGACAAGGAGGTGAAGATCGACGGGTTTTACATGCGCATGACCCTGAAAGTGCTGACCCTGAGCGA |
| CGATCTGGGGGTGTACCGCAACGACAGGATGCACCGCGCGGTGAGCGCCAGCAGGCGGCGCGAGCTGAG |
| CGACCAGGAGCTGATGCACAGCCTGCAGCGGGCCCTGACCGGGGCCGGGACCGAGGGGGAGAGCTACTT |
| TGACATGGGCGCGGACCTGCACTGGCAGCCCAGCCGCCGGGCCTTGGAGGCGGCAGGCGGTCCCCCCTA |
| CATAGAAGAGGTGGACGATGAGGTGGACGAGGAGGGCGAGTACCTGGAAGACTGATGGCGCGACCGTAT |
| TTTTGCTAGATGCAACAACAGCCACCTCCTGATCCCGCGATGCGGGCGGCGCTGCAGAGCCAGCCGTCC |
| GGCATTAACTCCTCGGACGATTGGACCCAGGCCATGCAACGCATCATGGCGCTGACGACCCGCAACCCC |
| GAAGCCTTTAGACAGCAGCCCCAGGCCAACCGGCTCTCGGCCATCTTGGAGGCCGTGGTGCCCTCGCGC |
| TCCAACCCCACGCACGAGAAGGTCCTGGCCATCGTGAACGCGCTGGTGGAGAACAAGGCCATCCGCGGC |
| GACGAGGCCGGCCTGGTGTACAACGCGCTGCTGGAGCGCGTGGCCCGCTACAACAGCACCAACGTGCAG |
| ACCAACCTGGACCGCATGGTGACGACGTGCGCGAGGCCGTGGCCCAGCGCGAGCGGTTCCACCGCGAG |
| TCCAACCTGGGATCCATGGTGGCGCTGAACGCCTTCCTCAGCACCCAGCCCGCCAACGTGCCCCGGGGC |
| CAGGAGGACTACACCAACTTCATCAGCGCCCTGCGCCTGATGGTGACCGAGGTGCCCCAGAGCGAGGTG |
| TACCAGTCCGGGCCGGACTACTTCTTCCAGACCAGTCGCCAGGGCTTGCAGACCGTGAACCTGAGCCAG |
| GCGTTCAAGAACTTGCAGGGCCTGTGGGGCGTGCAGGCCCCGGTCGGGACCGCGCGACGGTGTCGAGC |
| CTGCTGACGCCGAACTCGCGCCTGCTGCTGCTGCTGCTGGTGGCCCCCTTCACGGACAGCGGCAGCATCAAC |
| CGCAACTCGTACCTGGGCTACCTGATTAACCTGTACCGCGAGGCCCATCGGCCAGGCGCACGTGGACGAG |
| CAGACCTACCAGGAGATCACCCACGTGAGCCGCGCCCTGGGCCAGGACGACCCGGGCAATCTGGAAGCC |
| ACCCTGAACTTTTTGCTGACCAACCCGGTCGCAGAAGATCCCGCCCCAGTACACGCTCAGCGCCGAGGAG |
| GAGCGCATCCTGCGATACGTGCAGCAGAGCGTGGGCCTGTTCCTGATGCAGGAGGGGGCCACCCCCAGC |
| GCCGCGCTCGACATGACGCGCGCAACATGGAGCCCAGCATGTACGCCAGCAACCGCCCGTTCATCAAT |
| AAACTGATGGACTACTTGCATGGGCGGCCGCCATGAACTCTGACTATTTCACCAACGCCATCCTGAAT |
| CCCCACTGGCTCCCGCCGCCGGGGTTCTACACGGGCGAGTACGACATGCCCGACCCCAATGACGGGTTC |
| CTGTGGGACGATGTGGACAGCAGCGTGTTCTCCCCCGACCGGGTGCTAACGAGCGCCCCTTGTGGAAG |
| AAGGAAGGCAGCGACCGACGCCCGTCCTCGGCGCTGTCCGGCCGCGAGGGTGCTGCCGCGGCGGTGCCC |
| GAGGCCGCCAGTCCTTTCCCGAGCTTGCCCTTCTCGCTGAACAGTATTCGCAGCAGCGAGCTGGGCAGG |
| ATCACGCGCCCGCGCTTGCTGGGCGAGGAGGAGTACTTGAATGACTCGCTGTTGAGACCCGAGCGGGAG |

| Sequences |
|---|
| AAGAACTTCCCCAATAACGGGATAGAGAGCCTGGTGGACAAGATGAGCCGCTGGAAGACGTATGCGCAG |
| GAGCACAGGGACGATCCGTCGCAGGGGGCCACGAGCCGGGGCAGCGCCGCCCGTAAACGCCGGTGGCAC |
| GACAGGCAGCGGGGACTGATGTGGGACGATGAGGATTCCGCCGACGACAGCAGCGTGTTGGACTTGGGT |
| GGGAGTGGTAACCCGTTCGCTCACCTGCGCCCCCGCATCGGGCGCATGATGTAAGAGAAACCGAAAATA |
| AATGATACTCACCAAGGCCATGGCGACCAGCGTGCGTTCGTTTCTTCTCTGTTGTTGTATCTAGTATGA |
| TGAGGCGTGCGTACCCGGAGGGTCCTCCTCCCTCGTACGAGAGCGTGATGCAGCAGGCGATGGCGGCGG |
| CGGCGGCGATGCAGCCCCCGCTGGAGGCTCCTTACGTGCCCCCGCGGTACCTGGCGCCTACGGAGGGGC |
| GGAACAGCATTCGTTACTCGGAGCTGGCACCCTTGTACGATACCACCCGGTTGTACCTGGTGGACAACA |
| AGTCGGCGGACATCGCCTCGCTGAACTACCAGAACGACCACAGCAACTTCCTGACCACCGTGGTGCAGA |
| ACAATGACTTCACCCCCACGGAGGCCAGCACCCAGACCATCAACTTTGACGAGCGCTCGCGGTGGGGCG |
| GTCAGCTGAAAACCATCATGCACACCAACATGCCCAACGTGAACGAGTTCATGTACAGCAACAAGTTCA |
| AGGCGCGGGTGATGGTCTCCCGCAAGACCCCCAACGGGGTGACAGTGACAGATGGTAGTCAGGATATCT |
| TGGAGTATGAATGGGTGGAGTTTGAGCTGCCCGAAGGCAACTTCTCGGTGACCATGACCATCGACCTGA |
| TGAACAACGCCATCATCGACAATTACTTGGCGGTGGGGCGGCAGAACGGGGTCCTGGAGAGCGATATCG |
| GCGTGAAGTTCGACACTAGGAACTTCAGGCTGGGCTGGGACCCCGTGACCGAGCTGGTCATGCCCGGGG |
| TGTACACCAACGAGGCCTTCCACCCCGATATTGTCTTGCTGCCCGGCTGCGGGGTGGACTTCACCGAGA |
| GCCGCCTCAGCAACCTGCTGGGCATTCGCAAGAGGCAGCCCTTCCAGGAGGGCTTCCAGATCATGTACG |
| AGGATCTGGAGGGGGGCAACATCCCCGCGCTCCTGGATGTCGACGCCTATGAGAAAAGCAAGGAGGAGA |
| GCGCCGCCGCGGCGACTGCAGCTGTAGCCACCGCCTCTACCGAGGTCAGGGGCGATAATTTTGCCAGCC |
| CTGCAGCAGTGGCAGCGGCCGAGGCGGCTGAAACCGAAAGTAAGATAGTCATTCAGCCGGTGGAGAAGG |
| ATAGCAAGGACAGGAGCTACAACGTGCTGCCGGACAAGATAAACACCGCCTACCGCAGCTGGTACCTGG |
| CCTACAACTATGGCGACCCCGAGAAGGGCGTGCGCTCCTGGACGCTGCTCACCACCTCGGACGTCACCT |
| GCGGCGTGGAGCAAGTCTACTGGTCGCTGCCCGACATGATGCAAGACCCGGTCACCTTCCGCTCCACGC |
| GTCAAGTTAGCAACTACCCGGTGGTGGCGCGAGCTCCTGCCCGTCTACTCCAAGAGCTTCTTCAACG |
| AGCAGGCCGTCTACTCGCAGCAGCTGCGCGCCTTCACCTCGCTCACGCACGTCTTCAACCGCTTCCCCG |
| AGAACCAGATCCTCGTCCGCCCGCCCGCGCCCACCATTACCACCGTCAGTGAAAACGTTCCTGCTCTCA |
| CAGATCACGGGACCCTGCCGCTGCGCAGCAGTATCCGGGGAGTCCAGCGCGTGACCGTTACTGACGCCA |
| GACGCGCACCTGCCCCTACGTCTACAAGGCCCTGGGCATAGTCGCGCCGCGCGTCCTCTCGAGCCGCA |
| CCTTCTAAAAAATGTCCATTCTCATCTCGCCCAGTAATAACACCGGTTGGGGCCTGCGCGCGCCCAGCA |
| AGATGTACGGAGGCGCTCGCCAACGCTCCACGCAACACCCCGTGCGCGTGCGCGGGCACTTCCGCGCTC |
| CCTGGGGCGCCCTCAAGGGCCGCGTGCGGTCGCGCACCACCGTCGACGACGTGATCGACCAGGTGGTGG |
| CCGACGCGCGCAACTACACCCCCGCGCCGCGCCCGTCTCCACCGTGGACGCCGTCATCGACAGCGTGG |
| TGGCCGACGCGCGCCGGTACGCCCGCGCCAAGAGCCGGCGGCGGCGCATCGCCCGGCGGCACCGGAGCA |
| CCCCCGCCATGCGCGCGGCGCGAGCCTTGCTGCGCAGGGCCAGGCGCACGGGACGCAGGGCCATGCTCA |
| GGGCGGCCAGACGCGCGGCTTCAGGCGCCAGCGCCGGCAGGACCCGGAGACGCGCGGCCACGGCGGCGG |
| CAGCGGCCATCGCCAGCATGTCCCGCCGCGGCGAGGGAACGTGTACTGGGTGCGCGACGCCGCCACCG |
| GTGTGCGCGTGCCCGTGCGCACCCGcCCCCCTCGCACTTGAAGATGTTCACTTCGCGATGTTGATGTGT |
| CCCAGCGGCGAGGAGGATGTCCAAGCGCAAATTCAAGGAAGAGATGCTCCAGGTCATCGCGCCTGAGAT |
| CTACGGCCCCGCGGTGGTGAAGGAGGAAAGAAAGCCCCGCAAAATCAAGCGGGTCAAAAAGGACAAAAA |
| GGAAGAAGATGACGATCTGGTGGAGTTTGTGCGCGAGTTCGCCCCCcGGCGGCGCGTGCAGTGGCGGG |
| GCGGAAAGTGCACCCGGTGCTGAGACCCGCACCACCGTGGTCTTCACGCCCGGCGAGCGCTCCGGCAG |
| CGCTTCCAAGCGCTCCTACGACGAGGTGTACGGGGACGAGGACATCCTCGAGCAGGCGGCCGAGCGCCT |
| GGGCGAGTTTGCTTACGGCAAGCGCAGCCGCCCCGCCCTGAAGGAAGAGGCGGTGTCCATCCCGCTGGA |
| CCACGGCAACCCCACGCCGAGCCTCAAGCCCGTGACCCTGCAGCAGGTGCTGCCGAGCGCAGCGCCGCG |
| CCGGGGGTTCAAGCGCGAGGGCGAGGATCTGTACCCCACCATGCAGCTGATGGTGCCCAAGCGCCAGAA |
| GCTGGAAGACGTGCTGGAGACCATGAAGGTGGACCCGGACGTGCAGCCCGAGGTCAAGGTGCGGCCCAT |
| CAAGCAGGTGGCCCCGGGCCTGGGCGTGCAGACCGTGGACATCAAGATCCCCACGGAGCCCATGGAAAC |
| GCAGACCGAGACCCATGATCAAGCCCAGCACCAGCACCATGGAGGTGCAGACGGATCCCTGGATGCCATC |
| GGCTCCTAGCCGAAGACCCCGGCGCAAGTACGGCGCGGCCAGCCTGCTGATGCCCAACTACGCGCTGCA |
| TCCTTCCATCATCCCCACGCCGGGCTACCGCGGCACGCGCTTCTACCGCGGTCATACAACCAGCCGCCG |
| CCGCAAGACCACCACCGCCGCCGCCGTCGCCGCACAGCCGCTGCATCTACCCCTGCCGCCCTGGTGCG |
| GAGAGTGTACCGCCGCGGCCGCGCGCCTCTGACCCTACCGCGCGCGCGCTACCACCCGAGCATCGCCAT |
| TTAAACTTTCGCCTGCTTTGCAGATGGCCCTCACATGCCGCCTCCGCGTTCCCATTACGGGCTACCGAG |
| GAAGAAAACCGCGCCGTAGAAGGCTGGCGGGAACGGGATGCGTCGCCACCACCATCGGCGGCGGCGCG |
| CCATCAGCAAGCGGTTGGGGgAGGCTTCCTGCCCGCGCTGATCCCCATCATCGCCGCGGCGATCGGGG |
| CGATCCCCGGCATTGCTTCCGTGGCGGTGCAGGCCTCTCAGCGCCACTGAGACACTTGGAAAACATCTT |
| GTAATAAACCAATGGACTCTGACGCTCCTGGTCCTGTGATGTGTTTTCGTAGACAGATGGAAGACATCA |
| ATTTTTCGTCCCTGGCTCCGCGACACGGCACGCGGCCGTTCATGGGCACCTGGAGCGACATCGGCACCA |
| GCCAACTGAACGGGGCGCCTTCAATTGGAGCAGTCTCTGGAGCGGGCTTAAGAATTTCGGGTCCACGC |
| TTAAAACCTATGGCAGCAAGGCGTGGAACAGCACCACAGGGCAGGCGCTGAGGGATAAGCTGAAAGAGC |
| AGAACTTCCAGCAGAAGGTGGTCGATGGGCTGCCTGGGCATCAACGGGGTGGTGGACCTGGCCAACC |
| AGGCCGTGCAGCGGCAGATCAACAGCCGCCTGGACCCGGTGCCGCCCGCCGGCTCCGTGGAGATGCCGC |
| AGGTGGAGGAGGAGCTGCCTCCCCTGGACAAGCGGGGCGAGAAGCGACCCCGCCCCGACGCGGAGGAGA |
| CGCTGCTGACGCACACGGACGAGCCGCCCCGTACGAGGAGGCGGTGAAACTGGGTCTGCCCACCACGC |
| GGCCCATCGCGCCCCTGGCCACCGGGGTGCTGAAACCCGAAAGTAATAAGCCCGCGACCCTGGACTTGC |
| CTCCTCCCGCTTCCCGCCCCTCTACAGTGGCTAAGCCCCTGCCGCCGGTGGCCGTGGCCCCGCGCGCAG |
| CCGGGGGCTCCGCCCGCCCTCATGCGAACTGGCAGAGCACTCTGAACAGCATCGTGGGTCTGGGAGTGC |
| AGAGTGTGAAGCGCCGCCGCTGCTATTAAACCTACCGTAGCGCTTAACTTGCTTGTCTGTGTGTATG |
| TATTATGTCGCCGCTGTCCGCCAGAAGGAGGAGTGAAGAGGCGCGTCGCCGAGTTGCAAGATGGCCACC |
| CCATCGATGCTGCCCCAGTGGGCGTACATGCACATCGCCGGACAGGACGCTTCGGAGTACCTGAGTCCG |
| GGTCTGGTGCAGTTCGCCCGCGCCACAGACACCTACTTCAGTCTGGGGAACAAGTTTAGGAACCCCACG |
| GTGGCGCCCACGCACGATGTGACCACCGACCGCAGCCAGCGGCTGACGCTGCGCTTCGTGCCCGTGGAC |
| CGCGAGGACAACACCTACTCGTACAAAGTGCGCTACACGCTGGCCGTGGGCGACAACCGCGTGCTGGAC |
| ATGGCCAGCACCTACTTTGACATCCGCGGCGTGCTGGATCGGGGCCCTAGCTTCAAACCCTACTCCGGC |
| ACCGCCTACAACAGCCTGGCTCCCAAGGGAGCGCCCAATTCCAGCAGTGGGAGCaAAAAAAGGCAGGC |
| AATGGTGACACTATGGAAACACACACATTTGGTGTGGCCCCAATGGGCGGTGAGAATATTACAATCGAC |
| GGATTACAAATTGGAACTGACGCTACAGCTGATCAGGATAAACCAATTTATGCTGACAAAACATTCCAG |

| Sequences |
| --- |
| CCTGAACCTCAAGTAGGAGAAGAAAATTGGCAAGAAACTGAAAGCTTTTATGGCGGTAGGGCTCTTAAA
AAAGACACAAGCATGAAACCTTGCTATGGCTCCTATGCTAGACCCACCAATGTAAAGGGAGGTCAAGCT
AAACTTAAAGTTGGAGCTGATGGAGTTCCTACCAAAGAATTTGACATAGACCTGGCTTTCTTTGATACT
CCCGGTGGCACAGTGAATGGACAAGATGAGTATAAAGCAGACATTGTCATGTATACCGAAAACACGTAT
CTGGAAACTCCAGACACGCATGTGGTATACAAACCAGGCAAGGATGATGCAAGTTCTGAAATTAACCTG
GTTCAGCAGTCCATGCCCAATAGACCCAACTATATTGGGTTCAGAGACAACTTTATTGGGCTCATGTAT
TACAACAGTACTGGCAATATGGGGGTGCTGGCTGGTCAGGCCTCACAGCTGAATGCTGTGGTCGACTTG
CAAGACAGAAACACCGAGCTGTCATACCAGCTCTTGCTTGACTCTTTGGGTGACAGAACCCGGTATTTC
AGTATGTGGAATCAGGCGGTGGACAGTTATGATCCTGATGTGCGCATTATTGAAAACCATGGTGTGGAA
GACGAACTTCCCAACTATTGCTTCCCCCTGGATGGGTCTGGCACTAATGCCGCTTACCAAGGTGTGAAA
GTAAAAAATGGTAACGATGGTGATGTTGAGAGCGAATGGGAAAATGATGATACTGTCGCAGCTCGAAAT
CAATTATGCAAGGGCAACATTTTTGCCATGGAAATTAACCTCCAAGCCAACCTGTGGAGAAGTTTCCTC
TACTCGAACGTGGCCCTGTACCTGCCCGACTCTTACAAGTACACGCCAGCCAACATCACCCTGCCCACC
AACACCAACACTTATGATTACATGAACGGGAGAGTGGTGCCTCCCTCGCTGGTGGACGCCTACATCAAC
ATCGGGGCGCGCTGGTCGCTGGACCCCATGGACAACGTCAATCCCTTCAACCACCACCGCAACGCGGGC
CTGCGCTACCGCTCCATGCTCCTGGGCAACGGGCGCTACGTGCCCTTCCACATCCAGGTGCCCCAGAAA
TTTTTCGCCATCAAGAGCCTCCTGCTCCTGCCCGGGTCCTACACCTACGAGTGGAACTTCCGCAAGGAC
GTCAACATGATCCTGCAGAGCTCCCTCGGCAACGACCTGCGCACGGACGGGGCCTCCATCTCCTTCACC
AGCATCAACCTCTACGCCACCTTCTTCCCCATGGCGCACAACACGGCCTCCACGCTCGAGGCCATGCTG
CGCAACGACGACCAACGACCAGTCCTTCAACGACTACCTCTCGGCGGCCAACATGCTCTACCCCATCCCG
GCCAACGCCACCAACGTGCCCATCTCCATCCCCTCGCGCAACTGGGCCGCCTTCCGCGGCTGGTCCTTC
ACGCGCCTCAAGACCAAGGAGACGCCCTCGCTGGGCTCCGGGTTCGACCCCTACTTCGTCTACTCGGGC
TCCATCCCCTACCTCGACGGCACCTTCTACCTCAACCACACCTTCAAGAAGGTCTCCATCACCTTCGAC
TCCTCCGTCAGCTGGCCCGGCAACGACCGGCTCCTGACGCCCAACGAGTTCGAAATCAAGCGCACCGTC
GACGGCGAGGGATACAACGTGGCCCAGTGCAACATGACCAAGGACTGGTTCCTGGTCCAGATGCTGGCC
CACTACAACATCGGCTACCAGGGCTTCTACGTGCCCGAGGGCTACAAGGACCGCATGTACTCCTTCTTC
CGCAACTTCCAGCCCATGAGCCGCCAGGTGGTGGACGAGGTCAACTACAAGGACTACCAGGCCGTCACC
CTGGCCTACCAGCACAACAACTCGGGCTTCGTCGGCTACCTCGCGCCCACCATGCGCCAGGGCCAGCCC
TACCCCGCCAACTACCCGTACCCGCTCATCGGCAAGAGCGCCGTCACCAGCGTCACCCAGAAAAAGTTC
CTCTGCGACAGGGTCATGTGGCGCATCCCCTTCTCCAGCAACTTCATGTCCATGGGCGCGCTCACCGAC
CTCGGCCAGAACATGCTCTATGCCAACTCCGCCCACGCGCTAGACATGAATTTCGAAGTCGACCCCATG
GATGAGTCCACCCTTCTCTATGTTGTCTTCGAAGTCTTCGACGTCGTCCGAGTGCACCAGCCCCACCGC
GGCGTCATCGAGGCCGTCTACCTGCGCACCCCCTTCTCGGCCGGTAACGCCACCACCTAAATTGCTACT
TGCATGATGGCTGAGCCCACAGGCTCCGGCGAGCAGGAGCTCAGGGCCATCATCCGCGACCTGGGCTGC
GGGCCCTACTTCCTGGGCACCTTCGATAAGCGCTTCCCGGGATTCATGGCCCCGCACAAGCTGGCCTGC
GCCATCGTCAACACGGCCGGCCGCGAGACCGGGGGCGAGCACTGGCTGGCCTTCGCCTGGAACCCGCGC
TCGAACACCTGCTACCTCTTCGACCCCTTCGGGTTCTCGGACGAGCGCCTCAAGCAGATCTACCAGTTC
GAGTACGAGGGCCTGCTGCGCCGTAGCGCCCTGGCCACCGAGGACCGCTGCGTCACCCTGGAAAAGTCC
ACCCAGACCGTGCAGGGTCCGCGCTCGGCCGCCTGCGGGCTCTTCTGCTGCATGTTCCTGCACGCCTTC
GTGCACTGGCCGACCGCCCATGGACAAGAACCCCACCATGAACTTGCTGACGGGGGTGCCCAACGGC
ATGCTCCAGTCGCCCCAGGTGGAACCCACCCTGCGCCGCAACCAGGAGGCGCTCTACCGCTTCCTCAAC
TCCCACTCCGCCTACTTTCGCTCCCACCGCGCGCATCGAGAAGGCCACCGCCTTCGACCGCATGAAC
AATCAAGACATGTAAACCGTGTGTGTATGTTTAAAATATCTTTTAATAAACAGCACTTTAATGTTACAC
ATGCATCTGAGATGATTTTATTTTAGAAATCGAAAGGGTTCTGCCGGGTCTCGGCATGGCCCGCGGGCA
GGGACACGTTGCGGAACTGGTACTTGGCCAGCCACTTGAACTCGGGGATCAGCAGTTTGGGCAGCGGGG
TGTCGGGGAAGGAGTCGGTCCACAGCTTCCGCGTCAGCTGCAGGGCGCCCAGCAGGTCGGGCGCGGAGA
TCTTGAAATCGCAGTTGGGACCCGCGTTCTGCGCGCGAGAGTTGCGGTACACGGGGTTGCAGCACTGGA
ACACCATCAGGGCCGGGTGCTTCACGCTCGCCAGCACCGCCGCGTCGGTGATGCTCTCCACGTCGAGGT
CCTCGGCGTTGGCCATCCCGAAGGGGGTCATCTTGCAGGTCTGCGTTCCCATGGTGGGCACGCACCCGG
GCTTGTGGTTGCAATCGCAGTGCAGGGGGATCAGCATCATCTGGGCCTGGTCGGCGTTCATCCCCGGGT
ACATGGCCTTCATGAAAGCCTCCAATTGCCTGAACGCCTGCTGGGCCTTGGCTCCTCGGTGAAGAAGA
CCCCGCAGGACTTGCTAGAGAACTGGTTGGTGGCACAGCCGGCATCGTGCACGCAGCAGCGCGCGTCGT
TGTTGGCCAGCTGCACCACGCTGCGCCCCAGCGGTTCTGGGTGATCTTGGCCCGGTCGGGGTTCTCCT
TCAGCGCGCGCTGCCCGTTCTCGCTCGCCACATCCATCTCGATCATGTGCTCCTTCTGGATCATGGTGG
TCCCGTGCAGGCACCGCAGTTTGCCCTCGGCCTCGGTGCACCCGTGCAGCCACAGCGCGCACCCGGTGC
ACTCCCAGTTCTTGTGGGCGATCTGGGAATGCGCGTGCACGAACCCTTGCAGGAAGCGGCCCATCATGG
TCGTCAGGGTCTTGTTGCTAGTGAAGGTCAACGGGATGCCGCGGTGCCTCCTTGTTGATGTACAGGTGC
AGATGCGGCGGTACACCTCGCCCTGCTCGGGCATCAGTTGGAAGTTGGCTTTCAGGTCGGTCTCCACGC
GGTAGCGGTCCATCAGCATAGTCATGATTTCCATGCCCTTCTCCCAGGCCGAGACGATGGGCAGGCTCA
TAGGGTTCTTCACCATCATCTTAGCACTAGCAGCCGCGGCCAGGGGGTCGCTCTCATCCAGGGTCTCAA
AGCTCCGCTTGCCGTCCTTCTCGGTGATCCGCACCGGGGGGTAGCTGAAGCCCACGGCCGCCAGCTCCT
CCTCGGCCTGTCTTTCGTCCTCGCTGTCCTGGCTGACGTCCTGCATGACCACATGCTTGGTCTTGCGGG
GTTTCTTCTTGGGCGGCAGTGGCGGCGGAGATGCTTGTGGCGAGGGGAGCGCGAGTTCTCGCTCACCA
CTACTATCTCTTCCTCTTCTTGGTCCGAGGCCACGCGGCGGTAGGTATGTCTTCGGGGGCAGAGGCG
GAGGCGACGGGCTCTCGCCGCCGCGACTTGGCGGATGGCTGGCAGAGCCCCTTCCGCGTTCGGGGGTGC
GCTCCCGGCGGCGCTCTGACTGACTTCCTCCGCGGCCGGCCATTGTGTTCTCCTAGGGAGGAACACAA
GCATGGAGACTCAGCCATCGCCAACCTCGCCATCTGCCCCCACCGCGGCGACGAGAAGCAGCAGCAGC
AGAATGAAAGCTTAACCGCCCCGCCGCCCAGCCCCGCCTCCGACGCAGCCGCGGTCCCAGACATGCAAG
AGATGGAGGAATCCATCGAGATTGACCTGGGCTATGTGACGCCCGCGGAGCATGAGGAGGAGCTGGCAG
TGCGCTTTCAATCGTCAAGCCAGGAAGATAAAGAACAGCCAGAGCAGGAAGCAGAGAACGAGCAGAGTC
AGGCTGGGCTCGAGCATGGCGACTACCTCCACCTGAGCGGGGAGGAGGACGCGCTCATCAAGCATCTGG
CCCGGCAGGCCACCATCGTCAAGGACGCGCTGCTCGACCGCACCGAGGTGCCCCTCAGCGTGGAGGAGC
TCAGCCGCGCCTACGAGCTCAACCTCTTCTCGCGCGCGTGCCCCCAAGCGCCAGCCCAACGGCACCTT
GCGAGCCCAACCCCCGCCTCAACTTCTACCCGGTCTTCGCGGTGCCCGAGGCCCTGGCCACCTACCACA
TCTTTTTtCAAGAACCAAAAGATCCCCGTCCTGCCGCGCCAACCGCACCCGCGCCGACGCCCTCTTCA
ACCTGGGTCCCGGCGCCCGCCTACCTGATATCGCCTCCTTGGAAGAGGTTCCCAAGATCTTCGAGGGTC
TGGGCAGCGACGAGACTCGGGCCGCGAACGCTCTGCAAGGAGAAGGAGGAGGAGAGCATGAGCACCACA |

| Sequences |
| --- |
| GCGCCCTGGTCGAGTTGGAAGGCGACAACGCGCGGCTGGCGGTGCTCAAACGCACGGTCGAGCTGACCC |
| ATTTCGCCTACCCGGCTCTGAACCTGcCCCCGAAAGTCATGAGCGCGGTCATGGACCAGGTGCTCATCA |
| AGCGCGCGTCGCCCATCTCCGAGGACGAGGGCATGCAAGACTCCGAGGAGGGCAAGCCCGTGGTCAGCG |
| ACGAGCAGCTGGCCCGGTGGCTGGGTCCTAATGCTACCCCTCAAAGTTTGGAAGAGCGGCGCAAGCTCA |
| TGATGGCCGTGGTCCTGGTGACCGTGGAGCTGGAGTGCCTGCGCCGCTTCTTCGCCGACGCGGAGACCC |
| TGCGCAAGGTCGAGGAGAACCTGCACTACCTCTTCAGGCACGGGTTCGTGCGCCAGGCCTGCAAGATCT |
| CCAACGTGGAGCTGACCAACCTGGTCTCCTACATGGGCATCTTGCACGAGAACCGCCTGGGGCAGAACG |
| TGCTGCACACCACCCTGCGCGGGGAGGCCCGCCGCGACTACATCCGCGACTGCGTCTACCTCTACCTCT |
| GCCACACCTGGCAGACGGGCATGGGCGTGTGGCAGCAGTGTCTGGAGGAGCAGAACCTGAAAGAGCTCT |
| GCAAGCTCCTGCAAAAGAACCTCAAGGGTCTGTGGACCGGGTTCGACGAGCGGACCACCGCCTCGGACC |
| TGGCCGACCTCATCTTCCCCGAGCGCCTCAGGCTGACGCTGCGCAACGGCCTGCCCGACTTTATGAGCC |
| AAAGCATGTTGCAAACTTTCGCTCTTTCATCCTCGAACGCTCCGGAATCCTGCCCGCCACCTGCTCCG |
| CGCTGCCCTCGGACTTCGTGCCGCTGACCTTCCGCGAGTGCCCCCGCCGCTGTGGAGCCACTGCTACC |
| TGCTGCGCCTGGCCAACTACCTGGCCTACCACTCGGACGTGATCGAGGACGTCAGCGGCGAGGGCCTGC |
| TCGAGTGCCACTGCCGCTGCAACCTCTGCACGCCGCACCGCTCCCTGGCCTGCAACCCCCAGCTGCTGA |
| GCGAGACCCAGATCATCGGCACCTTCGAGTTGCAAGGGCCCAGCGAGGGCGAGGAGCCAAGGGGGGTC |
| TGAAACTCACCCCGGGGCTGTGGACCTCGGCCTACTTGCGCAAGTTCGTGCCCGAGGATTACCATCCCT |
| TCGAGATCAGGTTCTACGAGGACCAATCCCAGCCGCCCAAGGCCGAGTCTGTCGGCCTGCGTCATCACCC |
| AGGGGGCGATCCTGGCCCAATTGCAAGCCATCCAGAAATCCCGCCAAGAATTCTTGCTGAAAAAGGGCC |
| GCGGGGTCTACCTCGACCCCCAGACCGGTGAGGAGCTCAACCCCGGCTTCCCCCAGGATGCCCCGAGGA |
| AACAAGAAGCTGAAAGTGGAGCTGCCGCCCGTGGAGGATTGGAGGAAGACTGGGAGAACAGCAGTCAG |
| GCAGAGGAGATGGAGGAAGACTGGGACAGCACTCAGGCAGAGGAGGACAGCCTGCAAGACAGTCTGGAG |
| GAAGACGAGGAGGAGGCAGAGGAGGAGGTGGAAGAAGCAGCCGCCGCCAGACCGTCGTCCTCGGCGGGG |
| GAGAAAGCAAGCAGCACGGATACCATCTCCGCTCCGGGTCGGGGTCCCGCTCGGCCCCACAGTAGATGG |
| GACGAGACCGGGCGATTCCCGAACCCCACCACCCAGACCGGTAAGAAGGAGCGGCAGGGATACAAGTCC |
| TGGCGGGGGCACAAAAACGCCATCGTCTCCTGCTTGCAGGCCTGCGGGGGCAACATCTCCTTCACCCGG |
| CGCTACCTGCTCTTCCACCGCGGGGTGAACTTCCCCCGCAACATCTTGCATTACTACCGTCACCTCCAC |
| AGCCCCTACTACTTCCAAGAAGAGGCAGCAGCAGCAGaAAAAGACCAGAAAACCAGCTAGAAAATCCAC |
| AGCGGCGGCAGCGGCAGGTGGACTGAGGATCGCGGCGAACGAGCCGGCGCAGACCCGGGAGCTGAGGAA |
| CCGGATCTTTCCCACCCTCTATGCCATCTTCCAGCAGAGTCGGGGCAGGAGCAGGAACTGAAAGTCAA |
| GAACCGTTCTCTGCGCTCGCTCACCCGCAGTTGTCTGTATCACAAGAGCGAAGACCAACTTCAGCGCAC |
| TCTCGAGGACGCCGAGGCTCTCTTCAACAAGTACTGCGCGCTCACTCTTAAAGAGTAGCCCGCGCCCGC |
| CCAGTCGCAGAAAAGGCGGGAATTACGTCACCTGTGCCCTTCGCCCTAGCCGCCTCCACCCAGCACCG |
| CCATGAGCAAAGAGATTCCCACGCCTTACATGTGGAGCTACCAGCCCCAGATGGGCCTGGCCGCCGGCG |
| CCGCCCAGGACTACTCCACCCGCATGAATTGGCTCAGCGCCGGGCCCGCGATGATCTCACGGGTGAATG |
| ACATCCGCGCCCACCGAAACCAGATCCTCTAGAACAGTCAGCGCTCACCGCCACGCCCCGCAATCACC |
| TCAATCCGCGTAATTGGCCCGCCGCCCTGGTGTACCAGGAAATTCCCCAGCCCACGACCGTACTACTTC |
| CGCGAGACGCCCAGGCCGAAGTCCAGCTGACTAACTCAGGTGTCCAGCTGGCGGGCGGCGCCACCCTGT |
| GTCGTCACCGCCCCGCTCAGGGTATAAAGCGGCTGGTGATCGGGGCAGAGGCACACAGCTCAACGACG |
| AGGTGGTGAGCTCTTCGCTGGGGTCTGCGACCTGACGGAGTCTTCCAACTCGCCGGATCGGGGAGATCTT |
| CCTTCACGCCTCGTCAGGCGGTCCTGACTTTGGAGAGTTCGTCCTCGCAGCCCCGCTCGGGCGGCATCG |
| GCACTCTCCAGTTCGTGGAGGAGTTCACTCCCTCGGTCTACTTCAACCCCTTCTCCGGCTCCCCGGCC |
| ACTACCCGGACGAGTTCATCCCGAACTTTGACGCCATCAGCGAGTCGGTGGACGGCTACGATTGATTAA |
| TTAATCAACTAACCCCTTACCCCTTTACCCTCCAGTAAAAATAAAGATTAAAAATGATTGAATTGATCA |
| ATAAAGAATCACTTACTTGAAATCTGAAACCAGGTCTCTGTCCATGTTTTCTGTCAGCAGCACTTCACT |
| CCCCTCTTCCCAACTCTGGTACTGCAGGCCCCGGCGGGCTGCAAACTTCCTCCACACTCTGAAGGGGAT |
| GTCAAATTCCTCCTGTCCCTCAATCTTCATTTTTATCTTCTATCAGATGTCCAAAAAGCGCGCGCGGGT |
| GGATGATGGCTTCGACCCCGTGTACCCCTACGATGCAGACAACGCACCGACTGTGCCCTTCATCAACCC |
| TCCCTTCGTCTCTTCAGATGGATTCCAAGAAAAGCCCCTGGGGGTGTTGTCCTGCGACTGCCGACCC |
| CGTCACCACCAAGAATGGGGCTGTCACCCTCAAGCTGGGGGAGGGGGTGGACCTCGACGACTCGGGAAA |
| ACTCATCTCCAAAAATGCCACCAAGGCCACTGCCCCTCTCAGTATTTCCAACGGCACCATTTCCCTTAA |
| CATGGCTGCCCCTTTTTACAACAACAATGGAACGTTAAGTCTCAATGTTTCTACACCATTAGCAGTATT |
| TCCCACTTTTAACACTTTAGGTATCAGTCTTGGAAACGGTCTTCAAACTTCTAATAAGTTGCTGACTGT |
| ACAGTTAACTCATCCTCTTACATTCAGCTCAAATAGCATCACAGTAAAAACAGACAAAGGACTCTATAT |
| TAATTCTAGTGGAAACAGAGGGCTTGAGGCTAACATAAGCCTAAAAAGAGGACTGATTTTTGATGGTAA |
| TGCTATTGCAACATACCTTGGAAGTGGTTTAGACTATGGATCCTATGATAGCGATGGGAAAACAAGACC |
| CATCATCACCAAATTGGAGCAGGTTTGAATTTTGATGCTAATAATGCCATGGCTGTGAAGCTAGGCAC |
| AGGTTTAAGTTTTGACTCTGCCGGTGCCTTAACAGCTGGAAACAAAGAGGATGACAAGCTAACACTTTG |
| GACTACACCTGACCCAAGCCCTAATTGTCAATTACTTTCAGACAGAGATGCCAAATTTACCCTATGTCT |
| TACAAAATGCGGTAGTCAAATACTAGGCACTGTTGCAGTAGCTGCTGTTACTGTAGGTTCAGCACTAAA |
| TCCAATTAATGACACAGTAAAAAGCGCCATAGTATTCCTTAGATTTCGACGTGTGCTCATGTC |
| AAACTCATCAATGGTAGGTGATTACTGGAACTTTAGGGAAGGACAGACCACCCAAAGTGTGGCCTATAC |
| AAATGCTGTGGGATTCATGCCCAATCTAGGTGCATATCCTAAAACCCAAAGCAAAACACCAAAAAATAG |
| TATAGTAAGTCAGGTATATTTAAATGGAGAAACTACTATGCCAATGACACTGACAATAACTTTCAATGG |
| CACTGATGAAAAGACACAACACCTGTGAGCACTTACTCCATGACTTTTACATGGCAGTGGACTGGAGA |
| CTATAAGGACAAGAATATTACCTTTGCTACCAACTCCTTTACTTTCTCCTACATGGCCCAAGAATAAAC |
| CCTGCATGCCAACCCCATTGTTCCCACCACTATGGAAAATCTGAAGCAGAAAAAATAAAGGTTCAAGT |
| GTTTTATTGATTCAACAGTTTTCACAGAATTCGAGTAGTTATTTTCCTCCTCCCTCCCAACTCATGGA |
| ATACACCACCCTCTCCCACGCACAGCCTTAAACATCTGAATGCCATTGGTAATGGACATGGTTTTGGT |
| CTCCACATTCCACACAGTTTCAGAGCGAGCCAGTCTCGGGTCGGTCAGGGAGATGAAACCCTCCGGGCA |
| CTCCTGCATCTGCACCTCAAAGTTCAGTAGCTGAGGGCTGTCCTCGGTGTCGGGGATCACAGTTATCTG |
| GAAGAAGAGCGGTGAGAGTCATAATCCGGAACGGGATCGGGCGGTTGTGGCGCATCAGGCCCCGCAGC |
| AGTCGCTGTCTGCGCCGCTCCGTCAAGCTGCTGCTCAAGGGGTCTGGGTCCAGGGACTCCTGCGCATG |
| ATGCCGATGGCCCTGAGCATCAGTCGCCTGGTGCGGCGGGCGCAGCAGCGGATCGGATCTCACTCAGG |
| TCGGAGCAGTACGTGCAGCACAGCACTACCAAGTTGTTCAACAGTCCATAGTTCAACGTGCTCCAGCCA |
| AAACTCATCTGTGGAACTATGCTGCCCACATGTCCATCGTACCAGATCCTGATGTAAATCAGGTGGCGC |
| CCCCTCCAGAACACACTGCCCATGTACATGATCTCCTTGGGCATGTGCAGGTTCACCACCTCCCGGTAC |

-continued

Sequences

CACATCACCCGCTGGTTGAACATGCAGCCCTGGATAATCCTGCGGAACCAGATGGCCAGCACCGCCCCG
CCCGCCATGCAGCGCAGGGACCCCGGGTCCTGGCAATGGCAGTGGAGCACCCACCGCTCACGGCCGTGG
ATTAACTGGGAGCTGAACAAGTCTATGTTGGCACAGCACAGGCACACGCTCATGCATGTCTTCAGCACT
CTCAGTTCCTCGGGGGTCAGGACCATGTCCCAGGGCACGGGGAACTCTTGCAGGACAGTGAACCCGGCA
GAACAGGGCAGCCCTCGCACACAACTTACATTGTGCATGGACAGGGTATCGCAATCAGGCAGCACCGGA
TGATCCTCCACCAGAGAAGCGCGGGTCTCGGTCTCCTCACAGCGAGGTAAGGGGCCGGCGGTTGGTAC
GGATGATGGCGGGATGACGCTAATCGTGTTCTGGATCGTGTCATGATGGAGCTGTTTCCTGACATTTTC
GTACTTCACGAAGCAGAACCTGGTACGGGCACTGCACACCGCTCGCCGGCGACGGTCTCGGCGCTTCGA
GCGCTCGGTGTTGAAGTTATAGAACAGCCACTCCCTCAGAGCGTGCAGTATCTCCTGAGCCTCTTGGGT
GATGAAAATCCCATCCGCTCTGATGGCTCTGATCACATCGGCCACGGTGGAATGGGCCAGACCCAGCCA
GATGATGCAATTTTGTTGGGTTTCGGTGACGGAGGGAGAGGGAAGAACAGGAAGAACCATGATTAACTT
TATTCCAAACGGTCTCGGAGCACTTCAAAATGCAGGTCCCGAGGTGGCACCTCTCGCCCCCACTGTGT
TGGTGGAAAATAACAGCCAGGTCAAAGGTGACACGGTTCTCGAGATGTTCCACGGTGGCTTCCAGCAAA
GCCTCCACGCGCACATCCAGAAACAAGAGGACAGCGAAAGCGGGAGCGTTTTCTAATTCCTCAATCATC
ATATTCACTCCTGCACCATCCCCAGATAATTTTCATTTTTCAGCCTTGAATGATTCGTATTAGTTCC
TGAGGTAAATCCAAGCCAGCCATGATAAAAAGCTCGCGCAGAGCGCCCTCCACCGGCATTCTTAAGCAC
ACCCTCATAATTCCAAGAGATTCTGCTCCTGGTTCACCTGCAGCAGATTAACAATGGGAATATCAAAAT
CTCTGCCGCGATCCCTAAGCTCCTCCCTCAACAATAACTGTATGTAATCTTTCATATCATCTCCGAAAT
TTTTAGCCATAGGGCCGCCAGGAATAAGAGCAGGGCAAGCCACATTACAGATAAAGCGAAGTCCTCCCC
AGTGAGCATTGCCAAATGTAAGATTGAAATAAGCATGCTGGCTAGCACCTGTGATATCTTCCAGATAAC
TGGACAGAAAATCAGGCAAGCAATTTTTAAGAAAATCAACAAAAGAAAAGTCGTCCAGGTGCAGGTTTA
GAGCCTCAGGAACAACGATGGAATAAGTGCAAGGAGTGCGTTCCAGCATGGTTAGTGtTTTTTTGGTGA
TCTGTAGAACAAAAAATAAACATGCAATATTAAACCATGCTAGCCTGGCGAACAGGTGGGTAAATCACT
CTTTCCAGCACCAGGCAGGCTACGGGGTCTCCGGCGCGACCCTCGTAGAAGCTGTCGCCATGATTGAAA
AGCATCACCGAGAGACCTTCCCGGTGGCCGGCATGGATGATTCGAGAAGAAGCATACACTCCGGGAACA
TTGGCATCCGTGAGTGAAAAAAaGCGACCTATAAAGCCTCGGGGCACTACAATGCTCAATCTCAATTCC
AGCAAAGCCACCCCATGCGGATGGAGCACAAAATTGGCAGGTGCGTAAAAAATGTAATTACTCCCCTCC
TGCACAGGCAGCAAAGCCCCGCTCCCTCCAGAAACACATACAAAGCCTCAGCGTCCATAGCTTACCGA
GCACGGCAGGCGCAAGAGTCAGAGAAAAGGCTGAGCTCTAACCTGACTGCCCGCTCCTGTGCTAATAT
ATAGCCCTAACCTACACTGACGTAAAGGCCAAAGTCTAAAAATACCCGCCAAAATGACACACACGCCCA
GCACACGCCCAGAAACCGGTGACACACTCAAAAAAATACGTGCGCTTCCTCAAACGCCCAAACCGGCGT
CATTTCCGGGTTCCCACGCTACGTCACCGCTCAGCGACTTTCAAATTCCGTCGACCGTTAAAAACGTCA
CTCGCCCCGCCCCTAACGGTCGCCCTTCTCTCGGCCAATCACCTTCCTCCCTTCCCAAATTCAAACGCC
TCATTTGCATATTAACGCGCACAAAAAGTTTGAGGTATATATTTGAATGATG (AdHu5 E4Orf6/7)
SEQ ID NO. 39
MTTSGVPFGMTLRPTRSRLSRRTPYSRDRLPPFETETRATILEDHPLLPECNTLTMHNAWTSPSPPVKQ
PQVGQQPVAQQLDSDMNLSELPGEFINITDERLARQETVWNITPKNMSVTHDNIMLFKASRGERTVYSV
CWEGGGRLNTRVL (AdHu5 E4Orf6)
SEQ ID NO. 40
MTTSGVPFGMTLRPTRSRLSRRTPYSRDRLPPFETETRATILEDHPLLPECNTLTMHNVSYVRGLPCSV
GFTLIQEWVVPWDMVLTREELVILRKCMEVCLCCANIDIMTSMIMINGYESWALHCHCSSPGSLQCIAG
GQVLASWFRMVVDGAMFNQRFIWYREVVNYNMPKEVMFMSSVFMRGRHLIYLRLWYDGHVGSVVPAMSE
GYSALHCGILNNIVVLCCSYCADLSEIRVRCCARRTRRLMLRAVRIIAEETTAMLYSCRTERRRQQFIR
ALLQIIHRPILMHDYDSTPM (AdHu5 E4orf4)
SEQ ID NO. 41
MVLPALPAPPVCDSQNECVGWLGVAYSAVVDVIRAAAHEGVYIEPEARGRLDALREWIYYNYYTERSKR
RDRRRRSVCHARTWFCFRKYDYVRRSIWHDTTTNTISVVSAHSVQ (*Mycobacterium tuberculosis* protein Ag85A-nucleic acid sequence)
SEQ ID NO. 42
ATGGACGCCATGAAGAGGGGCCTGTGCTGCGTGCTGCTGCTGTGTGGCGCCGTGTTCGTGTCCCCCAGC
CAGGAAATCCACGCCCGGTTCAGACGGGGCAGCATGCAGCTGGTGGACAGAGTCAGAGGCGCCGTGACC
GGCATGAGCAGACGGCTGGTCGTGGGAGCTGTCGGAGCCGCTCTGGTGTCTGGACTCGTGGGAGCCGTG
GGCGGAACAGCTACAGCCGGCGCTTTCAGCAGACCCGGCCTGCCCGTGGAATATCTGCAGGTCCCCAGC
CCCAGCATGGGCCGGGACATCAAGGTGCAGTTCCAGTCTGGCGGACCCAACAGCCCTGCTCTGTACCTG
CTGGACGGCCTGAGAGCCCAGGACGACTTCAGCGGCTGGGACATCAACACCCCCGCCTTCGAGTGGTAC
GACCAGAGCGGCCTGTCTGTGGTCATGCCTGTGGGCGGCCAGAGCAGCTTCTACAGCGACTGGTATCAG
CCCGCTTGTGGCAAGGCCGGCTGCCAGACCTACAAGTGGGAGACATTCCTGACCAGCGAGCTGCCCGGC
TGGCTGCAGGCCAACAGACACGTGAAGCCCACCGGCTCTGCCGTCGTGGGCCTGTCTATGGCTGCCAGC
TCTGCCCTGACCCTGGCCATCTACCACCCCCAGCAGTTCGTATACGCTGGCGCCATGTCTGGCCTGCTG
GATCCTTCTCAGGCCATGGGACCCACCCTGATCGGACTGGCTATGGGAGATGCCGGCGGATACAAGGCC
AGCGACATGTGGGGCCCTAAAGAGGACCCCGCCTGGCAGAGAAACGACCCCCTGCTGAACGTGGGCAAG
CTGATCGCCAACAACACCAGAGTGTGGGTGTACTGCGGCAACGGCAAGCTGAGCGACCTGGGCGGCAAC
AACCTGCCCGCCAAGTTCCTGGAAGGCTTCGTGCGGACCAGCAACATCAAGTTCCAGGACGCCTACAAC
GCTGGCGGCGGACACAACGGCGTGTTCGACTTCCCCGACAGCGGCACCCACAGCTGGGAGTATTGGGGA
GCCCAGCTGAATGCCATGAAGCCCGACCTGCAGAGAGGCAGCATCCCTAATCCTCTGCTGGGCCTGGAC
TGA

| Sequences |
| --- |

(*Mycobacterium tuberculosis* protein Ag85A-amino acid sequence)

SEQ ID NO. 43

MDAMKRGLCCVLLLCGAVFVSPSQEIHARFRRGSMQLVDRVRGAVTGMSRRLVVGAVGAALVSGLVGAV
GGTATAGAFSRPGLPVEYLQVPSPSMGRDIKVQFQSGGANSPALYLLDGLRAQDDFSGWDINTPAFEWY
DQSGLSVVMPVGGQSSFYSDWYQPACGKAGCQTYKWETFLTSELPGWLQANRHVKPTGSAVVGLSMAAS
SALTLAIYHPQQFVYAGAMSGLLDPSQAMGPTLIGLAMGDAGGYKASDMWGPKEDPAWQRNDPLLNVGK
LIANNTRVWVYCGNGKLSDLGGNNLPAKFLEGFVRTSNIKFQDAYNAGGGHNGVFDFPDSGTHSWEYWG
AQLNAMKPDLQRGSIPNPLLGLD.

(synthetic peptide corresponding to the known immunodominant CD8+ T cell H-$2^d$ restricted epitopes in Ag85A-p11)

SEQ ID NO. 44

WYDQSGLSV (synthetic peptide corresponding to the known immunodominant $CD4^+$ T cell H-$2^d$ restricted epitopes in Ag85A-p15)

SEQ ID NO. 45

TFLTSELPGWLQANRHVKPT (nucleoprotein (NP) and matrix protein 1 (M1) of influenza A virus-nucleic acid sequence)

SEQ ID NO. 46

ATGGCCAGCCAGGGCACCAAGCGGAGCTACGAGCAGATGGAAACCGACGGCGACCGGCAGAACGCCACC
GAGATCCGGGCCAGCGTGGGCAAGATGATCGACGGCATCGGCCGGTTCTACATCCAGATGTGCACCGAG
CTGAAGCTGTCCGACTACGAGGGCCGGCTGATCCAGAACAGCCTGACCATCGAGAAGATGGTGCTGTCC
GCCTTCGACGAGCGGCGGAACAGATACCTGGAAGAGCACCCCAGCGCCGGCAAGGACCCCAAGAAAACC
GGCGGACCCATCTACCGGCGGGTGGACGGCAAGTGGATGCGGGAGCTGGTGCTGTACGACAAAGAGGAA
ATCCGGCGGATCTGGCGGCAGGCCAACAACGGCGAGGACGCCACAGCCGGCCTGACCCACATGATGATC
TGGCACAGCAACCTGAACGACACCACCTACCAGCGGACCAGGGCCCTCGTGCGGACCGGCATGGACCCC
CGGATGTGCAGCCTGATGCAGGGCAGCACACTGCCCAGAAGAAGCGGAGCTGCCGGAGCCGCCGTGAAG
GGCATCGGCACCATGGTGATGGAACTGATCCGGATGGTGAAGCGGGGCATCAACGACCGGAATTTTTGG
AGGGGCGAGAACGGCAGAAAGACTAGAAGCGCCTACGAGCGGATGTGCAACATCCTGAAGGGCAAGTTC
CAGACAGCCGCCCAGCGGGCCATGGTGGACCAGGTCCGGGAGAGCCGGAACCCCGGCAACGCCGAGATC
GAGGACCTGATCTTCCTGGCCCGGTCCGCCCTGATCCTGCGGGGCAGCGTGGCCCACAAGAGCTGCCTG
CCCGCCTGCGTGTACGGCCCTGCCGTGAGCAGCGGCTACGACTTCGAGAAAGAGGGCTACAGCCTGGTC
GGCATCGACCCCTTCAAGCTGCTGCAGAACAGCCAGGTGTACAGCCTGATCCGGCCCAACGAGAACCCC
GCCCACAAGTCCCAGCTGGTCTGGATGGCCTGCCACAGCGCCGCCTTCGAGGATCTGCGGCTGCTGTCC
TTCATCCGGGGCACCAAGGTGTCCCCCAGGGGCAAGCTGTCCACCAGAGGCGTGCAGATCGCCAGCAAC
GAGAACATGGACAACATGGGCAGCAGCACCCTGGAACTGCGGAGCGGCTACTGGGCCATCCGGACCCGG
TCCGGCGGCAACACCAACCAGCAGCGGGCCAGCGCCGGACAGATCAGCGTGCAGCCCACCTTCTCCGTG
CAGCGGAACCTGCCCTTCGAGAAGAGCACCGTGATGGCCGCCTTCACCGGCAACACCGAGGGCCGGACC
AGCGACATGCGGGCCGAGATTATCCGGATGATGGAAGGCGCCAAGCCCGAGGAAGTGAGCTTCCGGGGC
AGGGGCGTGTTCGAGCTGTCCGATGAGAAGGCCACCAACCCCATCGTGCCCAGCTTCGAGATGAGCAAC
GAGGGCAGCTACTTCTTCGGCGACAACGCCGAGGAATACGACAATGGCGGCGGACCAGGCGGCGGAATG
AGCCTGCTGACCGAGGTGGAGACCTACGTGCTGTCCATCGTGCCTAGCGGCCCTCTGAAGGCCGAGATC
GCCCAGCGGCTGGAAGATGTGTTCGCCGGCAAGAACACCGACCTGGAAGCCCTGATGGAATGGCTGAAA
ACCCGGCCCATCCTGAGCCCCCTGACCAAGGGCATCCTGGGCTTCGTGTTCACCCTGACCGTGCCCAGC
GAGCGGGGCCTGCAGCGGCGGAGATTCGTGCAGAACGCCCTGAACGGCAACGGCGACCCCAACAACATG
GATAAGGCCGTGAAGCTGTACCGGAAGCTGAAGCGGGAGATCACCTTCCACGGCGCCAAAGAGATCGCC
CTGAGCTACAGCGCCGGAGCCCTGGCCAGCTGCATGGGCCTGATCTACAACCGGATGGGCGCCGTGACC
ACCGAGGTGGCCTTCGGCCTGGTCTGCGCCACCTGCGAGCAGATCGCCGACAGCCAGCACAGATCCCAC
CGGCAGATGGTGGCCACAACCAACCCTCTGATCAAGCACGAGAACCGGATGGTGCTGGCTAGCACCACC
GCCAAGGCCATGGAACAGATGGCCGGCAGCAGCGAGCAGGCCGCCGAAGCCATGGAAATCGCCAGCCAG
GCCAGACAGATGGTGCAGGCCATGCGGACCGTGGGCACCCACCCCAGCAGCTCCACCGGCCTGCGGGAC
GACCTGCTGGAAAACCTGCAGACCTACCAGAAACGGATGGGGGTGCAGATGCAGCGGTTCAAGTGA (nucleoprotein (NP) and matrix protein 1 (M1) of influenza A virus-amino acid sequence)

SEQ ID NO. 47

MASQGTKRSYEQMETDGDRQNATEIRASVGKMIDGIGRFYIQMCTELKLSDYEGRLIQNSLTIEKMVL
SAFDERRNRYLEEHPSAGKDPKKTGGPIYRRVDGKWMRELVLYDKEEIRRIWRQANNGEDATAGLTHM
MIWHSNLNDTTYQRTRALVRTGMDPRMCSLMQGSTLPRRSGAAGAAVKGIGTMVMELIRMVKRGINDR
NFWRGENGRKTRSAYERMCNILKGKFQTAAQRAMVDQVRESRNPGNAEIEDLIFLARSALILRGSVAH
KSCLPACVYGPAVSSGYDFEKEGYSLVGIDPFKLLQNSQVYSLIRPNENPAHKSQLVWMACHSAAFED
LRLLSFIRGTKVSPRGKLSTRGVQIASNENMDNMGSSTLELRSGYWAIRTRSGGNTNQQRASAGQISV
QPTFSVQRNLPFEKSTVMAAFTGNTEGRTSDMRAEIIRMMEGAKPEEVSFRGRGVFELSDEKATNPIV
PSFEMSNEGSYFFGDNAEEYDNGGGPGGGMSLLTEVETYVLSIVPSGPLICAEIAQRLEDVFAGKNTD
LEALMEWLKTRPILSPLTKGILGFVFTLTVPSERGLQRRFVQNALNGNGDPNNMDKAVKLYRKLKRE
ITFHGAKEIALSYSAGALASCMGLIYNRMGAVTTEVAFGLVCATCEQIADSQHRSHRQMVATTNPLIK
HENRMVLASTTAKAMEQMAGSSEQAAEAMEIASQARQMVQAMRTVGTHPSSSTGLRDDLLENLQTYQK
RMGVQMQRFK.

-continued

| Sequences |
|---|

(immunodominant CD8+ T cell H-2d restricted epitope in NP)
SEQ ID NO. 48
TYQRTRALV (linker sequence)
SEQ ID NO. 49
IPNPLLGLD

---

The invention claimed is:

1. An adenovirus vector comprising a capsid, wherein said capsid comprises one or more capsid proteins from chimpanzee adenovirus AdY25 and encapsidates a nucleic acid molecule comprising an exogenous nucleotide sequence of interest operably linked to expression control sequences which direct the expression thereof in an animal cell and an adenoviral packaging signal sequence, and wherein the nucleotide sequence that encodes the wild-type chimpanzee adenovirus AdY25 is SEQ ID No. 1.

2. The vector of claim 1 wherein said vector comprises an AdY25 genome that lacks a functional E1 locus.

3. The vector of claim 1 wherein said vector comprises an AdY25 genome that lacks an E3 locus.

4. The vector of claim 1 wherein the vector comprises an AdY25 genome wherein at least one of the E4 open reading frame (Orf) is heterologous.

5. The vector of claim 4 wherein the vector lacks a native E4 locus and the at least one E4Orf is the entire E4 locus.

6. The vector of claim 5 wherein the E4Orf6 open reading frame is from AdHu5.

7. The vector of claim 4 having an E4 locus that comprises E4Orf1, E4Orf2, and E4Orf3 from AdY25 and E4Orf4, Orf6 and Orf6/7 from AdHu5.

8. The vector of claim 1 wherein the exogenous nucleotide sequence of interest encodes a protein or a polypeptide.

9. The vector of claim 8 wherein the protein or the polypeptide is selected from the group comprising an antigen, a molecular adjuvant, an immunostimulatory protein or a recombinase.

10. The vector of claim 9, wherein said antigen is Ag85A from *Mycobacterium tuberculosis*.

11. The vector of claim 1 wherein said exogenous nucleotide sequence of interest is an miRNA or an immunostimulatory RNA sequence.

12. The vector of claim 1 wherein said capsid comprises one or more capsid proteins selected from the group consisting of:
   (a) an AdY25 hexon protein comprising the amino acid sequence of SEQ ID NO. 2:
   (b) an AdY25 penton protein comprising the amino acid sequence of SEQ ID NO. 3; and
   (c) an AdY25 fibre protein comprising the amino acid sequence of SEQ ID NO. 4.

13. An isolated nucleic acid molecule having a sequence identical to SEQ ID NO. 1 over its entire length.

* * * * *